United States Patent
Cohen et al.

(10) Patent No.: US 10,052,360 B2
(45) Date of Patent: *Aug. 21, 2018

(54) METHODS FOR TREATING DERMATOMYOSITIS OR POLYMYOSITIS BY ADMINISTERING A SOLUBLE CTLA4 MOLECULE

(71) Applicant: BRISTOL-MYERS SQUIBB COMPANY, Princeton, NJ (US)

(72) Inventors: Robert Cohen, Newtown, PA (US); Suzette Belder-Carr, Hopewell, NJ (US); David Hagerty, Cardiff by the Sea, CA (US); Robert James Peach, San Diego, CA (US); Jean-Claude Becker, New York, NY (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 227 days.

This patent is subject to a terminal disclaimer.

(21) Appl. No.: 15/047,849

(22) Filed: Feb. 19, 2016

(65) Prior Publication Data

US 2016/0158318 A1 Jun. 9, 2016

Related U.S. Application Data

(63) Continuation of application No. 14/193,687, filed on Feb. 28, 2014, now Pat. No. 9,296,808, which is a continuation of application No. 13/795,545, filed on Mar. 12, 2013, now Pat. No. 8,703,718, which is a continuation of application No. 13/788,970, filed on Mar. 7, 2013, now Pat. No. 8,722,632, which is a continuation of application No. 13/404,384, filed on Feb. 24, 2012, now Pat. No. 8,497,247, which is a continuation of application No. 13/191,923, filed on Jul. 27, 2011, now Pat. No. 8,148,332, which is a continuation of application No. 12/720,064, filed on Mar. 9, 2010, now Pat. No. 8,227,420, which is a continuation of application No. 10/419,008, filed on Apr. 18, 2003, now abandoned, which is a continuation-in-part of application No. 09/898,195, filed on Jul. 2, 2001, now Pat. No. 7,455,835.

(60) Provisional application No. 60/407,246, filed on Aug. 30, 2002, provisional application No. 60/373,852, filed on Apr. 19, 2002, provisional application No. 60/215,913, filed on Jul. 3, 2000.

(51) Int. Cl.
| | |
|---|---|
| C07K 14/705 | (2006.01) |
| A61K 38/17 | (2006.01) |
| A61K 39/00 | (2006.01) |
| A61K 39/395 | (2006.01) |
| A61K 47/48 | (2006.01) |
| A61K 38/00 | (2006.01) |

(52) U.S. Cl.
CPC ...... *A61K 38/1774* (2013.01); *A61K 39/0008* (2013.01); *A61K 39/395* (2013.01); *A61K 47/48415* (2013.01); *C07K 14/70521* (2013.01); *A61K 38/00* (2013.01); *C07K 2319/00* (2013.01)

(58) Field of Classification Search
None
See application file for complete search history.

(56) References Cited

U.S. PATENT DOCUMENTS

| | | |
|---|---|---|
| 4,399,216 A | 8/1983 | Axel et al. |
| 4,603,102 A | 7/1986 | Himmelmann et al. |
| 5,110,802 A | 5/1992 | Cantin et al. |
| 5,194,428 A | 3/1993 | Agrawal et al. |
| 5,354,678 A | 10/1994 | Lebkowski et al. |
| 5,397,703 A | 3/1995 | De Boer et al. |
| 5,434,131 A | 7/1995 | Linsley et al. |
| 5,521,288 A | 5/1996 | Linsley et al. |
| 5,539,082 A | 7/1996 | Nielsen et al. |
| 5,580,756 A | 12/1996 | Linsley et al. |
| 5,624,823 A | 4/1997 | Sachs et al. |
| 5,637,481 A | 6/1997 | Ledbetter et al. |
| 5,708,037 A | 1/1998 | Yagita |
| 5,747,034 A | 5/1998 | De Boer et al. |
| 5,770,197 A | 6/1998 | Linsley et al. |
| 5,773,253 A | 6/1998 | Linsley et al. |
| 5,789,446 A | 8/1998 | Uchiyama et al. |
| 5,824,655 A | 10/1998 | Border |
| 5,844,095 A | 12/1998 | Linsley et al. |
| 5,851,795 A | 12/1998 | Linsley et al. |
| 5,883,223 A | 3/1999 | Gray |
| 5,885,579 A | 3/1999 | Linsley et al. |
| 5,885,796 A | 3/1999 | Linsley et al. |
| 5,916,560 A | 6/1999 | Larsen et al. |
| 5,958,403 A | 9/1999 | Strom et al. |

(Continued)

FOREIGN PATENT DOCUMENTS

| | | |
|---|---|---|
| EP | 0 682 039 A1 | 11/1985 |
| EP | 0 613 944 A2 | 9/1994 |

(Continued)

OTHER PUBLICATIONS

Mayoclinic.com, Juvenile rheumatoid arthritis, Definition (by Mayo Clinic Staff) Mar. 8, 2013.
http://my.clevelandclinic.org/childrens-hospital/health-info/diseases-conditions/rheumatology/hic-juvenile-idiopathic-arthritis.aspx, "Juvenile Idiopathic Arthritis", Mar. 8, 2013.
Ruperto, et al., "Abatacept in children with juvenile idiopathic arthritis: a randomized, double-blind, placebo-controlled withdrawal trial", The Lancet, vol. 372, pp. 383-391 (2008).
Ruperto, et al., "Long-Term Safety and Efficacy of Abatacept in Children With Juvenile Idiopathic Arthritis", Arthritis Rheumatism, vol. 62 (6), pp. 1792-1802 (2010).

(Continued)

*Primary Examiner* — Ilia I Ouspenski
(74) *Attorney, Agent, or Firm* — Nickki L. Parlet

(57) ABSTRACT

The present invention relates to compositions and methods for treating autoimmune diseases by administering to a subject a CTLA4 molecule that block endogenous B7 molecules from binding their ligands.

16 Claims, 102 Drawing Sheets

(56) References Cited

U.S. PATENT DOCUMENTS

| | | |
|---|---|---|
| 5,968,510 A | 10/1999 | Linsley et al. |
| 5,977,318 A | 11/1999 | Chou |
| 5,993,800 A | 11/1999 | Linsley et al. |
| 6,040,292 A | 3/2000 | Sommer |
| 6,090,914 A | 7/2000 | Linsley et al. |
| 6,113,898 A | 9/2000 | Anderson et al. |
| 6,132,992 A | 10/2000 | Ledbetter et al. |
| 6,352,694 B1 | 3/2002 | June et al. |
| 6,444,792 B1 | 9/2002 | Gray et al. |
| 6,534,055 B1 | 3/2003 | June et al. |
| 6,641,809 B1 | 11/2003 | Brady et al. |
| 6,685,941 B1 | 2/2004 | Thompson et al. |
| 6,719,972 B1 | 4/2004 | Gribben et al. |
| 6,750,334 B1 | 6/2004 | Gray et al. |
| 6,830,937 B1 | 12/2004 | Brady et al. |
| 6,887,471 B1 | 5/2005 | Linsley et al. |
| 6,905,680 B2 | 6/2005 | June et al. |
| 7,094,874 B2 | 8/2006 | Bajorath et al. |
| 7,304,033 B2 | 12/2007 | Larsen et al. |
| 7,307,064 B2 | 12/2007 | Rusnak |
| 7,332,303 B2 | 2/2008 | Schilling et al. |
| 7,439,230 B2 | 10/2008 | Peach et al. |
| 7,455,835 B2 | 11/2008 | Cohen et al. |
| 7,541,164 B2 | 6/2009 | Schilling et al. |
| 7,700,556 B2 | 4/2010 | Peach et al. |
| 7,915,222 B2 | 3/2011 | Vratsanos et al. |
| 8,148,332 B2 | 4/2012 | Cohen et al. |
| 8,227,420 B2 | 7/2012 | Cohen et al. |
| 8,435,952 B2 | 5/2013 | Vratsanos et al. |
| 8,497,247 B2 | 7/2013 | Cohen et al. |
| 8,703,718 B2 * | 4/2014 | Cohen ............. C07K 14/70521 514/21.2 |
| 8,722,632 B2 * | 5/2014 | Cohen ............. C07K 14/70521 514/21.2 |
| 9,296,808 B2 * | 3/2016 | Cohen ............. C07K 14/70521 |
| 9,309,316 B2 * | 4/2016 | Dali ................... C07K 16/2827 |
| 2001/0053361 A1 | 12/2001 | Thompson et al. |
| 2002/0031510 A1 | 3/2002 | Larsen et al. |
| 2002/0039577 A1 | 4/2002 | Townsend et al. |
| 2003/0007968 A1 | 1/2003 | Adams et al. |
| 2003/0219863 A1 | 11/2003 | Peach et al. |
| 2004/0014171 A1 | 1/2004 | Peach et al. |

FOREIGN PATENT DOCUMENTS

| | | |
|---|---|---|
| JP | A-2000-86519 | 3/2000 |
| WO | WO94/01547 | 1/1984 |
| WO | WO1990/05541 | 5/1990 |
| WO | WO93/00431 | 1/1993 |
| WO | WO93/19757 | 10/1993 |
| WO | WO84/29436 | 12/1994 |
| WO | WO 94/28912 | 12/1994 |
| WO | WO95/06481 | 3/1995 |
| WO | WO95/28957 | 11/1995 |
| WO | WO 95/33770 | 12/1995 |
| WO | WO95/33823 | 12/1995 |
| WO | WO95/34320 | 12/1995 |
| WO | WO96/14865 | 5/1996 |
| WO | WO 96/23071 | 8/1996 |
| WO | WO97/28267 | 8/1997 |
| WO | WO98/31820 | 7/1998 |
| WO | WO98/33 513 | 8/1998 |
| WO | WO 98/56417 | 12/1998 |
| WO | WO1999/50282 | 10/1999 |
| WO | WO1999/51275 | 10/1999 |
| WO | WO1999/62525 | 12/1999 |
| WO | WO00/23115 | 4/2000 |
| WO | WO01/54732 A1 | 8/2001 |
| WO | WO01/90122 A2 | 11/2001 |
| WO | WO01/92337 | 12/2001 |
| WO | WO01/95928 | 12/2001 |
| WO | WO 02/02638 A2 | 1/2002 |
| WO | WO02/094202 | 11/2002 |
| WO | WO2004/058800 | 7/2004 |
| WO | WO2004/058944 | 7/2004 |
| WO | WO2005/016266 | 2/2005 |

OTHER PUBLICATIONS

Chakravarty, E., "A Pilot Study of Abatecept for the Treatment of Patients with Diffuse Cutaneous Systemic Sclerosis", ACR/ARHP Scientific Meeting, Nov. 6, 2011, 707, 2 pgs.

Chakravarty, Eliza F., et al., "Gene expression changes reflect clinical response in a placebo-controlled randomized trial of abatacept in patients with diffuse cutaneous systemic sclerosis", Arthritis Research & Therapy, 2015, vol. 17, 159 (14 pages).

de Paoli, FV, et al., "Abatacept induces clinical improvement in patients with severe systemic sclerosis", Scand J Rheumatol, 2014, vol. 43(4), pp. 342-345.

Elhai, M., et al., "Outcomes of patients with systemic sclerosis-associated polyarthritis and myopathy treated with tocilizumab or abatacept: a EUSTAR observational study", Ann Rheum Dis, ARD Online First, Dec. 19, 2012; 00:1-4; total of 6 pgs.

Elhai, M., et al., "Outcomes of patients with systemic sclerosis-associated polyarthritis and myopathy treated with tocilizumab or abatacept: a EUSTAR observational study", Ann Rheum Dis, 2013, vol. 72(7), pp. 1217-1220 (Abstract only—1 page).

A. Tjärnlund, et al., "[SAT0436] Abatacept in the Treatment of Adult Dermatomyositis and Polymyositis: Artemis, a Randomized, Treatment Delayed-Start Trial", Ann Rheum Dis 2015;74(Suppl2): 817, Abstract.

Orban, et al., "Co-stimulation modulation with abatacept in patients with recent-onset type 1 diabetes: a randomized, double-blind, placebo-controlled trial", Lancet. Jul. 30, 2011;378(9789):412-9. doi: 0.1016/S0140-6736(11)60886-6. Epub Jun. 28, 2011.

Roep, B.O., "New hope for immune intervention therapy in type 1 diabetes", Lancet, Jul. 30, 2011;378(9789):376-8. doi: 10.1016/S0140-6736(11)60977-X. Epub Jun. 28, 2011.

ClinicalTrials.gov "Intravenous CTLA4-Ig Treatment in Recent Onset Type 1 Diabetes Mellitus," accessed online at clinicaltrials.gov/ct2/show/NCT00505375 on Oct. 30, 2012, 4 pages.

Wikipedia, "Diabetes mellitus type 2," accessed at en.wikipedia.org/wiki/Diabetes_mellitus_type_2 on Oct. 30, 2012, 1 page.

Winer et al., Nature Medicine, 2011, 17:610-617.

Mallat, Nature Medicine, 2011, 17:539-540.

Croft, M. et al., "Naive Versus memory CD4 T Cell Response to Antigen", Journal of Immunology, vol. 152, pp. 2675-2685 (1994).

Cush, JJ. Et al., "Cellular basis for rheumatoid Inflammation", Clin. Orthop Relat Res., vol. 265, pp. 9-22 (1991).

Dougados, M. et al., "Abatacept provides increasing improvements in clinical measures of disease activity over time: results from the aim trial", Ann Rheum Dis, vol. 66(Suppl II) p. 429 (2007).

Dougados, M. et al., "Efficacy of Abatacept or infliximab treatment in rheumatoid arthritis patients with an inadequate response to methotrexate", Ann Rheum Dis, vol. 66(Suppl II), p. 88 (2007).

Dougados, M. et al., "Abatacept reduces fatigue and pain severity and sleep problems through 2 years in rheumatoid arthritis patients in the aim and attain trails", Ann Rheum Dis, vol. 66(Suppl II), p. 429 (2007).

Hegen, M. et al., "Utility of animal models for identification of potential therapeutics for Rheumatoid Arthritis", Ann Rheum Dis, ARD Online published Nov. 29, 2007.

Isaacs, J., "T cell Immunomodulation—the Holy Grail of therapeutic tolerance", Current opinion in Pharmacology, vol. 7, pp. 418-425 (2007).

Malmstrom, V. et al., "Modulating co-stimulation: a rational strategy in the treatment of rheumatoid arthritis?", Arthritis Res Ther, vol. 7(Suppl 2), p. S15-S20, (2005).

Qin, S. et al., ""Infectious" transplantation tolerance", Science, vol. 259(5097), pp. 974-977 (1993).

Sibilia, J. et al., "Sustained improvements in disease activity score 28 )DAS28) and patient (PT)-reported outcomes (PRO) with abatacept (ABA) in Rheumatoid arthritis (RA) PTS with an inad-

(56) References Cited

OTHER PUBLICATIONS equate response to anti-TNF Therapy: the long term extension (LTE) of the attain trial", Ann Rheum Dis, vol. 65(Suppl II), p. 501 (2006).
Wells, G.A. et al., "Minimal disease activity state for patients with Rheumatoid arthritis treated with abatacept", Ann Rheum Dis, vol. 66(Suppl II), p. 341 (2007).
Keystone, E., "Abandoned therapies and unpublished trials in rheumatoid arthritis", Opin Rheumatol., vol. 15, pp. 253-258 (2003).
Gallon, L. et al., "Differential Effects of B7-1 Blockade in the Rat Experimental Autoimmune Encephalomyelitis Model", The J. of Immunology, vol. 159, pp. 4212-4216 (1997).
Khoury, S. et al., Ex Vivo Treatment of Antigen-Presenting Cells with CTLA4lg and Encephalitogenic Peptide Prevents Experimental Autoimmune Encephalomyelitis in the Lewis Rat, The J. of Immunology, vol. 157, pp. 3700-3705 (1996).
Lin, H. et al., :CD28 blockade alters cytokine mRNA profiles in cardiac transplantation, Surgery, vol. 122(2) pp. 129-137 (1997).
Wagener, M. et al., "Alloantigen-Driven T Cell Death Mediated by Fas Figand and Tumor Necrosis Factor-[alpha] is not essential for the induction of Allograft Acceptance", Transplantation, vol. 69(11), pp. 2428-2432 (2000).
Bolling, S. et al., "The Effect of Combination Cyclosporine and CTLA4-lg Therapy on Cardiac Allograft Survival", Journal of Surgical Research, vol. 57, pp. 60-64 (1994).
Choi, H. et al., "A Cost-Effectiveness Analysis of Treatment Options for Patients with Methotrexate-Resistant Rheumatoid Arthritis", Arthritis & Rheumatism, vol. 43(10), pp. 2316-2327 (2000).
Merriam-Webster Dictionary (visited online on Feb. 12, 2008), entry for "adequate".
Brockbank, J. et al., "Psoriatic arthritis", Expert Opinion on Investigational Drugs, vol. 9(7), pp. 1511-1522 (2000).
Mease, P. et al., "Abatacept in the Treatment of Patients With Psoriatic Arthritis", Arthritis & Rheumatism, vol. 63(4), pp. 939-944 (2011).
Schett et al., Arthritis Research and Therapy, 13 (Suppl. 1), S4, pp. 1-9 (2011).
Battleman, David S. et al., "HSV-1 Vector-Mediated Gene Transfer of the Human Nerve Growth Factor Receptor p75.sup.hNSFR Defines High Affinity NGF Binding," The Journal of Neuroscience, Mar. 1993, 13(3):941-51 (Exhibit 6).
Broach, James R., "Construction of High Copy Yeast Vectors Using 2-μm Circle Sequences", Methods in Enzymology, 1983, 101:307-25 (Exhibit 7).
Byrn, Randal A. et al., "Characterization of In Vitro Inhibition of Human Immunodeficiency Virus by Purified Recombinant CD4," Journal of Virology, Oct. 1989, 63(10):4370-5 (Exhibit 8).
Carroll, R. et al., "SZ 401 Construction and Characterization of Replication-Defective HIV-1 Packaging Cell Lines," Journal of Cell Biochemistry, 1993, 17E:241 (Exhibit 9).
Clarke, Louise et al., "Selection Procedure for Isolation of Centromere DNAs from Saccharomyces cerevisiae," Methods in Enzymology, 1983, 101:300-7 (Exhibit 10).
Cohen, Stanley N. et al., "Nonchromosomal Antibiotic Resistance in Bacteria: Genetic Transformation of Escherichia coli by R-Factor DNA," Proc. Nat'l. Acad. Sci. USA, Aug. 1972, 69[8]:2110-4 (Exhibit 11).
Darievach, Fiona et al., "Human ig Superfamily CTLA-4 Gene: Chromosomal Localization and Identity of Protein Sequence Between Murine and Human CTLA-4 Cytoplasmic Domains," Eur. J. Immunol., 1988, 18:1901-6 [Exhibit 12].
Dash, Bret et al., "Deletion of a Single N-linked Glycosylation Site From the Transmembrane Envelope Protein of Human Immunodeficency Virus Type 1 Stops Cleavage and Transport of gp 160 Preventing anv-mediated Fusion," Journal of General Virology, 1994, 75:1389:97 (Exhibit 13).
Davison, Elliott, "Obtaining Infectious Virus From Recombinant Plasmids" in Molecular Virology: A Practical Approach. Chapter 7 [IRL Press, New York, NY, 1993], pp. 184-186 (Exhibit 14).
Falk, Kirsten et al., "Both Human and Mouse Cells Expressing H-2K$^b$ and Ovalbumin Pocess the Same Peptide, SIINFEKL," Cellular Immunology, 1993, 150:447-52 (Exhibit 15).
FDA CDER Guideline for the Clinical Evaluation of Anti-Inflammatory and Antirheuraetic Drugs, Apr. 1988 (Exhibit 16).
FDA Guidance for Industry: Clinical Development Programs for Drugs, Devices and Biological Products for the Treatment of Rheumatoid Arthritis [RA]. Feb. 1999. (Exhibit 17).
Felson, David T. et al., "The American College of Rheumatology Preliminary Core Set of Disease Activity Measures for Rheumatoid Arthritis Clinical Trials", Arthritis and Rheumatism, Jun. 1993, 36(6):729-40, (Exhibit 18).
Felson, David T. et al., "American College of Rheumatology Preliminary Definition of Improvement in Rheumatoid Arthritis," Arthritis and Rheumatism, Jun. 1995, 38(6):727-35 (Exhibit 19).
Fiers, W. et al., "Complete Nucleotide Sequence of SV4O DNA," Nature, May 1978, 273:113-20 (Exhibit 20).
Fries, James F. et al., "The Dimensions of Health Outcomes: The Health Assessment Questionnaire, Disability and Pain Scales," Journal of Rheumatology, 1982, 9(5):789-93 (Exhibit 21).
Fujikawa, Kiyomi et al., "Nuclear Localization and Transforming Activity of Human Papillomavirus Type 16 E7-β-Galactosidase Fusion Protein: Characterization of the Nuclear Localization Sequence," Virology, 1994, 204:789-93 (Exhibit 22).
Gerard, C. et al., "Production and Characterization of Polyclonal Antibodies Recognizing the Intracytoplasmic Third Loop of the 5-Hydroxytryptamine, Receptor," Neuroscience, 1994, 62(3):721-39 (Exhibit 23).
Goeddel, David V. et al., "Synthesis of Human Fibroblast Interferon by E. coli," Nucleuc Acids Research, 1980 8(18):4057-74 (Exhibit 24).
Greene, JoAnne L. et al. "Covalent Dimerization of CD28/CTLA-4 and Oligomerization of CD8O/CD86 Regulate T Cell Costimulatory Interactions," The Journal of Biological Chemistry, Oct. 25, 1996, 271(43):26762-71 (Exhibit 25).
Hansen, John A. et al., "Monoclonal Antibodies Identifying a Novel T-Cell Antigen and la Antigens of Human Lymphocytes," Immunogentics, 1980, 10:247:60 (Exhibit 26).
Hartley, R. D. et al., "Toxic Metabolites of Aspergillus Flavus," Nature, Jun. 15, 1963, 198:1056-8 (Exhibit 27).
Hess, B. et al., "Cooperation of Glycolytic Enzymes," Advances in Enzyme Regulation, 1969, 7:149-67 (Exhibit 28).
Hitzeman, Ronald A. et al., "Isolation and Characterization of the Yeast 3-Phosphogiycerokinase Gene [PGK] by an Immunological Screening Technique," The Journal of Biological Chemistry, 1980, 255(24):12073-80 (Exhibit 29).
Holland, Michael J. and Janice P. Holland, "Isolation and Identification of Yeast Messenger Ribonucleic Acids Coding for Enolase, Glyceraldehyde-3-phosphate Dehydrogenase, and Phosphoglycerate Kinase," Biochemistry, Nov. 1978, 17(23):4900-7 (Exhibit 30).
Ikeda, Toshido et al., "Isolation of a cDNA Encoding the Chicken p50B/p97 (Lyt-10) Transcription Factor," Gene, 1994, 138:193-6 (Exhibit 31).
Johnsson, Bo et al., "Immobilization of Proteins to a Carboxymethyidexytran-Modified Gold Surface for Biospecific Interaction Analysis in Surface Plasmon Resonance Sensors," Anal Biochem, Nov. 1991, 198:269-77 (Exhibit 32).
Jones, Nancy H. et al., "Isolation of Complementary DNA Clones Encoding the Human Lymphocyte Glycoprotein T 1/Leu-1," Nature, Sep. 1986, 323:346-9 (Exhibit 33).
Karin, Michael and Robert I. Richards, "Human Metallothionem Genes—Primary Structure of the Metallothioneln-II Gene and a Related Procesed Gene," Nature, Oct. 1882, 299(58BS):797-802 (Exhibit 34).
Khilko, Sergei N. et al., "Direct Detection of Major Histocompatibility-Complex Class 1 Binding to Antigenic Peptides Using Surface Plasmon Resonance Peptide Immobilization and Characterization of Binding Specificity," Journal of Biological Chemistry, Jul. 1993, 268(21):15425-34 (Exhibit 35).

(56) References Cited

OTHER PUBLICATIONS

Kolheker, Apama S. et al., "Peptidylglycine α-Hydroxylating Monooxygenase Active Site Residues, Disulfide Linkages and a Two-Domain Model of the Catalytic Core," *Biochemistry*, 1997, 36:10901-9 (Exhibit 35).
Kriegler, Michael, ed., "Gene Transfer and Expression, Laboratory Manual," 1991, 96-8 (Exhibit 37).
Larsen, Arvi et al., "Radiographic Evaluation of Rheumatoid Arthritis and Related Conditions by Standard Reference Films," *Acta-Radiologica-Diagnosis*, Jul. 1997, 18(4):481-91 (Exhibit 38).
Lasky, Laurence A. et al., "Neutralization of the AIDS Retrovirus by Antitbodies to a Recombinant Envelope Glycoprotein," *Science*, 1986, 233i4760I:209-12 (Exhibit 39).
Lenschow, Deborah J. et al., "Long-Term Survival of Xenogeneic Pancreatic Islet Grafts Induced by CTLA4lg," *Science*, Aug. 1992, 257:789-92 (Exhibit 40).
Linsley, Peter S. et al., "Binding Stoichiometry of the Cytotoxic T Lymphocyte-associated Molecule-4 (CTLA-4) A Disulfide-Linked Homodimer Binds Two CD85 Molecules," *The Journal of Biological Chemistry*, 1995, 270(25):15417-24- (Exhibit 41).
Linsley, Peter S. et al., "Co-expression and Functional Cooperation of CTLA-4 and CD28 on Activated T Lymphocytes," *J. Exp. Med.* Dec. 1992, 176:1595-1604 (Exhibit 42).
Linsley, Peter S. and Jeffrey Ledbetter, "The Role of the CD28 Receptor During T Cell Responses to Antigen," *Annu. Rev. Immunol.*, 1993, 11:191-212 (Exhibit 43).
Linsley, Peter S. et al., "Human B7-1 (CD8O) and B7-2.(CD86) Bind with Similar Avidities but Distinct Kinetics CD28 and CTLA-4 Receptors," *Immunity*, Dec. 1994, 1:783-801 (Exhibit 44).
Linsley, Peter S. et al., "Immunosuppression in Vivo by a Soluble Form of the CTLA-4 T Cell Activation Molecule," *Science*, Aug. 1992, 257:792-5 [Exhibit 45].
Lipsky, Peter E., et al., "Rheumatoid Arthritis," *Harrison's Principles of Internal Medicine 13th Edition*, Isselbacher, et al., eds., 1992, 2:1648-55 (Exhibit 46).
Maini, Ravinder et al., "Infiximab (Chimeric Anti-Tumour Necrosis Factor α Monoclonal Antibody) Versus Placebo in Rheumatoid Arthritis Patients Receiving Concomitant Methotrexate: A Randomised Phase III Trial," *The Lancet*, Dec. 1999, 354:1932-9 (Exhibit 47).
Malik, Najima et al., "Molecular Cloning, Sequence Analysis and Functional Expression of a Novel Growth Regulator, Oncostatin M," *Molecular and Cellular Biology*, Jul. 1989, 9(7):2847-53 (Exhibit 48).
Martin, Paul J. et al., "Preincubation of Donor Bone Marrow Cells with a Combination of Murine Monoclonal Anti-T-Cell Antibodies Without Complement Does Not Prevent Graft-Versus-Host Disease After Allogenic Marrow Transplantation," *Journal of Clinical Immunology*, 1984, 4(1):18-22 (Exhibit 49).
Mathiesen, T. et al., "Prolonged Survival and Vascularization of Xenografted Human Glioblastoma Cells in the Central Nervous System of Cyclosporine A Treated Rats," *Cancer Letters*, 1989, 44:151-6 (Exhibit 50).
Metzler, William J. et al., "Solution Structore of Human CTLA-4 and Delineation of a CD8O/CD86 Binding Site Conserved in CD28," *Nature Structural Biology*, Jun. 1997, 4(7):527-31 (Exhibit 51).
Moreland, Larry W. et al., "Etanercept Therapy in Rheumatoid Arthritis A Randomized, Controlled Trial," *Ann. Intern. Med.*, 1999, 130:478-86 (Exhibit 52).
Mueller, Daniel L. et al., "Clonal Expansion Versus Functional Clonal Inactivation: A Costimulatory Signalling Pathway Determines the Outcome of T Cell Antigen Receptor Occupancy," *Ann. Rev. Immunol.*, 1989, 7:445-80 (Exhibit 53).
O'Shannessy, Daniel J. et al., "Determinations of Rate and Equilibrium Binding Constants for Macromolecular Interactions Using Surface Plasmon Resonance: Use of Nonlinear Least Squares Analysis Methods," *Analytical Biochemistry*, 1993, 212:457-68 (Exhibit 54).
Oaks, Martin K. et al., "A Native Soluble Form of CTLA-4," *Molecular Immunology*, 2000, 201:144-53 (Exhibit 55).
Peach, Robert J. et al., "Complementarity Determining Region 1 (CDR1)- and CDR3-analogous Regions in CTLA-4 and CD28 Determine the Binding to B7-1," *J. Exp. Med.*, Dec. 1994, 180:2049-58 (Exhibit 56).
Rammensee, Hans-Georg et al., "Peptides Naturally Presented by MHC Class I Molecules," *Annu. Rev. Immunol.*, 1993, 11:213-44 (Exhibit 57).
Ruddy S. et al., Kelley's Textbook of Rheumatology, 6th Edition. W. B. Saunders Company 2001; vol. 1:823-633 (Exhibit 58).
Ruddy S. et al., Kelley's Textbook of Rheumatology, 6th Edition, W. B. Saunders Company 2001; vol. 2:1001-1022 (Exhibit 59).
Sharp, John T. et al., "How Many Joints in the Hands and Wrists Should be Included in a Score of Radiologic Abnormalities Used to Assess Rheumatoid Arthritis" *Arthritis and Rheumatism*, Dec. 1985, 28(12):1326-35 (Exhibit 60).
Shimatake, Hiroyuki and Martin Rosenberg, "Purified λ Regulatory Protein cll Positively Activates Promoters for Lysogenic Development," *Nature*, Jul. 1981, 292:128-32 (Exhibit 61).
Smith, Douglas H. et al., "Blocking of HIV-1 Infectivity by a Soluble, Secreted Form of the CD4 Antigen," *Science*, Dec. 1987, 238:1704-7 (Exhibit 62).
Stinchcornb, D. T. et al., "Isolation and Characterisation of a Yeast Chromosomal Replicater," *Nature*, Nov. 1979, 282:39-43 (Exhibit 63).
Tan, Patrick et al., "Induction of Alloantigen-specific Hyporesponsiveness in Human T Lymphocytes by Blocking Interaction of CD28 with its Natural Ligand B7/BB1," *J. Exp. Med.*, Jan. 1993, 177:165-73 (Exhibit 64).
Turka, Laurence A. et al., "T-Cell Activation by the CD28 Ligand B7 is Required for Cardiac Allograft Rejection In Vivo," *Proc. Nat'l. Acad. Sci, USA*, Nov. 1992, 89:11102-5 (Exhibit 65).
Toyama, Reiko and Hiroto Okayama, "Human Chorionic Gonadotropin α and Human Cytomegalovirus Promoters are Extremely Active in the Fission Yeast *Schizosaccharomyces pombe*," *FEBS*, Jul. 1990, 268(1):217-21 (Exhibit 66).
Tschumper, Gary and John Carbon, "Sequence of a Yeast DNA Fragment Containing a Chromosomal Replicater and the TRP1 Gene," *Gene*, 1980, 10:157-66 (Exhibit 67).
Urlaub, Gail et al., "Effect of Gamma Rays at the Dihydrotolate Reductase Locus: Deletions and Inversions," *Somatic Cell and Molecular Genetics*; 1986, 12(6):656-66. (Exhibit 68).
Weinblatt, Michael E. et al., "A Trial of Elanercept, A Recombinant Tumor Necrosis Factor Receptor:Fc Fusion Protein, in Patients with Rheumatold Arthritis Receiving Methotrexate," *The New England Journal of Medicine*, Jan. 28, 1999, 340(4):253-9 (Exhibit 69).
Williams, R. Sanders et al., "Introduction of Foreign Genes into Tissues of Living Mice By DNA-coated Microprojectiles," *Proc. Nat'l. Acad. Sci. USA*, Apr. 1991, 88:2726-3D (Exhibit 70).
Yokochi, Takashi et al., "B Lymphoblast Antigen (BB-1) Expressed on Epstein-Barr Virus-Activated B Cell Blasts, B Lymphoblastoid Cell Lines and Burkitt's Lymphomas," *The Journal of Immunology*, Feb. 1982, 128(2):823-7 (Exhibit 71).
American College of Rheumatology Ad Hoc Committee on Clinical Guidelines, "Guidelines for the Management of Rheumatoid Arthritis," *Arthritis & Rheumatism*, 1998, 39:713-22 (Exhibit 227).
Berkner, Kathleen L., "Development of Adenovirus Vectors for the Expression of Heterologous Genes," *Biotechniques*, 1988, 6:616-30 (Exhibit 228).
Bitter, Grant A. et al., "Expression and Secretion Vectors for Yeast," *Methods in Enzymology*, Wu and Grossman (eds.), 1987, 153:5)6-44 (Exhibit 229).
Cochran, William G., "Some Methods for Strengthening the Common $x^2$ Tests," *Biometrics*, 1954, 10:417-51 (Exhibit 230).
Dugas, Hermann and Christopher Penney, *Bioorganic Chemistry: A Chemical Approach to Enzyme Action*, 1981, Springer-Verlag, NY, 54-92 (Exhibit 231).
Egholm, Michael et al., "Peptide Nucleic Acids (PNA): A Novel Approach to Sequence-Selective Recognition of Double-Stranded DNA," *Innovation and Perspectives in Solid Phase Synthesis: Peptides, Polypeptides and Oligonucleotides*, Roger Epton (ed.), 1992, pp. 325-328 (Exhibit 232).

(56) References Cited

OTHER PUBLICATIONS

Freeman, Gordon J. et al., "B7, A New Member of the Ig Superfamily with Unique Expression on Activated and Neoplastic B Cells," *The Journal of Immunology*, 1989, 143-2714-22 (Exhibit 233).
Handschumacher, Robert E., "Immunosuppressive Agents," *Goodman and Gilman's: The Pharmacological Basis of Therapeutics*, Pergamon Press, NY, 1990, 1264-76 (Exhibit 234).
Koch, Gary G. and Stuart A. Ganstry, "Statistical Considerations for Muitiplicity in Confirmatory Protocols," *Drug Information Journal*, 1996, 30:523-34 (Exhibit 235).
Mantel, Nathan and Wiliam Haenszel, "Statistical Aspects of the Analysis of Data From Retrospective Studies of Disease," *Journal of the National Cancer Institute*, 1959, 22:719-48 (Exhibit 236).
Linsley, Peter S, et al., "CTLA-4 Is a Second Receptor for the B Cell Activation Antigen B7" *The Journal Experimental Medicine*, 1991, 174:561-9 (Exhibit 72).
Gimmi, Claude D. et al., "Human T-cell clonal energy is induced by antigen presentation in the absence of B7 costimulation" *Proc. Natl. Acad. Sci. USA*, 1993, 90:6586-90 (Exhibit 73).
Azuma, Miyuki et al., "B70 antigen is a second ligand for CTLA-4 and CD28," *Nature*, 1993, 366:76-9 (Exhibit 74).
Ronchese, Franca et al., "Mice Transgenic for a Soluble Form of Murine CTLA-4 Show Enhanced Expansion Antigen-specific CD4+ T Cells and Defective Antibody Production In Vivo" *The Journal of Experimental Medicine*, 1994, 179:809-17 (Exhibit 75).
Griggs, Nathan D. et al., "The Relative Contribution of the CD28 and gp39 Costimulatory Pathways in the Clonal Expansion and Pathogenic Acquisition of Self-reactive T Cells" *The Journal of Experimental Medicine*, 1996, 183:801-10 (Exhibit 76).
Verwilghen, Jo et al., "Expression of Functional B7 and CTLA4 on Rheumatoid Synovial T Cells" *The Journal of Immunology*, 1994, 153:1378-85 (Exhibit 77).
Blazar, Bruce R. et al., "In Vivo Blockade of CD28/CTLA4: B7/BB1 Interaction With CTLA4-lg Reduces Lethal Murine Graft-Versus-Host Disease Across the Major Histocompatibility Complex Barrier in Mice" *Blood*, 1994, B3:3815-26 (Exhibit 78).
Finck, Bathara K., et al., "Treatment of Murine Lupus with CTLA4lg" *Science*, 1994, 265:1225-7 (Exhibit 79).
Perrin, Peter J. et al., "Role of B7:CD28/CTLA-4 in the Induction of Chronic Relapsing Experimental Allergic Encephalomyelitis" *The Journal of Immunology*, 1995, 154:1481-90 (Exhibit 90).
Pearson, Thomas C. et al., "Transplantation Tolerance Induced By CTLA4-lg" *Transplantation*, 1984, 57:1701-6 (Exhibit 81).
Baliga, Prabhaker et al., "CTLA4lg Prolongs Allograft Survival While Suppressing Cell-Mediated Immunity" *Transplantation*, 1994, 58:1082-90 (Exhibit 82).
Tepper, M. A. et al., "Tolerance Inductiun by Soluble CTLA4 in a Mouse Skin Transplant Model" *Transplantation Proceedings*, 1994, 25:3151-4 (Exhibit 83).
Perico, Norberto et al., "Toward novel antirejection strategies: In vivo immunosuppressive properties of CTLA4lg" *Kidney International*, 1995, 47:241-6 (Exhibit 84).
Finck, B. K. et al., "Effects of CTLA4lg in Murine Lupus" *Arthritis and Rheumatism*, 1994, 37:S222 (Exhibit 85).
Nishikawa, Kazuhiro et al., "Effect of CTLA-4 chimeric protein on rat autoimmune anti-glomerular basement membrane glomerulonephritis" *Eur. J. Immunol*, 1994, 24:1249-54 (Exhibit 86).
Wallace, Philip M. et al., "CTLA4-lg Treatment Ameliorates the Lethality of Murine Graft-Versus-Host Disease Across Major Histocompatibility Complex Barriers" *Transplantation*, 1994, 58:602-10 (Exhibit 87).
Damle, Nitin K. et al., "Costimulation of T Lymphocytes with Integrin Ligands Intercellular Adhesion Molecule-1 or Vascillar Cell Adhesion Molecule-1 Induces Functional Expression of CTLA-4, a Second Receptor for B7" *The Journal of Immunology*, 1994, 152:2686-97 (Exhibit 88).

Milich, David R, et al., "Soluble CTLA-4 Can Suppress Autoantibody Production and Elicit Long Term Unresponsiveness in a Novel Transgenic Model," *The Journal of Immunology*, 1994, 153:429-35 (Exhibit 89).
Webb, Louise M. C. et al., "Prevention and amelioration of collagen-induced arthritis by blockade of the CD28 co-stimulatory pathway: requirement for both B7-1 and B7-2" *European Journal of Immunology*, 1996, 23:2320-8 (Exhibit 90).
Van Oosterhout, A. J. M. et al., "Murine CTLA4-lgG Treatment Inhibits Airway Eosinophilla and Hyperresponsiveness and Attenuates IgE Upregulation in a Murine Model of Allergic Asthma," *American Journal of Respiratory Cell and Molecular Biology*, 1997, 17:386-92 (Exhibit 91).
Abrams, Judith R. et al., "CTLA4lg-mediated blockade of T-cell constimulation in patients with psoriasis vulgaris," *The Journal of Clinical Investigation*, 1999, 103:1243-52 (Exhibit 92).
Ibrahim, Sherif et al., "CTLA4lg inhibits Alloantibody Response to Repeated Blood Transfusions," *Blood*, 198, 88:4594-6OO (Exhibit 93).
Lenschow, Deborah J. et al., "Differential Effects of Anti-B7-1 and Anti-B7-2 Monoclonal Antibody Treatment on the Development of Diabetes in the Nonobese Diabetic Mouse," *J. Exp. Med.*, 1995, 181:1145-55 (Exhibit 94).
Lenschow, Deborah J. et al., "Long-Term Survival of Xenogeneic Pancreatic Islet Grafts Induced by CTLAlg," *Science*, 1992, 257:789-92 (Exhibit 95).
Sayegh, Mohamed H., "Finally, CTLA4lg graduates to the clinic," *The Journal of Clinical Investigation*, 1999, 103:1223-5 (Exhibit 96).
Wolfe, Frederick, "The epidemiology of drug treatment failure in rheumatoid arthritis," *Bailliere's Clinical Rheumatology*, 1995, 9:619-32 (Exhibit 97).
Hochberg, Marc C. and Timothy D. Spector, "Epidermiology of Rheumatoid Arthritis: Update!," *Epidemiologic Reviews*, 1990, 12:247-52 (Exhibit 98).
Spector, Tim D., "Rheumatoid Arthritis," *Rheumatic Disease Clinics of North America*, 1990, 16:513-37 (Exhibit 99).
Liu, Ming Fei, et al., "The Presence of Constimulatory Molecules CD85 and CD28 in Rheumatoid Arthritis Synovium," *Arthritis & Rheumatism*, 1996, 39:110-4 (Exhibit 100).
Sfikakis, Petros P. and Charles S. Via "Expression of CD28, CTLA4, CD80, and CD86 Molecules in Patients Autoimmune Rheumatic Diseases: Implications for Immunotherapy," *Clinical Immunology and Immunopathology*, 1997, 83: 195-8 [Exhibit 101].
Sayegh, Mohamed H., et al., "CD28-B7 Blockade after Alloantigenic Challenge In Vivo Inhibits Th1 Cytokines but Spares Th2," *J. Exp. Med.*, 1995, 181: 1869-74 [Exhibit 102].
Racusen, Lorraine C., et al., "The Banff 97 working classification of renal allograft pathology," *Kidney International*, 1999, 55: 713-23 [Exhibit 103].
Parkin, David, et al., "Treatment of multiple sclerosis with interferon β: an appraisal of cost-effectiveness and quality of life," *J. Neurol. Neurosurg. Psychiatry*, 2000, 68:144-9 [Exhibit 104].
Nortvedt, Monica W. et al., "Quality of life in multiple sclerosis: Measuring the disease effects more broadly," *Neurology*, 1999, 53:1098-1103 (Exhibit 105).
Pearson, Thomas C. et al., "Transplantation Tolerance Induced By CTLA4-lg" *Transplantation*, 1994, 57:1701-6 (Exhibit 106).
Liao, Hua-Xin and Barton F. Haynes, "Role of Adhesion Molecules in the Pathogenesis of Rheumatoid Arthritis," *Rheumatic Disease Clinics of North America*, 1995, 21:715-40 (Exhibit 107).
Thomas, Ranjeny and Christopher Quinn, "Functional Differentiation of Dendritic Cells in Rheumatoid Arthritis: Role of CD86 in the Synovium," *The Journal of Immunology*. 1996, 156:3074-86 (Exhibit 109).
Verhoeven, A. C. et al., "Combination Therapy in Rheumatoid Arthritis: Updated Systematic Review," *British Journal of Rheumatology*, 1998, 37:612-9 (Exhibit 110).
Schiff, Michael, "Emerging Treatments for Rheumatoid Arthritis" *Am. J. Med.*, 1997, 102: 115-155 [Exhibit 111].

(56) References Cited

OTHER PUBLICATIONS

Balsa, A. et al., "Differential Expression of the Costimulatory Molecules B7.1 (CD8O) and B7.2 (CD86) in Rheumatoid Synovial Tissue," *British Journal of Rheumatology*, 1996, 35:33-7 (Exhibit 112).

Ranheim Erik A. and Thomas J. Kipps, "Elevated Expression of CD80 (B7/BB1) and Other Accessory Molecules on Synovial Fluid Mononuclear Cell Subsets in Rheumatoid Arthritis," *Arthritis & Rheumatism*, 1994, 37:1637-46 (Exhibit 113).

Freeman, Gordon J. et al., "Cloning of B7-2; A CTLA-4 Counter-Receptor that Costimulates Human T Cell Proliferation," *Science*, 1993, 262:909-11 (Exhibit 114).

Becker, J.C., Abstract and Presentation of "A multi-center, randomized, double-blind, placebo controlled study to evaluate the safety and preliminary clinical activity of multiple doses of CTLA4Ig and LEA29Y administration.intravenously to subjects with rheumatoid arthritis," presented at American College of Rheumatology Conference: "2001 Innovative Therapies in Autoimmune Diseases," San Francisco, California, Mar. 8, 2001 (Exhibit 115).

Aruffo, S., Presentation of "Approaches to Immune Regulation" at BIO 2000 in Boston, Massachusetts, Mar. 27, 2000 (Exhibit 116).

Abrams, Judith R. et al., "Blockade of T Lymphocyte Costimulation with Cytotoxic T Lymphocyte-associated Antigen 4-Immunogloblin (CTLA4Ig) Reverse the Cellular Pathology of Psoriatic plaques, including the Activation of Keratinocytes, Dendritic Cells, and Endothelial Cells," *Journal of Experimental Medicine*, 2000, 192:681-93 (Exhibit 117).

Srinivas, N. R. et al., "Pharmacokinetics and Pharmacodynamics of CTLA4Ig (BMS-16957), a Novel Immunosuppressive Agent, in Monkeys following Multiple Doses," *Journal of Pharmaceutical Sciences*, 1996, 85:1-4 (Exhibit 118).

Gandhi, Rajesh S. et al., Abstract and Presentation of "Physical and Chemical Characterization of BMS-224818, A Recombinant Fusion Protein," in San Francisco, California, *PharmSci Supplement*, Nov. 18, 1998, 1:S-535 (Exhibit 119).

Flesher, Alan R, Presentation of "Transgenic Production, A Comparative Study" at Bio 99 in Seattle, Washington, Apr. 15, 1999 (Exhibit 120).

Greve, Kimberly F., "Capillary electrophoretic examination of underivatized aligosaccharide mixtures released from immunoglobulin G anitbodies and CTLA4g fusion protein," *Journal of Chromatography*, 1996, 749:237-245 (Exhibit 121).

Srinivas, Nuggehally R. et al., "Assessment of Dose Proportionality, Absolute Bioavailability, and Immunogenicity Response of CTLA4Ig (BMS-188667), a Novel Immunosuppressive Agent, Following Subcutaneous and Intravenous Administration to Rats," *Phramaceutical Research*, 1997, 14:911-6 (Exhibit 122).

Weiner, R. et al., Abstract and Presentation of "Validation and PK Application of a Double Antibody Sandwich Enzyme Immunoassay for the Quantitation of Human CTLA4Ig Fusion Protein (BMS-188667) in Mouse Serum," Nov. 6-10, 1994 (Exhibit 123).

Weiner, Russell S. et al., "A sensitive enzyme immunoassay for the quantitation of human CTLA4Ig fusion protein in mouse serum: pharmacokinetic application to optimizing cell line selection," *Journal of Pharmaceutical and Biomedical Analysis*, 1997, 15:571-579 (Exhibit 124).

Warner, G. L. et al., Abstract and Presentation of "Bioactivity of BMS-188657 (CTLA4Ig) in Cynomolgus Monkeys," in Seattle, Washington, Mar. 16-22, 1995 (Exhibit 125).

Weiner, Russell S., Abstract and Presentation of "Industial Perspectives of Primary Analytical Tools for Macromolecules—Principles and Applications with Examples" Mar. 1, 2000 (Exhibit 126).

Weiner, Russell et al., Abstract and Presentation of "Validation of an Enzyme immunoassay for the Quantitation of Human CTLA4Ig Fusion Protein in Human Serum," in Miami, Florida, Nov. 1995 (Exhibit 127).

Weiner, Russell, Abstract and Presentation of "Automation and Validation of an EIA for Quantitation of Human CTLA4Ig in Monkey Serum," in Miami, Florida, Nov. 1995 (Exhibit 128).

Webb, Louise M. C. et al., "Prevention and amalioration of collagen-induced arthritis by blockade of the CD28 co-stimulatory pathway: requirement for both B7-1 and B7-2" *European Journal of Immunology*, 1995, 26:2320-8 (Exhibit 129).

Knoerzer, Debbie Barney et al., "Collagen-induced Arthritis in the BB Rat Prevention of Disease by Treatment with CTLA-4-Ig," *Journal of Clinical Investigation*, 1995, 96:957-93 (Exhibit 130).

Larsen, Christian P. et al., Abstract of "Prolongation of Renal Allograft Survival by a Chimeric Anti-Human CD4D Monoclonal Antibody in Nonhuman Primates," in *Transplantation*, 2000, 69:S123, #45 (Exhibit 131).

Larsen, Christian P. et al., Presentation of "Prolongation of Renal Allograft Survival With Blockade of the CD28 Pathway Using a Novel Mutant CTLA4-Ig Fusion Protein in Non-Human Primates" at the American Society of Transplantation Meeting in Chicago, Illinois, Mar. 3-4, 2000 (Exhibit 132).

Larsen, Christian P., Presentation of "Manipulation of Costimulatory Pathways: Targeting CD80 and CD86" at the XVII congress of the Transplantation Society in Rome, Italy, Aug. 27-Sep. 1, 2000 (Exhibit 133).

Larsen, Christian P., Presentation of "Costimulation blockade: progress toward clinical application" at Canadian Society of Transplantation Annual Scientific meeting in Mont Tremblant, Quebec, Canada, Mar. 3-4, 2000 (Exhibit 134).

Larsen, Christian P., Presentation of "Costimulation blockade: Progress toward clinical application" at the American Society of Transplantation Meeting in Las Croabas, Puerto Rico, Jan. 13-17, 2000 (Exhibit 135).

Hathcock, Karen S. et al., "Identification of an Alternative CTLA-4 Ligand Costimulatory for T Cell Activation," *Science*, 1993, 262:905-911 (Exhibit 136).

Sfikakis, Peter P. et al., "CD28 Expression on T Cell Subsets In Vivo and CD28-Mediated T Cell Response In Vitro in Patients with Rheumatoid Arthritis," *Arthritis & Rheumatism*, 1995, 38:649-54 (Exhibit 137).

Lakkis, Fadi G. et al., "Blocking the CD28-B7 T Cell Costimulaton Pathway Induces Long Term Cardiac Allograft Acceptance in the Absence of IL-4," *The Journal of Immunology*, 1997, 158:2443-8 (Exhibit 140).

Pearson, Thomas C. et al., "Analysis of the B7 Costimulatory Pathway in Allograft Rejection," *Transplantation*, 1997, 53:1463-9 (Exhibit 141).

Pearson, Thomas C. et al., "Transplantation Tolerance Induced by CTLA4-Ig" *Transplantation*, 1994, 57:1701-6 (Exhibit 142).

Alexander, Diane Z. et al., "Analysis of a Functional Role for Chimerism in CTLA4-Ig Plus Bone Marrow-Treaded Cardiac Allograft Recipients," *Transplantation*, 1994, 91:418-8 (Exhibit 143).

Larsen, Christian P. et al., "CD40-gp39 Interactions Play a Critical Role During Allograft Rejection," *Transplantation*, 1996, 61:4-9 (Exhibit 144).

Pearson, Thomas C. et al., "CTLA4-Ig Plus Bone Marrow Induces Long-Term Allograft Survival and Dorior-Specific Unresponsiveness in the Murine Model," *Transplantation*, 1996, 61:997-1004 (Exhibit 145).

Weber, C. J. et al, "CTLA4-Ig Prolongs Survival of Microencapsulated Rabbit Islet Xenografts in Spontaneously Diabetic Nod Mice," *Transplantation Proceedings*, 1996, 25:821-3 (Exhibit 146).

Alexander, D. Z., et al., "Analysis of effector mechanisms in murine cardiac allografs rejection," *Transplant Immunology*, 1996, 4:46-8 (Exhibit 147).

Larsen, Christian P. et al., "Long-Term acceptance of skin and cardiac allografts after blocking CD40 and CD28 pathways," *Nature*, 1996, 381:434-8 (Exhibit 148).

Elwood, Eric T. et al., "Microchimerism and rejection in clinical transplantation," *The Lancet*, 1997, 349:1358-60 (Exhibit 149).

Larsen, Christian P. and Thomas C. Peterson, "The CD40 pathway in allograft rejection, acceptance, and tolerance," *Current Opinion in Immunology*, 1997, 9:641-7 (Exhibit 150).

Konieczny, Bogumila T. et al., "1FN-γ Critical for Long-Term Allograft Survival Induced by Blocking the CD28 and CD40 Ligand T Cell Constimulation Pathways," *The Journal of Immunology*, 1998, 160:2059-64 (Exhibit 151).

(56) References Cited

OTHER PUBLICATIONS

Elwood, Eric T. et al., "Prolonged Accpetance of Concordant and Discordant Xenografts with Combined CD40 and CD28 Pathway Blockade," *Transplantation*, 1998, 65:1422-8 (Exhibit 152).

Niimi, Masanori et al., "The Role of the CD40 Pathway in Alloantigen-Induced Hyporesponsiveness In Vivo," *The Journal of Immunology*, 1998, 161:5331-7 (Exhibit 153).

Whitmire, Jason K. et al., "CD40-CD40 Ligand Costimulation is Required for Generating Antiviral CD4 T Cell Responses But is Dispensable for CD8 T Cell Responses," *Journal of Immunology*, 1999, 163:3194-201 (Exhibit 154).

Bingaman, Adam W. et al., "Vigorous Allograft Rejection in the Absence of Danger," *The Journal of Immunology*, 2000, 164:3065-71 (Exhibit 155).

Bingaman, Adam W. et al., "Transplantation of the Bone Marrow Microenvironment Leads to Hematopoietic Chimarism Without Cytoreductive Conditioning," *Transplantation*, 2000, 69:2491-6 (Exhibit 156).

Durham, Megan M. et al., "Cutting Edge: Administration of Anti-CD40 Ligand and Donor Bone Marrow Leads to Hemopoietic Chimerism and Donor-Specific Tolerance Without Cytoreductive Conditioning," *The Journal of Immunology*, 2000, 165:1-4 [Exhibit 157].

Williams, Matthew A. et al., "Genetic Characterization of Strain Differences in the Ability to Mediate CD40/CD28-Independent Rejection of Skin Allografts," *The Journal of Immunology*, 2000, 165:6849-57 (Exhibit 158).

Bingaman, Adam W. et al., "The role of CD40L in T cell-dependent nitric oxide production by murine macrophages," *Transplant Immunology*, 2000, 8:195-202 (Exhibit 159).

Adams, Andrew B. et al., "Costimulation Blockade, Busulfan, and Bone Marrow Promote Titratable Macrochimersim, Induce Transplantation Tolerance, and Correct Genetic Hemoaglobinopathies with Minimal Myelosuppression," *Journal of Immunology*, 2001, 167:1103-11 (Exhibit 160).

Meng, L. et al., "Blockade of the CD40 Pathway Fails to Prevent CD8 T Cell-Mediated intestinal Allograft Rejection," *Transplantation Proceedings*, 2001, 33:418-20 (Exhibit 161).

Guo, Zhong et al., "CD8 T Cell-Mediated Rejection of Intestinal Allografts is Resistant to Inhibition of the CD40/CD154 Costimulatory Pathway," *Transplantation*, 2001, 71:1351-4 (Exhibit 162).

Ha, Jongwon et al., "Aggressive skin allograft rejection in CD28-/- mice independent of the CD40/CD40L costimulatory pathway," *Transplant Immnunology*,2001, 9:13-7 (Exhibit 163).

Bingman, Adam W. et al., "Analysis of the CD40 and CD28 Pathways on Alloimmune Responses by CD4+ T Cells In Vivo," *Transplantation*, 2001, 72:1286-92 (Exhibit 164).

Adams, Andrew B. et al., "Calcineurin Inhibitor—Free CD28 Blockade Based Protocol Protects Allogeneic Islets in Nonhuman Primates," *Diabetes*, 2002, 51:265-70 (Exhibit 165).

Whelchel, J. D. et al., "Evolving Strategies in Immunosuppressive Therapy: The Emory Experience," *Clinical Transplants*, J. Michael Cacka, Ph.D. and Paul I. Terasaki, Ph.D., (eds.), 1996, 249-55 (Exhibit 166).

Ritchie, Shannon C. et al., "Regulation of Immunostimulatory Function and B7 Molecule Expression on Murine Dendritic Cells," *Journal of Cellular Biochemistry*, 1995, 21A:C1-215 (Exhibit 167).

Alexander, Diane Z. et al., "Analysis of the Mechanisms of CTLA4-lg Plus Bone Marrow Induced Transplantation Tolerance," *Journal of Cellular Biochemistry*, 1995, 21A:C1-301 (Exhibit 168).

Alexander, Diane Z. et al., "CTLA4-lg-Induced Transplantation Tolerance: Analysis of Donor Cell Chimerism," *Surgical Forum*, 1994, 45:402-4 (Exhibit 169).

Pearson, Thomas C. et al., "CTLA4-lg + Bone Marrow Induces Transplantation Tolerance in the Murine Model," *Journal of Cellular Biochemistry*, 1995, 21A: C1-327 (Exhibit 170).

Lakkis, Fadi G. et al., "CTLA4lg Induces Longterm Cardiac Allograft Survival in the Absence of Interleukin-4," *Journal of the American Society of Nephrology*, 1996, 7:1887 (Exhibit 171).

A letter dated Jul. 9, 1998 including a report submitted to the U.S. Food and Drug Administration in connection with an Investigational New Drug (IND) application (Exhibit 172).

An investigator Brochure dated Jan. 26, 1999 (Exhibit 173).

Morton, Phillip A. et al., "Differential Effects of CTLA-4 Substitutions on the Binding of Human CD80 (B7-1) and CD8B (B7-2)," *Journal of Immunology*, 1996, 156:1047-1054 (Exhibit 189).

Sun, Hong et al., "Prevention of Chronic Rejection in Mouse Aortic Allografts by Combined Treatment with CTLA4-lg and Anti-CD40 Ligand Monoclonal Antibody," *Transplantation*, 1997, 64:1838-56 (Exhibit 191).

Souza, D. et al., "Synergistic Inhibition of Established Collagen Induced Arthritis (CIA) Through Dual Inhibition of ICAM-1 and CD40L Pathways," *Arthritis and Rheumatism*, 1999, 42:S6D (Exhibit 192).

Blazar, Bruce R. et al., "Coblockade of the LFA1:ICAM and CD28/CTLA4:B7 Pathways Is A Highly Effective Means of Preventing Acute Lethal Graft-Versus-Host Disease Induced by Fully Major Histocompatibility Complex-Disparate Donor Grafts," *Blood*, 1995, 85:2607-18 (Exhibit 193).

Alegro, Maria-Luisa et al., "Immunomodulation of Transplant Rejection Using Monoclonal Antibodies and Soluble Receptors," *Digestive Diseases and Sciences*, 1995, 40:58-64 (Exhibit 196).

Murakami, Masaaki et al., "Identification and characterization of an alternative cytotoxic T lymphocyte-associated protein 4 binding molecule on B cells," *Proceedings of the National Academy of Sciences USA*, 1996, 93:7838-7842 (Exhibit 197).

Peach, Robert J. et al., "Both Extracellular Immunoglobin-like Domains of CD80 Contain Residues Critical for Binding T Cell Surface Receptors CTLA-4 and CD28," *Journal of Biological Chemistry*, 1995, 270:21181-21187 (Exhibit 198).

Fargeas, Christine et al., "Identification of Residues in the V Domain of CD80 (B7-1) Implicated in Functional Interactions with CD28 and CTLA4," *Journal of Experimental Medicine*, 1995, 182-667-675 (Exhibit 199).

Steurer, Wolfgang et al., "Ex Vivo Coating of Islet Cell Allografts with Murin CTLA4/Fc Promotes Graft Tolerance," *Journal of Immunology*, 1995, 155:1165-1174 (Exhibit 200).

Guo, Yong et al., "Mutational Analysis and an Alternatively Spliced Production of B7 Defines Its CD28/CTLA4-binding Site on Immunoglobulin C-like Domain," *Journal of Experimental Medicine*, 1995, 181:1345-1355 (Exhibit 201).

Peach, Robert J. and Peter S. Linsely, "CTLA4lg: A Novel Immunoglobulin Chimera with Immunosuppressive Properties," *Methods*, 1995, 8:116-123 (Exhibit 202).

Rattis, Frédérique-Marie et al., "Expression and function of B7-1 (CD80) and B7-2 (CD86) on human epidermal Langerhans cells," *European Journal of Immunology*, 1996, 26:449-453 (Exhibit 203).

Najafian, Nader and Mohamed H. Sayegh, "CTLA4-lg: a novel immunosuppressive agent," *Exp. Opin. Invest. Drugs*, 2000, 9:2147-2157 (Exhibit 206).

Schwartz, R., "Costimulation of T Lymphocytes: The Role of CD28, CTLA-4, and B7/BB1 in Interleukin-2 Production and Immunotherapy," *Cell*, 1992, 71:1085-1088 (Exhibit 215).

Mitchell, Donald, *Rheumatoid Arthritis*, Peter D. Utsinger et al. (eds.), 1985, pp. 133-150 (Exhibit 237).

Nielsen, Peter E. et al., "Peptide nucleic acids (PNAs): Potential anti-sense and ant-gene agents," *Anti-cancer Drug Design*, 1993, B:53-63 (Exhibit 238).

Scharf, Klaus-Dieter et al., "Heat Stress Promoters and Transcription Factors," *Results and Problems in Cell Differentiation*, 1994, 20:125-62 (Exhibit 239).

Smolen, Josef S. et al., "Validity and Reliability of the Twenty-Eight-Joint Count for the Assessment of Rheumatoid Arthritis Activity," *Arthritis & Rheumatism*, 1995, 38:38-43 (Exhibit 240).

Zamecnik, Paul C. and Mary L. Stephenson, "Inhibition of Rous sarcoma virus replication and cell transformation by a specific oligodeoxyneucleotide," *Proceedings of the National Academy of Sciences USA*, 1978, 75:280-4 (Exhibit 241).

(56) References Cited

OTHER PUBLICATIONS

Zarnecnik, Paul C. et al., "Inhibition of replication and expression of human T-cell lymphotrophic virus type III in cultured cells by exogenous synthetic oligonucleotides complementary to viral RNA," *Proceedings of the National Academy of Sciences USA*, 1986, 83:4143-6 (Exhibit 242).

Bluestone, Jeffrey A., "New Perspectives of CD2B-B7-Mediated T Cell Costimulation," *Immunity*, 1995, 2:555-9 (Exhibit 247).

Bluestone, J. A. et al., "Costimulation and its role in organ transplantation," *Clin. Transplantation*, 1996, 10:104-9 [Exhibit 248].

Chen, Fang-An et al., "Human Antibody Response in Human Peripheral Blood Leukocyte/Severe Combined Immunodeficient Chimeric Model is Dependent on B and T Cell Costimulation via CD40/CD40 Ligand," *Journal of Immunology*, 1995, 155:2833-40 (Exhibit 249).

Duria, Fiona H. et al., "Pevention of Collagen-Induced Arthritis with an Antibody to gp39, the Ligand for CD4" *Science*, 1993, 261:1328-30 (Exhibit 250).

Durie, Fiona H. et al., "Antibody to the Ligand of CD40, gp39, Blocks the Occurence of the Acute and Chronic Forms of Graft-vs-Host Disease," *Journal of Clinical Investigation*, 1994, 94:1333-B (Exhibit 251).

Griggs, Nathan et al., "Contribution of CD28/CTLA4/B7 and gp39/CD40 Constimulation Pathways in Clonal Expansion and Functional Acquistion of Self Reactive T Cells," *Journal of Cellular Biochemistry*, 1995, Supplement, p. 141, Abstract C2-427 (Exhibit 252).

Jenkins, Marc K. et al., "CD28 Delivers a Costimulatory Signal Involved in Antigen-Specific IL-2 Production by Human T Cells," *Journal of Immunology*, 1991, 147:2461-6 (Exhibit 263).

Lenschow, Deborah J. et al., "Inhibition of Transplant Rejection Following Treatment with Anti-B7-2 and Anti-B7-1 Antibodies," *Transplantation*, 1995, 60:1171-8 (Exhibit 254).

Rossini, Aldo et al., "Induction of Immunological Tolerance to Islet Allografts," *Cell Transplantation*, 1996, 5:49-52 (Exhibit 255).

Roy, Meenakshi et al., "Studies on the interdependence of gp39 and B7 expression and function during antigen-specific immune response," *European Journal of Immunology*, 1995, 25:595-603 (Exhibit 256).

Schaub, M. et al., "Synergistic effect of CD40L/CD40 and CD28/B7 Blockade in murine EAE," *Journal of Allergy and Clinical Immunology*, 1997, 99:5206 Abstact 834 [Exhibit 257].

Tang, Aimin et al., "Suppression of Murine Allergic Contact Dermatitis by CTLA4Ig: Tolerance induction of Th2 Responses Requires Additional Blockade of CD40-Ligand," *Journal of Immunology*, 1996, 157:117-25 (Exhibit 258).

\* cited by examiner

Demographic - 1 -

|  |  | Placebo N=32 | CTLA.5 N=26 | CTLA 2 N=32 | CTLA 10 N=32 | LEA.5 N=32 | LEA 2 N=29 | LEA 10 N=31 | Total N=214 |
|---|---|---|---|---|---|---|---|---|---|
| Gender | Male | 6 (19%) | 4 (15%) | 9 (28%) | 10 (31%) | 9 (28%) | 9 (31%) | 7 (23%) | 54 (25%) |
|  | Female | 26 (81%) | 22 (85%) | 23 (72%) | 22 (69%) | 23 (72%) | 20 (69%) | 24 (77%) | 160 (75%) |
| Race | White | 30 (94%) | 23 (88%) | 30 (94%) | 30 (94%) | 29 (91%) | 25 (86%) | 27 (87%) | 194 (91%) |
|  | Black | 2 (6%) | 0 (0%) | 0 (0%) | 1 (3%) | 1 (3%) | 3 (10%) | 2 (6%) | 9 (4%) |
|  | Other | 0 (0%) | 3 (12%) | 2 (6%) | 1 (3%) | 2 (6%) | 1 (3%) | 2 (6%) | 11 (5%) |
| Disease Duration | < 2 years | 12 (38%) | 5 (19%) | 8 (25%) | 12 (38%) | 10 (31%) | 10 (34%) | 11 (35%) | 68 (32%) |
|  | 2-5 years | 14 (44%) | 11 (42%) | 18 (56%) | 13 (41%) | 14 (44%) | 14 (48%) | 12 (39%) | 96 (45%) |
|  | 5-7 years | 6 (19%) | 8 (31%) | 6 (19%) | 6 (19%) | 6 (19%) | 5 (17%) | 7 (23%) | 44 (21%) |
|  | > 7 years | 0 (0%) | 2 (8%) | 0 (0%) | 1 (3%) | 2 (6%) | 0 (0%) | 1 (3%) | 6 (3%) |
| Duration Disease (years) | N | 32 | 26 | 32 | 32 | 32 | 29 | 31 | 214 |
|  | Mean | 3.2 | 4.2 | 3.3 | 3.4 | 3.7 | 3.1 | 3 | 3.4 |
|  | Sd | 2 | 2 | 1.7 | 2.1 | 2 | 1.8 | 2.2 | 2 |
|  | Min | 0.3 | 0.2 | 0.4 | 0 | 0.7 | 0.4 | 0 | 0 |
|  | Max | 7 | 7.5 | 6.8 | 7.3 | 7.6 | 7 | 7.1 | 7.6 |

FIG. 1A

Demographic -2-

| | Placebo N=32 | CTLA.5 N=26 | CTLA 2 N=32 | CTLA 10 N=32 | LEA.5 N=32 | LEA 2 N=29 | LEA 10 N=31 | Total N=214 |
|---|---|---|---|---|---|---|---|---|
| Gender Male | 6 (19%) | 4 (15%) | 9 (28%) | 10 (31%) | 9 (28%) | 9 (31%) | 7 (23%) | 54 (25%) |
| Female | 26 (81%) | 22 (85%) | 23 (72%) | 22 (69%) | 23 (72%) | 20 (69%) | 24 (77%) | 160 (75%) |
| Age N | 32 | 26 | 32 | 32 | 32 | 29 | 31 | 214 |
| Mean | 48.3 | 46.9 | 46.2 | 51.5 | 49.3 | 50.8 | 45.6 | 48.4 |
| Sd | 11.7 | 12.2 | 13.4 | 11.5 | 8.8 | 10.7 | 10.1 | 11.3 |
| Min | 22 | 25 | 21 | 24 | 27 | 24 | 28 | 21 |
| Max | 66 | 64 | 64 | 66 | 66 | 65 | 64 | 66 |
| Weight (kg) N | 32 | 26 | 32 | 32 | 32 | 29 | 31 | 214 |
| Mean | 72.9 | 70.6 | 72.7 | 70 | 69.8 | 68.9 | 71.7 | 71 |
| Sd | 13.5 | 17.4 | 14.4 | 16.7 | 12.8 | 12.1 | 15.8 | 14.6 |
| Min | 46.7 | 45 | 50 | 40.1 | 48 | 47 | 39.2 | 39.2 |
| Max | 98.2 | 101.3 | 99 | 101.3 | 95 | 93.8 | 99 | 101.3 |
| Disease activity (patient) N | 32 | 26 | 32 | 32 | 32 | 29 | 31 | 215 |
| Mean | 3.6 | 3.6 | 3.7 | 3.6 | 3.5 | 3.6 | 3.5 | 3.6 |
| Sd | 0.9 | 0.9 | 0.9 | 0.9 | 0.8 | 0.8 | 0.7 | 0.8 |
| Min | 2 | 2 | 2 | 2 | 2 | 2 | 2 | 2 |
| Max | 5 | 5 | 5 | 5 | 5 | 5 | 5 | 5 |

FIG. 1B

Demographic - Disease -

| | | Placebo N=32 | CTLA.5 N=26 | CTLA.2 N=32 | CTLA.10 N=32 | LEA.5 N=32 | LEA.2 N=29 | LEA.10 N=31 | Total N=214 |
|---|---|---|---|---|---|---|---|---|---|
| Disease activity (physician) | N | 32 | 26 | 32 | 32 | 32 | 29 | 31 | 214 |
| | Mean | 3.6 | 3.5 | 3.5 | 3.7 | 3.4 | 3.4 | 3.5 | 3.5 |
| | Sd | 0.7 | 0.6 | 0.8 | 1 | 0.6 | 0.8 | 0.6 | 0.7 |
| | Min | 2 | 3 | 2 | 2 | 2 | 2 | 2 | 2 |
| | Max | 5 | 5 | 5 | 5 | 5 | 5 | 5 | 5 |
| ESR | N | 32 | 26 | 32 | 32 | 32 | 29 | 30 | 213 |
| | Mean | 43.3 | 35.2 | 41.6 | 36.3 | 29.8 | 40.9 | 39.3 | 38.1 |
| | Sd | 29.4 | 22.5 | 27.4 | 27.9 | 24.2 | 30.2 | 24.6 | 26.8 |
| | Min | 2 | 4 | 4 | 3 | 0 | 6 | 2 | 0 |
| | Max | 116 | 90 | 94 | 98 | 91 | 110 | 102 | 116 |
| Physical function (score) | N | 32 | 26 | 31 | 32 | 32 | 29 | 31 | 213 |
| | Mean | 16.8 | 15.5 | 16.2 | 17.1 | 15.3 | 16.3 | 16.1 | 16.2 |
| | Sd | 5.4 | 4.2 | 5.5 | 5.7 | 3.7 | 4.8 | 3.8 | 4.8 |
| | Min | 8 | 8 | 8 | 8 | 8 | 8 | 9 | 8 |
| | Max | 32 | 23 | 26 | 28 | 24 | 26 | 26 | 32 |
| CRP | N | 30 | 23 | 31 | 31 | 31 | 28 | 31 | 205 |
| | Mean | 56.7 | 26.4 | 48 | 33.6 | 28.1 | 48.1 | 37.5 | 40.1 |
| | Sd | 62.7 | 30.3 | 47.3 | 46 | 39.1 | 64.5 | 35.2 | 48.6 |
| | Min | 2 | 5 | 3 | 3 | 3 | 3 | 3 | 2 |
| | Max | 248 | 115 | 198 | 182 | 200 | 333 | 135 | 333 |

FIG. 1C

Demographic – Disease –

| | | Placebo N=32 | CTLA.5 N=26 | CTLA.2 N=32 | CTLA.10 N=32 | LEA.5 N=32 | LEA.2 N=29 | LEA.10 N=31 | Total N=214 |
|---|---|---|---|---|---|---|---|---|---|
| Tender joints (score) | N | 32 | 26 | 32 | 32 | 32 | 29 | 31 | 214 |
| | Mean | 32.1 | 32.5 | 32.1 | 29.4 | 25.6 | 30.7 | 30.6 | 30.4 |
| | Sd | 14.8 | 14.8 | 15 | 14.6 | 12 | 13.3 | 12.9 | 13.9 |
| | Min | 12 | 14 | 11 | 12 | 12 | 12 | 12 | 11 |
| | Max | 63 | 64 | 68 | 68 | 61 | 63 | 59 | 68 |
| Swollen joints (score) | N | 32 | 26 | 32 | 32 | 32 | 29 | 31 | 214 |
| | Mean | 23.9 | 18.6 | 26.9 | 22.7 | 18.3 | 22.6 | 19.9 | 21.9 |
| | Sd | 10 | 6.3 | 11.4 | 12.7 | 7.6 | 8.5 | 8.9 | 10 |
| | Min | 10 | 10 | 10 | 10 | 10 | 10 | 10 | 10 |
| | Max | 51 | 33 | 53 | 58 | 36 | 40 | 44 | 58 |
| Pain (score) | N | 32 | 26 | 32 | 32 | 32 | 29 | 31 | 214 |
| | Mean | 3.5 | 3.4 | 3.5 | 3.5 | 3.5 | 3.3 | 3.5 | 3.5 |
| | Sd | 0.9 | 0.6 | 0.6 | 1 | 0.7 | 0.8 | 0.7 | 0.8 |
| | Min | 2 | 2 | 2 | 1 | 2 | 2 | 3 | 1 |
| | Max | 5 | 5 | 5 | 5 | 5 | 5 | 5 | 5 |
| AM stiffness (min.) | N | 31 | 26 | 32 | 31 | 32 | 29 | 30 | 211 |
| | Mean | 156.6 | 211.5 | 145.2 | 149.5 | 160.9 | 160.3 | 147.5 | 160.5 |
| | Sd | 121.5 | 370.6 | 102.1 | 148.7 | 151.1 | 152.3 | 258.3 | 198.1 |
| | Min | 30 | 0 | 5 | 35 | 30 | 0 | 15 | 0 |
| | Max | 600 | 1440 | 420 | 720 | 600 | 720 | 1440 | 1440 |

FIG. 1D

Demographic - Prior treatments -

|  |  | Placebo N=32 | CTLA.5 N=26 | CTLA.2 N=32 | CTLA10 N=32 | LEA.5 N=32 | LEA.2 N=29 | LEA 10 N=31 | Total N=214 |
|---|---|---|---|---|---|---|---|---|---|
| Etanercept | Yes | 0 (0%) | 0 (0%) | 0 (0%) | 0 (0%) | 0 (0%) | 0 (0%) | 0 (0%) | 0 (0%) |
|  | No | 32 (100%) | 26 (100%) | 32 (100%) | 32 (100%) | 32 (100%) | 29 (100%) | 31 (100%) | 214 (100%) |
| Methotrexate | Yes | 23 (72%) | 22 (85%) | 26 (81%) | 24 (75%) | 24 (75%) | 21 (72%) | 28 (90%) | 168 (79%) |
|  | No | 9 (28%) | 4 (15%) | 6 (19%) | 8 (25%) | 8 (25%) | 8 (28%) | 3 (10%) | 46 (21%) |
| Other DMARDs | Yes | 28 (86%) | 23 (88%) | 25 (78%) | 26 (81%) | 28 (86%) | 24 (83%) | 25 (81%) | 179 (84%) |
|  | No | 4 (13%) | 3 (12%) | 7 (22%) | 6 (19%) | 4 (13%) | 5 (17%) | 6 (19%) | 35 (16%) |
| C-Steroids | Yes | 31 (97%) | 26 (100%) | 29 (91%) | 27 (84%) | 27 (84%) | 28 (97%) | 24 (77%) | 192 (90%) |
|  | No | 1 (3%) | 0 (0%) | 3 (9%) | 5 (16%) | 5 (16%) | 1 (3%) | 7 (23%) | 22 (10%) |
| NSAIDs | Yes | 27 (84%) | 20 (77%) | 30 (94%) | 29 (91%) | 26 (81%) | 25 (86%) | 25 (77%) | 181 (85%) |
|  | No | 5 (16%) | 6 (23%) | 2 (6%) | 3 (9%) | 6 (19%) | 4 (14%) | 7 (23%) | 33 (15%) |
| Other | Yes | 30 (94%) | 22 (85%) | 29 (91%) | 30 (94%) | 31 (97%) | 29 (100%) | 29 (94%) | 200 (93%) |
|  | No | 2 (6%) | 4 (15%) | 3 (9%) | 2 (6%) | 1 (3%) | 0 (0%) | 2 (6%) | 14 (7%) |

FIG. 1E

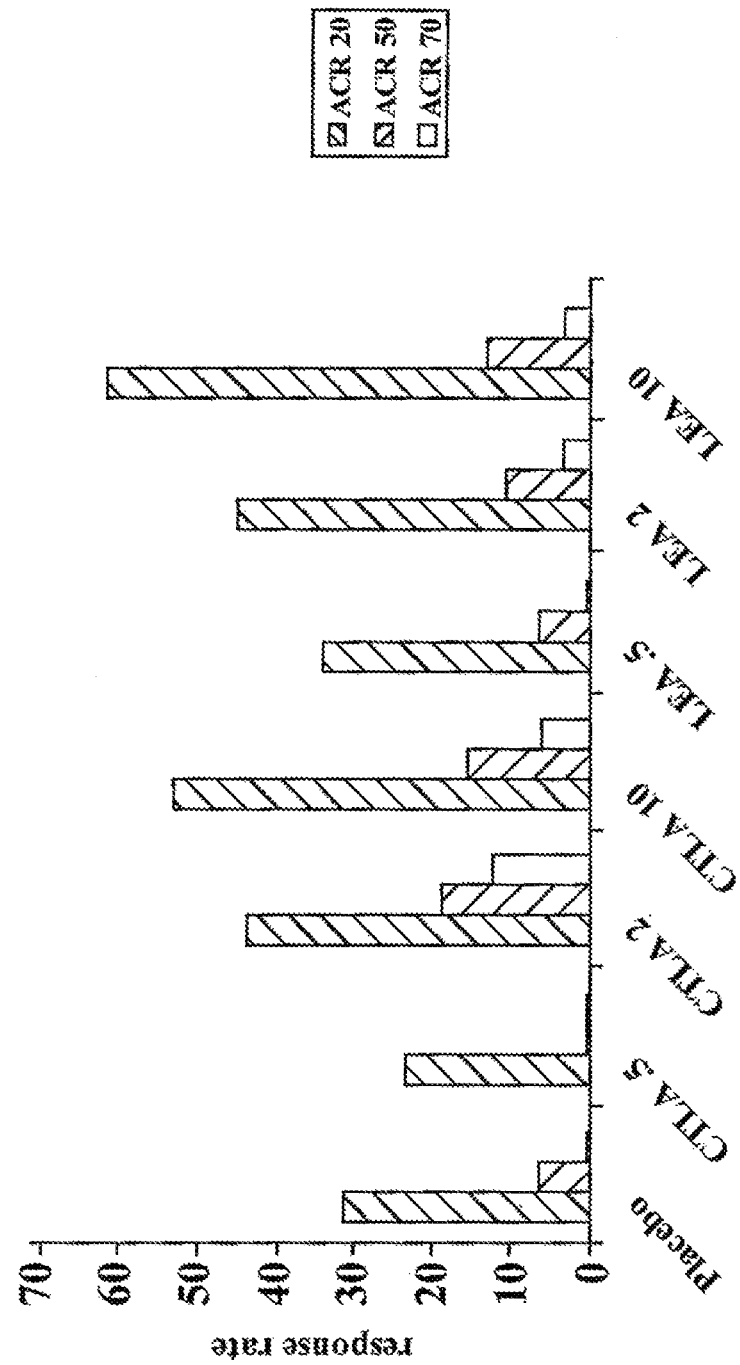

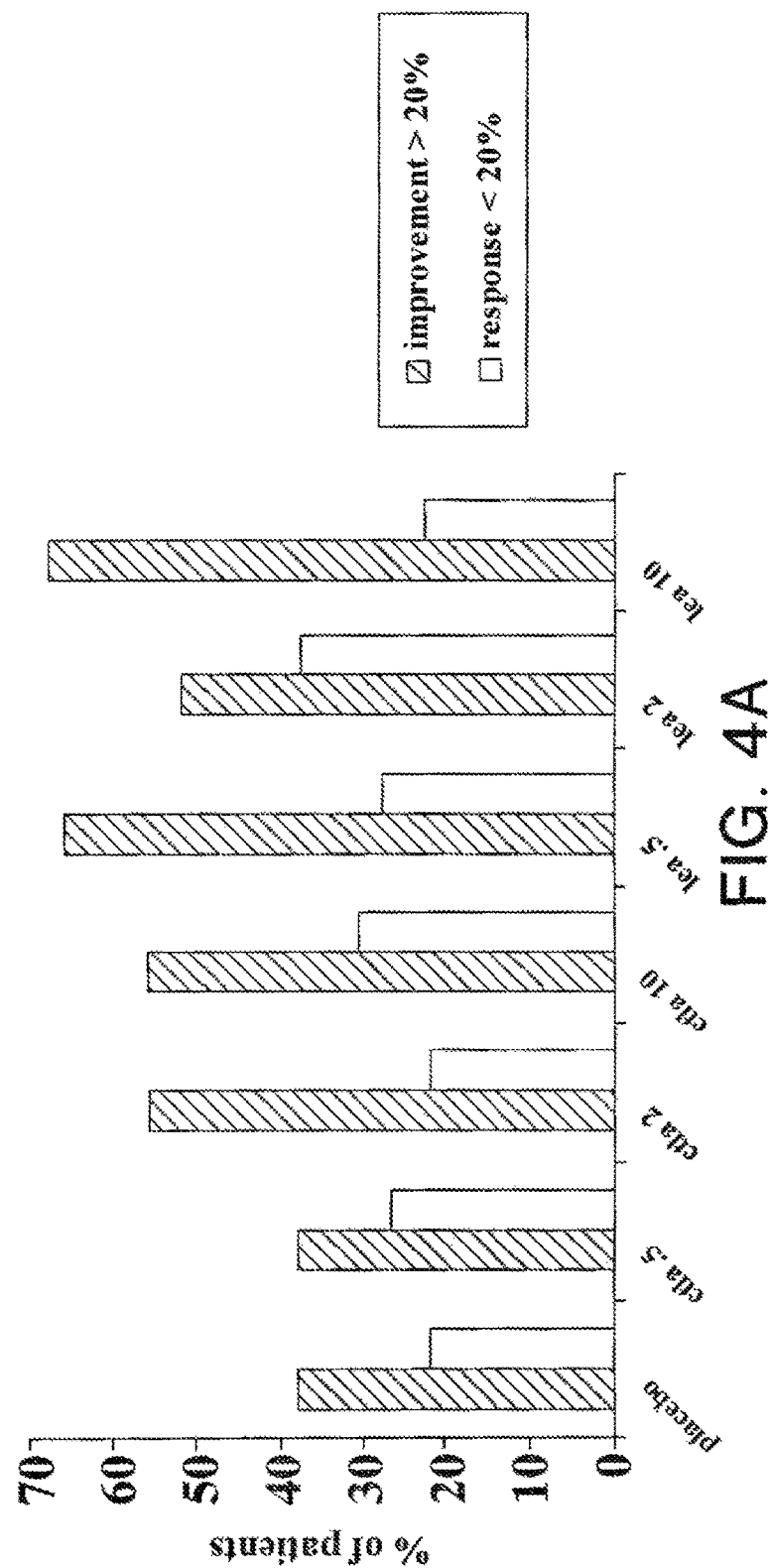

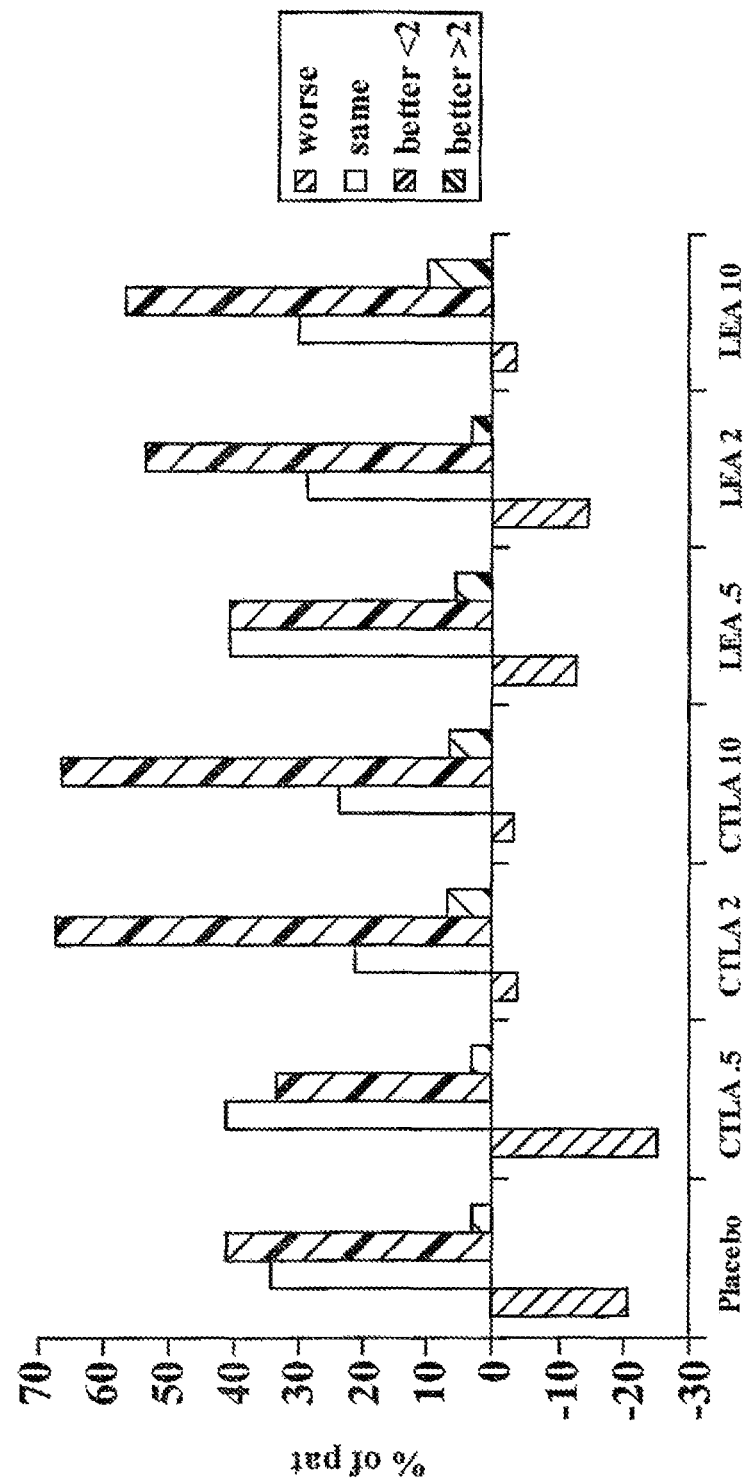

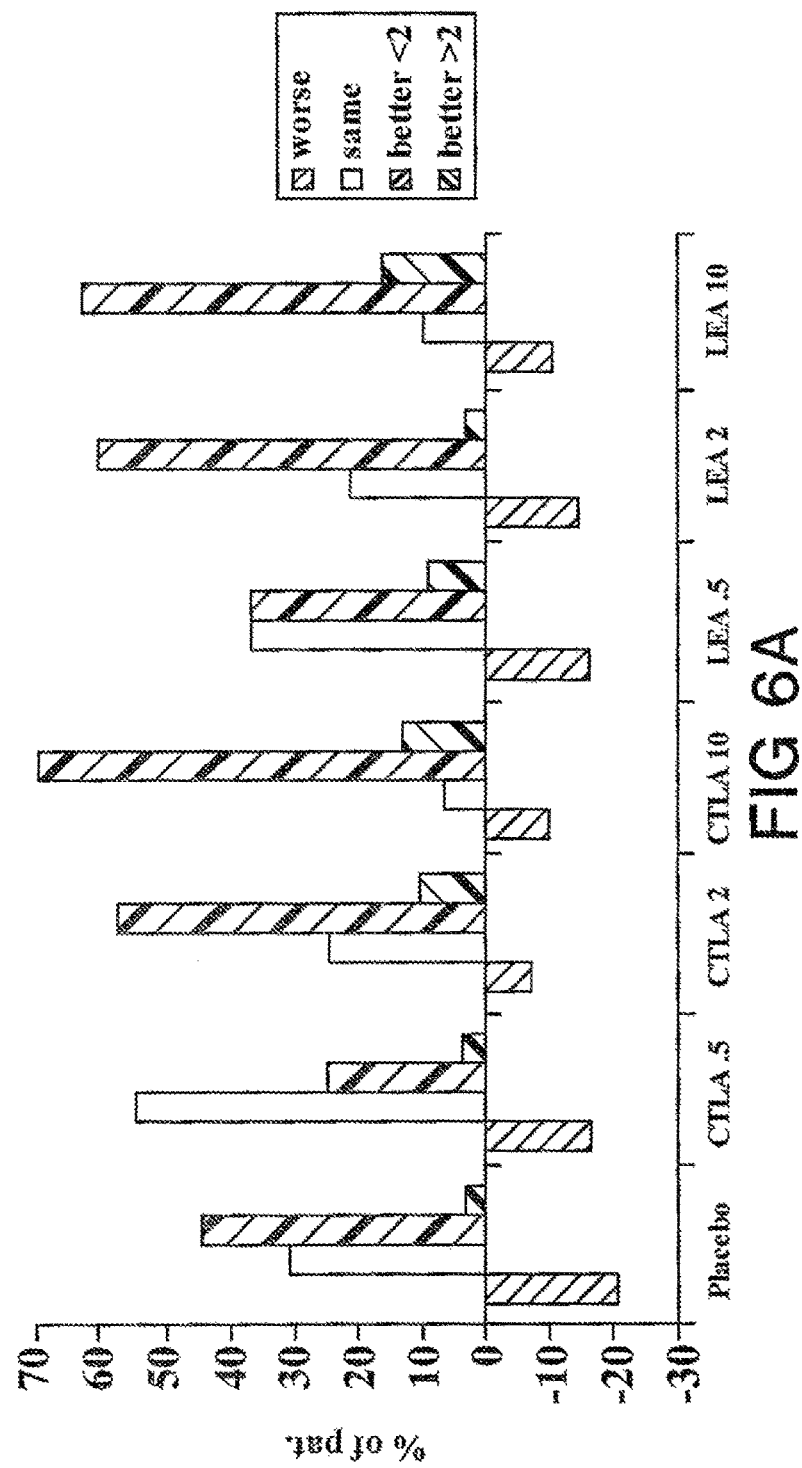

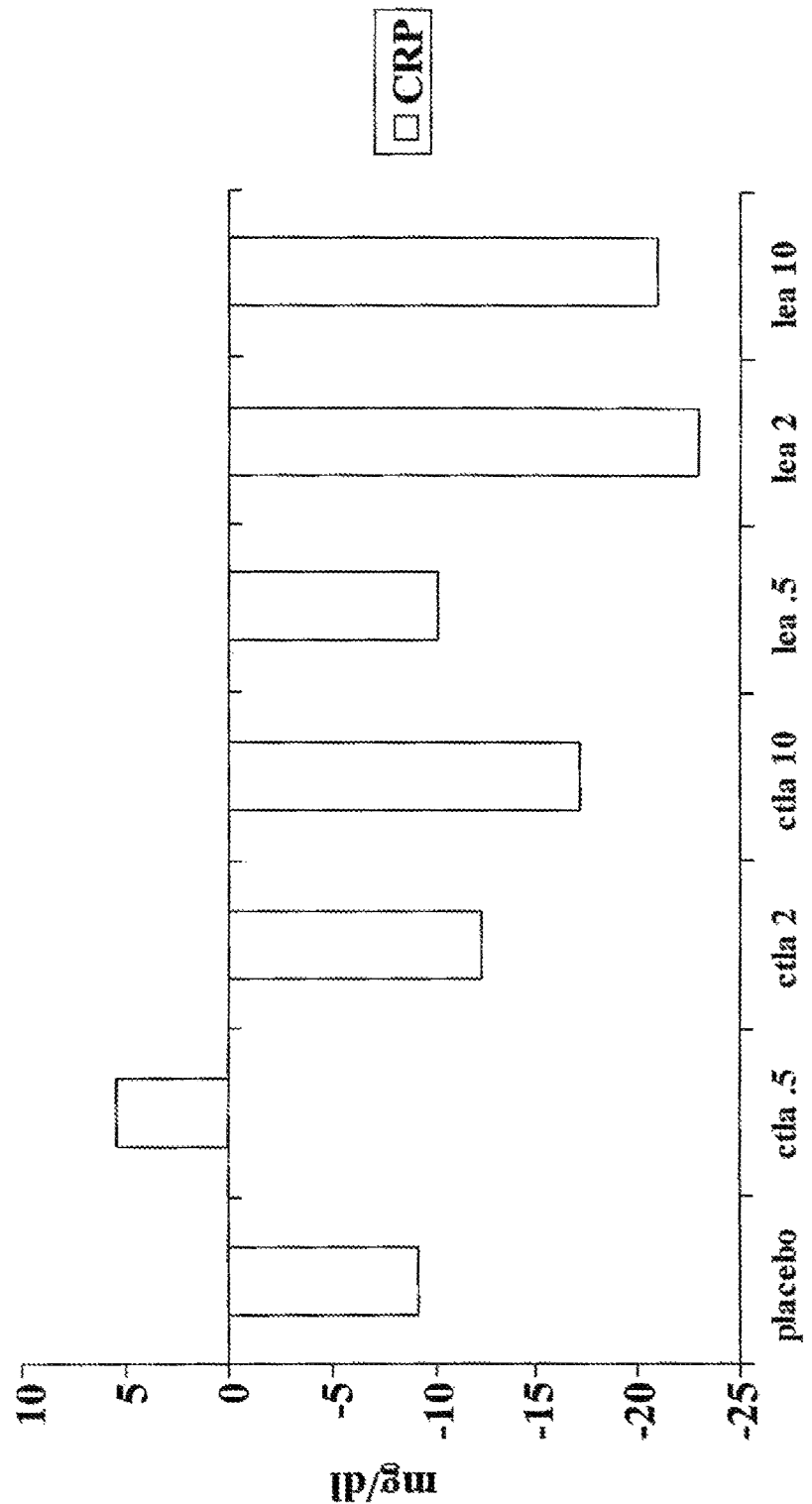

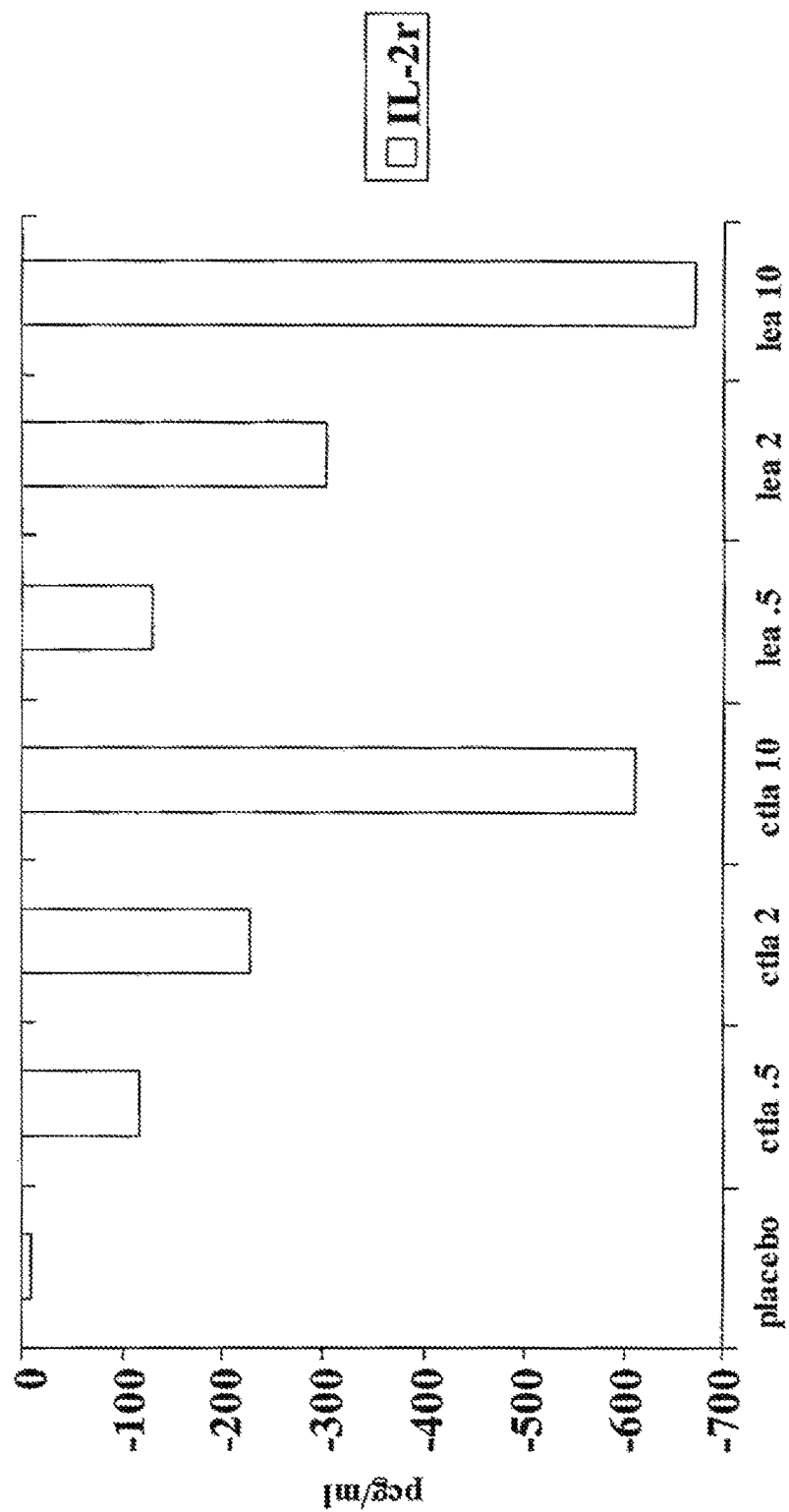

```
ATGGGTGTACTGCTCACACAGAGGACGCTGCTCAGTCTGGTCCTTGCACTCCTGTTTCCA      -19
M~~G~~V~~L~~L~~T~~Q~~R~~T~~L~~L~~S~~L~~V~~L~~A~~L~~L~~F~~P~~       -7

AGCATGGCGAGCATGGCAATGCACGTGGCCCAGCCTGCTGTGGTACTGGCCAGCAGCCGA      +42
S~~M~~A~~S~~M~~A~~M~~H~~V~~A~~Q~~P~~A~~V~~V~~L~~A~~S~~S~~R~~      +14
                    +1

GGCATCGCTAGCTTTGTGTGTGAGTATGCATCTCCAGGCAAAGCCACTGAGGTCCGGGTG     +102
G~~I~~A~~S~~F~~V~~C~~E~~Y~~A~~S~~P~~G~~K~~A~~T~~E~~V~~R~~V~~      +34

ACAGTGCTTCGGCAGGCTGACAGCCAGGTGACTGAAGTCTGTGCGGCAACCTACATGATG     +162
T~~V~~L~~R~~Q~~A~~D~~S~~Q~~V~~T~~E~~V~~C~~A~~A~~T~~Y~~M~~M~~      +54

GGGAATGAGTTGACCTTCCTAGATGATTCCATCTGCACGGGCACCTCCAGTGGAAATCAA     +222
G~~N~~E~~L~~T~~F~~L~~D~~D~~S~~I~~C~~T~~G~~T~~S~~S~~G~~N~~Q~~      +74

GTGAACCTCACTATCCAAGGACTGAGGGCCATGGACACGGGACTCTACATCTGCAAGGTG     +282
V~~N~~L~~T~~I~~Q~~G~~L~~R~~A~~M~~D~~T~~G~~L~~Y~~I~~C~~K~~V~~      +94

GAGCTCATGTACCCACCGCCATACTACGAGGGCATAGGCAACGGAACCCAGATTTATGTA     +342
E~~L~~M~~Y~~P~~P~~P~~Y~~Y~~E~~G~~I~~G~~N~~G~~T~~Q~~I~~Y~~V~~     +114

ATTGATCCAGAACCGTGCCCAGATTCTGATCAGGAGCCCAAATCTTCTGACAAAACTCAC     +402
I~~D~~P~~E~~P~~C~~P~~D~~S~~D~~Q~~E~~P~~K~~S~~S~~D~~K~~T~~H~~     +134

ACATCCCCACCGTCCCCAGCACCTGAACTCCTGGGGGGATCGTCAGTCTTCCTCTTCCCC     +462
T~~S~~P~~P~~S~~P~~A~~P~~E~~L~~L~~G~~G~~S~~S~~V~~F~~L~~F~~P~~     +154

CCAAAACCCAAGGACACCCTCATGATCTCCCGGACCCCTGAGGTCACATGCGTGGTGGTG     +522
P~~K~~P~~K~~D~~T~~L~~M~~I~~S~~R~~T~~P~~E~~V~~T~~C~~V~~V~~V~~     +174

GACGTGAGCCACGAAGACCCTGAGGTCAAGTTCAACTGGTACGTGGACGGCGTGGAGGTG     +582
D~~V~~S~~H~~E~~D~~P~~E~~V~~K~~F~~N~~W~~Y~~V~~D~~G~~V~~E~~V~~     +194

CATAATGCCAAGACAAAGCCGCGGGAGGAGCAGTACAACAGCACGTACCGTGTGGTCAGC     +642
H~~N~~A~~K~~T~~K~~P~~R~~E~~E~~Q~~Y~~N~~S~~T~~Y~~R~~V~~V~~S~~     +214

GTCCTCACCGTCCTGCACCAGGACTGGCTGAATGGCAAGGAGTACAAGTGCAAGGTCTCC     +702
V~~L~~T~~V~~L~~H~~Q~~D~~W~~L~~N~~G~~K~~E~~Y~~K~~C~~K~~V~~S~~     +234

AACAAAGCCCTCCCAGCCCCCATCGAGAAAACCATCTCCAAAGCCAAAGGGCAGCCCCGA     +762
N~~K~~A~~L~~P~~A~~P~~I~~E~~K~~T~~I~~S~~K~~A~~K~~G~~Q~~P~~R~~     +254

GAACCACAGGTGTACACCCTGCCCCCATCCCGGGATGAGCTGACCAAGAACCAGGTCAGC     +822
E~~P~~Q~~V~~Y~~T~~L~~P~~P~~S~~R~~D~~E~~L~~T~~K~~N~~Q~~V~~S~~     +274

CTGACCTGCCTGGTCAAAGGCTTCTATCCCAGCGACATCGCCGTGGAGTGGGAGAGCAAT     +882
L~~T~~C~~L~~V~~K~~G~~F~~Y~~P~~S~~D~~I~~A~~V~~E~~W~~E~~S~~N~~     +294

GGGCAGCCGGAGAACAACTACAAGACCACGCCTCCCGTGCTGGACTCCGACGGCTCCTTC     +942
G~~Q~~P~~E~~N~~N~~Y~~K~~T~~T~~P~~P~~V~~L~~D~~S~~D~~G~~S~~F~~     +314

TTCCTCTACAGCAAGCTCACCGTGGACAAGAGCAGGTGGCAGCAGGGGAACGTCTTCTCA    +1002
F~~L~~Y~~S~~K~~L~~T~~V~~D~~K~~S~~R~~W~~Q~~Q~~G~~N~~V~~F~~S~~     +334

TGCTCCGTGATGCATGAGGCTCTGCACAACCACTACACGCAGAAGAGCCTCTCCCTGTCT    +1062
C~~S~~V~~M~~H~~E~~A~~L~~H~~N~~H~~Y~~T~~Q~~K~~S~~L~~S~~L~~S~~     +354

CCGGGTAAATGA
P~~G~~K~~*
```

FIG. 18

```
ATGGGTGTACTGCTCACACAGAGGACGCTGCTCAGTCTGGTCCTTGCACTCCTGTTTCCA      -19
M~~G~~V~~L~~T~~Q~~R~~T~~L~~L~~S~~L~~V~~L~~A~~L~~L~~F~~P~~          -7

AGCATGGCGAGCATGGCAATGCACGTGGCCCAGCCTGCTGTGGTACTGGCCAGCAGCCGA      +42
S~~M~~A~~S~~M~~A~~M~~H~~V~~A~~Q~~P~~A~~V~~V~~L~~A~~S~~S~~R~~      +14
                      +1

GGCATCGCTAGCTTTGTGTGTGAGTATGCATCTCCAGGCAAATATACTGAGGTCCGGGTG     +102
G~~I~~A~~S~~F~~V~~C~~E~~Y~~A~~S~~P~~G~~K~~Y~~T~~E~~V~~R~~V~~      +34

ACAGTGCTTCGGCAGGCTGACAGCCAGGTGACTGAAGTCTGTGCGGCAACCTACATGATG     +162
T~~V~~L~~R~~Q~~A~~D~~S~~Q~~V~~T~~E~~V~~C~~A~~A~~T~~Y~~M~~M~~      +54

GGGAATGAGTTGACCTTCCTAGATGATTCCATCTGCACGGGCACCTCCAGTGGAAATCAA     +222
G~~N~~E~~L~~T~~F~~L~~D~~D~~S~~I~~C~~T~~G~~T~~S~~S~~G~~N~~Q~~      +74

GTGAACCTCACTATCCAAGGACTGAGGGCCATGGACACGGGACTCTACATCTGCAAGGTG     +282
V~~N~~L~~T~~I~~Q~~G~~L~~R~~A~~M~~D~~T~~G~~L~~Y~~I~~C~~K~~V~~      +94

GAGCTCATGTACCCACCGCCATACTACGAGGGCATAGGCAACGGAACCCAGATTTATGTA     +342
E~~L~~M~~Y~~P~~P~~P~~Y~~Y~~E~~G~~I~~G~~N~~G~~T~~Q~~I~~Y~~V~~     +114

ATTGATCCAGAACCGTGCCCAGATTCTGATCAGGAGCCCAAATCTTCTGACAAAACTCAC     +402
I~~D~~P~~E~~P~~C~~P~~D~~S~~D~~Q~~E~~P~~K~~S~~S~~D~~K~~T~~H~~     +134

ACATCCCCACCGTCCCCAGCACCTGAACTCCTGGGGGGATCGTCAGTCTTCCTCTTCCCC     +462
T~~S~~P~~P~~S~~P~~A~~P~~E~~L~~L~~G~~G~~S~~S~~V~~F~~L~~F~~P~~     +154

CCAAAACCCAAGGACACCCTCATGATCTCCCGGACCCCTGAGGTCACATGCGTGGTGGTG     +522
P~~K~~P~~K~~D~~T~~L~~M~~I~~S~~R~~T~~P~~E~~V~~T~~C~~V~~V~~V~~     +174

GACGTGAGCCACGAAGACCCTGAGGTCAAGTTCAACTGGTACGTGGACGGCGTGGAGGTG     +582
D~~V~~S~~H~~E~~D~~P~~E~~V~~K~~F~~N~~W~~Y~~V~~D~~G~~V~~E~~V~~     +194

CATAATGCCAAGACAAAGCCGCGGGAGGAGCAGTACAACAGCACGTACCGTGTGGTCAGC     +642
H~~N~~A~~K~~T~~K~~P~~R~~E~~E~~Q~~Y~~N~~S~~T~~Y~~R~~V~~V~~S~~     +214

GTCCTCACCGTCCTGCACCAGGACTGGCTGAATGGCAAGGAGTACAAGTGCAAGGTCTCC     +702
V~~L~~T~~V~~L~~H~~Q~~D~~W~~L~~N~~G~~K~~E~~Y~~K~~C~~K~~V~~S~~     +234

AACAAAGCCCTCCCAGCCCCCATCGAGAAAACCATCTCCAAAGCCAAAGGGCAGCCCCGA     +762
N~~K~~A~~L~~P~~A~~P~~I~~E~~K~~T~~I~~S~~K~~A~~K~~G~~Q~~P~~R~~     +254

GAACCACAGGTGTACACCCTGCCCCCATCCCGGGATGAGCTGACCAAGAACCAGGTCAGC     +822
E~~P~~Q~~V~~Y~~T~~L~~P~~P~~S~~R~~D~~E~~L~~T~~K~~N~~Q~~V~~S~~     +274

CTGACCTGCCTGGTCAAAGGCTTCTATCCCAGCGACATCGCCGTGGAGTGGGAGAGCAAT     +882
L~~T~~C~~L~~V~~K~~G~~F~~Y~~P~~S~~D~~I~~A~~V~~E~~W~~E~~S~~N~~     +294

GGGCAGCCGGAGAACAACTACAAGACCACGCCTCCCGTGCTGGACTCCGACGGCTCCTTC     +942
G~~Q~~P~~E~~N~~N~~Y~~K~~T~~T~~P~~P~~V~~L~~D~~S~~D~~G~~S~~F~~     +314

TTCCTCTACAGCAAGCTCACCGTGGACAAGAGCAGGTGGCAGCAGGGGAACGTCTTCTCA    +1002
F~~L~~Y~~S~~K~~L~~T~~V~~D~~K~~S~~R~~W~~Q~~Q~~G~~N~~V~~F~~S~~     +334

TGCTCCGTGATGCATGAGGCTCTGCACAACCACTACACGCAGAAGAGCCTCTCCCTGTCT    +1062
C~~S~~V~~M~~H~~E~~A~~L~~H~~N~~H~~Y~~T~~Q~~K~~S~~L~~S~~L~~S~~     +354

CCGGGTAAATGA
P~~G~~K~~*
```

FIG. 19

```
ATGGGTGTACTGCTCACACAGAGGACGCTGCTCAGTCTGGTCCTTGCACTCCTGTTTCCA
M   G   V   L   L   T   Q   R   T   L   L   S   L   V   L   A   L   L   P   F

AGCATGGCGAGCATGGCAATGCACGTGGCCCAGCCTGCTGTGGTACTGGCCAGCAGCCGA
S   M   A   S   M   A   M   H   V   A   Q   P   A   V   V   L   A   S   S   R
                    +1

GGCATCGCTAGCTTTGTGTGTGAGTATGCATCTCCAGGCAAATTGACTGAGGTCCGGGTG
G   I   A   S   F   V   C   E   Y   A   S   P   G   K   L   T   E   V   R   V

ACAGTGCTTCGGCAGGCTGACAGCCAGGTGACTGAAGTCTGTGCGGCAACCTACATGATG
T   V   L   R   Q   A   D   S   Q   V   T   E   V   C   A   A   T   Y   M   M

GGGAATGAGTTGACCTTCCTAGATGATTCCATCTGCACGGGCACCTCCAGTGGAAATCAA
G   N   E   L   T   F   L   D   D   S   I   C   T   G   T   S   S   G   N   Q

GTGAACCTCACTATCCAAGGACTGAGGGCCATGGACACGGGACTCTACATCTGCAAGGTG
V   N   L   T   I   Q   G   L   R   A   M   D   T   G   L   Y   I   C   K   V

GAGCTCATGTACCCACCGCCATACTACGAGGGCATAGGCAACGGAACCCAGATTTATGTA
E   L   M   Y   P   P   P   Y   Y   E   G   I   G   N   G   T   Q   I   Y   V

ATTGATCCAGAACCGTGCCCAGATTCTGATCAGGAGCCCAAATCTTCTGACAAAACTCAC
I   D   P   E   P   C   P   D   S   D   Q   E   P   K   S   S   D   K   T   H

ACATCCCCACCGTCCCCAGCACCTGAACTCCTGGGGGGATCGTCAGTCTTCCTCTTCCCC
T   S   P   P   S   P   A   P   E   L   L   G   G   S   S   V   F   L   F   P

CCAAAACCCAAGGACACCCTCATGATCTCCCGGACCCCTGAGGTCACATGCGTGGTGGTG
P   K   P   K   D   T   L   M   I   S   R   T   P   E   V   T   C   V   V   V

GACGTGAGCCACGAAGACCCTGAGGTCAAGTTCAACTGGTACGTGGACGGCGTGGAGGTG
D   V   S   H   E   D   P   E   V   K   F   N   W   Y   V   D   G   V   E   V

CATAATGCCAAGACAAAGCCGCGGGAGGAGCAGTACAACAGCACGTACCGTGTGGTCAGC
H   N   A   K   T   K   P   R   E   E   Q   Y   N   S   T   Y   R   V   V   S

GTCCTCACCGTCCTGCACCAGGACTGGCTGAATGGCAAGGAGTACAAGTGCAAGGTCTCC
V   L   T   V   L   H   Q   D   W   L   N   G   K   E   Y   K   C   K   V   S

AACAAAGCCCTCCCAGCCCCCATCGAGAAAACCATCTCCAAAGCCAAAGGGCAGCCCCGA
N   K   A   L   P   A   P   I   E   K   T   I   S   K   A   K   G   Q   P   R

GAACCACAGGTGTACACCCTGCCCCCATCCCGGGATGAGCTGACCAAGAACCAGGTCAGC
E   P   Q   V   Y   T   L   P   P   S   R   D   E   L   T   K   N   Q   V   S

CTGACCTGCCTGGTCAAAGGCTTCTATCCCAGCGACATCGCCGTGGAGTGGGAGAGCAAT
L   T   C   L   V   K   G   F   Y   P   S   D   I   A   V   E   W   E   S   N

GGGCAGCCGGAGAACAACTACAAGACCACGCCTCCCGTGCTGGACTCCGACGGCTCCTTC
G   Q   P   E   N   N   Y   K   T   T   P   P   V   L   D   S   D   G   S   F

TTCCTCTACAGCAAGCTCACCGTGGACAAGAGCAGGTGGCAGCAGGGGAACGTCTTCTCA
F   L   Y   S   K   L   T   V   D   K   S   R   W   Q   Q   G   N   V   F   S

TGCTCCGTGATGCATGAGGCTCTGCACAACCACTACACGCAGAAGAGCCTCTCCCTGTCT
C   S   V   M   H   E   A   L   H   N   H   Y   T   Q   K   S   L   S   L   S

CCGGGTAAATGA
P   G   K   *
```

ONCOSTATIN M SIGNAL PEPTIDE

```
  M   G   V   L   L   T   Q   R   T   L   L   S   L   V   L
 ATG GGT GTA CTG CTC ACA CAG AGG ACG CTG CTC AGT CTG GTC CTT     45
                                     ←─┐
                                    -1 +1

A   L   L   F   P   S   M   A   S   M   A   M   H   V   A
 GCA CTC CTG TTT CCA AGC ATG GCG AGC ATG GCA ATG CAC GTG GCC     90

Q   P   A   V   V   L   A   S   S   R   G   I   A   S   F
 CAG CCT GCT GTG GTA CTG GCC AGC AGC CGA GGC ATC GCC AGC TTT    135

V   C   E   Y   A   S   P   G   K   A   T   E   V   R   V
 GTG TGT GAG TAT GCA TCT CCA GGC AAA GCC ACT GAG GTC CGG GTG    180

T   V   L   R   Q   A   D   S   Q   V   T   E   V   C   A
 ACA GTG CTT CGG CAG GCT GAC AGC CAG GTG ACT GAA GTC TGT GCG    225

A   T   Y   M   M   G   N   E   L   T   F   L   D   D   S
 GCA ACC TAC ATG ATG GGG AAT GAG TTG ACC TTC CTA GAT GAT TCC    270

I   C   T   G   T   S   S   G   N   Q   V   N   L   T   I
 ATC TGC ACG GGC ACC TCC AGT GGA AAT CAA GTG AAC CTC ACT ATC    315

Q   G   L   R   A   M   D   T   G   L   Y   I   C   K   V
 CAA GGA CTG AGG GCC ATG GAC ACG GGA CTC TAC ATC TGC AAG GTG    360
                                                GLYCOSYLATION SITE
                                                       ┌─────
  E   L   M   Y   P   P   P   Y   Y   L   G   I   G   N   G
 GAG CTC ATG TAC CCA CCG CCA TAC TAC CTG GGC ATA GGC AAC GGA    405
 ←─┐
  T   Q   I   Y   V   I   D   P   E   P   C   P   D   S   D
 ACC CAG ATT TAT GTA ATT GAT CCA GAA CCG TGC CCA GAT TCT GAC    450

F   L   L   W   I   L   A   A   V   S   S   G   L   F   F
 TTC CTC CTC TGG ATC CTT GCA GCA GTT AGT TCG GGG TTG TTT TTT    495

Y   S   F   L   L   T   A   V   S   L   S   K   M   L   K
 TAT AGC TTT CTC CTC ACA GCT GTT TCT TTG AGC AAA ATG CTA AAG    540

K   R   S   P   L   T   T   G   V   Y   V   K   M   P   P
 AAA AGA AGC CCT CTT ACA ACA GGG GTC TAT GTG AAA ATG CCC CCA    585

T   E   P   E   C   E   K   Q   F   Q   P   Y   F   I   P
 ACA GAG CCA GAA TGT GAA AAG CAA TTT CAG CCT TAT TTT ATT CCC    630

I   N
 ATC AAT                                                        636
```

FIG. 23

```
ATGGGTGTACTGCTCACACAGAGGACGCTGCTCAGTCTGGTCCTTGCACTCCTGTTTCCA    -19
M~~G~~V~~L~~L~~T~~Q~~R~~T~~L~~L~~S~~L~~V~~L~~A~~L~~L~~F~~P~~    -7

AGCATGGCGAGCATGGCAATGCACGTGGCCCAGCCTGCTGTGGTACTGGCCAGCAGCCGA    +42
S~~M~~A~~S~~M~~A~~M~~H~~V~~A~~Q~~P~~A~~V~~V~~L~~A~~S~~S~~R~~    +14
       +1

GGCATCGCTAGCTTTGTGTGTGAGTATGCATCTCCAGGCAAAGCCACTGAGGTCCGGGTG    +102
G~~I~~A~~S~~F~~V~~C~~E~~Y~~A~~S~~P~~G~~K~~A~~T~~E~~V~~R~~V~~    +34

ACAGTGCTTCGGCAGGCTGACAGCCAGGTGACTGAAGTCTGTGCGGCAACCTACATGATG    +162
T~~V~~L~~R~~Q~~A~~D~~S~~Q~~V~~T~~E~~V~~C~~A~~A~~T~~Y~~M~~M~~    +54

GGGAATGAGTTGACCTTCCTAGATGATTCCATCTGCACGGGCACCTCCAGTGGAAATCAA    +222
G~~N~~E~~L~~T~~F~~L~~D~~D~~S~~I~~C~~T~~G~~T~~S~~S~~G~~N~~Q~~    +74

GTGAACCTCACTATCCAAGGACTGAGGGCCATGGACACGGGACTCTACATCTGCAAGGTG    +282
V~~N~~L~~T~~I~~Q~~G~~L~~R~~A~~M~~D~~T~~G~~L~~Y~~I~~C~~K~~V~~    +94

GAGCTCATGTACCCACCGCCATACTACCTGGGCATAGGCAACGGAACCCAGATTTATGTA    +342
E~~L~~M~~Y~~P~~P~~P~~Y~~Y~~L~~G~~I~~G~~N~~G~~T~~Q~~I~~Y~~V~~    +114

ATTGATCCAGAACCGTGCCCAGATTCTGATCAGGAGCCCAAATCTTCTGACAAAACTCAC    +402
I~~D~~P~~E~~P~~C~~P~~D~~S~~D~~Q~~E~~P~~K~~S~~S~~D~~K~~T~~H~~    +134

ACATCCCCACCGTCCCCAGCACCTGAACTCCTGGGTGGATCGTCAGTCTTCCTCTTCCCC    +462
T~~S~~P~~P~~S~~P~~A~~P~~E~~L~~L~~G~~G~~S~~S~~V~~F~~L~~F~~P~~    +154

CCAAAACCCAAGGACACCCTCATGATCTCCCGGACCCCTGAGGTCACATGCGTGGTGGTG    +522
P~~K~~P~~K~~D~~T~~L~~M~~I~~S~~R~~T~~P~~E~~V~~T~~C~~V~~V~~V~~    +174

GACGTGAGCCACGAAGACCCTGAGGTCAAGTTCAACTGGTACGTGGACGGCGTGGAGGTG    +582
D~~V~~S~~H~~E~~D~~P~~E~~V~~K~~F~~N~~W~~Y~~V~~D~~G~~V~~E~~V~~    +194

CATAATGCCAAGACAAAGCCGCGGGAGGAGCAGTACAACAGCACGTACCGGGTGGTCAGC    +642
H~~N~~A~~K~~T~~K~~P~~R~~E~~E~~Q~~Y~~N~~S~~T~~Y~~R~~V~~V~~S~~    +214

GTCCTCACCGTCCTGCACCAGGACTGGCTGAATGGCAAGGAGTACAAGTGCAAGGTCTCC    +702
V~~L~~T~~V~~L~~H~~Q~~D~~W~~L~~N~~G~~K~~E~~Y~~K~~C~~K~~V~~S~~    +234

AACAAAGCCCTCCCAGCCCCCATCGAGAAAACCATCTCCAAAGCCAAAGGGCAGCCCCGA    +762
N~~K~~A~~L~~P~~A~~P~~I~~E~~K~~T~~I~~S~~K~~A~~K~~G~~Q~~P~~R~~    +254

GAACCACAGGTGTACACCCTGCCCCCATCCCGGGATGAGCTGACCAAGAACCAGGTCAGC    +822
E~~P~~Q~~V~~Y~~T~~L~~P~~P~~S~~R~~D~~E~~L~~T~~K~~N~~Q~~V~~S~~    +274

CTGACCTGCCTGGTCAAAGGCTTCTATCCAAGCGACATCGCCGTGGAGTGGGAGAGCAAT    +882
L~~T~~C~~L~~V~~K~~G~~F~~Y~~P~~S~~D~~I~~A~~V~~E~~W~~E~~S~~N~~    +294

GGGCAGCCGGAGAACAACTACAAGACCACGCCTCCCGTGCTGGACTCCGACGGCTCCTTC    +942
G~~Q~~P~~E~~N~~N~~Y~~K~~T~~T~~P~~P~~V~~L~~D~~S~~D~~G~~S~~F~~    +314

TTCCTCTACAGCAAGCTCACCGTGGACAAGAGCAGGTGGCAGCAGGGGAACGTCTTCTCA    +1002
F~~L~~Y~~S~~K~~L~~T~~V~~D~~K~~S~~R~~W~~Q~~Q~~G~~N~~V~~F~~S~~    +334

TGCTCCGTGATGCATGAGGCTCTGCACAACCACTACACGCAGAAGAGCCTCTCCCTGTCT    +1062
C~~S~~V~~M~~H~~E~~A~~L~~H~~N~~H~~Y~~T~~Q~~K~~S~~L~~S~~L~~S~~    +354

CCGGGTAAATGA
P~~G~~K~~*
```

FIG. 24

Protocol: IM101-100

Working Table : Univariate of Methotrexate Dose at Screening/Enrollment
By Treatment Group Page: 1

------- GROUP=BMS 10 -------
Univariate Procedure

Variable=MEDDOSE     Dose

Moments

| | | | |
|---|---|---|---|
| N | 134 | Sum Wgts | 134 |
| Mean | 14.35366 | Sum | 1923.39 |
| Std Dev | 4.861737 | Variance | 23.63648 |
| Skewness | -0.09914 | Kurtosis | 0.445504 |
| USS | 30751.33 | CSS | 3143.652 |
| CV | 33.87107 | Std Mean | 0.41999 |
| T:Mean=0 | 34.17618 | Pr>|T| | 0.0001 |
| Num ^= 0 | 134 | Num > 0 | 134 |
| M(Sign) | 67 | Pr>=|M| | 0.0001 |
| Sgn Rank | 4522.5 | Pr>=|S| | 0.0001 |

Quantiles(Def=5)

| | | | | | |
|---|---|---|---|---|---|
| 100% Max | 25 | 99% | 25 | | |
| 75% Q3 | 17.5 | 95% | 22.5 | | |
| 50% Med | 15 | 90% | 20 | | |
| 25% Q1 | 10 | 10% | 10 | | |
| 0% Min | 0.4 | 5% | 10 | | |
| | | 1% | 0.8 | | |
| Range | 24.6 | | | | |
| Q3-Q1 | 7.5 | | | | |
| Mode | 10 | | | | |

Extremes

| Lowest | Obs | Highest | Obs |
|---|---|---|---|
| 0.4( | 119) | 25( | 74) |
| 0.8( | 120) | 25( | 76) |
| 0.8( | 75) | 25( | 88) |
| 2.14( | 70) | 25( | 93) |
| 7.5( | 19) | 25( | 111) |

Missing Value
Count            3
% Count/Nobs  0.74

Protocol: IM101-100

Working Table : Univariate of Methotrexate Dose at Screening/Enrollment
By Treatment Group

------GROUP=PLACEBO------

Univariate Procedure

Variable=MEDDOSE

| Moments | | Dose | |
|---|---|---|---|
| N | 143 | Sum Wgts | 143 |
| Mean | 15.13839 | Sum | 2164.79 |
| Std Dev | 4.875206 | Variance | 23.76763 |
| Skewness | -0.4482 | Kurtosis | 0.569695 |
| USS | 36146.44 | CSS | 3375.003 |
| CV | 32.20425 | Std Mean | 0.407685 |
| T:Mean=0 | 37.13255 | Pr>|T| | 0.0001 |
| Num ^= 0 | 143 | Num > 0 | 143 |
| M(Sign) | 71.5 | Pr>=|M| | 0.0001 |
| Sgn Rank | 5148 | Pr>=|S| | 0.0001 |

Quantiles(Def=5)

| 100% Max | 25 | 99% | 25 |
| 75% Q3 | 20 | 95% | 22.5 |
| 50% Med | 15 | 90% | 20 |
| 25% Q1 | 12.5 | 10% | 10 |
| 0% Min | 0.05 | 5% | 10 |
| | | 1% | 0.6 |

Range 24.95
Q3-Q1 7.5
Mode 15

Extremes

| Lowest | Obs | Highest | Obs |
|---|---|---|---|
| 0.05 | 80 | 25 | 93 |
| 0.6 | 6 | 25 | 99 |
| 2 | 76 | 25 | 104 |
| 2.14 | 79 | 25 | 105 |
| 5 | 72 | 25 | 118 |

Missing Value
Count            3
% Count/Nobs  2.05

FIG. 59

Protocol: IM101-100    Working Table : Univariate of Methotrexate Dose During DB Up to and Including Day 180 Period
By Treatment Group

--- GROUP=BMS 10 ---

Univariate Procedure

Variable=MEDDOSE    Dose

Moments

| | | | |
|---|---|---|---|
| N | 147 | Sum Wgts | 147 |
| Mean | 14.18973 | Sum | 2085.89 |
| Std Dev | 4.814626 | Variance | 23.18062 |
| Skewness | −0.12195 | Kurtosis | 0.530994 |
| USS | 32982.58 | CSS | 3384.371 |
| CV | 33.93036 | Std Mean | 0.397104 |
| T:Mean=0 | 35.73306 | Pr>|T| | 0.0001 |
| Num ^= 0 | 147 | Num > 0 | 147 |
| M(Sign) | 73.5 | Pr>=|M| | 0.0001 |
| Sgn Rank | 5439 | Pr>=|S| | 0.0001 |

Quantiles(Def=5)

| | | | | | |
|---|---|---|---|---|---|
| 100% Max | 25 | 99% | 25 | | |
| 75% Q3 | 17.5 | 95% | 20 | | |
| 50% Med | 15 | 90% | 20 | | |
| 25% Q1 | 10 | 10% | 10 | | |
| 0% Min | 0.4 | 5% | 7.5 | | |
| | | 1% | 0.8 | | |
| Range | 24.6 | | | | |
| Q3−Q1 | 7.5 | | | | |
| Mode | 10 | | | | |

Extremes

| Lowest | Obs | Highest | Obs |
|---|---|---|---|
| 0.4 | 132 | 25 | 81 |
| 0.8 | 133 | 25 | 83 |
| 0.8 | 82 | 25 | 98 |
| 2.14 | 76 | 25 | 103 |
| 2.5 | 78 | 25 | 124 |

Missing Value
Count    1
% Count/Nobs    0.68

FIG. 60

Protocol: IM101-100    Working Table : Univariate of Methotrexate Dose During DB Up to and Including Day 180 Period    Page: 2
By Treatment Group ------- GROUP=BMS 2 -------
Univariate Procedure Variable=MEDDOSE    Dose

| Moments | | | | |
|---|---|---|---|---|
| N | 142 | Sum Wgts | | 142 |
| Mean | 15.00211 | Sum | | 2130.3 |
| Std Dev | 5.383696 | Variance | | 28.98418 |
| Skewness | -0.06585 | Kurtosis | | 0.579653 |
| USS | 36045.77 | CSS | | 4086.769 |
| CV | 35.88625 | Std Mean | | 0.45179 |
| T:Mean=0 | 33.20596 | Pr>|T| | | 0.0001 |
| Num ^= 0 | 142 | Num > 0 | | 142 |
| M(Sign) | 71 | Pr>=|M| | | 0.0001 |
| Sgn Rank | 5076.5 | Pr>=|S| | | 0.0001 |

| Quantiles(Def=5) | | | | Extremes | | | |
|---|---|---|---|---|---|---|---|
| 100% Max | 30 | 99% | 25 | Lowest | Obs | Highest | Obs |
| 75% Q3 | 20 | 95% | 25 | 0.5 (141) | | 25 (134) | |
| 50% Med | 15 | 90% | 20 | 0.7 (140) | | 25 (135) | |
| 25% Q1 | 10 | 10% | 10 | 0.8 (128) | | 25 (136) | |
| 0% Min | 0.5 | 5% | 10 | 0.8 (127) | | 25 (137) | |
| | | 1% | 0.7 | 2.5 (88) | | 30 (113) | |
| Range | 29.5 | | | | | | |
| Q3-Q1 | 10 | | | | | | |
| Mode | 15 | | | | | | |

FIG. 61

Protocol: IM101-100    Working Table : Univariate of Methotrexate Dose During DB Up to and Including Day 180 Period
By Treatment Group Page: 3

----------GROUP=PLACEBO----------
Univariate Procedure

Variable=MEDDOSE    Dose

| Moments | | | |
|---|---|---|---|
| N | 161 | Sum Wgts | 161 |
| Mean | 17.0018 | Sum | 2737.29 |
| Std Dev | 19.69515 | Variance | 387.8839 |
| Skewness | 10.61733 | Kurtosis | 124.5489 |
| USS | 108602.7 | CSS | 62063.83 |
| CV | 115.8416 | Std Mean | 1.552195 |
| T:Mean=0 | 10.95339 | Pr>|T| | 0.0001 |
| Num ^= 0 | 161 | Num > 0 | 161 |
| M(Sign) | 80.5 | Pr>=|M| | 0.0001 |
| Sgn Rank | 6520.5 | Pr>=|S| | 0.0001 |

| Quantiles(Def=5) | | | | Extremes | | | |
|---|---|---|---|---|---|---|---|
| 100% Max | 250 | 99% | 250 | Lowest | Obs | Highest | Obs |
| 75% Q3 | 20 | 95% | 25 | 0.05( | 87) | 25( | 114) |
| 50% Med | 15 | 90% | 20 | 0.6( | 6) | 25( | 132) |
| 25% Q1 | 12.5 | 10% | 10 | 2( | 82) | 30( | 146) |
| 0% Min | 0.05 | 5% | 7.5 | 2.14( | 86) | 75( | 52) |
| | | 1% | 0.6 | 5( | 76) | 250( | 115) |

Range 249.95
Q3-Q1 7.5
Mode 15

Missing Value
Count              3
% Count/Nobs    1.83

FIG. 62

```
ATGGGTGTAC TGCTCACACA GAGGACGCTG CTCAGTCTGG TCCTTGCACT CCTGTTTCCA
AGCATGGCGA GCATGGCAAT GCACGTGGCC CAGCCTGCTG TGGTACTGGC CAGCAGCCGA
GGCATCGCCA GCTTTGTGTG TGAGTATGCA TCTCCAGGCA AAGCCACTGA GGTCCGGGTG
ACAGTGCTTC GGCAGGCTGA CAGCCAGGTG ACTGAAGTCT GTGCGGCAAC CTACATGATG
GGGAATGAGT TGACCTTCCT AGATGATTCC ATCTGCACGG GCACCTCCAG TGGAAATCAA
GTGAACCTCA CTATCCAAGG ACTGAGGGCC ATGGACACGG GACTCTACAT CTGCAAGGTG
GAGCTCATGT ACCCACCGCC ATACTACCTG GGCATAGGCA ACGGAACCCA GATTTATGTA
ATTGATCCAG AACCGTGCCC AGATTCTGAT CAGGAGCCCA AATCTTCTGA CAAAACTCAC
ACATCCCCAC CGTCCCCAGC ACCTGAACTC CTGGGGGGAT CGTCAGTCTT CCTCTTCCCC
CCAAAACCCA AGGACACCCT CATGATCTCC CGGACCCCTG AGGTCACATG CGTGGTGGTG
GACGTGAGCC ACGAAGACCC TGAGGTCAAG TTCAACTGGT ACGTGGACGG CGTGGAGGTG
CATAATGCCA AGACAAAGCC GCGGGAGGAG CAGTACAACA GCACGTACCG TGTGGTCAGC
GTCCTCACCG TCCTGCACCA GGACTGGCTG AATGGCAAGG AGTACAAGTG CAAGGTCTCC
AACAAAGCCC TCCCAGCCCC CATCGAGAAA ACCATCTCCA AAGCCAAAGG GCAGCCCCGA
GAACCACAGG TGTACACCCT GCCCCCATCC CGGGATGAGC TGACCAAGAA CCAGGTCAGC
CTGACCTGCC TGGTCAAAGG CTTCTATCCC AGCGACATCG CCGTGGAGTG GGAGAGCAAT
GGGCAGCCGG AGAACAACTA CAAGACCACG CCTCCCGTGC TGGACTCCGA CGGCTCCTTC
TTCCTCTACA GCAAGCTCAC CGTGGACAAG AGCAGGTGGC AGCAGGGGAA CGTCTTCTCA
TGCTCCGTGA TGCATGAGGC TCTGCACAAC CACTACACGC AGAAGAGCCT CTCCCTGTCT
CCGGGTAAAT GA
```

FIG. 66

```
MGVLLTQRTL LSLVLALLFP SMASMAMHVA QPAVVLASSR GIASFVCEYA        50

SPGKATEVRV TVLRQADSQV TEVCAATYMM GNELTFLDDS ICTGTSSGNQ       100

VNLTIQGLRA MDTGLYICKV ELMYPPPYYL GIGNGTQIYV IDPEPCPDSD       150

QEPKSSDKTH TSPPSPAPEL LGGSSVFLFP PKPKDTLMIS RTPEVTCVVV       200

DVSHEDPEVK FNWYVDGVEV HNAKTKPREE QYNSTYRVVS VLTVLHQDWL       250

NGKEYKCKVS NKALPAPIEK TISKAKGQPR EPQVYTLPPS RDELTKNQVS       300

LTCLVKGFYP SDIAVEWESN GQPENNYKTT PPVLDSDGSF FLYSKLTVDK       350

SRWQQGNVFS CSVMHEALHN HYTQKSLSLS PGK
```

FIG. 67

* Indicates a significantly significant result for comparison of BMS-188667 vs placebo.

* Indicates a significantly significant result for comparison of 10 mg/kg vs placebo.

METHODS FOR TREATING DERMATOMYOSITIS OR POLYMYOSITIS BY ADMINISTERING A SOLUBLE CTLA4 MOLECULE

CROSS-REFERENCE TO RELATED APPLICATIONS

This application is a continuation of U.S. Ser. No. 14/193,687, filed Feb. 28, 2014, currently allowed; which is a continuation of U.S. Ser. No. 13/795,545, filed Mar. 12, 2013, granted as U.S. Pat. No. 8,703,718; which is a continuation of U.S. Ser. No. 13/788,970, filed Mar. 7, 2013, granted as U.S. Pat. No. 8,722,632; which is a continuation of U.S. Ser. No. 13/404,384, filed Feb. 24, 2012, granted as U.S. Pat. No. 8,497,247; which is a continuation of U.S. Ser. No. 13/191,923, filed Jul. 27, 2011, granted as U.S. Pat. No. 8,148,332; which is a continuation of U.S. Ser. No. 12/720,064, filed Mar. 9, 2010, granted as U.S. Pat. No. 8,227,420; which is a continuation of U.S. Ser. No. 10/419,008, filed Apr. 18, 2003, now abandoned; which is a continuation-in-part of U.S. Ser. No. 09/898,195, filed Jul. 2, 2001, granted as U.S. Pat. No. 7,455,835; which claims the priorities of provisional applications, U.S. Ser. No. 60/215,913, filed Jul. 3, 2000, U.S. Ser. No. 60/373,852, filed Apr. 19, 2002, and U.S. Ser. No. 60/407,246, filed Aug. 30, 2002, the contents of which are hereby incorporated by reference in their entirety into this application.

Throughout this application various publications are referenced. The disclosures of these publications in their entireties are hereby incorporated by reference into this application in order to more fully describe the state of the art to which this invention pertains.

FIELD OF THE INVENTION

The present invention relates generally to the field of immune system diseases regulated by B7 interactions. In particular, the invention relates to methods and compositions for treating immune system diseases regulated by B7 interactions by administering to a subject an effective amount of soluble CTLA4 molecules in conjunction with a corticosteroid. The invention also relates to a method for blocking B7 interactions with CTLA4 and/or CD28 comprising the use of a soluble CTLA4 molecule.

BACKGROUND OF THE INVENTION

No cure currently exists for rheumatic diseases. Rather, therapeutic agents are used to treat the symptoms. Typically, the therapeutic agents are administered over long periods of time and the therapeutic value is often diminished by adverse side effects.

Rheumatic diseases encompass a group of diseases that affect the musculoskeletal and connective tissues of the body. These diseases are characterized by chronic inflammation that often leads to permanent tissue damage, deformity, atrophy and disability. Rheumatic diseases affect the joints, bone, soft tissue, or spinal cord (Mathies, H., *Rheuma* (1983)) and are classified as inflammatory rheumatism, degenerative rheumatism, extra-articular rheumatism, or collagen diseases. Some rheumatic diseases are known to be autoimmune diseases caused by a subject's altered immune response.

Rheumatoid arthritis is a progressive rheumatic disease, affecting approximately 2% of the adult population of developed countries (Utsinger, P. D. et al., *Rheumatoid Arthritis*, p. 140 (1985)). This disease is characterized by persistent inflammatory synovitis that causes destruction of cartilage and bone erosion, leading to structural deformities in the peripheral joints. The symptoms associated with rheumatoid arthritis include joint swelling, joint tenderness, inflammation, morning stiffness, and pain, especially upon flexing. Subjects having advanced stages of arthritis suffer from structural damage, including joint destruction with bone erosion (in *Harrison's Principals of Internal Medicine,* 13th Edition, pp. 1648-1655 (1994)). In addition, patients can present other clinical symptoms of various organic lesions, including lesions of the skin, kidney, heart, lung, central nervous system, and eyes due to vasculitis related to the autoimmune process.

Other symptoms that correlate with rheumatoid arthritis include elevated erythrocyte sedimentation rates, and elevated levels of serum C-reactive protein (CRP) and/or soluble IL-2 receptor (IL-2r). The erythrocyte sedimentation rate is increased in nearly all patients with active rheumatoid arthritis. The level of serum C-reactive protein is also elevated and correlates with disease activity and the likelihood of progressive joint damage. Additionally, the level of soluble IL-2r, a product of activated T-cells, is elevated in blood serum and synovial fluid of patients with active rheumatoid arthritis (see *Harrison's Principals of Internal Medicine,* 13th Edition, p. 1650 (1994)).

Rheumatoid arthritis is believed to be a T-cell-mediated autoimmune disease involving antigen-nonspecific intercellular interactions between T-lymphocytes and antigen-presenting cells. In general, the magnitude of the T-cell response is determined by the co-stimulatory response elicited by the interaction between T-cell surface molecules and their ligands (Mueller et al., *Ann. Rev. Immunol.,* 7:445-480 (1989)). Key co-stimulatory signals are provided by the interaction between T-cell surface receptors, CD28 and CTLA4, and their ligands, such as B7-related molecules CD80 (i.e., B7-1) and CD86 (i.e., B7-2), on antigen presenting cells (Linsley, P. et al., *Ann. Rev. Immunol.,* 11:191-212 (1993)).

T-cell activation in the absence of co-stimulation results in anergic T-cell response (Schwartz, R. H., *Cell,* 71:1065-1068 (1992)) wherein the immune system becomes nonresponsive to stimulation.

Since rheumatoid arthritis is thought to be a T-cell-mediated immune system disease, one strategy to develop new agents to treat rheumatoid arthritis is to identify molecules that block co-stimulatory signals between T-lymphocytes and antigen presenting cells, by blocking the interaction between endogenous CD28 or CTLA4 and B7. Potential molecules include soluble CTLA4 molecules that are modified (i.e., CTLA4 mutant molecules) to bind to B7 with higher avidity than wild-type CTLA4 (the sequence of which is shown in FIG. 23) or CD28, thereby blocking the co-stimulatory signals.

Soluble forms of CD28 and CTLA4 have been constructed by fusing variable (V)-like extracellular domains of CD28 and CTLA4 to immunoglobulin (Ig) constant domains resulting in CD28Ig and CTLA4Ig. A nucleotide and amino acid sequence of CTLA4Ig is shown in FIG. 24 with the protein beginning with methionine at position +1 or alanine at position −1 and ending with lysine at position +357. CTLA4Ig binds both CD80-positive and CD86-positive cells more strongly than CD28Ig (Linsley, P. et al., *Immunity,* 1:793-780 (1994)). Many T-cell-dependent immune responses have been found to be blocked by CTLA4Ig both in vitro and in vivo. (Linsley, P. et al. (1991), supra; Linsley, P. et al., *Science,* 257:792-795 (1992); Linsley, P. et al., *J. Exp. Med.,* 176:1595-1604 (1992); Lenschow, D. J. et al., *Science,* 257:789-792 (1992); Tan, P. et al., *J. Exp. Med.,* 177:165-173 (1992); Turka, L. A., *Proc. Natl. Acad. Sci. USA,* 89:11102-11105 (1992)).

To alter binding affinity to natural ligands, such as B7, soluble CTLA4Ig fusion molecules were modified by mutation of amino acids in the CTLA4 portion of the molecules. Regions of CTLA4 that, when mutated, alter the binding affinity or avidity for B7 ligands include the complementarity determining region 1 (CDR-1 as described in U.S. Pat. Nos. 6,090,914, 5,773,253 and 5,844,095; in U.S. Patent Application Ser. No. 60/214,065; and by Peach et al., *J. Exp. Med.,* 180:2049-2058 (1994)) and complementarity determining region 3 (CDR-3)-like regions (CDR-3 is the conserved region of the CTLA4 extracellular domain as described in U.S. Pat. Nos. 6,090,914, 5,773,253 and 5,844,095; in U.S. Patent Application Ser. No. 60/214,065; and by Peach, R. J. et al., *J. Exp. Med.,* 180:2049-2058 (1994); the CDR-3-like region encompasses the CDR-3 region and extends, by several amino acids, upstream and/or downstream of the CDR-3 motif). The CDR-3-like region includes a hexapeptide motif MYPPPY (SEQ ID NO.: 20) that is highly conserved in all CD28 and CTLA4 family members. Alanine scanning mutagenesis through the hexapeptide motif in CTLA4, and at selected residues in CD28Ig, reduced or abolished binding to CD80 (Peach, R. J. et al., *J. Exp. Med.,* 180:2049-2058 (1994); U.S. Pat. Nos. 5,434,131, 6,090,914 and 5,773,253).

Further modifications were made to soluble CTLA4Ig molecules by interchanging homologous regions of CTLA4 and CD28. These chimeric CTLA4/CD28 homologue mutant molecules identified the MYPPPY hexapeptide motif common to CTLA4 and CD28, as well as certain non-conserved amino acid residues in the CDR-1- and CDR-3-like regions of CTLA4, as regions responsible for increasing the binding avidity of CTLA4 with CD80 (Peach, R. J. et al., *J. Exp. Med.,* 180:2049-2058 (1994)).

Soluble CTLA4 molecules, such as CTLA4Ig, CTLA4 mutant molecules or chimeric CTLA4/CD28 homologue mutants as described, supra, introduce a new group of therapeutic drugs to treat rheumatic diseases.

Present treatments for rheumatic diseases, such as rheumatoid arthritis, include administering nonspecific cytotoxic immunosuppressive drugs known as Disease Modifying Anti-Rheumatic Drugs (DMARDs), such as methotrexate, infliximab, cyclophosphamide, azathioprine, cyclosporin A, sulfasalazine, hydroxychloroquine, leflunomide, etanercept, and tumor necrosis factor-alpha (TNFα) or other cytokine blockers or antagonists. These immunosuppressive drugs suppress the entire immune system of the subject, and long-term use increases the risk of infection and oncogenesis. Moreover, these drugs merely slow down the progress of the rheumatoid arthritis, which resumes at an accelerated pace after the therapy is discontinued. Additionally, prolonged therapy with these nonspecific drugs produces toxic side effects, including a tendency towards development of certain malignancies, kidney failure, bone marrow suppression, pulmonary fibrosis, malignancy, diabetes, and liver function disorders. These drugs may also gradually cease being effective after about 2-5 years (*Kelley's Textbook of Rheumatology,* Sixth Edition, pp. 1001-1022 (2001)). Newer, biologically based, DMARDs such as cytokine blockers may be more potent and may have longer lasting effects than older DMARDS such as hydrochloroquine, however, the long term safety of these newer drugs is still unknown. Reports of multiple sclerosis and lupus exist with the use of TNF blockers.

Alternatively, therapeutic agents that are non-specific immunosuppressive and anti-inflammatory drugs have been used to obtain symptomatic relief. These drugs are dose-dependent and do not protect from disease progression. These drugs include Non-Steroidal Anti-Inflammatory Drugs (NSAIDS) as well as steroid compounds (e.g., corticosteroids or glucocorticoids), such as prednisone and methylprednisolone. Steroids also have significant toxic side effects associated with their long-term use. (*Kelley's Textbook of Rheumatology,* Sixth Edition, pp. 829-833 (2001)).

Thus, current treatments for rheumatoid arthritis are of limited efficacy, involve significant toxic side effects, and cannot be used continuously for prolonged periods of time.

Accordingly, there exists a need for treatments that are effective and more potent for treating rheumatic diseases, such as rheumatoid arthritis, and avoids the disadvantages of old conventional methods and agents, by targeting a pathophysiological mechanism of autoimmunity.

SUMMARY OF THE INVENTION

The present invention provides compositions and methods for treating immune system diseases, by administering to a subject soluble CTLA4 molecules, which bind to B7 molecules on B7-positive cells, thereby inhibiting endogenous B7 molecules from binding CTLA4 and/or CD28 on T-cells. Soluble CTLA4 molecules used in the methods of the invention include CTLA4Ig and soluble CTLA4 mutant molecule L104EA29YIg.

Alternatively, the present invention provides compositions and methods for treating immune system diseases, by administering to a subject a combination of a DMARD and a molecule that blocks B7 interaction with CTLA4 and/or CD28.

The present invention also provides methods for inhibiting T-cell function, but not causing T-cell depletion, in a human by contacting B7-positive cells in the human with soluble CTLA4. Examples of soluble CTLA4 include CTLA4Ig and soluble CTLA4 mutant molecules, such as L104EA29YIg.

The present invention also provides methods for treating (e.g., reducing symptoms of) rheumatic diseases, such as rheumatoid arthritis, by administering to a subject suffering from symptoms of arthritis, soluble CTLA4 molecules such as CTLA4Ig and/or soluble CTLA4 mutant molecule L104EA29YIg and/or a mix of any soluble CTLA4 molecule. The CTLA4 mutant molecule L104EA29YIg, e.g., beginning with methionine at position +1 or alanine at position −1 and ending with lysine at position +357, as shown in FIG. 19, is preferred for use in the methods of the invention.

The present invention also provides methods for treating (e.g., reducing symptoms of) rheumatic diseases, such as rheumatoid arthritis, by administering to the subject a combination of 1) a DMARD, such as methotrexate or a molecule that blocks TNF interactions, and 2) soluble CTLA4 molecules, such as CTLA4Ig.

The present invention also provides methods for reducing pathophysiological changes associated with an immune system disease (e.g., rheumatic disease), such as structural damage, by administering to the subject diagnosed with the immune system disease (e.g., rheumatoid arthritis), soluble CTLA4 molecules alone or in conjunction with other therapeutic drugs, such as a DMARD.

The present invention also provides a pharmaceutical composition for treating immune system diseases, such as rheumatic diseases, comprising a pharmaceutically acceptable carrier and a biologically effective agent, such as soluble CTLA4 molecules, alone or in conjunction with other therapeutic drugs, such as a DMARD, an NSAID, a corticosteroid and/or a glucocorticoid.

Kits comprising pharmaceutical compositions therapeutic for immune system disease are also encompassed by the invention. In one embodiment, a kit comprising one or more of the pharmaceutical compositions of the invention is used to treat an immune system disease, e.g., rheumatoid arthritis. For example, the pharmaceutical composition comprises an effective amount of soluble CTLA4 molecules that bind to B7 molecules on B7-positive cells, thereby blocking the B7 molecules from binding CTLA4 and/or CD28 on T-cells. Further, the kit may contain one or more immunosuppressive agents used in conjunction with the pharmaceutical compositions of the invention. Potential immunosuppressive agents include, but are not limited to, corticosteroids, non-steroidal antiinflammatory drugs (e.g., Cox-2 inhibitors), prednisone, cyclosporine, cyclosporin A, azathioprine, methotrexate, TNFα blockers or antagonists, hydroxychloroquine, sulphasalazopyrine (sulfasalazine), gold salts, infliximab, etanercept, anakinra and any biological agent targeting an inflammatory cytokine.

The present invention also provides methods for reducing the erythrocyte sedimentation rate that is associated with rheumatoid arthritis.

Additionally, the present invention provides methods for reducing the levels of certain components of blood serum which are associated with rheumatoid arthritis, including C-reactive protein, IL-6, TNF-α, soluble ICAM-1, soluble E-selectin and/or soluble IL-2r.

BRIEF DESCRIPTION OF THE FIGURES

FIG. 1A: Demographic data of patient cohorts. Demographic data including gender, race, and disease duration as described in Example 3, infra.

FIG. 1B: Demographic data of patient cohorts. Demographic data including gender, age, weight, and disease activity, evaluated by the patient and by the physician, as described in Example 3, infra.

FIG. 1C: Demographic data of patient cohorts as described in Example 3, infra. Demographic data including disease activity, erythrocyte sedimentation rate (ESR), physical function (disability evaluated by health questionnaire), and C-reactive protein (CRP).

FIG. 1D: Demographic data of patient cohorts as described in Example 3, infra. Demographic data including joint swelling, joint tenderness, morning stiffness, and pain.

FIG. 1E: Demographic data of patient cohorts as described in Example 3, infra. Demographic data including prior treatments.

FIG. 3A: ACR responses at Day 85 as described in Example 3, infra. ACR-20, -50, and -70 responses.

FIG. 4A: Basic (20% improvement) clinical responses in swollen and tender joint count in percentage of patients at Day 85 as described in Example 3, infra. Basic clinical response, ACR-20.

FIG. 5D: Pain (by Likert scale by mean unit change from baseline) in percentage of patients at Day 85 as described in Example 3, infra. Pain changes from baseline.

FIG. 6A: Patient global assessment of disease activity change from baseline by range of 2 units at Day 85 as described in Example 3, infra. Disease activity improvement.

FIG. 7C: Mean reduction in C-reactive protein (CRP) levels at Day 85 as described in Example 3, infra. Mean change from baseline.

FIG. 8: Reduction in soluble IL-2 receptor levels mean change from baseline at Day 85 as described in Example 3, infra.

FIG. 18: Nucleotide and amino acid sequence of L104EIg (SEQ ID NOs: 6-7) as described in Example 1, infra.

FIG. 19: Nucleotide and amino acid sequence of L104EA29YIg (SEQ ID NOs: 8-9) as described in Example 1, infra.

FIG. 20: Nucleotide and amino acid sequence of L104EA29LIg (SEQ ID NOs: 10-11) as described in Example 1, infra.

FIG. 21: Nucleotide and amino acid sequence of L104EA29TIg (SEQ ID NOs: 12-13) as described in Example 1, infra.

FIG. 22: Nucleotide and amino acid sequence of L104EA29WIg (SEQ ID NOs: 14-15) as described in Example 1, infra.

FIG. 23: Nucleotide and amino acid sequence of CTLA4 receptor (SEQ ID NOs: 16-17).

FIG. 24: Nucleotide and amino acid sequence of CTLA4Ig (SEQ ID NOs: 18-19).

FIG. 26 (right depiction) shows an expanded view of the CDR-1 (S25-R33) region and the MYPPPY region indicating the location and side-chain orientation of the avidity enhancing mutations, L104 and A29.

FIG. 57: A table of the univariate methotrexate dose at screening/enrollment for treatment group BMS 10—treated with CTLA4Ig at 10 mg/kg body weight as described in Example 5, infra.

Figure 58:
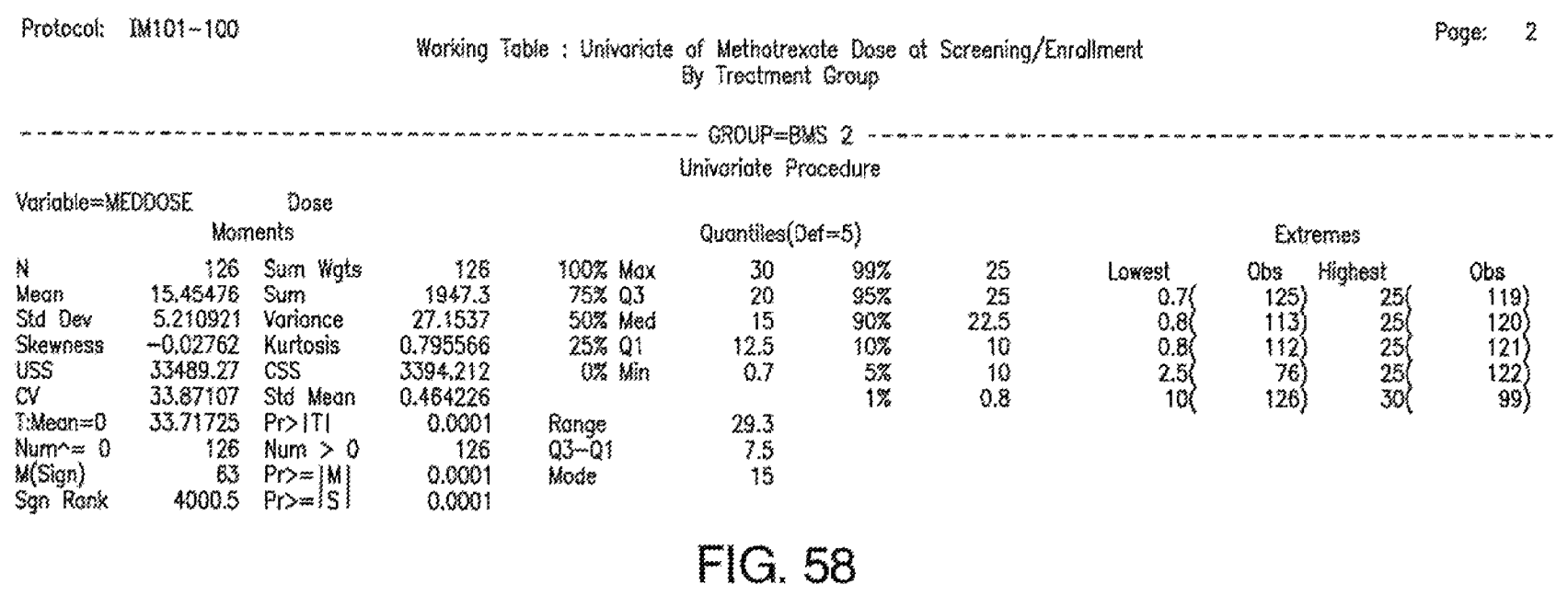

FIG. 58: A table of the univariate methotrexate dose at screening/enrollment for treatment group BMS 2—treated with CTLA4Ig at 2 mg/kg body weight as described in Example 5, infra.

FIG. 59: A table of the univariate methotrexate dose at screening/enrollment for the placebo group, as described in Example 5, infra.

FIG. 60: A table of the univariate methotrexate dose up to and including Day 180 of the study for treatment group BMS 10—treated with CTLA4Ig at 10 mg/kg body weight as described in Example 5, infra.

FIG. 61: A table of the univariate methotrexate dose up to and including Day 180 of the study for treatment group BMS 2—treated with CTLA4Ig at 2 mg/kg body weight as described in Example 5, infra.

FIG. 62: A table of the univariate methotrexate dose up to and including Day 180 of the study for the placebo group, as described in Example 5, infra.

FIG. 64a. Tender Joint Count. FIG. 64b. Swollen Joint Count. FIG. 64c. Pain Assessment.

FIG. 66: Nucleotide sequence of a CTLA4Ig encoding a signal peptide; a wild-type amino acid sequence of the extracellular domain of CTLA4 starting at methionine at position +1 to aspartic acid at position +124, or starting at alanine at position −1 to aspartic acid at position +124; and an Ig region (SEQ ID NO.: 21).

FIG. 67: Amino acid sequence of a CTLA4Ig having a signal peptide; a wild-type amino acid sequence of the extracellular domain of CTLA4 starting at methionine at position +1 to aspartic acid at position +124, or starting at alanine at position −1 to aspartic acid at position +124; and an Ig region (SEQ ID NO.: 22).

DETAILED DESCRIPTION OF THE INVENTION

Definitions

Figure 2:
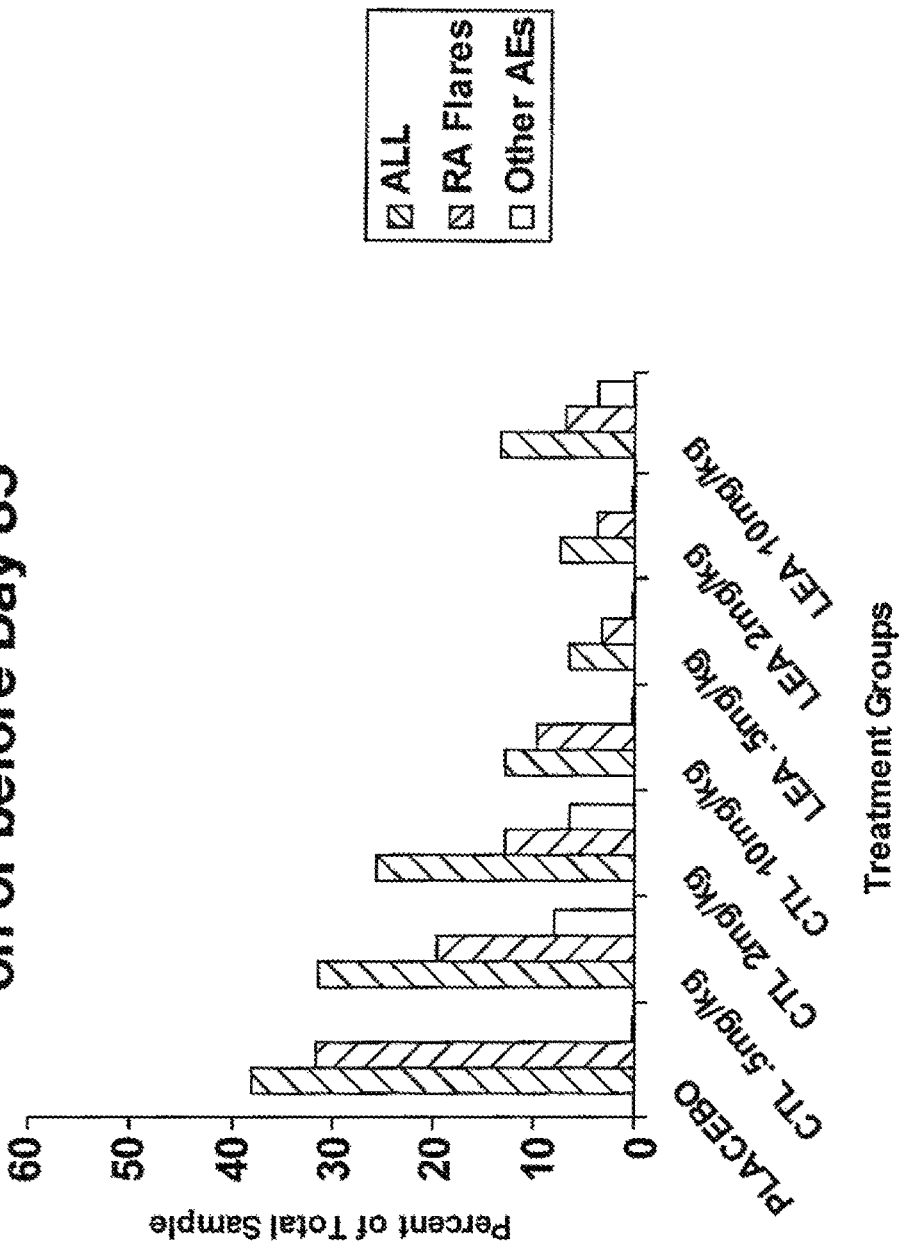
FIG. 2: Summary of discontinuations at Day 85 by reason as described in Example 3, infra.

All scientific and technical terms used in this application have meanings commonly used in the art unless otherwise specified. As used in this application, the following words or phrases have the meanings specified.

As used herein, DMARD refers to a Disease Modifying Anti-Rheumatic Drug. A DMARD is any agent that modifies the symptoms and/or progression associated with an immune system disease, including autoimmune diseases (e.g., rheumatic diseases), graft-related disorders and immunoproliferative diseases. DMARDs modify one or more of the symptoms and/or disease progression associated with rheumatic disease. Symptoms of rheumatic diseases, include the following: joint swelling, pain, tenderness, morning stiffness, structural damage, an elevated level of serum C-reactive protein (CRP), an elevated level of soluble IL-2r, an elevated level of soluble ICAM-1, an elevated level of soluble E-selectin, an elevated level of rheumatoid factor, an elevated level of IL-6 or an elevated erythrocyte sedimentation rate (ESR). These symptoms and the reduction of these symptoms can be evaluated by any well-known evaluation methods including: Health Questionnaire Assessments; ACR 20, 50, 70; and/or Medical Outcomes Study Short Form-36.

DMARDs include, but are not limited to, dihydrofolic acid reductase inhibitors, e.g., methotrexate; cyclophosphamide; cyclosporine; cyclosporin A; chloroquine; hydroxychloroquine; sulfasalazine (sulphasalazopyrine) gold salts D-penicillamine; leflunomide; azathioprine; anakinra; TNF blockers, e.g., infliximab (REMICADE®) or etanercept; and a biological agent that targets an inflammatory cytokine.

As used herein, NSAID refers to a Non-Steroidal Anti-Inflammatory Drug. NSAIDs reduce inflammatory responses in a subject. NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors, meloxicam and tramadol.

As used herein, "ligand" refers to a molecule that specifically recognizes and binds another molecule, for example, a ligand for CTLA4 is a B7 molecule. In a further example, a ligand for the B7 molecule is a CTLA4 and/or CD28 molecule. The interaction of a molecule and its ligand can be regulated by compositions of the invention. For example, CTLA4 interaction with its ligand B7 can be blocked by administration of CTLA4Ig molecules. Alternatively, Tumor Necrosis Factor (TNF) interaction with its ligand, TNF receptor (TNFR), can be blocked by administration of etanercept or other TNF/TNFR blocking molecules.

As used herein "wild-type CTLA4" or "non-mutated CTLA4" has the amino acid sequence of naturally occurring, full length CTLA4 as shown in FIG. 23 (also as described in U.S. Pat. Nos. 5,434,131, 5,844,095 and 5,851,795 herein incorporated by reference in their entirety), or any portion or derivative thereof, that recognizes and binds a B7 or interferes with a B7 so that it blocks binding to CD28 and/or CTLA4 (e.g., endogenous CD28 and/or CTLA4). In particular embodiments, the extracellular domain of wild-type CTLA4 begins with methionine at position +1 and ends at aspartic acid at position +124, or the extracellular domain of wild-type CTLA4 begins with alanine at position −1 and ends at aspartic acid at position +124 as shown in FIG. 23. Wild-type CTLA4 is a cell surface protein, having an N-terminal extracellular domain, a transmembrane domain, and a C-terminal cytoplasmic domain. The extracellular domain binds to target molecules, such as a B7 molecule. In a cell, the naturally occurring, wild-type CTLA4 protein is translated as an immature polypeptide, which includes a signal peptide at the N-terminal end. The immature polypeptide undergoes post-translational processing, which includes cleavage and removal of the signal peptide to generate a CTLA4 cleavage product having a newly generated N-terminal end that differs from the N-terminal end in the immature form. One skilled in the art will appreciate that additional post-translational processing may occur, which removes one or more of the amino acids from the newly generated N-terminal end of the CTLA4 cleavage product. Alternatively, the signal peptide may not be removed completely, generating molecules that begin before the common starting amino acid methionine. Thus, the mature CTLA4 protein may start at methionine at position +1 or alanine at position −1. The mature form of the CTLA4 molecule includes the extracellular domain or any portion thereof, which binds to B7.

As used herein, a "CTLA4 mutant molecule" means wild-type CTLA4 as shown in FIG. 23 or any portion or derivative thereof that has a mutation or multiple mutations (preferably in the extracellular domain of wild-type CTLA4). A CTLA4 mutant molecule has a sequence that it is similar but not identical to the sequence of wild-type CTLA4 molecule, but still binds a B7. The mutations may include one or more amino acid residues substituted with an amino acid having conservative (e.g., substitute a leucine with an isoleucine) or non-conservative (e.g., substitute a glycine with a tryptophan) structure or chemical properties, amino acid deletions, additions, frameshifts, or truncations. CTLA4 mutant molecules may include a non-CTLA4 molecule therein or attached thereto. The mutant molecules may be soluble (i.e., circulating) or bound to a cell surface. Additional CTLA4 mutant molecules include those described in U.S. Patent Application Ser. Nos. 60/214,065 and 60/287,576; in U.S. Pat. Nos. 7,094,874, 6,090,914, 5,844,095 and 5,773,253; and as described by Peach, R. J. et al., in *J. Exp. Med.*, 180:2049-2058 (1994)). CTLA4 mutant molecules can be made synthetically or recombinantly.

"CTLA4Ig" is a soluble fusion protein comprising an extracellular domain of wild-type CTLA4 that binds B7, or a portion thereof, joined to an immunoglobulin constant region (Ig), or a portion thereof. A particular embodiment comprises the extracellular domain of wild-type CTLA4 (as shown in FIG. 23) starting at methionine at position +1 and ending at aspartic acid at position +124, or starting at alanine at position −1 to aspartic acid at position +124; a junction amino acid residue glutamine at position +125; and an immunoglobulin portion encompassing glutamic acid at position +126 through lysine at position +357 (DNA encoding CTLA4Ig was deposited on May 31, 1991 with the American Type Culture Collection (ATCC®), 10801 University Blvd., Manassas, Va. 20110-2209 under the provisions of the Budapest Treaty, and has been accorded ATCC® Accession No. ATCC® 68629; Linsley, P. et al., *Immunity*, 1:793-780 (1994)). CTLA4Ig-24, a Chinese Hamster Ovary (CHO) cell line expressing CTLA4Ig was deposited on May 31, 1991 with ATCC® Identification No. CRL-10762). The soluble CTLA4Ig molecules used in the methods and/or kits of the invention may or may not include a signal (leader) peptide sequence. Typically, in the methods and/or kits of the invention, the molecules do not include a signal peptide sequence.

"L104EA29YIg" is a fusion protein that is a soluble CTLA4 mutant molecule comprising an extracellular domain of wild-type CTLA4 with amino acid changes A29Y (a tyrosine amino acid residue substituting for an alanine at position 29) and L104E (a glutamic acid amino acid residue substituting for a leucine at position +104), or a portion thereof that binds a B7 molecule, joined to an Ig tail (included in FIG. 19; DNA encoding L104EA29YIg was deposited on Jun. 20, 2000 with ATCC® No. PTA-2104; in U.S. patent application Ser. Nos. 09/579,927, 60/287,576 and 60/214,065, incorporated by reference herein). The soluble L104EA29YIg molecules used in the methods and/or kits of the invention may or may not include a signal (leader) peptide sequence. Typically, in the methods and/or kits of the invention, the molecules do not include a signal peptide sequence.

As used herein, "soluble" refers to any molecule, or fragments and derivatives thereof, not bound or attached to a cell, i.e., circulating. For example, CTLA4, B7 or CD28 can be made soluble by attaching an immunoglobulin (Ig) moiety to the extracellular domain of CTLA4, B7 or CD28, respectively. Alternatively, a molecule such as CTLA4 can be rendered soluble by removing its transmembrane domain. Typically, the soluble molecules used in the methods, compositions and/or kits of the invention do not include a signal (or leader) sequence.

As used herein, "soluble CTLA4 molecules" means non-cell-surface-bound (i.e., circulating) CTLA4 molecules or any functional portion of a CTLA4 molecule that binds B7 including, but not limited to: CTLA4Ig fusion proteins (e.g., encoded by DNA deposited with ATCC® Accession No. 68629), wherein the extracellular domain of CTLA4 is fused to an immunoglobulin (Ig) moiety such as IgCγ1 (IgCgamma1), IgCγ2 (IgCgamma2), IgCγ3 (IgCgamma3), IgCγ4 (IgCgamma4), IgCμ (IgCmu), IgCα1 (IgCalpha1), IgCα2 (IgCalpha2), IgCδ (IgCdelta) or IgCε (IgCepsilon), rendering the fusion molecule soluble, or fragments and derivatives thereof; proteins with the extracellular domain of CTLA4 fused or joined with a portion of a biologically active or chemically active protein such as the papillomavirus E7 gene product (CTLA4-E7), melanoma-associated antigen p97 (CTLA4-p97) or HIV env protein (CTLA4-env gp120) (as described in U.S. Pat. No. 5,844,095, herein incorporated by reference in its entirety), or fragments and derivatives thereof; hybrid (chimeric) fusion proteins such as CD28/CTLA4Ig (as described in U.S. Pat. No. 5,434,131, herein incorporated by reference in its entirety), or fragments and derivatives thereof; CTLA4 molecules with the transmembrane domain removed to render the protein soluble (Oaks, M. K. et al., *Cell. Immunol.*, 201:144-153 (2000), herein incorporated by reference in its entirety), or fragments and derivatives thereof "Soluble CTLA4 molecules" also include fragments, portions or derivatives thereof, and soluble CTLA4 mutant molecules, having CTLA4 binding activity. The soluble CTLA4 molecules used in the methods of the invention may or may not include a signal (leader) peptide sequence. Typically, in the methods, compositions and/or kits of the invention, the molecules do not include a signal peptide sequence.

As used herein "the extracellular domain of CTLA4" is the portion of CTLA4 that recognizes and binds CTLA4 ligands, such as B7 molecules. For example, an extracellular domain of CTLA4 comprises methionine at position +1 to aspartic acid at position +124 (FIG. 23). Alternatively, an extracellular domain of CTLA4 comprises alanine at position −1 to aspartic acid at position +124 (FIG. 23). The extracellular domain includes fragments or derivatives of CTLA4 that bind a B7 molecule. The extracellular domain of CTLA4 as shown in FIG. 23 may also include mutations that change the binding avidity of the CTLA4 molecule for a B7 molecule.

As used herein, the term "mutation" means a change in the nucleotide or amino acid sequence of a wild-type molecule, for example, a change in the DNA and/or amino acid sequences of the wild-type CTLA4 extracellular domain. A mutation in DNA may change a codon leading to a change in the amino acid sequence. A DNA change may include substitutions, deletions, insertions, alternative splicing, or truncations. An amino acid change may include substitutions, deletions, insertions, additions, truncations, or processing or cleavage errors of the protein. Alternatively, mutations in a nucleotide sequence may result in a silent mutation in the amino acid sequence as is well understood in the art. In that regard, certain nucleotide codons encode the same amino acid. Examples include nucleotide codons CGU, CGG, CGC, and CGA encoding the amino acid, arginine (R); or codons GAU, and GAC encoding the amino acid, aspartic acid (D). Thus, a protein can be encoded by one or more nucleic acid molecules that differ in their specific nucleotide sequence, but still encode protein molecules having identical sequences. The amino acid coding sequence is as follows:

| Amino Acid | Symbol | One Letter Symbol | Codons |
| --- | --- | --- | --- |
| Alanine | Ala | A | GCU, GCC, GCA, GCG |
| Cysteine | Cys | C | UGU, UGC |
| Aspartic Acid | Asp | D | GAU, GAC |
| Glutamic Acid | Glu | E | GAA, GAG |
| Phenylalanine | Phe | F | UUU, UUC |
| Glycine | Gly | G | GGU, GGC, GGA, GGG |
| Histidine | His | H | CAU, CAC |
| Isoleucine | Ile | I | AUU, AUC, AUA |
| Lysine | Lys | K | AAA, AAG |
| Leucine | Leu | L | UUA, UUG, CUU, CUC, CUA, CUG |
| Methionine | Met | M | AUG |
| Asparagine | Asn | N | AAU, AAC |
| Proline | Pro | P | CCU, CCC, CCA, CCG |
| Glutamine | Gln | Q | CAA, CAG |
| Arginine | Arg | R | CGU, CGC, CGA, CGG, AGA, AGG |
| Serine | Ser | S | UCU, UCC, UCA, UCG, AGU, AGC |
| Threonine | Thr | T | ACU, ACC, ACA, ACG |
| Valine | Val | V | GUU, GUC, GUA, GUG |
| Tryptophan | Trp | W | UGG |
| Tyrosine | Tyr | Y | UAU, UAC |

The mutant molecule may have one or more mutations. As used herein, a "non-CTLA4 protein sequence" or "non-CTLA4 molecule" means any protein molecule that does not bind B7 and does not interfere with the binding of CTLA4 to its target. The non-CTLA4 molecule, attached to the extracellular domain of a CTLA4 molecule can alter the solubility or affinity of the CTLA4 molecule. An example includes, but is not limited to, an immunoglobulin (Ig) constant region or portion thereof. Preferably, the Ig constant region is a human or monkey Ig constant region, e.g., human C(gamma)1, including the hinge, CH2 and CH3 regions. The Ig constant region can be mutated to reduce its effector functions (U.S. Pat. Nos. 5,637,481, 5,844,095 and 5,434,131).

As used herein, a "fragment" or "portion" is any part or segment of a molecule, e.g., CTLA4 or CD28, preferably the extracellular domain of CTLA4 or CD28 or a part or segment thereof, that recognizes and binds its target, e.g., a B7 molecule.

As used herein, "B7" refers to the B7 family of molecules including, but not limited to, B7-1 (CD80) (Freeman et al., *J. Immunol.*, 143:2714-2722 (1989), herein incorporated by reference in its entirety), B7-2 (CD86) (Freeman et al., *Science*, 262:909-911 (1993) herein incorporated by reference in its entirety; Azuma et al., *Nature*, 366:76-79 (1993) herein incorporated by reference in its entirety) that may recognize and bind CTLA4 and/or CD28. A B7 molecule can be expressed on an activated B cell.

As used herein, "CD28" refers to the molecule that recognizes and binds B7 as described in U.S. Pat. Nos. 5,580,756 and 5,521,288 (herein incorporated by reference in their entirety).

As used herein, "B7-positive cells" are any cells with one or more types of B7 molecules expressed on the cell surface.

As used herein, a "derivative" is a molecule that shares sequence similarity and activity of its parent molecule. For example, a derivative of CTLA4 includes a soluble CTLA4 molecule having an amino acid sequence at least 70% similar to the extracellular domain of wild-type CTLA4, and which recognizes and binds B7, e.g., CTLA4Ig or soluble CTLA4 mutant molecule L104EA29YIg. A derivative means any change to the amino acid sequence and/or chemical quality of the amino acid, e.g., amino acid analogs.

As used herein, to "regulate" an immune response is to activate, stimulate, up-regulate, inhibit, block, down-regulate or modify the immune response. The autoimmune diseases described herein, may be treated by regulating an immune response, e.g., by regulating functional CTLA4- and/or CD28-positive cell interactions with B7-positive cells. For example, a method for regulating an immune response comprises contacting the B7-positive cells with a soluble CTLA4 molecule of the invention so as to form soluble CTLA4/B7 complexes, the soluble CTLA4 molecule interfering with reaction of an endogenous CTLA4 and/or CD28 molecule with said B7 molecule.

As used herein, to "block" or "inhibit" a receptor, signal or molecule means to interfere with the activation of the receptor, signal or molecule, as detected by an art-recognized test. For example, blockage of a cell-mediated immune response can be detected by determining reduction of rheumatic disease associated symptoms. Blockage or inhibition may be partial or total.

As used herein, "blocking B7 interaction" means to interfere with the binding of B7 to its ligands, such as CD28 and/or CTLA4, thereby obstructing T-cell and B7-positive cell interactions. Examples of agents that block B7 interactions include, but are not limited to, molecules such as an antibody (or portion or derivative thereof) that recognizes and binds to the any of CTLA4, CD28 or B7 molecules (e.g., B7-1, B7-2); a soluble form (or portion or derivative thereof) of the molecules such as soluble CTLA4; a peptide fragment or other small molecule designed to interfere with the cell signal through the CTLA4/CD28/B7-mediated interaction.

In a preferred embodiment, the blocking agent is a soluble CTLA4 molecule, such as CTLA4Ig (ATCC® 68629) or L104EA29YIg (ATCC® PTA-2104), a soluble CD28 molecule such as CD28Ig (ATCC® 68628), a soluble B7 molecule such as B7Ig (ATCC® 68627), an anti-B7 monoclonal antibody (e.g., ATCC® HB-253, ATCC® CRL-2223, ATCC® CRL-2226, ATCC® HB-301, ATCC® HB-11341) and monoclonal antibodies as described in by Anderson et al in U.S. Pat. No. 6,113,898 or Yokochi et al., J. Immunol., 128(2):823-827 (1982), an anti-CTLA4 monoclonal antibody (e.g., ATCC® HB-304, and monoclonal antibodies as described in references 82-83) and/or an anti-CD28 monoclonal antibody (e.g., ATCC® HB 11944 and mAb 9.3 as described by Hansen (Hansen et al., Immunogenetics, 10:247-260 (1980)) or Martin (Martin et al., J. Clin. Immunol., 4(1):18-22 (1984)). Blocking B7 interactions can be detected by art-recognized tests such as determining reduction of immune disease (e.g., rheumatic disease) associated symptoms, by determining reduction in T-cell/B7-cell interactions or by determining reduction in B7 interaction with CTLA4 and/or CD28. Blockage may be partial or total.

As used herein, an "effective amount" of a molecule is defined as an amount that blocks the interaction of the molecule with its ligand. For example, an effective amount of a molecule that blocks B7 interaction with CTLA4 and/or CD28 may be defined as the amount of the molecule that, when bound to B7 molecules on B7-positive cells, inhibit B7 molecules from binding endogenous ligands such as CTLA4 and CD28. Alternatively, an effective amount of a molecule that blocks B7 interaction with CTLA4 and/or CD28 may be defined as the amount of the molecule that, when bound to CTLA4 and/or CD28 molecules on T cells, inhibit B7 molecules from binding endogenous ligands such as CTLA4 and CD28. The inhibition or blockage may be partial or complete.

As used herein, "treating" a disease means to manage a disease by medicinal or other therapies. Treatment of a disease may ameliorate the symptoms of a disease, reduce the severity of a disease, alter the course of disease progression and/or ameliorate or cure the basic disease problem. For example, to treat an autoimmune disease may be accomplished by regulating an immune response, e.g., by regulating functional CTLA4- and/or CD28-positive cell interactions with B7-positive cells. Alternatively, treating an autoimmune disease may be accomplished by preventing the disease from occurring or progressing through the use of the compositions described herein.

As used herein, "immune system disease" means any disease mediated by T-cell interactions with B7-positive cells including, but not limited to, autoimmune diseases, graft related disorders and immunoproliferative diseases. Examples of immune system diseases include graft versus host disease (GVHD) (e.g., such as may result from bone marrow transplantation, or in the induction of tolerance), immune disorders associated with graft transplantation rejection, chronic rejection, and tissue or cell allo- or xenografts, including solid organs (e.g., kidney transplants), skin, islets, muscles, hepatocytes, neurons. Examples of immunoproliferative diseases include, but are not limited to, psoriasis, T-cell lymphoma, T-cell acute lymphoblastic leukemia, testicular angiocentric T-cell lymphoma, benign lymphocytic angiitis, lupus (e.g., lupus erythematosus, lupus nephritis), Hashimoto's thyroiditis, primary myxedema, Graves' disease, pernicious anemia, autoimmune atrophic gastritis, Addison's disease, diabetes (e.g., insulin dependent diabetes mellitus, type I diabetes mellitus, type II diabetes mellitus), Goodpasture syndrome, myasthenia gravis, pemphigus, Crohn's disease, sympathetic ophthalmia, autoimmune uveitis, multiple sclerosis, autoimmune hemolytic anemia, idiopathic thrombocytopenia, primary biliary cirrhosis, chronic action hepatitis, ulceratis colitis, Sjögren's syndrome, rheumatic diseases (e.g., rheumatoid arthritis, juvenile rheumatoid arthritis), polymyositis, scleroderma, and mixed connective tissue disease.

As used herein, "rheumatic diseases" means any disease that affects the joints, bone, soft tissue, or spinal cord (Mathies, H., Rheuma (1983)) and comprises inflammatory rheumatism, degenerative rheumatism, extra-articular rheumatism, and collagen diseases. Additionally, rheumatic diseases include, but are not limited to, chronic polyarthritis, psoriasis arthropathica, ankylosing spondylitis, rheumatoid arthritis, juvenile rheumatoid arthritis, panarteritis nodosa, systemic lupus erythematosus, progressive systemic scleroderma, periarthritis humeroscapularis, arthritis uratica, chondrocalcinosis, dermatomyositis, muscular rheumatism, myositis, and myogelosis. Some rheumatic diseases are known to be autoimmune diseases caused by a subject's altered immune response.

As used herein, "gene therapy" is a process to treat a disease by genetic manipulation. Gene therapy involves introducing a nucleic acid molecule into a cell and the cell expressing a gene product encoded by the nucleic acid molecule. For example, as is well known by those skilled in the art, introducing the nucleic acid molecule into a cell may be performed by introducing an expression vector containing the nucleic acid molecule of interest into cells ex vivo or in vitro by a variety of methods including, for example, calcium phosphate precipitation, diethyaminoethyl dextran, polyethylene glycol (PEG), electroporation, direct injection, lipofection or viral infection (Sambrook et al., Molecular Cloning: A Laboratory Manual, Cold Spring Harbor Laboratory Press (1989); Kriegler, M., Gene Transfer and Expression: A Laboratory Manual, W.H. Freeman and Co., New York, N.Y. (1993) and Wu, Method. Enzymol., Academic Press, New York (1993), each of which is incorporated herein by reference). Alternatively, nucleotide sequences of interest may be introduced into a cell in vivo using a variety of vectors and by a variety of methods including, for example, direct administration of the nucleic acid into a subject (Williams et al., Proc. Natl. Acad. Sci., 88:2726-2730 (1991)); or insertion of the nucleic acid molecule into a viral vector, production of the recombinant virus or viral particle, and infection of the subject with the recombinant virus (Battleman et al., J. Neurosci., 13:941-951 (1993); Carroll et al., J. Cell. Biochem., 17E:241 (1993); Lebkowski et al., U.S. Pat. No. 5,354,678; Davison et al., Molecular Virology: A Practical Approach, IRL Press, New York (1993)). Other methods used for in vivo transfer include encapsulation of the nucleic acid into liposomes, and direct introduction of the liposomes, or liposomes combined with a hemagglutinating Sendai virus, into a subject (U.S. Pat. No. 5,824,655, incorporated by reference herein). The transfected or infected cells express the protein products encoded by the nucleic acid in order to ameliorate a disease or the symptoms of a disease.

As used herein, "Health Questionnaire Assessments (HAQs)" refers to a set of questions used to evaluate patients for symptoms of disease activity. These symptoms included: joint swelling, joint tenderness, inflammation, morning stiffness, disease activity and disability evaluated by each patient in a self-administered questionnaire regarding their physical well-being and function, disease activity and disability as evaluated a physician, and pain (Fries, J. F. et al., J. Rheumatol., 9:789-793 (1982)).

As used herein, "ACR" refers to clinical response studies based on criteria established by the American College of Rheumatology. A subject satisfied the "ACR20" criterion if there was about a 20 percent improvement in tender and swollen joint counts and 20 percent improvement in three of five remaining symptoms measured, such as patient and physician global disease changes, pain, physical disability, and an acute phase reactant such as CRP or ESR (Felson, D. T. et al., *Arthritis Rheum.*, 36:729-740 (1993); Felson, D. T. et al., *Arthritis Rheum.*, 38:1-9 (1995)). Similarly, a subject satisfied the "ACR50" or "ACR70" criterion if there was about a 50 or 70 percent improvement, respectively, in tender and swollen joint counts and about 50 or 70 percent improvement, respectively, in three of five remaining symptoms measured, such as patient and physician global disease changes, pain, physical disability, and an acute phase reactant such as CRP or ESR.

As used herein, the "Medical Outcomes Study Short Form-36 (SF-36)" refers to forms used to evaluate the impact of a DMARD (e.g., methotrexate or etanercept) and CTLA4Ig therapy on health-related quality of life (HRQOL). The SF-36 consists of 36 items which covers four physical and four mental domains (physical function, role-physical, bodily pain, general health, vitality, social function, role emotional, and mental health). These individual domains are used to derive the physical and mental component summary scores which range from about 0 to 100, with higher scores indicating better quality of life. Absolute differences of 5 or more in the SF-36 scores were considered clinically meaningful.

As used herein, "alleviate" refers to lessening or making less severe, one or more of the symptoms of an immune disease (e.g., rheumatic disease) including, but not limited to, joint swelling, pain, tenderness, morning stiffness, structural damage, an elevated level of serum C-reactive protein (CRP), an elevated level of soluble IL-2r, an elevated level of soluble ICAM-1, an elevated level of soluble E-selectin, an elevated level of rheumatoid factor, an elevated level of IL-6 or an elevated erythrocyte sedimentation rate.

In order that the invention herein described may be more fully understood the following description is set forth.

Compositions and Methods of the Invention

The present invention provides compositions and methods for treating immune system diseases, such as rheumatic diseases, by administering to a subject an effective amount of a ligand that blocks B7 interactions with CTLA4 and/or CD28. For example, such ligands include: soluble CTLA4 molecules (such as CTLA4Ig, CTLA4-E7, CTLA4-p97, CTLA4-env gp120, and mutant CTLA4 molecules such as, CTLA4/CD28Ig, L104EA29YIg, L104EA29LIg, L104EA29TIg and/or L104EA29WIg), soluble CD28 molecules, soluble B7-1 molecules, soluble B7-2 molecules, and monoclonal antibodies that recognize and bind B7, CD28 and/or CTLA4 (e.g., an anti-CTLA4 monoclonal antibody, an anti-CD28 monoclonal antibody, an anti-B7-1 monoclonal antibody or an anti-B7-2 monoclonal antibody.

Further, the present invention provides compositions and methods for treating immune system diseases, such as rheumatic diseases, by administering to a subject a combination of an effective amount of 1) a DMARD (such as methotrexate or a molecule that blocks TNF interactions, e.g., blocks TNF interactions with its ligand) or other therapeutic agent, plus 2) an effective amount of a molecule that blocks B7 interaction with CTLA4 and/or CD28 such as soluble CTLA4 molecules (e.g., CTLA4Ig, CTLA4Ig/ CD28Ig, CTLA4-E7, CTLA4-p97, CTLA4-env gp120, L104EA29YIg, L104EA29LIg, L104EA29TIg and/or L104EA29WIg), soluble CD28 molecules, soluble B7-1 molecules, soluble B7-2 molecules, and monoclonal antibodies that recognize and bind B7, CD28 and/or CTLA4 (e.g., an anti-CTLA4 monoclonal antibody, an anti-CD28 monoclonal antibody, an anti-B7-1 monoclonal antibody or an anti-B7-2 monoclonal antibody).

An effective amount of a molecule that blocks B7 interaction with CTLA4 and/or CD28 may be defined as the amount of anti-B7 monoclonal antibodies, soluble CTLA4 and/or soluble CD28 molecules that, when bound to B7 molecules on B7-positive cells, inhibit B7 molecules from binding endogenous ligands such as CTLA4 and CD28. The inhibition may be partial or complete.

Alternatively, an effective amount of a molecule that blocks B7 interaction with CTLA4 and/or CD28 may be defined as the amount of anti-CTLA4 monoclonal antibody, anti-CD28 monoclonal antibody or soluble B7 (B7-1 or B7-2) molecules that, when bound to CTLA4 and/or CD28 molecules on T cells, inhibit B7 molecules from binding endogenous ligands such as CTLA4 and CD28. The inhibition may be partial or complete.

An effective amount of a molecule that blocks B7 interaction with CTLA4 and/or CD28 is an amount about 0.1 to 100 mg/kg weight of a subject. In another embodiment, the effective amount is an amount about 0.5 to 5 mg/kg weight of a subject, 0.1 to 5 mg/kg weight of a subject, about 5 to 10 mg/kg weight of a subject, about 10 to 15 mg/kg weight of a subject, about 15 to 20 mg/kg weight of a subject, about 20 to 25 mg/kg weight of a subject, about 25 to 30 mg/kg weight of a subject, about 30 to 35 mg/kg weight of a subject, about 35 to 40 mg/kg weight of a subject, about 40 to 45 mg/kg of a subject, about 45 to 50 mg/kg weight of a subject, about 50 to 55 mg/kg weight of a subject, about 55 to 60 mg/kg weight of a subject, about 60 to 65 mg/kg weight of a subject, about 65 to 70 mg/kg weight of a subject, about 70 to 75 mg/kg weight of a subject, about 75 to 80 mg/kg weight of a subject, about 80 to 85 mg/kg weight of a subject, about 85 to 90 mg/kg weight of a subject, about 90 to 95 mg/kg weight of a subject, or about 95 to 100 mg/kg weight of a subject.

In an embodiment, the effective amount of a molecule that blocks B7 interaction with CTLA4 and/or CD28 is an amount about 2 mg/kg to about 10 mg/kg weight of a subject. The preferred amount is 10 mg/kg weight of a subject. In another embodiment, the effective amount is an amount about 0.1 to 4 mg/kg weight of a subject. In another embodiment the effective amount is an amount about 0.1 to 0.5 mg/kg weight of a subject, about 0.5 to 1.0 mg/kg weight of a subject, about 1.0 to 1.5 mg/kg weight of a subject, about 1.5 to 2.0 mg/kg weight of a subject, about 2.0 to 2.5 mg/kg weight of a subject, about 2.5 to 3.0 mg/kg weight of a subject, about 3.0 to 3.5 mg/kg weight of a subject, about 3.5 to 4.0 mg/kg weight of a subject, about 4.0 to 4.5 mg/kg weight of a subject, about 4.5 to 5.0 mg/kg weight of a subject, about 5.0 to 5.5 mg/kg weight of a subject, about 5.5 to 6.0 mg/kg weight of a subject, about 6.0 to 6.5 mg/kg weight of a subject, about 6.5 to 7.0 mg/kg weight of a subject, about 7.0 to 7.5 mg/kg weight of a subject, about 7.5 to 8.0 mg/kg weight of a subject, about 8.0 to 8.5 mg/kg weight of a subject, about 8.5 to 9.0 mg/kg weight of a subject, about 9.0 to 9.5 mg/kg weight of a subject, about 9.5 to 10.0 mg/kg weight of a subject.

In another embodiment, the effective amount is an amount about 0.1 to 20 mg/kg weight of a subject. In another embodiment, the effective amount is an amount about 0.1 to 2 mg/kg weight of a subject, about 2 to 4 mg/kg weight of a subject, about 4 to 6 mg/kg weight of a subject, about 6 to 8 mg/kg weight of a subject, about 8 to 10 mg/kg weight of a subject, about 10 to 12 mg/kg weight of a subject, about 12 to 14 mg/kg weight of a subject, about 14 to 16 mg/kg weight of a subject, about 16 to 18 mg/kg weight of a subject or about 18 to 20 mg/kg weight of a subject.

In another embodiment, the effective amount is about 2 mg/kg weight of a subject. In yet another embodiment, the effective amount is about 10 mg/kg weight of a subject.

In a specific embodiment, the molecule that blocks B7 interaction with CTLA4 and/or CD28 is soluble CTLA4 and the effective amount of a soluble CTLA4 molecule is about 2 mg/kg weight of a subject. In another specific embodiment, the effective amount of a soluble CTLA4 molecule is about 10 mg/kg weight of a subject. In another specific embodiment, an effective amount of a soluble CTLA4 is 500 mg for a subject weighing less than 60 kg, 750 mg for a subject weighing between 60-100 kg and 1000 mg for a subject weighing more than 100 kg.

An effective amount of the molecule that blocks B7 interaction with CTLA4 and/or CD28 is soluble CTLA4 may be administered to a subject daily, weekly, monthly and/or yearly, in single or multiple times per hour/day/week/month/year, depending on need. For example, in one embodiment, the molecule may initially be administered once every two weeks for a month, and then once every month thereafter.

In a preferred embodiment, the immune disease is a rheumatic disease. Rheumatic diseases are any diseases which are characterized by (i) inflammation or degeneration of musculo-skeletal or connective tissue structures of the body, particularly the joints, and including muscles, tendons, cartilage, synovial and fibrous tissues, (ii) accompanied by joint swelling, joint tenderness, inflammation, morning stiffness, and/or pain, or impairment of locomotion or function of those structures and, in some cases, (iii) often accompanied by serological evidence of rheumatoid factor and other inflammatory surrogate markers.

Rheumatic diseases include, but are not limited to, rheumatoid arthritis. The symptoms of rheumatoid arthritis include joint swelling, joint tenderness, inflammation, morning stiffness, and pain leading to physical disability. Subjects afflicted with the advanced stages of arthritis suffer from symptoms of structural damage and debilitating pain. Other organs also can be impaired by the autoimmune mechanism.

In an embodiment of the invention used to treat an immune system disease, the DMARD is methotrexate or a molecule that blocks TNF interactions such as etanercept, and the molecule that blocks B7 interaction with CTLA4 and/or CD28 is a soluble CTLA4. In a further embodiment, the methods of the invention comprise administering to a subject an effective amount of methotrexate or a molecule that blocks TNF interactions in combination with an effective amount of soluble CTLA4 in order to treat rheumatic diseases such as rheumatoid arthritis.

Effective amounts of methotrexate range about 0.1 to 40 mg/week. In one embodiment, the effective amount includes ranges of about 0.1 to 5 mg/week, about 5 to 10 mg/week, about 10 to 15 mg/week, about 15 to 20 mg/week, about 20 to 25 mg/week, about 25 to 30 mg/week, about 30 to 35 mg/week, or about 35 to 40 mg/week. In one embodiment, methotrexate is administered in an amount ranging about 5 to 30 mg/week.

In one embodiment, the effective amount of a soluble CTLA4 molecule is about 2 mg/kg weight subject and the effective amount of methotrexate is about 10 to 30 mg/week. In another embodiment, the effective amount of a soluble CTLA4 molecule is about 10 mg/kg weight subject and the effective amount of methotrexate is about 10 to 30 mg/week.

In an embodiment of the invention used to treat an immune system disease, the DMARD is etanercept and the molecule that blocks B7 interaction with CTLA4 and/or CD28 is a soluble CTLA4. In a further embodiment, the methods of the invention comprise administering to a subject an effective amount of etanercept in combination with an effective amount of soluble CTLA4 in order to treat rheumatic diseases such as rheumatoid arthritis.

Effective amounts of etanercept range about 0.1 to 100 mg/week. In one embodiment, the effective amount includes ranges of about 10 to 100 mg/week, about 0.1 to 50 mg/week, about 0.1 to 5 mg/week, about 5 to 10 mg/week, about 10 to 15 mg/week, about 15 to 20 mg/week, about 20 to 25 mg/week, about 25 to 30 mg/week, about 30 to 35 mg/week, about 35 to 40 mg/week, about 40 to 45 mg/week, about 45 to 50 mg/week, about 50 to 55 mg/week, about 55 to 60 mg/week, about 60 to 65 mg/week, about 65 to 70 mg/week, about 70 to 75 mg/week, about 75 to 80 mg/week, about 80 to 85 mg/week, about 85 to 90 mg/week, about 90 to 95 mg/week or about 95 to 100 mg/week. In one embodiment, etanercept is administered in an amount of about 50 mg/week, alternatively etanercept may be administered in an amount of about 25 mg twice weekly.

In one embodiment, the effective amount of a soluble CTLA4 molecule is about 2 mg/kg weight subject and the effective amount of etanercept is about 25 mg twice a week. In another embodiment, the effective amount of a soluble CTLA4 molecule is about 10 mg/kg weight subject and the effective amount of etanercept is about 25 mg twice a week.

The invention also provides compositions and methods for treating immune system diseases, such as rheumatic diseases, by administering to a subject a combination of an effective amount of an NSAID and/or other therapeutic agent plus an effective amount of a molecule that blocks B7 interaction with CTLA4 and/or CD28.

The invention also provides compositions and methods for treating immune system diseases, such as rheumatic diseases, by administering to a subject an effective amount of a glucocorticoid, corticosteroid and/or other therapeutic agent plus an effective amount of a molecule that blocks B7 interaction with CTLA4 and/or CD28.

Compositions

Figure 22:
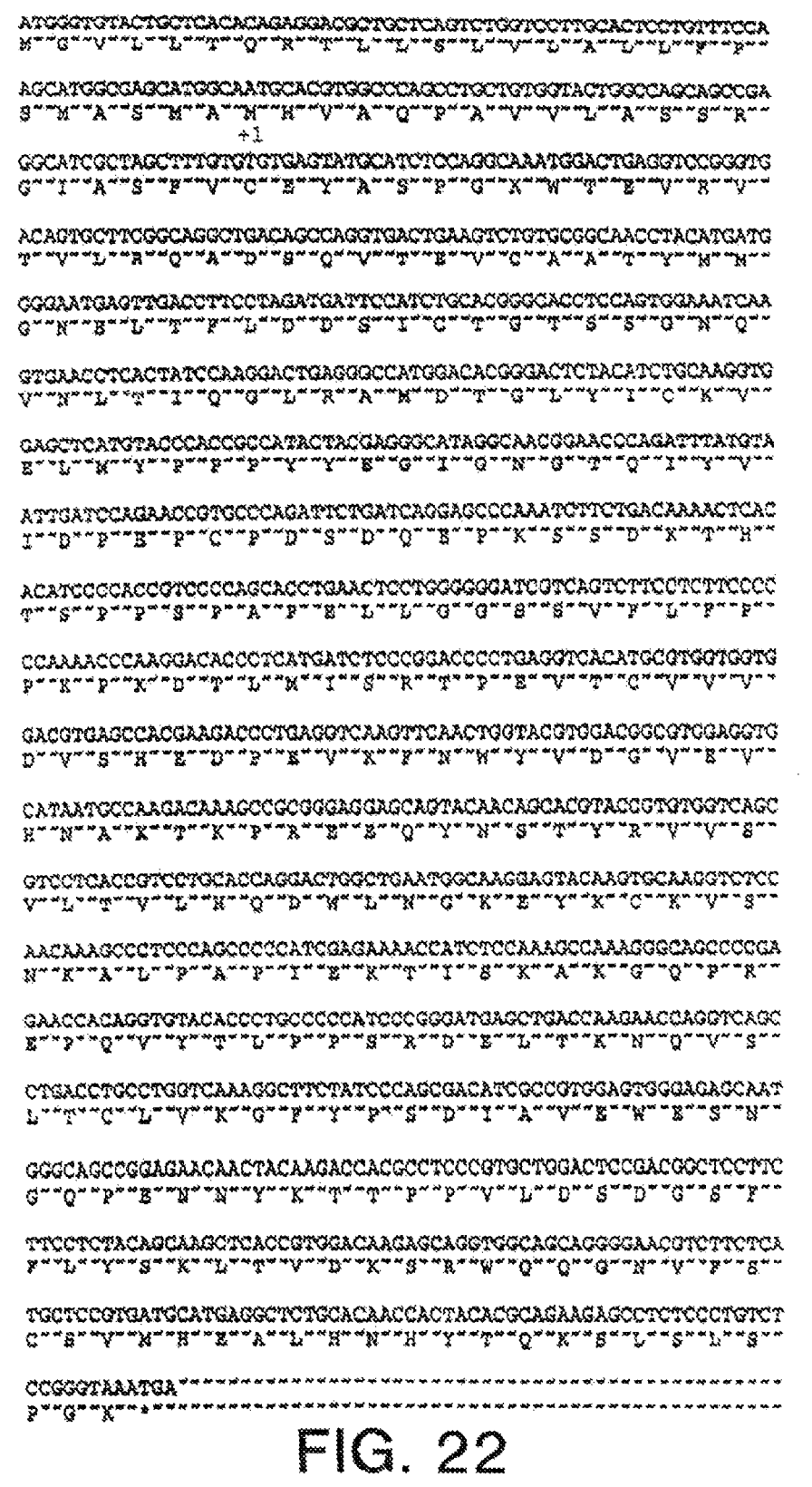

The present invention provides compositions for treating immune diseases, such as rheumatic diseases, comprising soluble CTLA4 molecules. Further, the present invention provides compositions comprising a biological agent that inhibits T-cell function but not T-cell depletion in a human by contacting B7-positive cells in the human with a soluble CTLA4. Examples of soluble CTLA4 include CTLA4Ig and soluble CTLA4 mutant molecules such as L104EA29YIg (FIG. 19), L104EA29LIg (FIG. 20), L104EA29Tig (FIG. 21), and L104EA29WIg (FIG. 22).

CTLA4 molecules, with mutant or wild-type sequences, may be rendered soluble by deleting the CTLA4 transmembrane segment (Oaks, M. K. et al., 2000 *Cell. Immunol.*, 201:144-153 (2000)).

Alternatively, soluble CTLA4 molecules, with mutant or wild-type sequences, may be fusion proteins, wherein the CTLA4 molecules are fused to non-CTLA4 moieties such as immunoglobulin (Ig) molecules that render the CTLA4 molecules soluble. For example, a CTLA4 fusion protein may include the extracellular domain of CTLA4 fused to an immunoglobulin constant domain, resulting in the CTLA4Ig molecule (FIG. 24) (Linsley, P. S. et al., *Immunity*, 1:793-

780 (1994)). Examples of immunoglobulin domains that may be fused to CTLA4 include, but are not limited to IgCγ1 (IgCgamma1), IgCγ2 (IgCgamma2), IgCγ3 (IgCgamma3), IgCγ4 (IgCgamma4), IgCμ (IgCmu), IgCα1 (IgCalpha1), IgCα2 (IgCalpha2), IgCδ (IgCdelta) or IgCε (IgCepsilon).

For clinical protocols, it is preferred that the immunoglobulin moiety does not elicit a detrimental immune response in a subject. The preferred moiety is the immunoglobulin constant region, including the human or monkey immunoglobulin constant regions. One example of a suitable immunoglobulin region is human Cγ1, including the hinge, CH2 and CH3 regions which can mediate effector functions such as binding to Fc receptors, mediating complement-dependent cytotoxicity (CDC), or mediate antibody-dependent cell-mediated cytotoxicity (ADCC). The immunoglobulin moiety may have one or more mutations therein, (e.g., in the CH2 domain, to reduce effector functions such as CDC or ADCC) where the mutation modulates the binding capability of the immunoglobulin to its ligand, by increasing or decreasing the binding capability of the immunoglobulin to Fc receptors. For example, mutations in the immunoglobulin moiety may include changes in any or all its cysteine residues within the hinge domain, for example, the cysteines at positions +130, +136, and +139 are substituted with serine (FIG. 24). The immunoglobulin moiety may also include the proline at position +148 substituted with a serine, as shown in FIG. 24. Further, the mutations in the immunoglobulin moiety may include having the leucine at position +144 substituted with phenylalanine, leucine at position +145 substituted with glutamic acid, or glycine at position +147 substituted with alanine.

Additional non-CTLA4 moieties for use in the soluble CTLA4 molecules or soluble CTLA4 mutant molecules include, but are not limited to, p97 molecule, env gp120 molecule, E7 molecule, and ova molecule (Dash, B. et al., *J. Gen. Virol.*, 75(Pt 6):1389-1397 (1994); Ikeda, T. et al., *Gene*, 138(1-2):193-196 (1994); Falk, K. et al., *Cell. Immunol.*, 150(2):447-452 (1993); Fujisaka, K. et al., *Virology*, 204(2):789-793 (1994)). Other molecules are also possible (Gerard, C. et al., *Neuroscience*, 62(3):721 (1994); Byrn, R. et al., *J. Virol.*, 63(10):4370 (1989); Smith, D. et al., *Science*, 238:1704 (1987); Lasky, L., *Science*, 233:209 (1996)).

The soluble CTLA4 molecule of the invention can include a signal peptide sequence linked to the N-terminal end of the extracellular domain of the CTLA4 portion of the molecule. The signal peptide can be any sequence that will permit secretion of the molecule, including the signal peptide from oncostatin M (Malik et al., *Mol. Cell. Biol.*, 9:2847-2853 (1989)), or CD5 (Jones, N. H. et al., *Nature*, 323:346-349 (1986)), or the signal peptide from any extracellular protein. The soluble CTLA4 molecule of the invention can include the oncostatin M signal peptide linked at the N-terminal end of the extracellular domain of CTLA4, and the human immunoglobulin molecule (e.g., hinge, CH2 and CH3) linked to the C-terminal end of the extracellular domain (wild-type or mutated) of CTLA4. This molecule includes the oncostatin M signal peptide encompassing an amino acid sequence having methionine at position −26 through alanine at position −1, the CTLA4 portion encompassing an amino acid sequence having methionine at position +1 through aspartic acid at position +124, a junction amino acid residue glutamine at position +125, and the immunoglobulin portion encompassing an amino acid sequence having glutamic acid at position +126 through lysine at position +357.

Specifically, the soluble CTLA4 mutant molecules of the invention, comprising the mutated CTLA4 sequences described, infra, can be fusion molecules comprising human Ig, e.g., IgC(gamma)1 (i.e., IgCγ1) moieties fused to the mutated CTLA4 fragments.

In one embodiment, the soluble CTLA4 mutant molecules comprise IgCγ1 (IgCgamma1) fused to an extracellular domain of CTLA4 comprising a single-site mutation in the extracellular domain. The extracellular domain of CTLA4 comprises methionine at position +1 through aspartic acid at position +124 (e.g., FIG. 23). The extracellular domain of the CTLA4 can comprise alanine at position −1 through aspartic acid at position +124 (e.g., FIG. 23). Examples of single-site mutations include the following wherein the leucine at position +104 is changed to any other amino acid:

| Single-site Mutant | Codon Change |
| --- | --- |
| L104EIg | Glutamic acid GAG |
| L104SIg | Serine AGT |
| L104TIg | Threonine ACG |
| L104AIg | Alanine GCG |
| L104WIg | Tryptophan TGG |
| L104QIg | Glutamine CAG |
| L104KIg | Lysine AAG |
| L104RIg | Arginine CGG |
| L104GIg | Glycine GGG |

Further, the invention provides mutant molecules having the extracellular domain of CTLA4 with two mutations, fused to an Ig Cγ1 (IgCgamma1) moiety. Examples include the following wherein the leucine at position +104 is changed to another amino acid (e.g., glutamic acid) and the glycine at position +105, the serine at position +25, the threonine at position +30 or the alanine at position +29 is changed to any other amino acid:

| Double-site Mutants | Codon Change |
| --- | --- |
| L104EG105FIg | Phenylalanine TTC |
| L104EG105WIg | Tryptophan TGG |
| L104EG105LIg | Leucine CTT |
| L104ES25RIg | Arginine CGG |
| L104ET30GIg | Glycine GGG |
| L104ET30NIg | Asparagine AAT |
| L104EA29YIg | Tyrosine TAT |
| L104EA29LIg | Leucine TTG |
| L104EA29TIg | Threonine ACT |
| L104EA29WIg | Tryptophan TGG |

Further still, the invention provides mutant molecules having the extracellular domain of CTLA4 comprising three mutations, fused to an IgCγ1 (IgCgamma1) moiety. Examples include the following wherein the leucine at position +104 is changed to another amino acid (e.g., glutamic acid), the alanine at position +29 is changed to another amino acid (e.g., tyrosine) and the serine at position +25 is changed to another amino acid:

| Triple-site Mutants | Codon Changes |
| --- | --- |
| L104EA29YS25KIg | Lysine AAA |
| L104EA29YS25KIg | Lysine AAG |
| L104EA29YS25NIg | Asparagine AAC |
| L104EA29YS25RIg | Arginine CGG |

Soluble CTLA4 mutant molecules may have a junction amino acid residue which is located between the CTLA4 portion and the Ig portion of the molecule. The junction amino acid can be any amino acid, including glutamine. The junction amino acid can be introduced by molecular or chemical synthesis methods known in the art.

The soluble CTLA4 proteins of the invention, and fragments thereof, can be generated by chemical synthesis methods. The principles of solid phase chemical synthesis of polypeptides are well known in the art and may be found in general texts relating to this area (Dugas, H. et al., *Bioorganic Chemistry*, pp. 54-92, Springer-Verlag, New York (1981)). The soluble CTLA4 proteins may be synthesized by solid-phase methodology utilizing an Applied Biosystems 430A peptide synthesizer (Applied Biosystems, Foster City, Calif.) and synthesis cycles supplied by Applied Biosystems. Protected amino acids, such as t-butoxycarbonyl-protected amino acids, and other reagents are commercially available from many chemical supply houses.

The present invention provides CTLA4 mutant molecules including a signal peptide sequence linked to the N-terminal end of the extracellular domain of the CTLA4 portion of the mutant molecule. The signal peptide can be any sequence that will permit secretion of the mutant molecule, including the signal peptide from oncostatin M (Malik et al., *Mol. Cell. Biol.*, 9:2847-2853 (1989)), or CD5 (Jones, N. H. et al., *Nature*, 323:346-349 (1986)), or the signal peptide from any extracellular protein.

The invention provides soluble CTLA4 mutant molecules comprising a single-site mutation in the extracellular domain of CTLA4 such as L104EIg (as included in FIG. 18) or L104SIg, wherein L104EIg and L104SIg are mutated in their CTLA4 sequences so that leucine at position +104 is substituted with glutamic acid or serine, respectively. The single-site mutant molecules further include CTLA4 portions encompassing methionine at position +1 through aspartic acid at position +124, a junction amino acid residue glutamine at position +125, and an immunoglobulin portion encompassing glutamic acid at position +126 through lysine at position +357. The immunoglobulin portion of the mutant molecule may also be mutated so that the cysteines at positions +130, +136, and +139 are substituted with serine, and the proline at position +148 is substituted with serine. Alternatively, the single-site soluble CTLA4 mutant molecule may have a CTLA4 portion encompassing alanine at position −1 through aspartic acid at position +124.

The invention provides soluble CTLA4 mutant molecules comprising a double-site mutation in the extracellular domain of CTLA4, such as L104EA29YIg, L104EA29LIg, L104EA29TIg or L104EA29WIg, wherein leucine at position +104 is substituted with a glutamic acid and alanine at position +29 is changed to tyrosine, leucine, threonine and tryptophan, respectively. The sequences for L104EA29YIg, L104EA29LIg, L104EA29TIg and L104EA29WIg, starting at methionine at position +1 and ending with lysine at position +357, plus a signal (leader) peptide sequence are shown in FIGS. 19-22, respectively. The double-site mutant molecules further comprise CTLA4 portions encompassing methionine at position +1 through aspartic acid at position +124, a junction amino acid residue glutamine at position +125, and an immunoglobulin portion encompassing glutamic acid at position +126 through lysine at position +357. The immunoglobulin portion of the mutant molecule may also be mutated, so that the cysteines at positions +130, +136, and +139 are substituted with serine, and the proline at position +148 is substituted with serine. Alternatively, these mutant molecules can have a CTLA4 portion encompassing alanine at position −1 through aspartic acid at position +124.

The invention provides soluble CTLA4 mutant molecules comprising a double-site mutation in the extracellular domain of CTLA4, such as L104EG105FIg, L104EG105WIg and L104EG105LIg, wherein leucine at position +104 is substituted with a glutamic acid and glycine at position +105 is substituted with phenylalanine, tryptophan and leucine, respectively. The double-site mutant molecules further comprise CTLA4 portions encompassing methionine at position +1 through aspartic acid at position +124, a junction amino acid residue glutamine at position +125, and an immunoglobulin portion encompassing glutamic acid at position +126 through lysine at position +357. The immunoglobulin portion of the may also be mutated, so that the cysteines at positions +130, +136, and +139 are substituted with serine, and the proline at position +148 is substituted with serine. Alternatively, these mutant molecules can have a CTLA4 portion encompassing alanine at position −1 through aspartic acid at position +124.

The invention provides L104ES25RIg which is a double-site mutant molecule comprising a CTLA4 portion encompassing methionine at position +1 through aspartic acid at position +124, a junction amino acid residue glutamine at position +125, and the immunoglobulin portion encompassing glutamic acid at position +126 through lysine at position +357. The portion having the extracellular domain of CTLA4 is mutated so that serine at position +25 is substituted with arginine, and leucine at position +104 is substituted with glutamic acid. Alternatively, L104ES25RIg can have a CTLA4 portion encompassing alanine at position −1 through aspartic acid at position +124.

The invention provides soluble CTLA4 mutant molecules comprising a double-site mutation in the extracellular domain of CTLA4, such as L104ET30GIg and L104ET30NIg, wherein leucine at position +104 is substituted with a glutamic acid and threonine at position +30 is substituted with glycine and asparagine, respectively. The double-site mutant molecules further comprise CTLA4 portions encompassing methionine at position +1 through aspartic acid at position +124, a junction amino acid residue glutamine at position +125, and an immunoglobulin portion encompassing glutamic acid at position +126 through lysine at position +357. The immunoglobulin portion of the mutant molecule may also be mutated, so that the cysteines at positions +130, +136, and +139 are substituted with serine, and the proline at position +148 is substituted with serine. Alternatively, these mutant molecules can have a CTLA4 portion encompassing alanine at position −1 through aspartic acid at position +124.

The invention provides soluble CTLA4 mutant molecules comprising a triple-site mutation in the extracellular domain of CTLA4, such as L104EA29YS25KIg, L104EA29YS25NIg, L104EA29YS25RIg, wherein leucine at position +104 is substituted with a glutamic acid, alanine at position +29 is substituted with tyrosine, and serine at position +25 is substituted with lysine, asparagine and arginine, respectively. The triple-site mutant molecules further comprise CTLA4 portions encompassing methionine at position +1 through aspartic acid at position +124, a junction amino acid residue glutamine at position +125, and an immunoglobulin portion encompassing glutamic acid at position +126 through lysine at position +357. The immunoglobulin portion of the mutant molecule may also be mutated, so that the cysteines at positions +130, +136, and +139 are substituted with serine, and the proline at position +148 is substituted with serine. Alternatively, these mutant molecules can have a CTLA4 portion encompassing alanine at position −1 through aspartic acid at position +124.

Additional embodiments of soluble CTLA4 mutant molecules include chimeric CTLA4/CD28 homologue mutant molecules that bind a B7 (Peach, R. J. et al., *J. Exp. Med.*, 180:2049-2058 (1994)). Examples of these chimeric CTLA4/CD28 mutant molecules include HS1, HS2, HS3, HS4, HS5, HS6, HS4A, HS4B, HS7, HS8, HS9, HS10, HS11, HS12, HS13 and HS14 (U.S. Pat. No. 5,773,253).

Preferred embodiments of the invention are soluble CTLA4 molecules such as CTLA4Ig (as shown in FIG. 24, starting at methionine at position +1 and ending at lysine at position +357) and soluble CTLA4 mutant L104EA29YIg (as shown in FIG. 19, starting at methionine at position +1 and ending at lysine at position +357).

The invention further provides nucleic acid molecules comprising nucleotide sequences encoding the amino acid sequences corresponding to the soluble CTLA4 molecules of the invention. In one embodiment, the nucleic acid molecule is a DNA (e.g., cDNA) or a hybrid thereof. For example, a CTLA4Ig molecule can comprise a GCT or GCC codon, encoding alanine, at nucleotide position +49 to +51 as shown in FIG. 24. In another example, a CTLA4Ig molecule can comprise a GGT or GGG codon, encoding glycine, at nucleotide position +436 to +438 as shown in FIG. 24. In yet another example, a CTLA4Ig molecule can comprise a CGG or CGT codon, encoding arginine, at nucleotide position +631 to +633 as shown in FIG. 24. DNA encoding CTLA4Ig (FIG. 24) was deposited on May 31, 1991 with the American Type Culture Collection (ATCC®), 10801 University Blvd., Manassas, Va. 20110-2209 and has been accorded ATCC® Accession No. ATCC® 68629. DNA encoding L104EA29YIg (sequence included in FIG. 19) was deposited on Jun. 19, 2000 with ATCC® and has been accorded ATCC® Accession No. PTA-2104. Alternatively, the nucleic acid molecules are RNA or a hybrid thereof.

The nucleic acid molecules of the invention also include derivative nucleic acid molecules which differ from DNA or RNA molecules, and anti-sense molecules. Derivative molecules include peptide nucleic acids (PNAs), and non-nucleic acid molecules, including phosphorothioate, phosphotriester, phosphoramidate, and methylphosphonate molecules, that bind to single-stranded DNA or RNA in a base pair-dependent manner (Zamecnik, P. C. et al., *Proc. Natl. Acad. Sci.*, 75:280-284 (1978); Goodchild, P. C. et al., *Proc. Natl. Acad. Sci.*, 83:4143-4146 (1986)). Peptide nucleic acid molecules comprise a nucleic acid oligomer to which an amino acid residue, such as lysine, and an amino group have been added. These small molecules, also designated anti-gene agents, stop transcript elongation by binding to their complementary (template) strand of nucleic acid (Nielsen, P. E. et al., *Anticancer Drug Des.*, 8:53-63 (1993)). Reviews of methods for synthesis of DNA, RNA, and their analogues can be found in Eckstein, F., ed., *Oligonucleotides and Analogues*, IRL Press, New York (1991); Gait, M. J., ed., *Oligonucleotide Synthesis*, IRL Press, Oxford, England (1984). Additionally, methods for antisense RNA technology are described in U.S. Pat. Nos. 5,194,428 and 5,110,802. A skilled artisan can readily obtain these classes of nucleic acid molecules using the herein described soluble CTLA4 polynucleotide sequences, see, for example, Egholm et al., *Innovative and Perspectives in Solid Phase Synthesis*, pp. 325-328 (1992) or U.S. Pat. No. 5,539,082.

Additionally, the invention provides a vector, which comprises the nucleotide sequences of the invention. The term vector includes, but is not limited to, plasmids, cosmids, and phagemids. In one embodiment, the vector can be an autonomously replicating vector comprising a replicon that directs the replication of the rDNA within the appropriate host cell. Alternatively, the vector can direct integration of the recombinant vector into the host cell. Various viral vectors may also be used, such as, for example, a number of well-known retroviral and adenoviral vectors (Berkner, *Biotechniques*, 6:616-629 (1988)).

The vectors can permit expression of the soluble CTLA4 transcript or polypeptide sequences in prokaryotic or eukaryotic host cells. The vectors include expression vectors, comprising an expression control element, such as a promoter sequence, which enables transcription of the inserted soluble CTLA4 nucleic acid sequences and can be used for regulating the expression (e.g., transcription and/or translation) of an operably linked soluble CTLA4 sequence in an appropriate host cell. Expression control elements are known in the art and include, but are not limited to, inducible promoters, constitutive promoters, secretion signals, enhancers, transcription terminators, and other transcriptional regulatory elements. Other expression control elements that are involved in translation are known in the art, and include the Shine-Dalgarno sequence (e.g., prokaryotic host cells), and initiation and termination codons.

Specific initiation signals may also be required for efficient translation of a soluble CTLA4 sequence. These signals include the ATG-initiation codon and adjacent sequences. In cases where the soluble CTLA4 initiation codon and upstream sequences are inserted into the appropriate expression vector, no additional translational control signals may be needed. However, in cases where only the coding sequence, or a portion thereof, is inserted, exogenous transcriptional control signals including the ATG-initiation codon may be provided. Furthermore, the initiation codon should be in the correct reading-frame to ensure translation of the entire insert. Exogenous transcriptional elements and initiation codons can be of various origins, both natural and synthetic. The efficiency of expression may be enhanced by the inclusion of enhancers appropriate to the cell system in use (Scharf, D. et al., *Results Probl. Cell. Differ.*, 20:125-162 (1994); Bittner et al., *Method. Enzymol.*, 153:516-544 (1987)).

The preferred vectors for expression of the soluble CTLA4 sequences in eukaryote host cells include expression control elements, such as the baculovirus polyhedrin promoter for expression in insect cells. Other expression control elements include promoters or enhancers derived from the genomes of plant cells (e.g., heat shock, RUBISCO, storage protein genes), viral promoters or leader sequences or from plant viruses, and promoters or enhancers from the mammalian genes or from mammalian viruses.

The preferred vector includes at least one selectable marker gene that encodes a gene product that confers drug resistance such as resistance to ampicillin or tetracycline. The vector also comprises multiple endonuclease restriction sites that enable convenient insertion of exogenous DNA sequences. Methods for generating a recombinant expression vector encoding the soluble CTLA4 proteins of the invention are well known in the art, and can be found in Sambrook et al., *Molecular Cloning; A Laboratory Manual*, Second Edition, Cold Spring Harbor Press (1989) and Ausubel et al., *Current Protocols in Molecular Biology*, John Wiley & Sons, New York, N.Y. (1989).

The preferred vectors for generating soluble CTLA4 transcripts and/or the encoded soluble CTLA4 polypeptides are expression vectors which are compatible with prokaryotic host cells. Prokaryotic cell expression vectors are well known in the art and are available from several commercial sources. For example, pET vectors (e.g., pET-21, Novagen Corp.), BLUESCRIPT® phagemid (Stratagene, LaJolla, Calif.), pSPORT (Gibco BRL, Rockville, Md.), or ptrp-lac hybrids may be used to express soluble CTLA4 polypeptides in bacterial host cells.

Alternatively, the preferred expression vectors for generating soluble CTLA4 transcripts and/or the encoded soluble CTLA4 polypeptides are expression vectors which are compatible with eukaryotic host cells. The more preferred vectors are those compatible with vertebrate cells. Eukaryotic cell expression vectors are well known in the art and are available from several commercial sources. Typically, such vectors are provided containing convenient restriction sites for insertion of the desired DNA segment. Typical of such vectors are PSVL and pKSV-10 (Pharmacia), pBPV-1/pML2d (International Biotechnologies, Inc.), pTDT1 (ATCC®, #31255), and similar eukaryotic expression vectors.

Examples of expression vectors for include, but are not limited to, vectors for mammalian host cells (e.g., BPV-1, pHyg, pRSV, pSV2, pTK2 (Maniatis); pIRES (Clontech); pRc/CMV2, pRc/RSV, pSFV1 (Life Technologies); pVPakc Vectors, pCMV vectors, pSGS vectors (Stratagene)), retroviral vectors (e.g., pFB vectors (Stratagene)), pCDNA-3 (Invitrogen) or modified forms thereof, adenoviral vectors; adeno-associated virus vectors, baculovirus vectors, yeast vectors (e.g., pESC vectors (Stratagene)).

A host vector system is also provided. The host vector system comprises the vector of the invention in a suitable host cell. Examples of suitable host cells include, but are not limited to, prokaryotic and eukaryotic cells. In accordance with the practice of the invention, eukaryotic cells are also suitable host cells. Examples of eukaryotic cells include any animal cell, whether primary or immortalized, yeast (e.g., *Saccharomyces cerevisiae, Schizosaccharomyces pombe*, and *Pichia pastoris*), and plant cells. Exemplary animal cells include cells from bovine, ovine, porcine, murine, equine, monkey and ape. Myeloma, COS and CHO cells are examples of animal cells that may be used as hosts. Particular CHO cells include, but are not limited to, DG44 (Chasin et al., *Somat. Cell. Molec. Genet.*, 12:555-556 (1986); Kolkekar, *Biochemistry*, 36:10901-10909 (1997)), CHO-K1 (ATCC® No. CCL-61), CHO-K1 Tet-On cell line (Clontech), CHO designated ECACC 85050302 (CAMR, Salisbury, Wiltshire, UK), CHO clone 13 (GEIMG, Genova, IT), CHO clone B (GEIMG, Genova, IT), CHO-K1/SF designated ECACC 93061607 (CAMR, Salisbury, Wiltshire, UK), and RR-CHOK1 designated ECACC 92052129 (CAMR, Salisbury, Wiltshire, UK). Exemplary plant cells include whole plants, cell culture, or callus, from tobacco, corn, soybean, and rice cells. Corn, soybean, and rice seeds are also acceptable.

The CTLA4 mutant molecules of the invention may be isolated as naturally-occurring polypeptides, or from any source whether natural, synthetic, semi-synthetic or recombinant. Accordingly, the CTLA4 mutant polypeptide molecules may be isolated as naturally-occurring proteins from any species, particularly mammalian, including bovine, ovine, porcine, murine, equine, and preferably human. Alternatively, the CTLA4 mutant polypeptide molecules may be isolated as recombinant polypeptides that are expressed in prokaryote or eukaryote host cells, or isolated as a chemically synthesized polypeptide.

A skilled artisan can readily employ standard isolation methods to obtain isolated CTLA4 mutant molecules. The nature and degree of isolation will depend on the source and the intended use of the isolated molecules.

CTLA4 mutant molecules and fragments or derivatives thereof, can be produced by recombinant methods. Accordingly, an isolated nucleotide sequence encoding wild-type CTLA4 molecules may be manipulated to introduce mutations, resulting in nucleotide sequences that encode the CTLA4 mutant polypeptide molecules. For example, the nucleotide sequences encoding the CTLA4 mutant molecules may be generated by site-directed mutagenesis methods, using primers and PCR amplification. The primers can include specific sequences designed to introduce desired mutations. Alternatively, the primers can be designed to include randomized or semi-randomized sequences to introduce random mutations. Standard recombinant methods (Sambrook et al., *Molecular Cloning; A Laboratory Manual*, Second Edition, Cold Spring Harbor Press (1989)) and PCR technology (U.S. Pat. No. 4,603,102) can be employed for generating and isolating CTLA4 mutant polynucleotides encoding CTLA4 mutant polypeptides.

The invention includes pharmaceutical compositions comprising pharmaceutically effective amounts of a molecule that blocks B7 interaction with CTLA4 and/or CD28 such as soluble CTLA4 molecules, CD28 molecules, B7 (B7-1 or B7-2) molecules, anti-CTLA4 monoclonal antibodies, anti-CD28 monoclonal antibodies or anti-B7 (B7-1 or B7-2) monoclonal antibodies. The pharmaceutical compositions of the invention are useful for treatment of immune system diseases. In certain embodiments, immune system diseases are mediated by CD28/CTLA4/B7 interactions. The soluble CTLA4 molecules are preferably soluble CTLA4 molecules with wild-type sequence and/or soluble CTLA4 molecules having one or more mutations in the extracellular domain of CTLA4. The pharmaceutical composition can include soluble CTLA4 protein molecules and/or nucleic acid molecules, and/or vectors encoding the molecules. In preferred embodiments, the soluble CTLA4 molecules have the amino acid sequence of the extracellular domain of CTLA4 as shown in either FIG. 24 or FIG. 19 (CTLA4Ig or L104EA29Y, respectively). Even more preferably, the soluble CTLA4 mutant molecule is L104EA29YIg as disclosed herein. The compositions may additionally include other therapeutic agents, including, but not limited to, DMARDs, NSAIDs, corticosteroids, glucocorticoids, drug toxins, alkylating agents, anti-neoplastic drugs, enzymes, antibodies, or conjugates.

An embodiment of the pharmaceutical composition of the invention comprises an effective amount of a molecule that blocks B7 interaction with CTLA4 and/or CD28, such as the molecules and the suitable amounts of the molecules described, supra, and an effective amount of a DMARD.

The amount of DMARDS administered to a subject varies depending on several factors including the efficacy of the drug on a specific subject and the toxicity (i.e., the tolerability) of a drug to a specific subject ("Guidelines for the Management of Rheumatoid Arthritis", *Arthritis Rheum.*, 39(5):713-722 (May 1996); *Physicians' Desk Reference*, Medical Economics Company, Inc., Montvale, N.J. (2002)). The following provides a range of drug dosages for each DMARD. An attending physician will determine specific dosages for each subject.

Depending on the DMARD, an effective amount can be in a range of about 1 to about 5000 mg/day. This range can be modified to an amount of about 1 to 10 mg/day, about 10 to 50 mg/day, about 50 to 100 mg/day, about 100 to 150 mg/day, about 150 to 200 mg/day, about 200 to 250 mg/day, about 250 to 300 mg/day, about 300 to 350 mg/day, about 350 to 400 mg/day, about 400 to 450 mg/day, about 450 to 500 mg/day, about 500 to 550 mg/day, about 550 to 600 mg/day, about 600 to 650 mg/day, about 650 to 700 mg/day, about 700 to 750 mg/day, about 750 to 800 mg/day, about 800 to 850 mg/day, about 850 to 900 mg/day, about 900 to 950 mg/day, about 950 to 1000 mg/day, about 1000 to 1100 mg/day, about 1100 to 1200 mg/day, about 1200 to 1300 mg/day, about 1300 to 1400 mg/day, about 1400 to 1500 mg/day, about 1500 to 1600 mg/day, about 1600 to 1700 mg/day, about 1700 to 1800 mg/day, about 1800 to 1900 mg/day, about 1900 to 2000 mg/day, about 2000 to 2500 mg/day, about 2500 to 3000 mg/day, about 3000 to 3500 mg/day, about 3500 to 4000 mg/day, about 4000 to 4500 mg/day or about 4500 to 5000 mg/day. It would be clear to one skilled in the art that dosage will vary depending on the particular DMARD being used. Specific examples of appropriate dosages, depending on the DMARD, are described below.

In another embodiment, an effective amount of a DMARD can be in a range of about 0.1 mg/week to 40 mg/week, 0.1 mg/week to 5 mg/week, 5 mg/week to 10 mg/week, 10 mg/week to 30 mg/week, 30 mg/week to 35 mg/week, 0.1 mg/week to 100 mg/week, or 30 mg/week to 50 mg/week. In another embodiment, a DMARD can be administered in an amount of about 50 mg/week or 25 mg twice weekly. It would be clear to one skilled in the art that dosage range will vary depending on the particular DMARD being used, for example, see below.

Methotrexate is an antimetabolite molecule that interferes with DNA synthesis, repair and cellular replication. Methotrexate functions as an inhibitor of dihydrofolic acid reductase, i.e., it is a folic acid antagonist. Methotrexate is commonly administered in an amount about 0.1 to 40 mg per week with a common dosage ranging about 5 to 30 mg per week. Methotrexate may be administered to a subject in various increments: about 0.1 to 5 mg/week, about 5 to 10 mg/week, about 10 to 15 mg/week, about 15 to 20 mg/week, about 20 to 25 mg/week, about 25 to 30 mg/week, about 30 to 35 mg/week, or about 35 to 40 mg/week. In one embodiment, an effective amount of a DMARD, including methotrexate, is an amount about 10 to 30 mg/week.

Cyclophosphamide, an alkylating agent, may be administered in dosages ranging about 1 to 10 mg/kg body weight per day.

Cyclosporine (e.g., NEORAL®) also known as Cyclosporin A, is commonly administered in dosages ranging from about 1 to 10 mg/kg body weight per day. Dosages ranging about 2.5 to 4 mg per body weight per day are commonly used.

Chloroquine or hydroxychloroquine (e.g., PLAQUENIL®), is commonly administered in dosages ranging about 100 to 1000 mg daily. Preferred dosages range about 200-600 mg administered daily.

Sulfasalazine (e.g., AZULFIDINE® EN-tabs) is commonly administered in amounts ranging about 50 to 5000 mg per day, with a common dosage of about 2000 to 3000 mg per day for adults. Dosages for children are commonly about 5 to 100 mg/kg of body weight, up to 2 grams per day.

Gold salts are formulated for two types of administration: injection or oral. Injectable gold salts are commonly prescribed in dosages about 5 to 100 mg doses every two to four weeks. Orally administered gold salts are commonly prescribed in doses ranging about 1 to 10 mg per day.

D-penicillamine or penicillamine (CUPRIMINE®) is commonly administered in dosages about 50 to 2000 mg per day, with preferred dosages about 125 mg per day up to 1500 mg per day.

Azathioprine is commonly administered in dosages of about 10 to 250 mg per day. Preferred dosages range about 25 to 200 mg per day.

Anakinra (e.g., KINERET®) is an interleukin-1 receptor antagonist. A common dosage range for anakinra is about 10 to 250 mg per day, with a recommended dosage of about 100 mg per day.

Infliximab (REMICADE®) is a chimeric monoclonal antibody that binds to tumor necrosis factor alpha (TNFα) and inhibits the activity of TNFα. Infliximab is commonly administered in dosages about 1 to 20 mg/kg body weight every four to eight weeks. Dosages of about 3 to 10 mg/kg body weight may be administered every four to eight weeks depending on the subject.

Etanercept (e.g., ENBREL®) is a dimeric fusion protein that binds the tumor necrosis factor (TNF) and blocks its interactions with TNF receptors. Commonly administered dosages of etanercept are about 10 to 100 mg per week for adults with a preferred dosage of about 50 mg per week. Dosages for juvenile subjects range about 0.1 to 50 mg/kg body weight per week with a maximum of about 50 mg per week. For adult patients, etanercept is commonly administered, e.g., injected, in 25 mg doses twice weekly, e.g., 72-96 hours apart in time.

Leflunomide (ARAVA®) is commonly administered at dosages about 1 and 100 mg per day. A common daily dosage is about 10 to 20 mg per day.

A further embodiment of the invention is a pharmaceutical composition comprising an effective amount of a soluble CTLA4, such as CTLA4Ig, and an effective amount of a DMARD, such as methotrexate or etanercept.

A pharmaceutical composition comprising soluble CTLA4 can be used for methods for blocking B7 interaction with CTLA4 and/or CD28; or for treating immune system diseases. Effective amounts of soluble CTLA4 in the pharmaceutical composition range about 0.1 to 100 mg/kg weight of the subject. In another embodiment, the effective amount is an amount about 0.5 to 5 mg/kg weight of a subject, about 5 to 10 mg/kg weight of a subject, about 10 to 15 mg/kg weight of a subject, about 15 to 20 mg/kg weight of a subject, about 20 to 25 mg/kg weight of a subject, about 25 to 30 mg/kg weight of a subject, about 30 to 35 mg/kg weight of a subject, about 35 to 40 mg/kg weight of a subject, about 40 to 45 mg/kg of a subject, about 45 to 50 mg/kg weight of a subject, about 50 to 55 mg/kg weight of a subject, about 55 to 60 mg/kg weight of a subject, about 60 to 65 mg/kg weight of a subject, about 65 to 70 mg/kg weight of a subject, about 70 to 75 mg/kg weight of a subject, about 75 to 80 mg/kg weight of a subject, about 80 to 85 mg/kg weight of a subject, about 85 to 90 mg/kg weight of a subject, about 90 to 95 mg/kg weight of a subject, or about 95 to 100 mg/kg weight of a subject.

In an embodiment, the effective amount of soluble CTLA4 is an amount about 2 mg/kg to about 10 mg/kg weight of a subject. In another embodiment, the effective amount is an amount about 0.1 to 4 mg/kg weight of a subject. In another embodiment the effective amount is an amount about 0.1 to 0.5 mg/kg weight of a subject, about 0.5 to 1.0 mg/kg weight of a subject, about 1.0 to 1.5 mg/kg weight of a subject, about 1.5 to 2.0 mg/kg weight of a subject, about 2.0 to 2.5 mg/kg weight of a subject, about 2.5 to 3.0 mg/kg weight of a subject, about 3.0 to 3.5 mg/kg weight of a subject or about 3.5 to 4.0 mg/kg weight of a subject. In another embodiment, the effective amount is an amount about 0.1 to 20 mg/kg weight of a subject. In another embodiment, the effective amount is an amount about 0.1 to 2 mg/kg weight of a subject, about 2 to 4 mg/kg weight of a subject, about 4 to 6 mg/kg weight of a subject, about 6 to 8 mg/kg weight of a subject, about 8 to 10 mg/kg weight of a subject, about 10 to 12 mg/kg weight of a subject, about 12 to 14 mg/kg weight of a subject, about 14 to 16 mg/kg weight of a subject, about 16 to 18 mg/kg weight of a subject or about 18 to 20 mg/kg weight of a subject. In an embodiment, the effective amount is 2 mg/kg weight of a subject. In another embodiment, the effective amount is about 10 mg/kg weight of a subject.

In a specific embodiment, an effective amount of soluble CTLA4 is 500 mg for a subject weighing less than 60 kg, 750 mg for a subject weighing between 60-100 kg and 1000 mg for a subject weighing more than 100 kg.

Effective amounts of methotrexate in the pharmaceutical composition range about 0.1 to 40 mg/week. In one embodiment, the effective amount is an amount about 0.1 to 5 mg/week, about 5 to 10 mg/week, about 10 to 15 mg/week, about 15 to 20 mg/week, about 20 to 25 mg/week, about 25 to 30 mg/week, about 30 to 35 mg/week, or about 35 to 40 mg/week. In one embodiment, an effective amount of a DMARD, including methotrexate, is an amount about 10 to 30 mg/week.

In one embodiment, the effective amount of a soluble CTLA4 molecule is about 2 mg/kg weight subject and the effective amount of methotrexate is about 10 to 30 mg/week. In another embodiment, the effective amount of a soluble CTLA4 molecule is about 10 mg/kg weight subject and the effective amount of methotrexate is about 10 to 30 mg/week.

Effective amounts of etanercept in the pharmaceutical composition range about 0.1 to 100 mg/week. In one embodiment, the effective amount is ranges about 0.1 to 5 mg/week, about 5 to 10 mg/week, about 10 to 15 mg/week, about 15 to 20 mg/week, about 20 to 25 mg/week, about 25 to 30 mg/week, about 30 to 35 mg/week, about 35 to 40 mg/week, about 40 to 45 mg/week, about 45 to 50 mg/week, about 50 to 55 mg/week, about 55 to 60 mg/week, about 60 to 65 mg/week, about 65 to 70 mg/week, about 70 to 75 mg/week, about 75 to 80 mg/week, about 80 to 85 mg/week, about 85 to 90 mg/week, about 90 to 95 mg/week or about 95 to 100 mg/week. In one embodiment, etanercept is administered in an amount ranging about 50 mg/week, e.g., 25 mg administered twice weekly.

In one embodiment, the effective amount of a soluble CTLA4 molecule is about 2 mg/kg weight subject and the effective amount of etanercept is about 25 mg twice a week. In another embodiment, the effective amount of a soluble CTLA4 molecule is about 10 mg/kg weight subject and the effective amount of etanercept is about 25 mg twice a week.

The compositions of the invention further encompass a pharmaceutical composition comprising soluble CTLA4 in combination with other treatments for rheumatic disease including, but not limited to: collagen, dnaJ, molecules that block TNF function (e.g., pegsunercept), molecules that block cytokine function (e.g., AMG719), molecules that block LFA-1 function (e.g., efalizumab) and stem cell transplants. These other treatments are currently being studied in clinical trials (www.clinicaltrials.gov) to determine their effect on rheumatoid arthritis.

Collagen, for example, in the form of bovine II collagen, may be orally administered to a patient suffering from rheumatoid arthritis in order to alleviate one or more symptoms of rheumatoid arthritis.

DnaJ is a small peptide which mimics a protein contained in a gene in many patients with rheumatoid arthritis. The peptide is derived from E. coli bacteria heat shock protein. DnaJ may be orally administered to a patient suffering from rheumatoid arthritis in order to alleviate one or more symptoms of rheumatoid arthritis.

TNF is a molecule involved in the inflammatory response of patients with rheumatoid arthritis. Conceivably, any molecule that blocks TNF function, e.g., by blocking TNF binding to the TNF receptor (TNFR), may help modify the progression of rheumatoid arthritis and alleviate some of its symptoms. Several TNF blockers such as infliximab and etanercept, have been shown to be efficacious in treating rheumatoid arthritis. Other TNF blockers such as pegsunercept are being developed and tested (Phase II clinical trial) for their efficacy in treating rheumatoid arthritis.

Cytokines, e.g., Interleukin-1 (IL-1), are cell secreted molecules involved in mediating immune responses. Conceivably, any molecule that blocks cytokine function, e.g., by blocking IL-1 interaction with its receptor, may help modify the progression of rheumatoid arthritis and alleviate one or more of its symptoms. Anakinra, a recombinant protein that blocks IL-1 interaction with its receptor (IL-1R) has been shown to be efficacious in treating rheumatoid arthritis. An IL-1 inhibitor, AMG719, is being developed and tested (Phase II clinical trial) for its efficacy in treating rheumatoid arthritis.

Lymphocyte function associated molecule 1 (LFA-1) is a molecule composed of two subunits, CD11a and CD18, which functions by mediating lymphocyte adhesion to various cell types such as endothelium. Conceivably, interference of LFA-1 function may help modify the progression of rheumatoid arthritis and alleviate one or more of its symptoms. An anti-LFA-1 antibody, efalizumab, is being developed and tested (Phase II clinical trial) for its efficacy in treating rheumatoid arthritis.

Blockage of TNF, cytokine or LFA-1 interaction to their ligands by a potentially therapeutic molecule can be determined by any number of assays known to those skilled in the art. For example, competition assays may be used to test blockage by the molecule of interest, e.g., a molecule can be exposed to a TNF/TNFR binding pair in order to compete with TNF to bind to TNFR. Alternatively, functional assays can be performed to test blockage, e.g., a molecule can be tested for its ability to inhibit an inflammatory cascade, or any part of an inflammatory reaction such as swelling, redness or pain, caused by a cytokine.

The present invention also provides pharmaceutical compositions comprising the molecules of the invention, e.g., CTLA4Ig and an acceptable carrier or adjuvant which is known to those of skill of the art. The pharmaceutical compositions preferably include suitable carriers and adjuvants which include any material which when combined with the molecules of the invention (e.g., a soluble CTLA4 molecule, such as, CTLA4Ig or L104EA29Y) retain the molecule's activity, and is non-reactive with the subject's immune system. These carriers and adjuvants include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, phosphate buffered saline solution, water, emulsions (e.g., oil/water emulsion), salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances and polyethylene glycol. Other carriers may also include sterile solutions; tablets, including coated tablets and capsules. Typically such carriers contain excipients such as starch, milk, sugar (e.g., sucrose, glucose, maltose), certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well-known conventional methods. Such compositions may also be formulated within various lipid compositions, such as, for example, liposomes as well as in various polymeric compositions, such as polymer microspheres.

In a further embodiment of the invention, the present invention provides kits (i.e., a packaged combination of reagents with instructions) containing the molecules of the invention useful for blocking B7 interactions with its ligands and/or for treating an immune system disease.

The kit can contain a pharmaceutical composition that includes one or more agents, for example, a soluble CTLA4 molecule alone, or with a second agent, and an acceptable carrier or adjuvant, e.g., pharmaceutically acceptable buffer, such as phosphate-buffered saline, Ringer's solution and dextrose solution. It may further include other materials desirable from a commercial and user standpoint, including other buffers, diluents, filters, needles, syringes, and package inserts with instructions for use. The agents may be provided as dry powders, usually lyophilized, including excipients that upon dissolving will provide a reagent solution having the appropriate concentration.

Second agents can include the following: steroids, glucocorticoids, drug toxins, alkylating agents, anti-neoplastic drugs, enzymes, antibodies, conjugates, immunosuppressive agents, corticosteroids, DMARDs, nonsteroidal antiinflammatory drugs (NSAIDs), prednisone, azathioprine, methotrexate, TNFα blockers or antagonists, infliximab, any biological agent targeting an inflammatory cytokine, chloroquine, hydroxychloroquine, sulfasalazine (sulphasalazopryine), gold salts, etanercept, anakinra, cyclophosphamide, leflunomide, collagen, dnaJ, a molecule that blocks TNF receptors (e.g., pegsunercept), a molecule that blocks cytokine function (e.g., AMG719), a molecule that blocks LFA-1 function (e.g., efalizumab), acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors, meloxicam, codeine phosphate, propoxyphene napsylate, oxycodone hydrochloride, oxycodone bitartrate, tramadol, dihydrofolic acid reductase inhibitor, cyclosporine, cyclosporin A or D-penicillamine.

The kit comprises a container with a label and/or instructions. Suitable containers include, for example, bottles, vials, and test tubes. The containers can be formed from a variety of materials such as glass or plastic. The container can have a sterile access port (for example, the container can be an intravenous solution bag or a vial having a stopper pierceable by a needle such as a hypodermic injection needle). The container can hold a pharmaceutical composition such as a pharmaceutical composition having an agent that is effective for blocking B7 interactions with its ligand and/or treating an immune system disease.

The kit can also comprise a second container comprising one or more second agents as described herein (e.g., any of the DMARDS or NSAIDS) and/or a pharmaceutically acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The kit may also suitably include a label and/or instructions on, or associated with the container. The label can provide directions for carrying out the preparation of the agents, for example, dissolving of the dry powders, and/or treatment for a specific immune system disease.

The label and/or the instructions can indicate directions for either in vivo or in vitro use of the pharmaceutical composition. The label and/or the instructions can indicate that the pharmaceutical composition is used alone, or in combination with a second agent.

The label can indicate appropriate dosages for the molecules of the invention. For example, the label can indicate that dosages for a molecule that is effective for blocking B7 interactions with its ligand and/or treating an immune system disease is about 0.1 to 100 mg/kg weight of the subject, about 0.5 to 5 mg/kg weight of a subject, about 5 to 10 mg/kg weight of a subject, about 10 to 15 mg/kg weight of a subject, about 15 to 20 mg/kg weight of a subject, about 20 to 25 mg/kg weight of a subject, about 25 to 30 mg/kg weight of a subject, about 30 to 35 mg/kg weight of a subject, about 35 to 40 mg/kg weight of a subject, about 40 to 45 mg/kg of a subject, about 45 to 50 mg/kg weight of a subject, about 50 to 55 mg/kg weight of a subject, about 55 to 60 mg/kg weight of a subject, about 60 to 65 mg/kg weight of a subject, about 65 to 70 mg/kg weight of a subject, about 70 to 75 mg/kg weight of a subject, about 75 to 80 mg/kg weight of a subject, about 80 to 85 mg/kg weight of a subject, about 85 to 90 mg/kg weight of a subject, about 90 to 95 mg/kg weight of a subject, about 95 to 100 mg/kg weight of a subject, about 2 to 10 mg/kg weight of a subject, about 0.1 to 4 mg/kg weight of a subject, about 0.1 to 0.5 mg/kg weight of a subject, about 0.5 to 1.0 mg/kg weight of a subject, about 1.0 to 1.5 mg/kg weight of a subject, about 1.5 to 2.0 mg/kg weight of a subject, about 2.0 to 2.5 mg/kg weight of a subject, about 2.5 to 3.0 mg/kg weight of a subject, about 3.0 to 3.5 mg/kg weight of a subject, about 3.5 to 4.0 mg/kg weight of a subject, about 4.0 to 4.5 mg/kg weight of a subject, about 4.5 to 5.0 mg/kg weight of a subject, about 5.0 to 5.5 mg/kg weight of a subject, about 5.5 to 6.0 mg/kg weight of a subject, about 6.0 to 6.5 mg/kg weight of a subject, about 6.5 to 7.0 mg/kg weight of a subject, about 7.0 to 7.5 mg/kg weight of a subject, about 7.5 to 8.0 mg/kg weight of a subject, about 8.0 to 8.5 mg/kg weight of a subject, about 8.5 to 9.0 mg/kg weight of a subject, about 9.0 to 9.5 mg/kg weight of a subject, about 9.5 to 10.0 mg/kg weight of a subject, about 0.1 to 2 mg/kg weight of a subject, about 2 to 4 mg/kg weight of a subject, about 4 to 6 mg/kg weight of a subject, about 6 to 8 mg/kg weight of a subject, about 8 to 10 mg/kg weight of a subject, about 10 to 12 mg/kg weight of a subject, about 12 to 14 mg/kg weight of a subject, about 14 to 16 mg/kg weight of a subject, about 16 to 18 mg/kg weight of a subject, about 18 to 20 mg/kg weight of a subject, about 0.5 mg/kg weight of the subject, 2 mg/kg weight of the subject, 10 mg/kg weight of the subject, about 0.5 mg/kg to 100 weight of the subject, about 0.5 to 10 mg/kg weight of a subject, about 0.1 to 20 mg/kg weight of a subject, about 500 mg for a subject weighing less than 60 kg, 750 mg for a subject weighing between 60-100 kg or 1000 mg for a subject weighing more than 100 kg.

The label and/or instructions can also indicate dosages for a second agent, such as a DMARD, is about 1 to about 5000 mg/day, about 1 to 10 mg/day, about 10 to 50 mg/day, about 50 to 100 mg/day, about 100 to 150 mg/day, about 150 to 200 mg/day, about 200 to 250 mg/day, about 250 to 300 mg/day, about 300 to 350 mg/day, about 350 to 400 mg/day, about 400 to 450 mg/day, about 450 to 500 mg/day, about 500 to 550 mg/day, about 550 to 600 mg/day, about 600 to 650 mg/day, about 650 to 700 mg/day, about 700 to 750 mg/day, about 750 to 800 mg/day, about 800 to 850 mg/day, about 850 to 900 mg/day, about 900 to 950 mg/day, about 950 to 1000 mg/day, about 1000 to 1100 mg/day, about 1100 to 1200 mg/day, about 1200 to 1300 mg/day, about 1300 to 1400 mg/day, about 1400 to 1500 mg/day, about 1500 to 1600 mg/day, about 1600 to 1700 mg/day, about 1700 to 1800 mg/day, about 1800 to 1900 mg/day, about 1900 to 2000 mg/day, about 2000 to 2500 mg/day, about 2500 to 3000 mg/day, about 3000 to 3500 mg/day, about 3500 to 4000 mg/day, about 4000 to 4500 mg/day or about 4500 to 5000 mg/day.

The label and/or the instructions can also indicate that the pharmaceutical composition can be used alone, or in combination, with a second agent to treat a condition of choice, e.g., immune system diseases, autoimmune diseases, immunoproliferative diseases, graft-related disorders, graft versus host disease (GVHD) (e.g., such as may result from bone marrow transplantation, or in the induction of tolerance), immune disorders associated with graft transplantation rejection, immune disorders associated with chronic rejection, immune disorders associated with tissue or cell allo- or xenografts (e.g., kidneys, skin, islets, muscles, hepatocytes, neurons, solid organs and the like), psoriasis, T cell lymphoma, T cell acute lymphoblastic leukemia, testicular angiocentric T cell lymphoma, benign lymphocytic angiitis, as lupus (e.g., lupus erythematosus, lupus nephritis), Hashimoto's thyroiditis, primary myxedema, Graves' disease, pernicious anemia, autoimmune atrophic gastritis, Addison's disease, diabetes (e.g., insulin dependent diabetes mellitus, type I diabetes mellitus, type II diabetes mellitus), Goodpasture syndrome, myasthenia gravis, pemphigus, Crohn's disease, sympathetic ophthalmia, autoimmune uveitis, multiple sclerosis, autoimmune hemolytic anemia, idiopathic thrombocytopenia, primary biliary cirrhosis, chronic action hepatitis, ulcerative colitis, Sjögren's syndrome, rheumatic diseases (e.g., rheumatoid arthritis, juvenile rheumatoid arthritis), polymyositis, scleroderma, mixed connective tissue disease, and the like.

In a specific embodiment of the invention, the kit comprises a pharmaceutical composition comprising a pharmaceutically acceptable carrier and an effective amount of a first agent, wherein the first agent is a molecule that blocks B7 interaction with CTLA4 and/or CD28 such as soluble CTLA4 molecules, CD28 molecules, B7 (B7-1 or B7-2) molecules, anti-CTLA4 monoclonal antibodies, anti-CD28 monoclonal antibodies or anti-B7 (B7-1 or B7-2) monoclonal antibodies. In preferred embodiments, the soluble CTLA4 molecules have the amino acid sequence of the extracellular domain of CTLA4 as shown in either FIG. 24 or FIG. 19 (CTLA4Ig or L104EA29Y, respectively).

Methods

The invention provides methods for regulating functional CTLA4- and CD28-positive cell interactions with B7-positive cells. The methods comprise contacting the B7-positive cells with a soluble CTLA4 molecule of the invention so as to regulate functional CTLA4- and CD28-positive cell interactions with B7-positive cells, e.g., by interfering with reaction of an endogenous CTLA4 and/or CD28 molecule with a B7 molecule. Suitable amounts of soluble CTLA4 for use in the methods of the invention are described, supra.

The present invention also provides methods for inhibiting T-cell function but not T-cell depletion in a human by contacting B7-positive cells in the human with a soluble CTLA4. Examples of soluble CTLA4 include CTLA4Ig and soluble CTLA4 mutant molecule, e.g., L104EA29YIg. The present invention further provides methods for treating immune system diseases and autoimmune diseases such as rheumatic diseases. The methods comprise administering a therapeutic composition, comprising soluble CTLA4 molecules of the invention, to a subject in an amount effective to relieve at least one of the symptoms associated with immune system diseases. Additionally, the invention may provide long-term therapy for immune system diseases by blocking the T-cell/B7-positive cell interactions, thereby blocking T-cell activation/stimulation by co-stimulatory signals such as B7 binding to CD28, leading to induction of T-cell anergy or tolerance. Immune system diseases include, but are not limited to, autoimmune diseases, immunoproliferative diseases, and graft-related disorders. Examples of graft-related diseases include graft versus host disease (GVHD) (e.g., such as may result from bone marrow transplantation, or in the induction of tolerance), immune disorders associated with graft transplantation rejection, chronic rejection, and tissue or cell allo- or xenografts, including allo- or xenografts solid organs (e.g., kidneys), skin, islets, muscles, hepatocytes, neurons. Examples of immunoproliferative diseases include, but are not limited to, psoriasis; T cell lymphoma; T cell acute lymphoblastic leukemia; testicular angiocentric T cell lymphoma; benign lymphocytic angiitis; and autoimmune diseases such as lupus (e.g., lupus erythematosus, lupus nephritis), Hashimoto's thyroiditis, primary myxedema, Graves' disease, pernicious anemia, autoimmune atrophic gastritis, Addison's disease, diabetes (e.g., insulin dependent diabetes mellitus, type I diabetes mellitus, type II diabetes mellitus), Goodpasture syndrome, myasthenia gravis, pemphigus, Crohn's disease, sympathetic ophthalmia, autoimmune uveitis, multiple sclerosis, autoimmune hemolytic anemia, idiopathic thrombocytopenia, primary biliary cirrhosis, chronic action hepatitis, ulcerative colitis, Sjögren's syndrome, rheumatic diseases (e.g., rheumatoid arthritis, juvenile rheumatoid arthritis), polymyositis, scleroderma, and mixed connective tissue disease.

The soluble CTLA4 molecules of the invention exhibit inhibitory properties in vivo. Under conditions where T-cell/B7-positive cell interactions, for example, T cell/B cell interactions, are occurring as a result of contact between T cells and B7-positive cells, binding of introduced CTLA4 molecules to react to B7-positive cells, for example, B cells, may interfere, i.e., inhibit, the T cell/B7-positive cell interactions resulting in regulation of immune responses.

The invention provides methods for regulating immune responses. Immune responses downregulated (reduced) by the soluble CTLA4 molecules of the invention may be by way of inhibiting or blocking an immune response already in progress or may involve preventing the induction of an immune response. The soluble CTLA4 molecules of the invention may inhibit the functions of activated T cells, such as T lymphocyte proliferation, cytokine secretion and/or cytokine production, by suppressing T cell responses or by inducing specific tolerance in T cells, or both. Further, the soluble CTLA4 molecules of this invention, interfering with the CTLA4/CD28/B7 pathway may inhibit T-cell proliferation and/or cytokine secretion, and thus result in reduced tissue destruction and induction of T-cell unresponsiveness or anergy.

A preferred embodiment of the invention comprises use of the soluble CTLA4 mutant molecule L104EA29YIg to regulate functional CTLA4- and CD28-positive cell interactions with B7-positive cells, to treat immune system diseases such as rheumatic diseases and/or to downregulate immune responses. The L104EA29YIg of the invention is a soluble CTLA4 mutant molecule comprising at least the two amino acid changes, the leucine (L) to glutamic acid (E) at position +104 and the alanine (A) to tyrosine (Y) change at position +29 (FIG. 19). The L104EA29YIg molecule may encompass further mutations beyond the two specified herein.

A preferred embodiment of the invention comprises use of a molecule to block the interaction of B7 with CTLA4 and/or CD28 in conjunction with a DMARD to regulate an immune response in order to treat an immune system disease such as a rheumatic disease. Suitable amounts of the molecule used to block the B7 interaction with CTLA4 and/or CD28 are described, supra. The molecule used to block the B7/CTLA4 interaction may be a soluble CTLA4 such as CTLA4Ig, CTLA4Ig/CD28Ig or L104EA29YIg, a soluble CD28 such as CD28Ig, a soluble B7 (B7-1 or B7-2) such as B7Ig, anti-CTLA4 monoclonal antibodies, anti-CD28 monoclonal antibodies or anti-B7 monoclonal antibodies. The DMARD may be a dihydrofolic acid reductase inhibitor such as methotrexate, cyclophosphamide, cyclosporine, cyclosporin A, chloroquine, hydroxychloroquine, sulfasalazine, sulphasalazopyrine, leflunomide, gold salts, D-penicillamine, azathioprine, anakinra, infliximab, etanercept, TNFα blockers or a biological agent that targets an inflammatory cytokine.

A preferred embodiment includes methods for treating a rheumatic disease, such as rheumatoid arthritis, by administering an effective amount of soluble CTLA4 molecules alone, or in conjunction with an effective amount of methotrexate or a molecule that blocks TNF interactions, to a subject. Administration of an effective amount of the therapeutic composition(s), thereby relieving the subject of at least one of the symptoms associated with the disease, including reducing: joint swelling, joint tenderness, inflammation, morning stiffness, and pain, and structural damage subsequently decreasing the physical disability. The methods of the invention also may be used to reduce at least one symptom associated with rheumatoid arthritis, including reducing erythrocyte sedimentation rates, serum levels of C-reactive protein, soluble ICAM-1, soluble E-selectin and/or soluble IL-2r.

The amount of symptom relief provided by the present invention can be measured using any of the accepted criteria established to measure and document symptom relief in a clinical setting. Acceptable criteria for measuring symptom relief may include scores based on the criteria established by the American College of Rheumatology (e.g., ACR 20), the four measures of symptom relief in *CDER Guideline for the Clinical Evaluation of Anti-Inflammatory and Antirheumatic Drugs* (FDA 1988), and the Health Assessment Questionnaire (HAQ) (Fries, J. F. et al., *J. Rheumatol.*, 9:789-793 (1982)). For a general description of these criteria, see *Guidance for Industry: Clinical Development Programs for Drugs, Devices, and Biological Products for the Treatment of Rheumatoid Arthritis (RA)* (February 1999).

The present invention provides improving ACR response rates using the methods of the invention. The embodiments of the invention include improving ACR response rates of ACR 20, 50, and/or 70, using the methods of the invention.

The subjects treated by the present invention include mammalian subjects, including, human, monkey, ape, dog, cat, cow, horse, goat, pig, rabbit, mouse and rat.

The present invention provides various methods, local or systemic, for administering the therapeutic compositions of the invention such as soluble CTLA4 molecule alone or in conjunction with a DMARD, such as methotrexate, a molecule that blocks TNF interactions and/or other therapeutic drug. The methods include intravenous, intramuscular, intraperitoneal, oral, inhalation and subcutaneous methods, as well as implantable pump, continuous infusion, gene therapy, liposomes, suppositories, topical contact, vesicles, capsules, biodegradable polymers, hydrogels, controlled release patch, and injection methods. The therapeutic agent, compounded with a carrier, is commonly lyophilized for storage and is reconstituted with water or a buffered solution with a neutral pH (about pH 7-8, e.g., pH 7.5) prior to administration.

As is standard practice in the art, the compositions of the invention may be administered to the subject in any pharmaceutically acceptable form.

In accordance with the practice of the invention, the methods comprise administering to a subject the soluble CTLA4 molecules of the invention to regulate CD28- and/or CTLA4-positive cell interactions with B7-positive cells. The B7-positive cells are contacted with an effective amount of the soluble CTLA4 molecules of the invention, or fragments or derivatives thereof, so as to form soluble CTLA4/B7 complexes. Suitable amounts of soluble CTLA4 are described, supra. The complexes interfere with interaction between endogenous CTLA4 and CD28 molecules with B7 family molecules.

The soluble CTLA4 molecules may be administered to a subject in an amount and for a time (e.g., length of time and/or multiple times) sufficient to block endogenous B7 molecules from binding their respective ligands, in the subject. Blockage of endogenous B7/ligand binding thereby inhibiting interactions between B7-positive cells with CD28- and/or CTLA4-positive cells. In an embodiment, soluble CTLA4 may be administered to a subject daily, weekly, monthly and/or yearly, in single or multiple times per day/week/month/year, depending on need. For example, in one embodiment, the molecule may initially be administered once every two weeks for a month, and then once every month thereafter.

Dosage of a therapeutic agent is dependent upon many factors including, but not limited to, the type of tissue affected, the type of autoimmune disease being treated, the severity of the disease, a subject's health and response to the treatment with the agents. Accordingly, dosages of the agents can vary depending on each subject and the mode of administration. The soluble CTLA4 molecules may be administered in an amount from about 0.1 to 100 mg/kg weight of the patient/day. Suitable amounts of soluble CTLA4 are described, supra. Methotrexate may be administered to a subject in an amount from about 0.1 to 100 mg/week. Suitable amounts of soluble methotrexate are described, supra. A molecule that blocks TNF interactions, e.g., etanercept, may be administered to a subject in an amount from about 0.1 to 100 mg/week. Suitable amounts of TNF blockers are described, supra.

The invention also encompasses the use of the compositions of the invention together with other pharmaceutical agents to treat immune system diseases. For example, rheumatic diseases may be treated with molecules of the invention in conjunction with, but not limited to, immunosuppressants such as corticosteroids, cyclosporin (Mathiesen, *Cancer Lett.*, 44(2):151-156 (1989)), prednisone, azathioprine (Handschumacher, R. E. in "Drugs Used for Immunosuppression", *Goodman & Gilman's The Pharmacological Basis of Therapeutics*, 8th Edition, pp. 1264-1276, Goodman-Gilman, A. et al., eds., McGraw-Hill, N.Y. (1990), TNFα blockers or antagonists (*New Engl. J. Med.*, 340:253-259 (1999); *The Lancet*, 354:1932-1939 (1999); *Ann. Int. Med.*, 130:478-486 (1999)), or any other biological agent targeting any inflammatory cytokine, nonsteroidal antiinflammatory drugs/Cox-2 inhibitors, hydroxychloroquine, sulphasalazopryine, gold salts, etanercept, infliximab, rapamycin, mycophenolate mofetil, azathioprine, tacrolimus, basiliximab, CYTOXAN®, interferon beta-1a, interferon beta-1b, glatiramer acetate, mitoxantrone hydrochloride, anakinra and/or other biologics.

The soluble CTLA4 molecules (preferably, L104EA29YIg) can also be used in combination with one or more of the following agents to regulate an immune response: soluble gp39 (also known as CD40 ligand (CD40L), CD154, T-BAM, TRAP), soluble CD29, soluble CD40, soluble CD80 (e.g., ATCC® 68627), soluble CD86, soluble CD28 (e.g., ATCC® Accession No. 68628), soluble CD56, soluble Thy-1, soluble CD3, soluble TCR, soluble VLA-4, soluble VCAM-1, soluble LECAM-1, soluble ELAM-1, soluble CD44, antibodies reactive with gp39 (e.g., ATCC® HB-10916, ATCC® HB-12055 and ATCC® HB-12056), antibodies reactive with CD40 (e.g., ATCC® HB-9110), antibodies reactive with B7 (e.g., ATCC® HB-253, ATCC® CRL-2223, ATCC® CRL-2226, ATCC® HB-301, ATCC® HB-11341, etc.), antibodies reactive with CD28 (e.g., ATCC® HB-11944 or mAb 9.3 as described by Martin et al. (*J. Clin. Immunol.*, 4(1):18-22 (1980)), antibodies reactive with LFA-1 (e.g., ATCC® HB-9579 and ATCC® TIB-213), antibodies reactive with LFA-2, antibodies reactive with IL-2, antibodies reactive with IL-12, antibodies reactive with IFN-gamma, antibodies reactive with CD2, antibodies reactive with CD48, antibodies reactive with any ICAM (e.g., ICAM-1 (ATCC® CRL-2252), ICAM-2 and ICAM-3), antibodies reactive with CTLA4 (e.g., ATCC® HB-304), antibodies reactive with Thy-1, antibodies reactive with CD56, antibodies reactive with CD3, antibodies reactive with CD29, antibodies reactive with TCR, antibodies reactive with VLA-4, antibodies reactive with VCAM-1, antibodies reactive with LECAM-1, antibodies reactive with ELAM-1, antibodies reactive with CD44. In certain embodiments, monoclonal antibodies are preferred. In other embodiments, antibody fragments are preferred. As persons skilled in the art will readily understand, the combination can include: the soluble CTLA4 molecules of the invention and one other immunosuppressive agent; the soluble CTLA4 molecules with two other immunosuppressive agents; the soluble CTLA4 molecules with three other immunosuppressive agents; and the like. The determination of the optimal combination and dosages can be determined and optimized using methods well known in the art.

Some specific combinations include the following: L104EA29YIg and CD80 monoclonal antibodies (mAbs); L104EA29YIg and CD86 mAbs; L104EA29YIg, CD80 mAbs, and CD86 mAbs; L104EA29YIg and gp39 mAbs; L104EA29YIg and CD40 mAbs; L104EA29YIg and CD28 mAbs; L104EA29YIg, CD80 and CD86 mAbs, and gp39 mAbs; L104EA29YIg, CD80 and CD86 mAbs and CD40 mAbs; and L104EA29YIg, anti-LFA1 mAb, and anti-gp39 mAb. A specific example of a gp39 mAb is MR1. Other combinations will be readily appreciated and understood by persons skilled in the art.

The soluble CTLA4 molecules of the invention, for example, L104EA29YIg, may be administered as the sole active ingredient or together with other drugs in immunomodulating regimens or other anti-inflammatory agents such as DMARDs, e.g., for the treatment or prevention of allo- or xenograft acute or chronic rejection or inflammatory or autoimmune disorders, or to induce tolerance. For example, it may be used in combination with a calcineurin inhibitor, e.g., cyclosporin A or FK506; an immunosuppressive macrolide, e.g., rapamycin or a derivative thereof (e.g., 40-O-(2-hydroxy)ethyl-rapamycin); a lymphocyte homing agent, e.g., FTY720 or an analog thereof; corticosteroids; cyclophosphamide; azathioprine; a dihydrofolic acid reductase inhibitor such as methotrexate; leflunomide or an analog thereof; mizoribine; mycophenolic acid; mycophenolate mofetil; 15-deoxyspergualine or an analog thereof; immunosuppressive monoclonal antibodies, e.g., monoclonal antibodies to leukocyte receptors, e.g., MHC, CD2, CD3, CD4, CD 11a/CD18, CD7, CD25, CD 27, B7, CD40, CD45, CD58, CD 137, ICOS, CD150 (SLAM), OX40, 4-1BB or their ligands; or other immunomodulatory compounds, e.g., CTLA4/CD28-Ig, or other adhesion molecule inhibitors, e.g., mAbs or low molecular weight inhibitors including LFA-1 antagonists, Selectin antagonists and VLA-4 antagonists. The compound is particularly useful in combination with a compound that interferes with CD40 and its ligand, e.g., antibodies to CD40 and antibodies to CD40-L.

Where the soluble CTLA4 mutant molecules of the invention are administered in conjunction with other immunosuppressive/immunomodulatory or anti-inflammatory therapy, e.g., as hereinabove specified, dosages of the co-administered immunosuppressant, immunomodulatory or anti-inflammatory compound will of course vary depending on the type of co-drug employed, e.g., whether it is a steroid or a cyclosporin, on the specific drug employed, on the condition being treated and so forth.

In accordance with the foregoing the present invention provides in a yet further aspect methods as defined above comprising co-administration, e.g., concomitantly or in sequence, of a therapeutically effective amount of soluble CTLA4 molecules of the invention, e.g., CTLA4Ig and/or L104EA29YIg, in free form or in pharmaceutically acceptable salt form, and a second drug substance, said second drug substance being an immunosuppressant, immunomodulatory or anti-inflammatory drug, e.g., as indicated above.

Further provided are therapeutic combinations, e.g., a kit, comprising a soluble CTLA4 molecule, in free form or in pharmaceutically acceptable salt form, to be used concomitantly or in sequence with at least one pharmaceutical composition comprising an immunosuppressant, immunomodulatory or anti-inflammatory drug, e.g., a DMARD, NSAID, glucocorticoid or corticosteroid. The kit may comprise instructions for its administration. The kits of the invention can be used in any method of the present invention.

The invention also provides methods for producing the soluble CTLA4 mutant molecules of the invention. Expression of soluble CTLA4 mutant molecules can be in prokaryotic cells or eukaryotic cells.

Prokaryotes most frequently are represented by various strains of bacteria. The bacteria may be a gram positive or a gram negative. Typically, gram-negative bacteria such as *E. coli* are preferred. Other microbial strains may also be used. Sequences encoding soluble CTLA4 mutant molecules can be inserted into a vector designed for expressing foreign sequences in prokaryotic cells such as *E. coli*. These vectors can include commonly used prokaryotic control sequences which are defined herein to include promoters for transcription initiation, optionally with an operator, along with ribosome binding site sequences, including such commonly used promoters as the beta-lactamase (penicillinase) and lactose (lac) promoter systems (Chang et al., *Nature*, 198:1056 (1977)), the tryptophan (trp) promoter system (Goeddel et al., *Nucleic Acids Res.*, 8:4057 (1980)) and the lambda derived PL promoter and N-gene ribosome binding site (Shimatake et al., *Nature*, 292:128 (1981)).

Such expression vectors will also include origins of replication and selectable markers, such as a beta-lactamase or neomycin phosphotransferase gene conferring resistance to antibiotics, so that the vectors can replicate in bacteria and cells carrying the plasmids can be selected for when grown in the presence of antibiotics, such as ampicillin or kanamycin.

The expression plasmid can be introduced into prokaryotic cells via a variety of standard methods, including but not limited to CaCl$_2$-shock (Cohen, *Proc. Natl. Acad. Sci. USA*, 69:2110 (1972), and Sambrook et al., eds., *Molecular Cloning: A Laboratory Manual*, Second Edition, Cold Spring Harbor Press (1989)) and electroporation.

In accordance with the practice of the invention, eukaryotic cells are also suitable host cells. Examples of eukaryotic cells include any animal cell, whether primary or immortalized, yeast (e.g., *Saccharomyces cerevisiae, Schizosaccharomyces pombe*, and *Pichia pastoris*), and plant cells. Myeloma, COS and CHO cells are examples of animal cells that may be used as hosts. Particular CHO cells include, but are not limited to, DG44 (Chasin et al., *Somat. Cell. Molec. Genet.*, 12:555-556 (1986); Kolkekar, *Biochemistry*, 36:10901-10909 (1997)), CHO-K1 (ATCC® No. CCL-61), CHO-K1 Tet-On cell line (Clontech), CHO designated ECACC 85050302 (CAMR, Salisbury, Wiltshire, UK), CHO clone 13 (GEIMG, Genova, IT), CHO clone B (GEIMG, Genova, IT), CHO-K1/SF designated ECACC 93061607 (CAMR, Salisbury, Wiltshire, UK), and RR-CHOK1 designated ECACC 92052129 (CAMR, Salisbury, Wiltshire, UK). Exemplary plant cells include tobacco (whole plants, cell culture, or callus), corn, soybean, and rice cells. Corn, soybean, and rice seeds are also acceptable.

Nucleic acid sequences encoding the CTLA4 mutant molecules can also be inserted into a vector designed for expressing foreign sequences in a eukaryotic host. The regulatory elements of the vector can vary according to the particular eukaryotic host.

Commonly used eukaryotic control sequences for use in expression vectors include promoters and control sequences compatible with mammalian cells such as, for example, CMV promoter (CDM8 vector) and avian sarcoma virus (ASV) (πLN vector). Other commonly used promoters include the early and late promoters from Simian Virus 40 (SV40) (Fiers et al., *Nature*, 273:113 (1973)), or other viral promoters such as those derived from polyoma, Adenovirus 2, and bovine papilloma virus. An inducible promoter, such as hMTII (Karin et al., *Nature*, 299:797-802 (1982)) may also be used.

Vectors for expressing CTLA4 mutant molecules in eukaryotes may also carry sequences called enhancer regions. These are important in optimizing gene expression and are found either upstream or downstream of the promoter region.

Examples of expression vectors for eukaryotic host cells include, but are not limited to, vectors for mammalian host cells (e.g., BPV-1, pHyg, pRSV, pSV2, pTK2 (Maniatis); pIRES (Clontech); pRc/CMV2, pRc/RSV, pSFV1 (Life Technologies); pVPakc Vectors, pCMV vectors, pSGS vectors (Stratagene)), retroviral vectors (e.g., pFB vectors (Stratagene)), pCDNA-3 (Invitrogen) or modified forms thereof, adenoviral vectors; Adeno-associated virus vectors, baculovirus vectors, yeast vectors (e.g., pESC vectors (Stratagene)).

Nucleic acid sequences encoding CTLA4 mutant molecules can integrate into the genome of the eukaryotic host cell and replicate as the host genome replicates. Alternatively, the vector carrying CTLA4 mutant molecules can contain origins of replication allowing for extrachromosomal replication.

For expressing the nucleic acid sequences in *Saccharomyces cerevisiae*, the origin of replication from the endogenous yeast plasmid, the 2µ circle can be used. (Broach, *Method. Enzymol.*, 101:307 (1983)). Alternatively, sequences from the yeast genome capable of promoting autonomous replication can be used (see, for example, Stinchcomb et al., *Nature*, 282:39 (1979)); Tschemper et al., *Gene*, 10:157 (1980); and Clarke et al., *Method. Enzymol.*, 101:300 (1983)).

Transcriptional control sequences for yeast vectors include promoters for the synthesis of glycolytic enzymes (Hess et al., *J. Adv. Enzyme Reg.*, 7:149 (1968); Holland et al., *Biochemistry*, 17:4900 (1978)). Additional promoters known in the art include the CMV promoter provided in the CDM8 vector (Toyama et al., *FEBS*, 268:217-221 (1990)); the promoter for 3-phosphoglycerate kinase (Hitzeman et al., *J. Biol. Chem.*, 255:2073 (1980)), and those for other glycolytic enzymes.

Other promoters are inducible because they can be regulated by environmental stimuli or by the growth medium of the cells. These inducible promoters include those from the genes for heat shock proteins, alcohol dehydrogenase 2, isocytochrome C, acid phosphatase, enzymes associated with nitrogen catabolism, and enzymes responsible for maltose and galactose utilization.

Regulatory sequences may also be placed at the 3' end of the coding sequences. These sequences may act to stabilize messenger RNA. Such terminators are found in the 3' untranslated region following the coding sequences in several yeast-derived and mammalian genes.

Exemplary vectors for plants and plant cells include, but are not limited to, *Agrobacterium* T$_i$ plasmids, cauliflower mosaic virus (CaMV), and tomato golden mosaic virus (TGMV).

General aspects of mammalian cell host system transformations have been described by Axel (U.S. Pat. No. 4,399,216, issued Aug. 16, 1983). Mammalian cells can be transformed by methods including but not limited to, transfection in the presence of calcium phosphate, microinjection, electroporation, or via transduction with viral vectors.

Methods for introducing foreign DNA sequences into eukaryote genomes, including plant and yeast genomes include: (1) mechanical methods, such as microinjection of DNA into single cells or protoplasts, vortexing cells with glass beads in the presence of DNA, or shooting DNA-coated tungsten or gold spheres into cells or protoplasts; (2) introducing DNA by making cell membranes permeable to macromolecules through polyethylene glycol treatment or subjection to high voltage electrical pulses (electroporation); or (3) the use of liposomes (containing cDNA) which fuse to cell membranes.

Once the CTLA4 mutant molecules of the inventions are expressed, they can be harvested by methods well known in the art such as cell lysis (e.g., sonication, lysozyme and/or detergents) and protein recovery performed using standard protein purification means, e.g., affinity chromatography or ion-exchange chromatography, to yield substantially pure product (Scopes, R., *Protein Purification, Principles and Practice*, Third Edition, Springer-Verlag (1994); Sambrook et al., eds., *Molecular Cloning: A Laboratory Manual*, Second Edition, Cold Spring Harbor Press, (1989)). Expression of CTLA4 mutant molecules can be detected by methods known in the art. For example, the mutant molecules can be detected by Coomassie staining SDS-PAGE gels and immunoblotting using antibodies that bind CTLA4.

EXAMPLES

The following Examples are presented to illustrate the present invention and to assist one of ordinary skill in making and using the same. The Examples are not intended in any way to otherwise limit the scope of the invention.

Example 1

The following provides a description of the methods used to generate the nucleotide sequences encoding the CTLA4 molecules of the invention.

A CTLA4Ig encoding plasmid was first constructed, and shown to express CTLA4Ig molecules as described in U.S. Pat. Nos. 5,434,131, 5,885,579 and 5,851,795. Then single-site mutant molecules (e.g., L104EIg) were generated from the CTLA4Ig encoding sequence, expressed and tested for binding kinetics for various B7 molecules. The L104EIg nucleotide sequence (as included in the sequence shown in FIG. 18) was used as a template to generate the double-site CTLA4 mutant sequences (as included in the sequences shown in FIGS. 19-22) which were expressed as proteins and tested for binding kinetics. The double-site CTLA4 mutant sequences include: L104EA29YIg, L104EA29LIg, L104EA29TIg, and L104EA29WIg. Triple-site mutants were also generated.

CTLA4Ig Construction

A genetic construct encoding CTLA4Ig comprising the extracellular domain of CTLA4 and an IgCgamma1 domain was constructed as described in U.S. Pat. Nos. 5,434,131, 5,844,095 and 5,851,795, the contents of which are incorporated by reference herein. The extracellular domain of the CTLA4 gene was cloned by PCR using synthetic oligonucleotides corresponding to the published sequence (Dariavach et al., *Eur. J. Immunol.*, 18:1901-1905 (1988)).

Because a signal peptide for CTLA4 was not identified in the CTLA4 gene, the N-terminus of the predicted sequence of CTLA4 was fused to the signal peptide of oncostatin M (Malik et al., *Mol. Cell. Biol.*, 9:2847 (1989)) in two steps using overlapping oligonucleotides. For the first step, the oligonucleotide, CTCAGTCTGGTCCTTGCACTCCT-GTTTCCAAGCATGGCGAGCATGGCAATGCA CGTG-GCCCAGCC (SEQ ID NO:1) (which encoded the C terminal 15 amino acids from the oncostatin M signal peptide fused to the N terminal 7 amino acids of CTLA4) was used as forward primer, and TTTGGGCTCCTGATCA-GAATCTGGGCACGGTTG (SEQ ID NO: 2) (encoding amino acid residues 119-125 of the amino acid sequence encoding CTLA4 receptor and containing a Bcl I restriction enzyme site) as reverse primer. The template for this step was cDNA synthesized from 1 micro g of total RNA from H38 cells (an HTLV II infected T-cell leukemic cell line provided by Drs. Salahudin and Gallo, NCI, Bethesda, Md.). A portion of the PCR product from the first step was reamplified, using an overlapping forward primer, encoding the N terminal portion of the oncostatin M signal peptide and containing a Hind III restriction endonuclease site, CTAGC-CACTGAAGCTTCACCAATGGGTGTACTGCTCA-CACAGAGGACGCTGC TCAGTCTGGTCCTTGCACTC (SEQ ID NO: 3) and the same reverse primer. The product of the PCR reaction was digested with Hind III and Bcl I and ligated together with a Bcl I/Xba I cleaved cDNA fragment encoding the amino acid sequences corresponding to the hinge, CH2 and CH3 regions of IgC(gamma)1 into the Hind III/Xba I cleaved expression vector, CDM8 or Hind III/Xba I cleaved expression vector piLN (also known as πLN).

DNA encoding the amino acid sequence corresponding to CTLA4Ig has been deposited with the ATCC® under the Budapest Treaty on May 31, 1991, and has been accorded ATCC® Accession No. 68629.

CTLA4Ig Codon Based Mutagenesis

A mutagenesis and screening strategy was developed to identify mutant CTLA4Ig molecules that had slower rates of dissociation ("off" rates) from CD80 and/or CD86 molecules, i.e., improved binding ability. In this embodiment, mutations were carried out in and/or about the residues in the CDR-1, CDR-2 (also known as the C' strand) and/or CDR-3 regions of the extracellular domain of CTLA4 (as described in U.S. Pat. Nos. 6,090,914, 5,773,253 and 5,844,095; in U.S. Patent Application Ser. No. 60/214,065; and by Peach, R. J. et al., *J. Exp. Med.*, 180:2049-2058 (1994). A CDR-like region encompasses the each CDR region and extends, by several amino acids, upstream and/or downstream of the CDR motif). These sites were chosen based on studies of chimeric CD28/CTLA4 fusion proteins (Peach et al., *J. Exp. Med.*, 180:2049-2058 (1994)), and on a model predicting which amino acid residue side chains would be solvent exposed, and a lack of amino acid residue identity or homology at certain positions between CD28 and CTLA4. Also, any residue which is spatially in close proximity (5 to 20 Angstrom Units) to the identified residues is considered part of the present invention.

To synthesize and screen soluble CTLA4 mutant molecules with altered affinities for a B7 molecule (e.g., CD80, CD86), a two-step strategy was adopted. The experiments entailed first generating a library of mutations at a specific codon of an extracellular portion of CTLA4 and then screening these by BIACORE® analysis to identify mutants with altered reactivity to B7. The BIACORE® assay system (Pharmacia, Piscataway, N.J.) uses a surface plasmon resonance detector system that essentially involves covalent binding of either CD80Ig or CD86Ig to a dextran-coated sensor chip which is located in a detector. The test molecule can then be injected into the chamber containing the sensor chip and the amount of complementary protein that binds can be assessed based on the change in molecular mass which is physically associated with the dextran-coated side of the sensor chip; the change in molecular mass can be measured by the detector system.

Specifically, single-site mutant nucleotide sequences were generated using non-mutated (e.g., wild-type) DNA encoding CTLA4Ig (U.S. Pat. Nos. 5,434,131, 5,844,095, 5,851, 795 and 5,885,796; ATCC® Accession No. 68629) as a template. Mutagenic oligonucleotide PCR primers were designed for random mutagenesis of a specific codon by allowing any base at positions 1 and 2 of the codon, but only guanine or thymine at position 3 (XXG/T or also noted as NNG/T). In this manner, a specific codon encoding an amino acid could be randomly mutated to code for each of the 20 amino acids. In that regard, XXG/T mutagenesis yields 32 potential codons encoding each of the 20 amino acids. PCR products encoding mutations in close proximity to the CDR3-like loop of CTLA4Ig (MYPPPY), were digested with SacI/XbaI and subcloned into similarly cut CTLA4Ig (as included in FIG. 24) πLN expression vector. This method was used to generate the single-site CTLA4 mutant molecule L104EIg (as included in FIG. 18).

For mutagenesis in proximity to the CDR-1-like loop of CTLA4Ig, a silent NheI restriction site was first introduced 5' to this loop, by PCR primer-directed mutagenesis. PCR products were digested with NheI/XbaI and subcloned into similarly cut CTLA4Ig or L104EIg expression vectors. This method was used to generate the double-site CTLA4 mutant molecule L104EA29YIg (as included in FIG. 19). In particular, the nucleic acid molecule encoding the single-site CTLA4 mutant molecule, L104EIg, was used as a template to generate the double-site CTLA4 mutant molecule, L104EA29YIg.

The double-site mutant nucleotide sequences encoding CTLA4 mutant molecules, such as L104EA29YIg (deposited on Jun. 19, 2000 with the American Type Culture Collection (ATCC®), 10801 University Blvd., Manassas, Va. 20110-2209 and accorded ATCC® Accession No. PTA-2104), were generated by repeating the mutagenesis procedure described above using L104EIg as a template. This method was used to generate numerous double-site mutants nucleotide sequences such as those encoding CTLA4 molecules L104EA29YIg (as included in the sequence shown in FIG. 19), L104EA29LIg (as included in the sequence shown in FIG. 20), L104EA29TIg (as included in the sequence shown in FIG. 21), and L104EA29WIg (as included in the sequence shown in FIG. 22). Triple-site mutants, such as those encoding L104EA29YS25KIg, L104EA29YS25NIg and L104EA29YS25RIg, were also generated.

The soluble CTLA4 molecules were expressed from the nucleotide sequences and used in the phase II clinical studies described in Example 3, infra.

As those skilled-in-the-art will appreciate, replication of nucleic acid sequences, especially by PCR amplification, easily introduces base changes into DNA strands. However, nucleotide changes do not necessarily translate into amino acid changes as some codons redundantly encode the same amino acid. Any changes of nucleotide from the original or wild-type sequence, silent (i.e., causing no change in the translated amino acid) or otherwise, while not explicitly described herein, are encompassed within the scope of the invention.

Example 2

The following Example provides a description of the screening methods used to identify the single- and double-site mutant CTLA polypeptides expressed from the constructs described in Example 1 that exhibited a higher binding avidity for B7 molecules, compared to non-mutated CTLA4Ig molecules.

Current in vitro and in vivo studies indicate that CTLA4Ig by itself is unable to completely block the priming of antigen specific activated T cells. In vitro studies with CTLA4Ig and either monoclonal antibody specific for CD80 or CD86 measuring inhibition of T cell proliferation indicate that anti-CD80 monoclonal antibody did not augment CTLA4Ig inhibition. However, anti-CD86 monoclonal antibody did augment the inhibition, indicating that CTLA4Ig was not as effective at blocking CD86 interactions. These data support earlier findings by Linsley et al., (*Immunity*, 1:793-801 (1994)) showing inhibition of CD80-mediated cellular responses required approximately 100 fold lower CTLA4Ig concentrations than for CD86-mediated responses. Based on these findings, it was surmised that soluble CTLA4 mutant molecules having a higher avidity for CD86 than wild-type CTLA4 should be better able to block the priming of antigen specific activated cells than CTLA4Ig.

To this end, the soluble CTLA4 mutant molecules described in Example 1 above were screened using a novel screening procedure to identify several mutations in the extracellular domain of CTLA4 that improve binding avidity for CD80 and CD86. This screening strategy provided an effective method to directly identify mutants with apparently slower "off" rates without the need for protein purification or quantitation since "off" rate determination is concentration independent (O'Shannessy et al., *Anal. Biochem.*, 212:457-468 (1993)).

COS cells were transfected with individual miniprep purified plasmid DNA and propagated for several days. Three day conditioned culture media was applied to BIACORE® biosensor chips (Pharmacia Biotech AB, Uppsala, Sweden) coated with soluble CD80Ig or CD86Ig. The specific binding and dissociation of mutant proteins was measured by surface plasmon resonance (O'Shannessy, D. J. et al., *Anal. Biochem.*, 212:457-468 (1997)). All experiments were run on BIACORE® or BIACORE® 2000 biosensors at 25° C. Ligands were immobilized on research grade NCMS sensor chips (Pharmacia) using standard N-ethyl-N'-(dimethylaminopropyl)carbodiimide N-hydroxysuccinimide coupling (Johnsson, B. et al., *Anal. Biochem.*, 198:268-277 (1991); Khilko, S. N. et al., *J. Biol. Chem.*, 268:5425-5434 (1993)).

Screening Method

COS cells grown in 24 well tissue culture plates were transiently transfected with mutant CTLA4Ig. Culture media containing secreted soluble mutant CTLA4Ig was collected 3 days later.

Conditioned COS cell culture media was allowed to flow over BIACORE® biosensor chips derivatized with CD86Ig or CD80Ig (as described in Greene et al., *J. Biol. Chem.*, 271:26762-26771 (1996)), and mutant molecules were identified with off-rates slower than that observed for wild-type CTLA4Ig. The DNAs corresponding to selected media samples were sequenced and more DNA prepared to perform larger scale COS cell transient transfection, from which CTLA4Ig mutant protein was prepared following protein A purification of culture media.

BIACORE® analysis conditions and equilibrium binding data analysis were performed as described in Greene, J. et al., *J. Biol. Chem.*, 271:26762-26771 (1996) and in U.S. patent application Ser. Nos. 09/579,927 and 60/214,065 which are herein incorporated by reference.

BIACORE® Data Analysis

Sensorgram baselines were normalized to zero response units (RU) prior to analysis. Samples were run over mock-derivatized flow cells to determine background RU values due to bulk refractive index differences between solutions. Equilibrium dissociation constants ($K_d$) were calculated from plots of $R_{eq}$ versus C, where $R_{eq}$ is the steady-state response minus the response on a mock-derivatized chip, and C is the molar concentration of analyte. Binding curves were analyzed using commercial nonlinear curve-fitting software (Prism, GraphPAD Software).

Experimental data were first fit to a model for a single ligand binding to a single receptor (1-site model, i.e., a simple Langmuir system, $A+B \leftrightarrows AB$), and equilibrium association constants ($K_d=[A]\cdot[B]\backslash[AB]$) were calculated from the equation $R=R_{max}\cdot C/(K_d+C)$. Subsequently, data were fit to the simplest two-site model of ligand binding (i.e., to a receptor having two non-interacting independent binding sites as described by the equation $R=R_{max1}\cdot C\backslash(K_{d1}+C)+R_{max2}\cdot C\backslash(K_{d2}+C)$.

The goodness-of-fits of these two models were analyzed visually by comparison with experimental data and statistically by an F test of the sums-of-squares. The simpler one-site model was chosen as the best fit, unless the two-site model fit significantly better (p<0.1).

Association and disassociation analyses were performed using BIA evaluation 2.1 Software (Pharmacia). Association rate constants $k_{on}$ were calculated in two ways, assuming both homogenous single-site interactions and parallel two-site interactions. For single-site interactions, $k_{on}$ values were calculated according to the equation $R_t=R_{eq}(1-\exp^{-ks(t-t0)})$, where $R_t$ is a response at a given time, t; $R_{eq}$ is the steady-state response; to is the time at the start of the injection; and $k_s=dR/dt=k_{on}\cdot Ck_{off}$, where C is a concentration of analyte, calculated in terms of monomeric binding sites. For two-site interactions $k_{on}$ values were calculated according to the equation $R_t=R_{eq1}(1-\exp^{-ks1(t-t0)})+R_{eq2}(1-\exp^{ks2(t-t0)})$. For each model, the values of $k_{on}$ were determined from the calculated slope (to about 70% maximal association) of plots of $k_s$ versus C.

Dissociation data were analyzed according to one site (AB=A+B) or two site (AiBj=Ai+Bj) models, and rate constants ($k_{off}$) were calculated from best fit curves. The binding site model was used except when the residuals were greater than machine background (2-10 RU, according to machine), in which case the two-binding site model was employed. Half-times of receptor occupancy were calculated using the relationship $t_{1/2}=0.693/k_{off}$.

Flow Cytometry

Murine mAb L307.4 (anti-CD80) was purchased from Becton Dickinson (San Jose, Calif.) and IT2.2 (anti-B7-0 [also known as CD86]), from Pharmingen (San Diego, Calif.). For immunostaining, CD80-positive and/or CD86-positive CHO cells were removed from their culture vessels by incubation in phosphate-buffered saline (PBS) containing 10 mM EDTA. CHO cells ($1-10\times10^5$) were first incubated with mAbs or immunoglobulin fusion proteins in DMEM containing 10% fetal bovine serum (FBS), then washed and incubated with fluorescein isothiocyanate-conjugated goat anti-mouse or anti-human immunoglobulin second step reagents (Tago, Burlingame, Calif.). Cells were given a final wash and analyzed on a FACScan (Becton Dickinson).

SDS-PAGE and Size Exclusion Chromatography

SDS-PAGE was performed on Tris/glycine 4-20% acrylamide gels (Novex, San Diego, Calif.). Analytical gels were stained with Coomassie Blue, and images of wet gels were obtained by digital scanning. CTLA4Ig (25 μg) and L104EA29YIg (25 μg) were analyzed by size exclusion chromatography using a TSK-GEL G300 SW$_{XL}$ column (7.8×300 mm, Tosohaas, Montgomeryville, Pa.) equilibrated in phosphate buffered saline containing 0.02% NAN$_3$ at a flow rate of 1.0 ml/min.

CTLA4X$_{C120S}$ and L104EA29YX$_{C120S}$

Single chain CTLA4X$_{C120S}$ was prepared as previously described (Linsley et al., J. Biol. Chem., 270:15417-15424 (1995)). Briefly, an oncostatin M CTLA4 (OMCTLA4) expression plasmid was used as a template, the forward primer, GAGGTGATAAAGCTTCACCAATGGGTGTACTGCTCACACAG (SEQ ID NO: 4) was chosen to match sequences in the vector; and the reverse primer, GTGGTGTATTGGTCTAGATCAATCAGAATCTGGGCACGGTTC (SEQ ID NO: 5) corresponded to the last seven amino acids (i.e., amino acids 118-124) in the extracellular domain of CTLA4, and contained a restriction enzyme site, and a stop codon (TGA). The reverse primer specified a C120S (cysteine to serine at position 120) mutation. In particular, the nucleotide sequence GCA (nucleotides 34-36) of the reverse primer shown above is replaced with one of the following nucleotide sequences: AGA, GGA, TGA, CGA, ACT, or GCT. As persons skilled in the art will understand, the nucleotide sequence GCA is a reversed complementary sequence of the codon TGC for cysteine. Similarly, the nucleotide sequences AGA, GGA, TGA, CGA, ACT, or GCT are the reversed complementary sequences of the codons for serine. Polymerase chain reaction products were digested with HindIII/XbaI and directionally subcloned into the expression vector πLN (Bristol-Myers Squibb Company, Princeton, N.J.). L104EA29YX$_{C120S}$ was prepared in an identical manner. Each construct was verified by DNA sequencing.

Identification and Biochemical Characterization of High Avidity Mutants 24 amino acids were chosen for mutagenesis and the resulting 2300 mutant proteins assayed for CD86Ig binding by surface plasmon resonance (SPR; as described, supra). The predominant effects of mutagenesis at each site are summarized in Table II, infra. Random mutagenesis of some amino acids in the CDR-1 region (S25-R33) apparently did not alter ligand binding. Mutagenesis of E31 and R33 and residues M97-Y102 apparently resulted in reduced ligand binding. Mutagenesis of residues, S25, A29, and T30, K93, L96, Y103, L104, and G105, resulted in proteins with slow "on" and/or slow "off" rates. These results confirm previous findings that residues in the CDR-1 (S25-R33) region, and residues in or near M97-Y102 influence ligand binding (Peach et al., J. Exp. Med., 180:2049-2058 (1994)).

Mutagenesis of sites S25, T30, K93, L96, Y103, and G105 resulted in the identification of some mutant proteins that had slower "off" rates from CD86Ig. However, in these instances, the slow "off" rate was compromised by a slow "on" rate that resulted in mutant proteins with an overall avidity for CD86Ig that was apparently similar to that seen with wild-type CTLA4Ig. In addition, mutagenesis of K93 resulted in significant aggregation that may have been responsible for the kinetic changes observed.

Random mutagenesis of L104 followed by COS cell transfection and screening by SPR of culture media samples over immobilized CD86Ig yielded six media samples containing mutant proteins with approximately 2-fold slower "off" rates than wild-type CTLA4Ig. When the corresponding cDNA of these mutants were sequenced, each was found to encode a leucine to glutamic acid mutation (L104E). Apparently, substitution of leucine 104 to aspartic acid (L104D) did not affect CD86Ig binding.

Mutagenesis was then repeated at each site listed in Table II, this time using L104E as the PCR template instead of wild-type CTLA4Ig, as described above. SPR analysis, again using immobilized CD86Ig, identified six culture media samples from mutagenesis of alanine 29 with proteins having approximately 4-fold slower "off" rates than wild-type CTLA4Ig. The two slowest were tyrosine substitutions (L104EA29Y), two were leucine (L104EA29L), one was tryptophan (L104EA29W), and one was threonine (L104EA29T). Apparently, no slow "off" rate mutants were identified when alanine 29 was randomly mutated, alone, in wild-type CTLA4Ig.

Figure 25A:
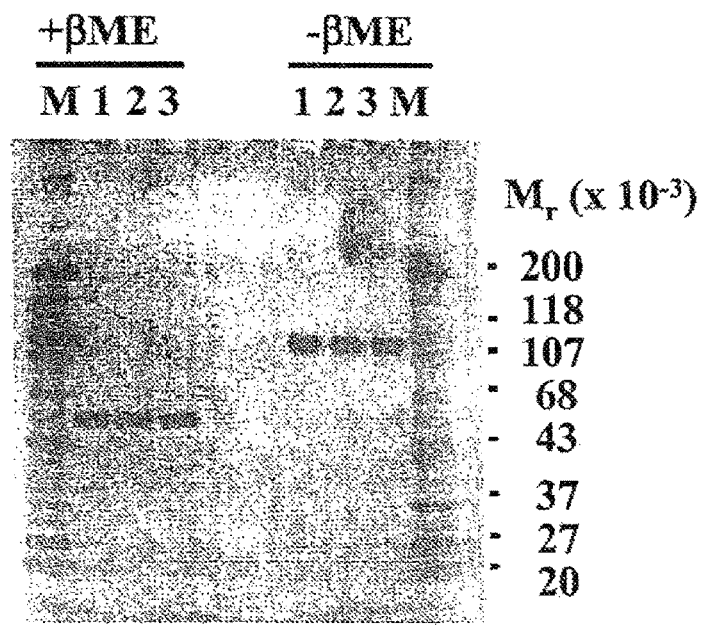
FIGS. 25A-25C: SDS gel (FIG. 25A) for CTLA4Ig (lane 1), L104EIg (lane 2), and L104EA29YIg (lane 3A); and size exclusion chromatographs of CTLA4Ig (FIG. 25B) and L104EA29YIg (FIG. 25C).
Figure 25B:
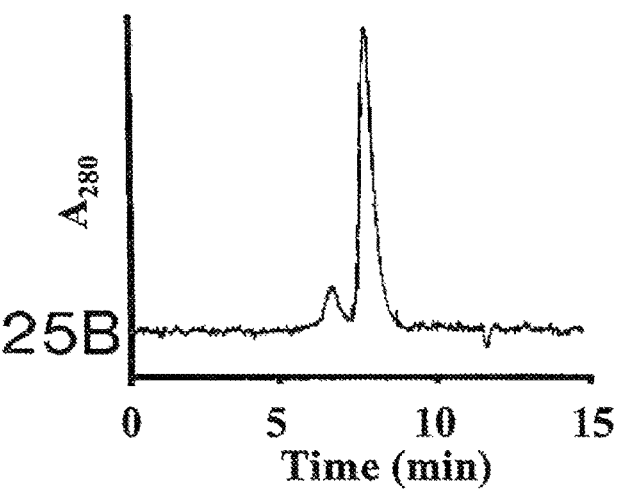
Figure 25C:
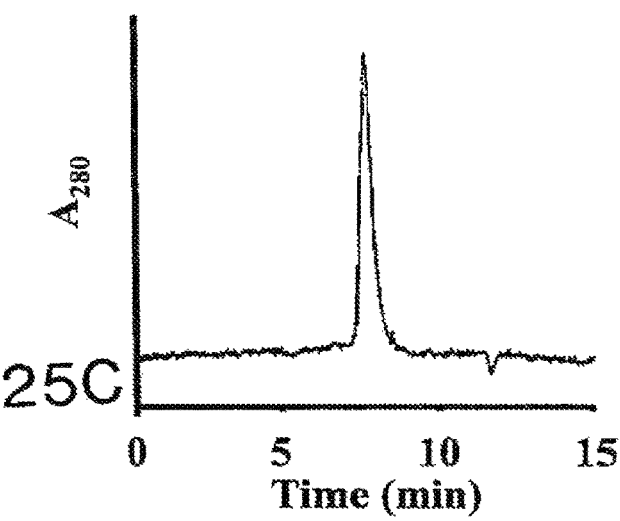

The relative molecular mass and state of aggregation of purified L104E and L104EA29YIg was assessed by SDS-PAGE and size exclusion chromatography. L104EA29YIg (~1 μg; lane 3) and L104EIg (~1 μg; lane 2) apparently had the same electrophoretic mobility as CTLA4Ig (~1 μg; lane 1) under reducing (~50 kDa; +βME; plus 2-mercaptoethanol) and non-reducing (~100 kDa; −βME) conditions (FIG. 25A). Size exclusion chromatography demonstrated that L104EA29YIg (FIG. 25C) apparently had the same mobility as dimeric CTLA4Ig (FIG. 25B). The major peaks represent protein dimer while the faster eluting minor peak in FIG. 25B represents higher molecular weight aggregates. Approximately 5.0% of CTLA4Ig was present as higher molecular weight aggregates but there was no evidence of aggregation of L104EA29YIg or L104EIg. Therefore, the stronger binding to CD86Ig seen with L104EIg and L104EA29YIg could not be attributed to aggregation induced by mutagenesis.

Equilibrium and Kinetic Binding Analysis

Equilibrium and kinetic binding analysis was performed on protein A purified CTLA4Ig, L104EIg, and L104EA29YIg using surface plasmon resonance (SPR). The results are shown in Table I, infra. Observed equilibrium dissociation constants ($K_d$; Table I) were calculated from binding curves generated over a range of concentrations (5.0-200 nM). L104EA29YIg binds more strongly to CD86Ig than does L104EIg or CTLA4Ig. The lower $K_d$ of L104EA29YIg (3.21 nM) than L104EIg (6.06 nM) or CTLA4Ig (13.9 nM) indicates higher binding avidity of L104EA29YIg to CD86Ig. The lower $K_d$ of L104EA29YIg (3.66 nM) than L104EIg (4.47 nM) or CTLA4Ig (6.51 nM) indicates higher binding avidity of L104EA29YIg to CD80Ig.

Kinetic binding analysis revealed that the comparative "on" rates for CTLA4Ig, L104EIg, and L104EA29YIg binding to CD80 were similar, as were the "on" rates for CD86Ig (Table I). However, "off" rates for these molecules were not equivalent (Table I). Compared to CTLA4Ig, L104EA29YIg had approximately 2-fold slower "off" rate from CD80Ig, and approximately 4-fold slower "off" rate from CD86Ig. L104E had "off" rates intermediate between L104EA29YIg and CTLA4Ig. Since the introduction of these mutations did not significantly affect "on" rates, the increase in avidity for CD80Ig and CD86Ig observed with L104EA29YIg was likely primarily due to a decrease in "off" rates.

To determine whether the increase in avidity of L104EA29YIg for CD86Ig and CD80Ig was due to the mutations affecting the way each monomer associated as a dimer, or whether there were avidity enhancing structural changes introduced into each monomer, single chain constructs of CTLA4 and L104EA29Y extracellular domains were prepared following mutagenesis of cysteine 120 to serine as described, supra, and by Linsley et al., *J. Biol. Chem.*, 270:15417-15424 (1995) (84). The purified proteins $CTLA4X_{C120S}$ and $L104EA29YX_{C120S}$ were shown to be monomeric by gel permeation chromatography (Linsley et al. (1995), supra), before their ligand binding properties were analyzed by SPR. Results showed that binding affinity of both monomeric proteins for CD86Ig was approximately 35-80-fold less than that seen for their respective dimers (Table I). This supports previously published data establishing that dimerization of CTLA4 was required for high avidity ligand binding (Greene et al., *J. Biol. Chem.*, 271: 26762-26771 (1996)).

$L104EA29YX_{C120S}$ bound with approximately 2-fold higher affinity than $CTLA4X_{C120S}$ to both CD80Ig and CD86Ig. The increased affinity was due to approximately 3-fold slower rate of dissociation from both ligands. Therefore, stronger ligand binding by L104EA29Y was most likely due to avidity enhancing structural changes that had been introduced into each monomeric chain rather than alterations in which the molecule dimerized.

Location and Structural Analysis of Avidity Enhancing Mutations

Figure 26:
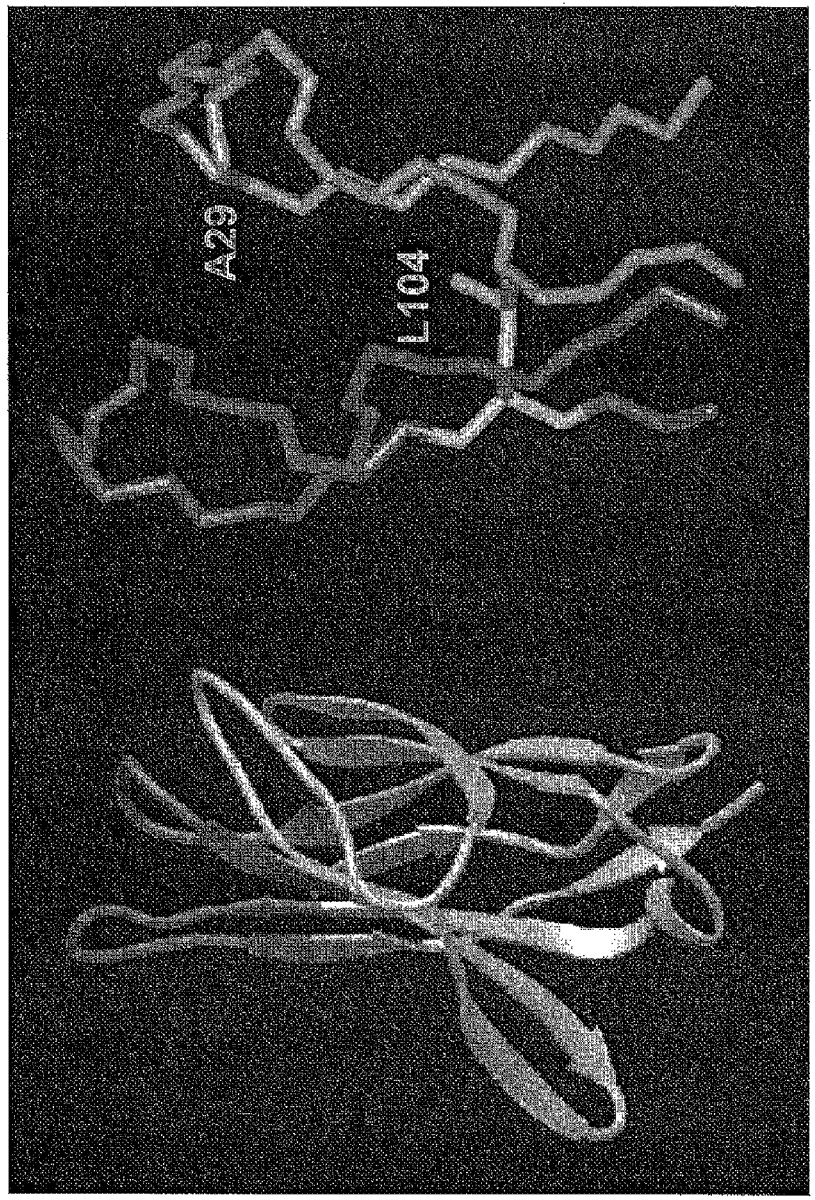
FIG. 26 (left and right depictions): A ribbon diagram of the CTLA4 extracellular Ig V-like fold generated from the solution structure determined by NMR spectroscopy.

The solution structure of the extracellular IgV-like domain of CTLA4 has recently been determined by NMR spectroscopy (Metzler et al., *Nat. Struct. Biol.*, 4:527-531 (1997)). This allowed accurate location of leucine 104 and alanine 29 in the three dimensional fold (FIG. 26, left and right depictions). Leucine 104 is situated near the highly conserved MYPPPY amino acid sequence. Alanine 29 is situated near the C-terminal end of the CDR-1 (S25-R33) region, which is spatially adjacent to the MYPPPY region. While there is significant interaction between residues at the base of these two regions, there is apparently no direct interaction between L104 and A29 although they both comprise part of a contiguous hydrophobic core in the protein. The structural consequences of the two avidity enhancing mutants were assessed by modeling. The A29Y mutation can be easily accommodated in the cleft between the CDR-1 (S25-R33) region and the MYPPPY region, and may serve to stabilize the conformation of the MYPPPY region. In wild-type CTLA4, L104 forms extensive hydrophobic interactions with L96 and V94 near the MYPPPY region. It is highly unlikely that the glutamic acid mutation adopts a conformation similar to that of L104 for two reasons. First, there is insufficient space to accommodate the longer glutamic acid side chain in the structure without significant perturbation to the CDR-1 (S25-R33 region). Second, the energetic costs of burying the negative charge of the glutamic acid side chain in the hydrophobic region would be large. Instead, modeling studies predict that the glutamic acid side chain flips out on to the surface where its charge can be stabilized by solvation. Such a conformational change can easily be accommodated by G105, with minimal distortion to other residues in the regions.

Binding of High Avidity Mutants to CHO Cells Expressing CD80 or CD86

FACS analysis (FIGS. 27A and 27B) of CTLA4Ig and mutant molecules binding to stably transfected CD80+ and CD86+CHO cells was performed as described herein. CD80-positive and CD86-positive CHO cells were incubated with increasing concentrations of CTLA4Ig, L104EA29YIg, or L104EIg, and then washed. Bound immunoglobulin fusion protein was detected using fluorescein isothiocyanate-conjugated goat anti-human immunoglobulin.

Figure 27A:
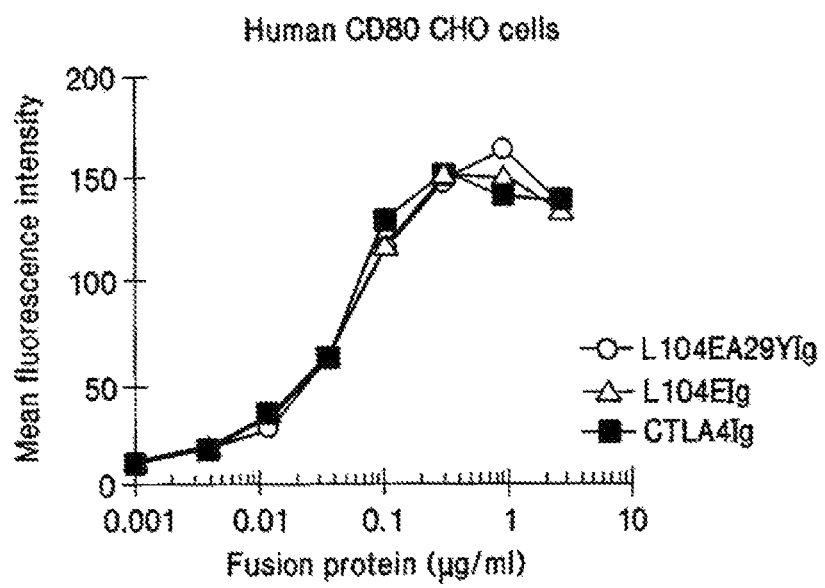
FIGS. 27A and 27B: FACS assays showing binding of L104EA29YIg, L104EIg, and CTLA4Ig to human CD80- or CD86-transfected CHO cells as described in Example 2, infra.
Figure 27B:
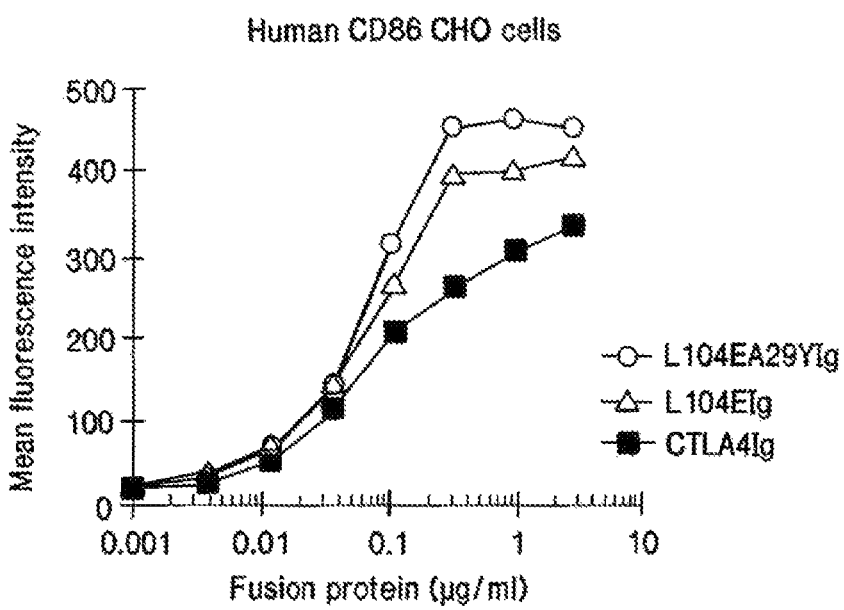

As shown in FIGS. 27A and 27B, CD80-positive or CD86-positive CHO cells ($1.5 \times 10^5$) were incubated with the indicated concentrations of CTLA4Ig (closed squares), L104EA29YIg (circles), or L104EIg (triangles) for 2 hr. at 23° C., washed, and incubated with fluorescein isothiocyanate-conjugated goat anti-human immunoglobulin antibody. Binding on a total of 5,000 viable cells was analyzed (single determination) on a FACScan, and mean fluorescence intensity (MFI) was determined from data histograms using PC-LYSYS. Data were corrected for background fluorescence measured on cells incubated with second step reagent only (MFI=7). Control L6 mAb (80 µg/ml) gave MFI<30. These results are representative of four independent experiments.

Binding of L104EA29YIg, L104EIg, and CTLA4Ig to human CD80-transfected CHO cells is approximately equivalent (FIG. 27A). L104EA29YIg and L104EIg bind more strongly to CHO cells stably transfected with human CD86 than does CTLA4Ig (FIG. 27B).

Functional Assays

Figure 28A:
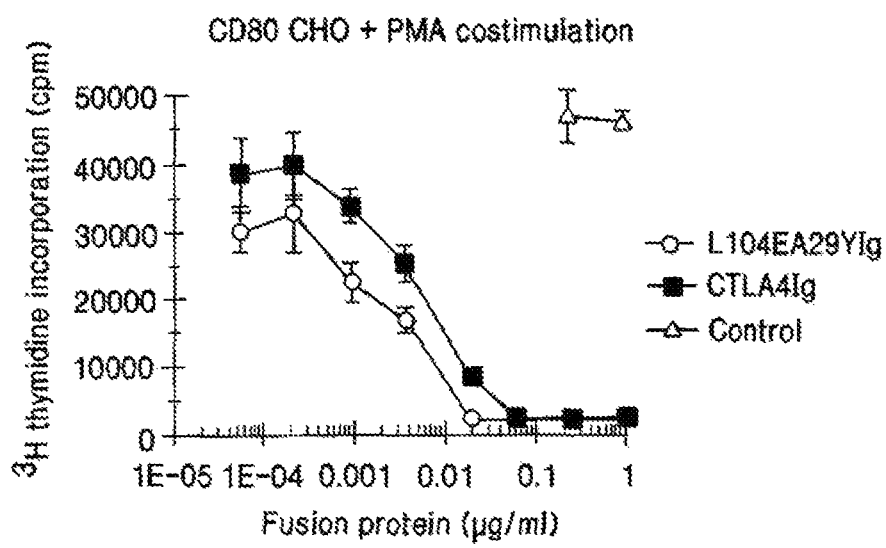
FIGS. 28A and 28B: Graphs showing inhibition of proliferation of CD80-positive and CD86-positive CHO cells as described in Example 2, infra.
Figure 28B:
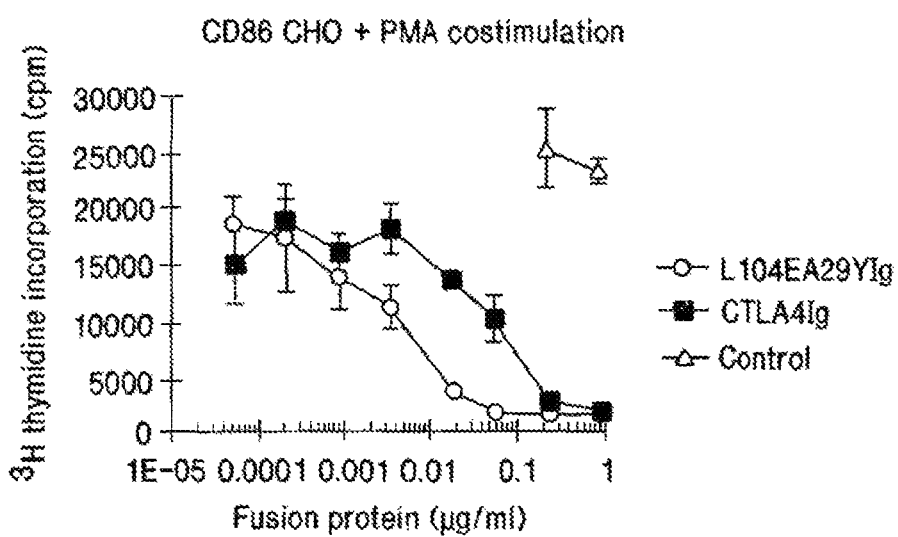

Human CD4-positive T cells were isolated by immunomagnetic negative selection (Linsley et al., *J. Exp. Med.*, 176:1595-1604 (1992)). Isolated CD4-positive T cells were stimulated with phorbol myristate acetate (PMA) plus CD80-positive or CD86-positive CHO cells in the presence of titrating concentrations of inhibitor. CD4-positive T cells ($8-10 \times 10^4$/well) were cultured in the presence of 1 nM PMA with or without irradiated CHO cell stimulators. Proliferative responses were measured by the addition of 1 µCi/well of [3H]thymidine during the final 7 hours of a 72 hour culture. Inhibition of PMA plus CD80-positive CHO, or CD86-positive CHO, stimulated T cells by L104EA29YIg and CTLA4Ig was performed. The results are shown in FIGS. 28A and 28B. L104EA29YIg inhibits proliferation of CD80-positive PMA treated CHO cells more than CTLA4Ig (FIG. 28A). L104EA29YIg is also more effective than CTLA4Ig at inhibiting proliferation of CD86-positive PMA treated CHO cells (FIG. 28B). Therefore, L104EA29YIg is a more potent inhibitor of both CD80- and CD86-mediated costimulation of T cells.

Figure 29A:
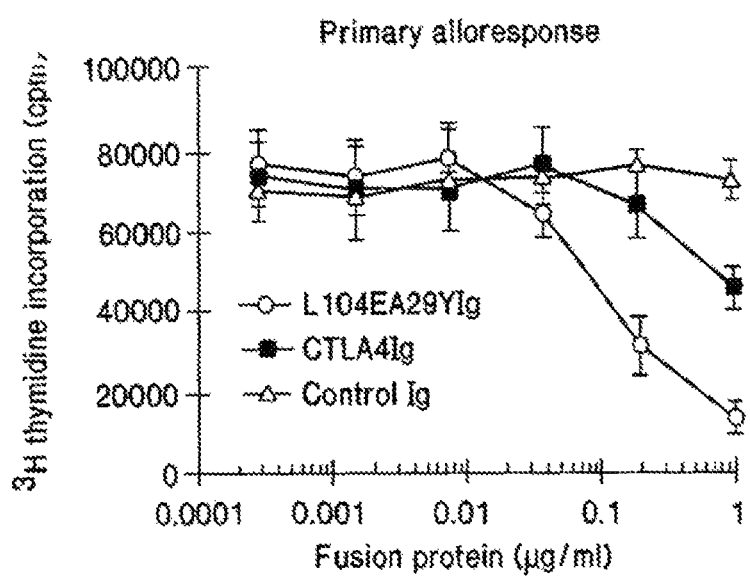
FIGS. 29A and 29B: Graphs showing that L104EA29YIg is more effective than CTLA4Ig at inhibiting proliferation of primary and secondary allostimulated T cells as described in Example 2, infra.
Figure 29B:
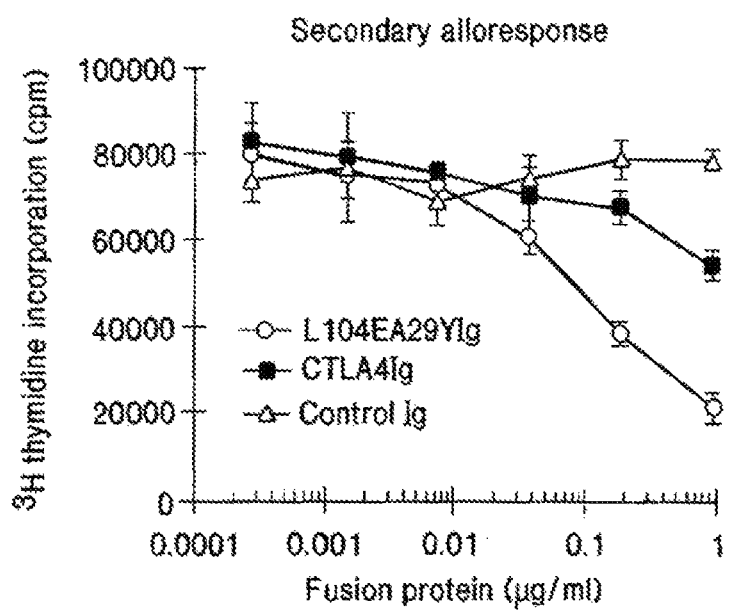

FIGS. 29A and 29B show inhibition by L104EA29YIg and CTLA4Ig of allostimulated human T cells prepared above, and further allostimulated with a human B lymphoblastoid cell line (LCL) called PM that expressed CD80 and CD86 (T cells at $3.0 \times 10^4$/well and PM at $8.0 \times 10^3$/well). Primary allostimulation occurred for 6 days, then the cells were pulsed with $^3$H-thymidine for 7 hours, before incorporation of radiolabel was determined.

Secondary allostimulation was performed as follows. Seven-day primary allostimulated T cells were harvested over lymphocyte separation medium (LSM) (ICN, Aurora, Ohio) and rested for 24 hours. T cells were then restimulated (secondary), in the presence of titrating amounts of CTLA4Ig or L104EA29YIg, by adding PM in the same ratio as above. Stimulation occurred for 3 days, then the cells were pulsed with radiolabel and harvested as above. The effect of L104EA29YIg on primary allostimulated T cells is shown in FIG. 29A. The effect of L104EA29YIg on secondary allostimulated T cells is shown in FIG. 29B. L104EA29YIg inhibits both primary and secondary T cell proliferative responses better than CTLA4Ig.

Figure 30A:
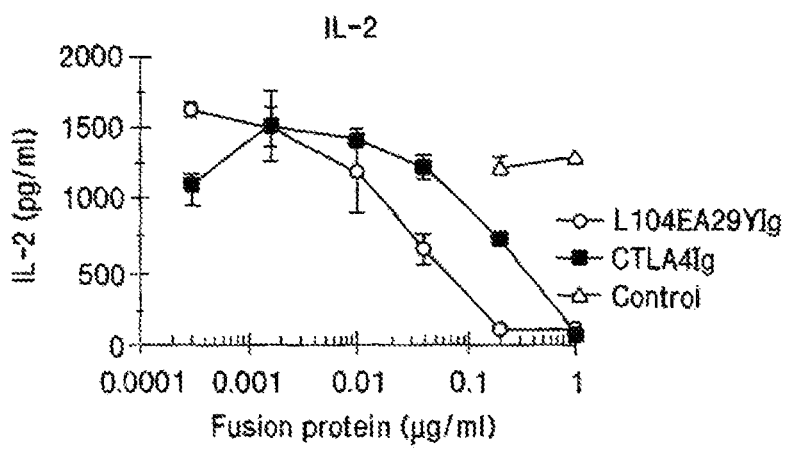
FIGS. 30A-30C: Graphs illustrating that L104EA29YIg is more effective than CTLA4Ig at inhibiting IL-2 (FIG. 30A), IL-4 (FIG. 30B), and gamma (γ)-interferon (FIG. 30C) cytokine production of allostimulated human T cells as described in Example 2, infra.
Figure 30B:
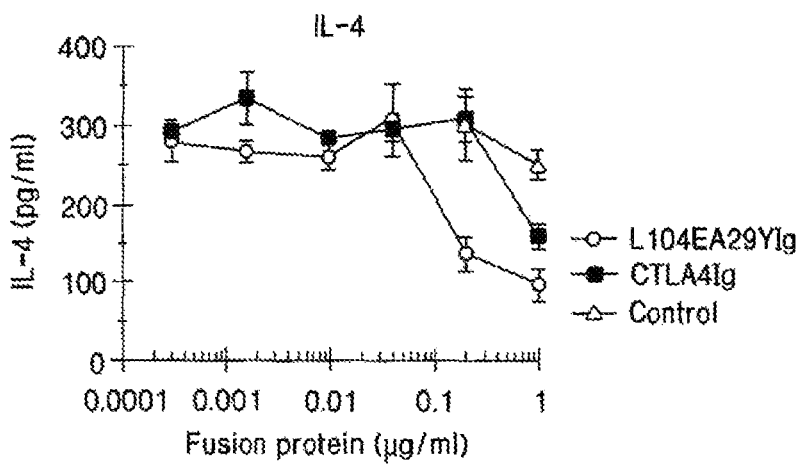
Figure 30C:
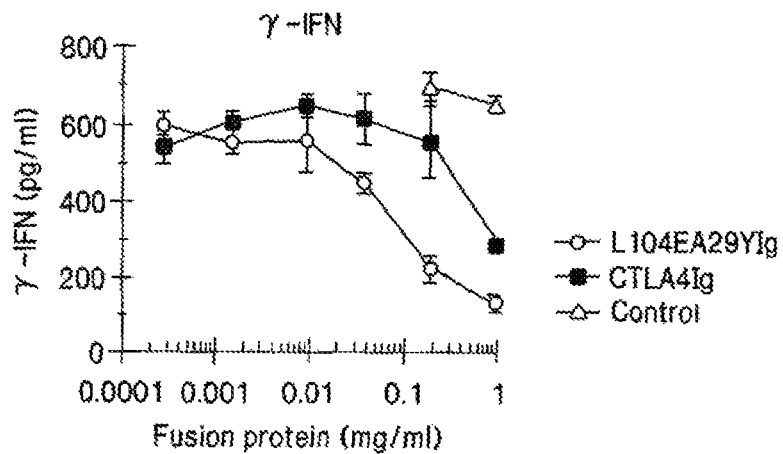

To measure cytokine production (FIGS. 30A-30C), duplicate secondary allostimulation plates were set up. After 3 days, culture media was assayed using ELISA kits (Biosource, Camarillo, Calif.) using conditions recommended by the manufacturer. L104EA29YIg was found to be more potent than CTLA4Ig at blocking T cell IL-2, IL-4, and γ-IFN (gamma-IFN) cytokine production following a secondary allogeneic stimulus (FIGS. 30A-30C).

Figure 31:
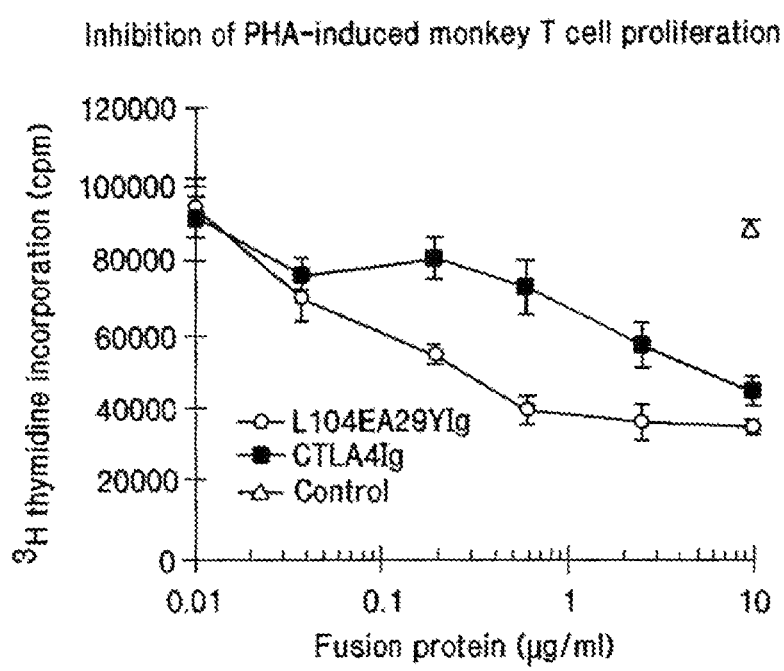
FIG. 31: A graph demonstrating that L104EA29YIg is more effective than CTLA4Ig at inhibiting proliferation of phytohemagglutinin-(PHA) stimulated monkey T cells as described in Example 2, infra.
Figure 32:
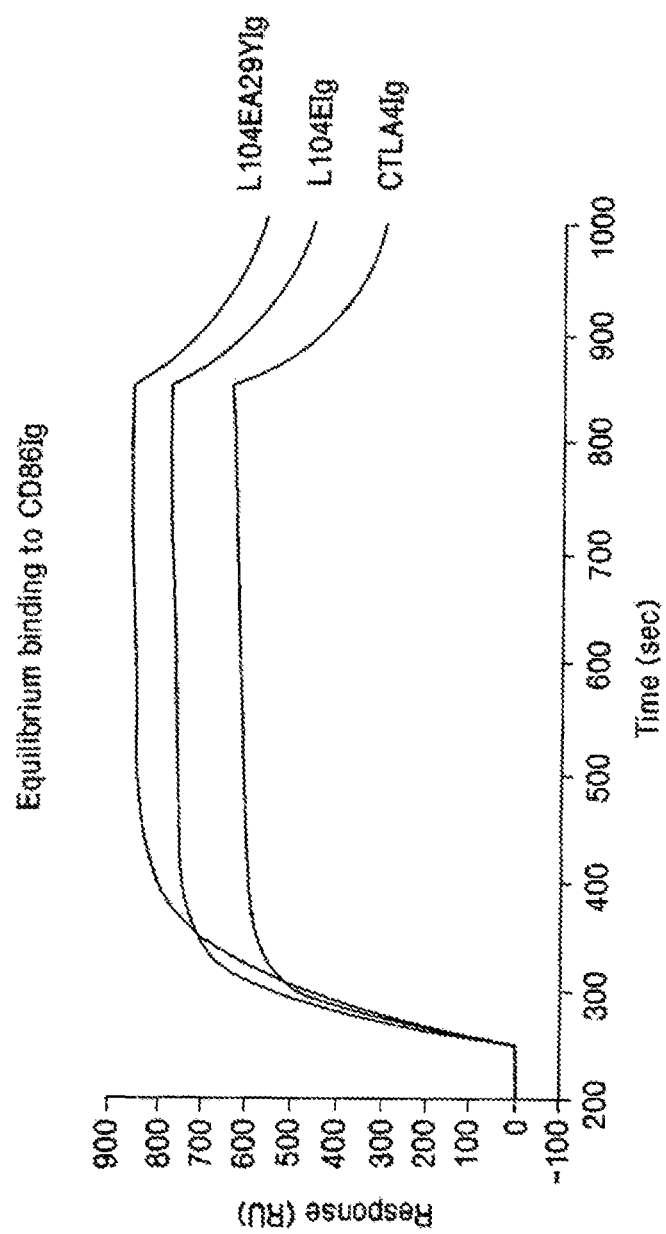
FIG. 32: A graph showing the equilibrium binding analysis of L104EA29YIg, L104EIg, and wild-type CTLA4Ig to CD86Ig.

The effects of L104EA29YIg and CTLA4Ig on monkey mixed lymphocyte response (MLR) are shown in FIG. 31. Peripheral blood mononuclear cells (PBMC'S; $3.5 \times 10^4$ cells/well from each monkey) from 2 monkeys were purified over lymphocyte separation medium (LSM) and mixed with 2 μg/ml phytohemagglutinin (PHA). The cells were stimulated 3 days then pulsed with radiolabel 16 hours before harvesting. L104EA29YIg inhibited monkey T cell proliferation better than CTLA4Ig.

TABLE I

| Immobilized Protein | Analyte | $k_{on}$ (×10$^5$) M$^{-1}$ S$^{-1}$ | $k_{off}$ (×10$^{-3}$) S$^{-1}$ | $K_d$ nM |
|---|---|---|---|---|
| CD80Ig | CTLA4Ig | 3.44 ± 0.29 | 2.21 ± 0.18 | 6.51 ± 1.08 |
| CD80Ig | L104EIg | 3.02 ± 0.05 | 1.35 ± 0.08 | 4.47 ± 0.36 |
| CD80Ig | L104EA29YIg | 2.96 ± 0.20 | 1.08 ± 0.05 | 3.66 ± 0.41 |
| CD80Ig | CTLA4X$_{C120S}$ | 12.0 ± 1.0 | 230 ± 10 | 195 ± 25 |
| CD80Ig | L104EA29YX$_{C120S}$ | 8.3 ± 0.26 | 71 ± 5 | 85.0 ± 2.5 |
| CD86Ig | CTLA4Ig | 5.95 ± 0.57 | 8.16 ± 0.52 | 13.9 ± 2.27 |
| CD86Ig | L104EIg | 7.03 ± 0.22 | 4.26 ± 0.11 | 6.06 ± 0.05 |
| CD86Ig | L104EA29YIg | 6.42 ± 0.40 | 2.06 ± 0.03 | 3.21 ± 0.23 |
| CD86Ig | CTLA4X$_{C120S}$ | 16.5 ± 0.5 | 840 ± 55 | 511 ± 17 |
| CD86Ig | L104EA29YX$_{C120S}$ | 11.4 ± 1.6 | 300 ± 10 | 267 ± 29 |

Equilibrium and apparent kinetic constants are given in the following Table (values are means±standard deviation from three different experiments).

TABLE II

Effects of Mutagenesis

| Mutagenesis Site | No Apparent Effect | Slow "on" rate/ slow "off" rate | Reduced ligand binding |
|---|---|---|---|
| S25 | | + | |
| P26 | + | | |
| G27 | + | | |
| K28 | + | | |
| A29 | | + | |
| T30 | | + | |
| E31 | | | + |
| R33 | | | + |
| K93 | | + | |
| L96 | | + | |
| M97 | | | + |
| Y98 | | | + |
| P99 | | | + |
| P100 | | | + |
| P101 | | | + |
| Y102 | | | + |
| Y103 | | + | |
| L104 | | + | |
| G105 | | + | |
| I106 | + | | |
| G107 | + | | |
| Q111 | + | | |
| Y113 | + | | |
| I115 | + | | |

The effect on CD86Ig binding by mutagenesis of CTLA4Ig at the sites listed was determined by SPR, described, supra. The predominant effect is indicated with a "+" sign.

Example 3

The following provides a description of phase II clinical studies of human patients administered soluble CTLA4 mutant molecule L104EA29YIg (also known as LEA29Y or LEA) or CTLA4Ig, to relieve at least one symptom associated with rheumatoid arthritis, including reducing: joint swelling, joint tenderness, inflammation, morning stiffness, and pain. The CTLA4Ig molecule used herein begins with methionine at position +1 (or alternatively with alanine at position −1) and ends with lysine at position +357 as shown in FIG. 24. DNA encoding an embodiment of the CTLA4Ig molecule has been deposited as ATCC® 68629. The L104EA29YIg molecule used herein begins with methionine at position +1 (or alternatively with alanine at position −1) and ends with lysine at position +357 as shown in FIG. 19. DNA encoding an embodiment of the L104EA29YIg molecule has been deposited as ATCC® PTA 2104.

Additionally, the following provides a description of human patients administered L104EA29YIg or CTLA4Ig to relieve at least one biological surrogate marker associated with rheumatoid arthritis, including reducing erythrocyte sedimentation rates, and serum levels of C-reactive protein and/or IL2 receptor.

Patient Cohorts

A total of 214 patients, including 54 males and 160 females, participated in the study (FIGS. 1A and 1B). The patients at baseline had a mean disease duration of 3.4 (±2.0) years and had failed at least one Disease Modifying Antirheumatic Drug (DMARD). Stable Nonsteroidal Anti-inflammatory Drugs (NSAIDS) or steroids 10 mg/day) were permitted and concomitant DMARDS were prohibited. The patients were randomized into groups of 25 to 32 patients per treatment group. 32 patients received a placebo, 92 received L104EA29YIg, and 90 received CTLA4Ig. The patients who followed protocol guidelines and did not discontinue before Day 57 received a total of 4 intravenous infusions, one infusion each on Days 1, 15, 29, and 57. All patients were evaluated on Days 1, 15, 29, 43, 57, 71, and 85. The doses administered included 0.5, 2.0, or 10.0 mg/kg of L104EA29YIg (denoted as LEA.5, LEA2 and LEA10, respectively in FIGS. 1A-1E) or of CTLA4Ig (denoted as CTLA.5, CTLA2 and CTLA10, respectively in FIGS. 1A-1E).

All subjects were monitored for peri-infusional adverse events and global safety by answering a questionnaire listing potential adverse events. The patients were questioned about potential adverse events that may have occurred within 24 hours post-infusion. In addition, the patients were encouraged to spontaneously report any adverse events that they experienced. The physicians routinely monitored laboratory samples from the patients for abnormalities in blood chemistry and hematology, e.g., assessed the levels of inflammatory response mediators such as cytokines (TNF, IL-6), tryptase and complement. The primary endpoint was the proportion of subjects meeting the ACR 20 criteria on Day 85.

Storage of Test Material

The CTLA4Ig and L104EA29YIg were supplied in single-use glass vials containing 200 mg/vial of CTLA4Ig or 100 mg/vial of L104EA29YIg, respectively. Prior to infusion, the CTLA4Ig and L104EA29YIg were diluted to a final concentration of 25 mg/ml with sterile water for injection (SWFI).

Administration Protocol

All infusions were administered intravenously over 1 hour (FIGS. 1-17). All subjects received at least one infusion of study medication.

Group 1: 32 patients, CTLA4Ig or L104EA29YIg matching placebo.
Group 2: 26 patients; dosage 0.5 mg/kg of CTLA4Ig.
Group 3: 32 patients; dosage 2.0 mg/kg of CTLA4Ig.
Group 4: 32 patients; dosage 10.0 mg/kg of CTLA4Ig.
Group 5: 32 patients; dosage 0.5 mg/kg of L104EA29YIg.
Group 6: 29 patients; dosage 2.0 mg/kg of L104EA29YIg.
Group 7: 31 patients; dosage 10.0 mg/kg of L104EA29YIg.

Clinical Monitoring

Patients were evaluated for baseline symptoms of disease activity prior to receiving any infusions. These baseline evaluations included: joint swelling, joint tenderness, inflammation, morning stiffness, disease activity evaluated by patient and physician as well as disability evaluated by Health Questionnaire Assessment (HAQ) (reported as a physical function score in FIG. 1C), and pain (FIGS. 1A-1D). Additionally, the baseline evaluations included erythrocyte sedimentation rates (ESR), and serum levels of C-reactive protein (CRP) and soluble IL-2 receptor (IL-2r) (FIGS. 1C and 1D).

The clinical response studies were based on the criteria established by the American College of Rheumatology (ACR). A subject satisfied the ACR20 criterion if there was a 20 percent improvement in tender and swollen joint counts and 20 percent improvement in three of the five remaining symptoms measured, such as patient and physician global disease changes, pain, disability, and an acute phase reactant (Felson, D. T. et al., *Arthritis Rheum.*, 36:729-740 (1993); Felson, D. T. et al., *Arthritis Rheum.*, 38:1-9 (1995)). Similarly, a subject satisfied the ACR50 or ACR70 criterion if there was a 50 or 70 percent improvement, respectively, in tender and swollen joint counts and 50 or 70 percent improvement, respectively, in three of the five remaining symptoms measured, such as patient and physician global disease changes, pain, physical disability, and an acute phase reactant such as CRP or ESR.

Biomarkers

Potential biomarkers of disease activity (rheumatoid factor, CRP, ESR, soluble IL-2R, soluble ICAM-1, soluble E-selectin, and MMP-3) were also assessed. Validated enzyme immunoassay (EIA) methods were used to determine the serum concentration of IL-2sRα, sICAM-1, sE-selectin and MMP-3. TNFα and IL-6 were assessed at infusion pre and 2 hours post, if necessary.

IL-2sRα, sICAM-1, and sE-selectin were measured using commercially available colorimetric EIA kits from R&D Systems, Inc. (Minneapolis, Minn.). The lower and upper limits of quantitation were 312-20,000 pg/mL, 40-907 ng/mL and 10-206 ng/mL, respectively. The inter-assay coefficient of variation ranged from 4.48-8.4%, 3.8-5.0% and 5.5-9.0% respectively. According to the kit manufacturer, normal serum values range from 676-2,132 pg/mL, respectively.

MMP-3 was measured using a commercially available colorimetric EIA kit from Amersham Pharmacia Biotech (Piscataway, N.J.). The lower and upper limits of quantitation were 30-7,680 ng/mL. The inter-assay coefficient of variation ranged from 6.3-10.6%. According to the kit manufacturer, normal serum values range from 28-99 ng/mL.

IL-6 and TNFα were measured using commercially available chemiluminescent EIA kits from R&D Systems, Inc. (Minneapolis, Minn.). The lower and upper limits of quantitation were 0.3-3,000 pg/mL and 0.7-7,000 pg/mL, respectively. The inter-assay coefficient of variation ranged from 3.1-5.7% and 6.4-20.7%, respectively. According to the kit manufacturer, normal serum values range from <0.3-12 pg/mL and <0.7-7.5 pg/mL.

Antibody Testing

Serum samples were obtained for assessment of drug-specific antibodies prior to dosing on Day 1, and approximately on Days 15, 29, 57, 85 and 169. Due to high, preexisting titers directed to the immunoglobulin (Ig) portion of the molecule, specific antibody formation against CTLA4Ig and LEA29Y without Ig constant regions was also assessed.

96-well IMMULON® II ELISA plates (Dynex, Chantilly, Va.) were coated with CTLA4Ig, CTLA4Ig without the Ig constant regions, LEA29Y, or LEA29Y without the Ig constant regions at 2, 4, 2, or 1 µg/ml in phosphate buffered saline (PBS), respectively, and incubated overnight at 2-8° C. The plates were washed with PBS containing 0.05% Tween 20 and blocked for 1 hour at 37° C. with PBS containing 1% bovine serum albumin (BSA). The plates were then washed and serial dilutions of the test sera or quality control (QC) sera were added to the appropriate wells and incubated for 2 hours at 37° C. Sera was diluted threefold in PBS with 0.25% BSA and 0.05% Tween 20 starting at a 1:10 dilution. Plates were washed and an alkaline-phosphatase-conjugated goat anti-human kappa and lambda (Southern Biotechnology Associates, Inc., Birmingham, Ala.) antibody cocktail was added. Following a 1-hour incubation at 37° C., the plates were washed and 1 mg/ml para-nitrophenyl phosphate in diethanolamine buffer was added to each well. After 30 minutes at 25° C., the reactions were stopped with 3N NaOH and the absorbance (dual wavelength: 405 nm and 550 nm) was recorded. Results were expressed as endpoint titer (EPT), defined as the reciprocal of the highest dilution that resulted in an absorbance reading fivefold greater than or equal to the mean plate-background absorbance. Plate background was determined as the absorbance measurement recorded in the absence of serum. Values were considered positive for seroconversion if they were at least two serial dilutions (ninefold) or greater relative to predose EPT values. Serum QC samples positive for either CTLA4Ig- or LEA29Y-specific antibodies were generated from immunized monkeys. An aliquot of the appropriate QC sample was assayed during each analytical run. Analytical runs were accepted only when the QC samples were within the assay acceptance criteria.

Results

CTLA4Ig and L104EA29YIg were generally well-tolerated at all dose-levels. Peri-infusional adverse events were similar across all dose groups, with the exception of headaches. Headache response of patients on Day 85 increased dose-dependently 23%, 44%, and 53% in CTLA4Ig-treated patients, and 34%, 45%, and 61% in L104EA29YIg-treated patients, at 0.5, 2.0, and 10.0 mg/kg respectively. In contrast, 31% of the patients administered placebos experienced headaches.

The percent of patients that discontinued from the clinical study due to arthritis flares and other adverse events is summarized in FIG. 2. A much higher percentage of patients on placebo discontinued treatment due to arthritis flare. The CTLA4Ig treated patients discontinued treatment less with increasing doses. Very few patients treated with L104EA29YIg discontinued treatment. These results indicate a good inverse dose-dependent response for CTLA4Ig, and a stronger therapeutic response with L104EA29YIg therapy.

Figure 3B:
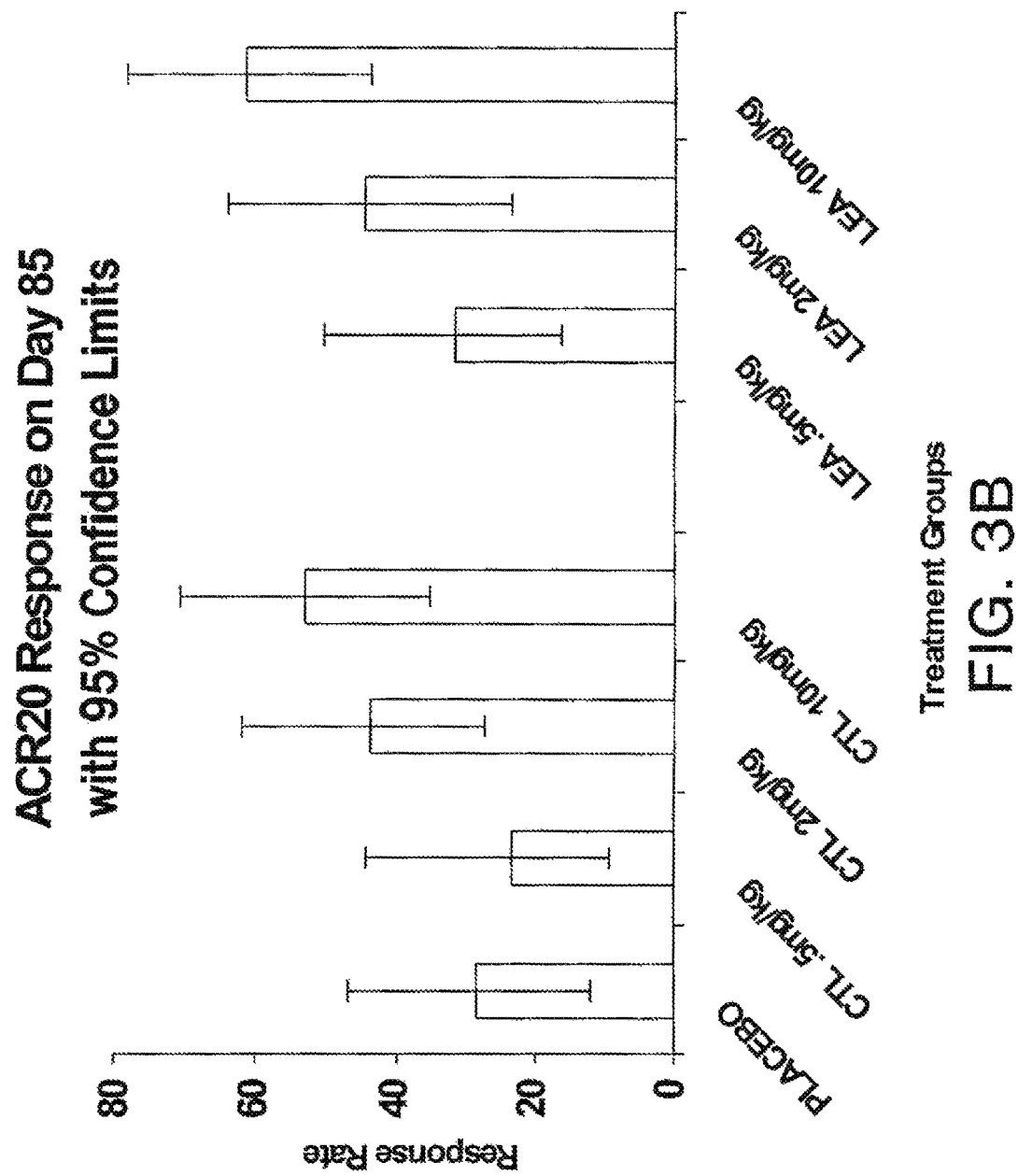
FIG. 3B: ACR-20 responses at Day 85, including placebo response, as described in Example 3, infra. ACR-20 response with 95% confidence limits.
Figure 3C:
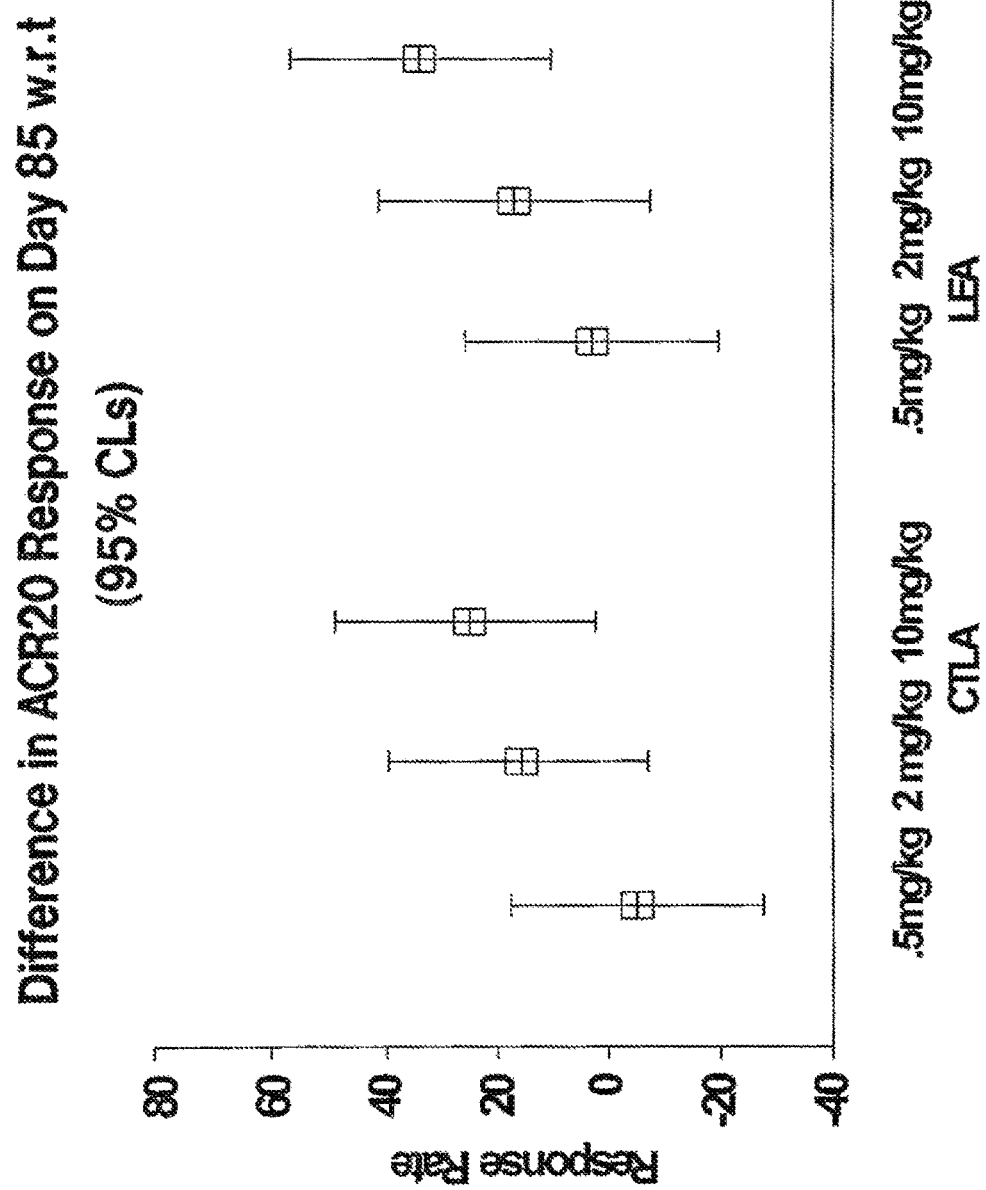
FIG. 3C: ACR-20 responses at Day 85 as described in Example 3, infra. Difference in ACR-20 response with respect to 95% confidence intervals.

The ACR-20, -50, and -70 responses of patients treated with CTLA4Ig, L104EA29YIg, or placebo at Day 85 are summarized in FIG. 3A. Similarly, FIGS. 3B and 3C describe the ACR-20 responses with 95% confidence limits. The responses appear to be dose-dependent with a clear significant response at 10 mg/kg per body weight of the patient.

Figure 4B:
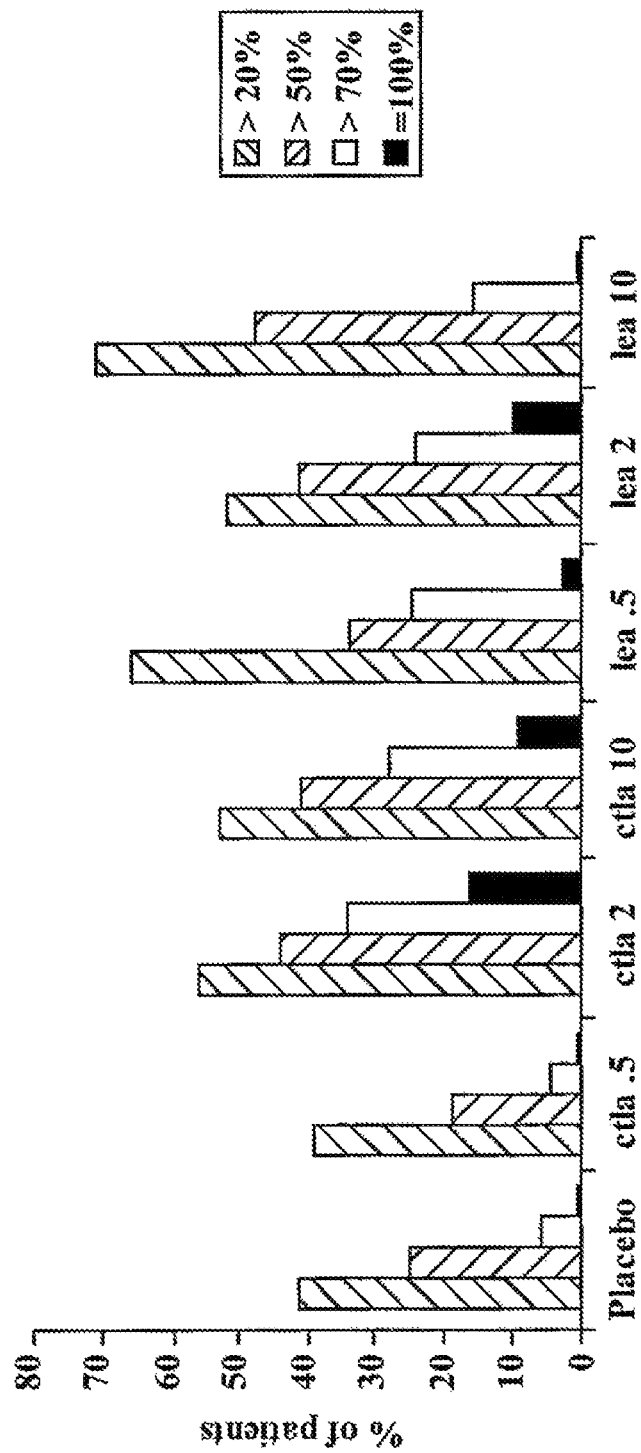
FIG. 4B: Clinical responses (in percentage improvement) in swollen and tender joint count in percentage of patients at Day 85 as described in Example 3, infra. Change in clinical response in percentage improvement.
Figure 5A:
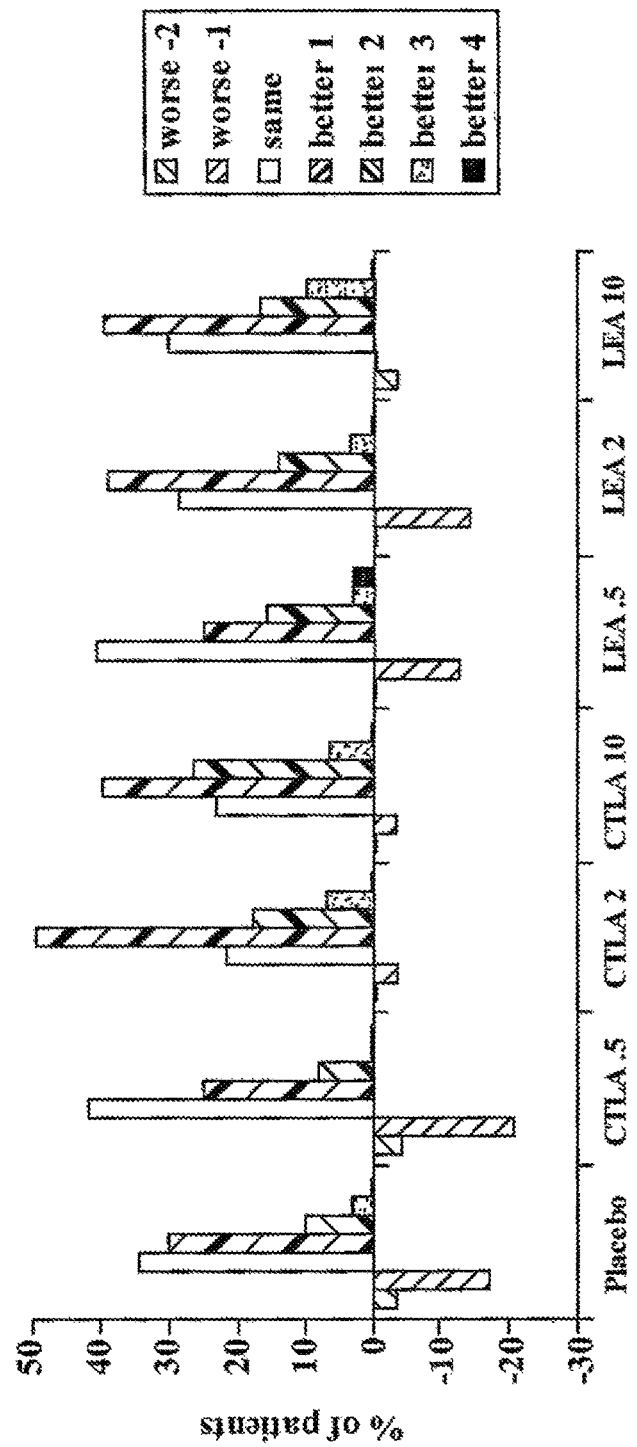
FIG. 5A: Pain response (by Likert scale by mean unit change from baseline) in percentage of patients at Day 85 as described in Example 3, infra. Pain score changes from baseline.
Figure 5B:
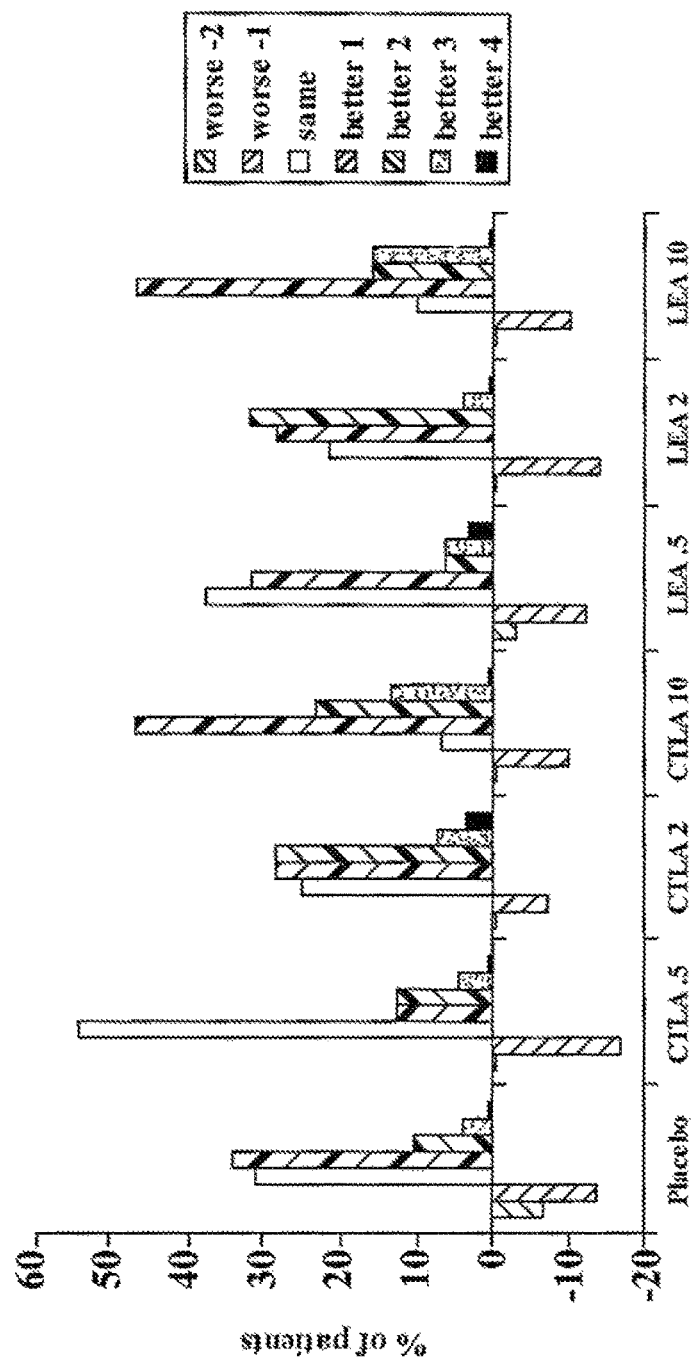
FIG. 5B: Patient global disease changes (by Likert scale by mean unit change from baseline) in percentage of patients at Day 85 as described in Example 3, infra. Patient global disease activity changes.
Figure 5C:
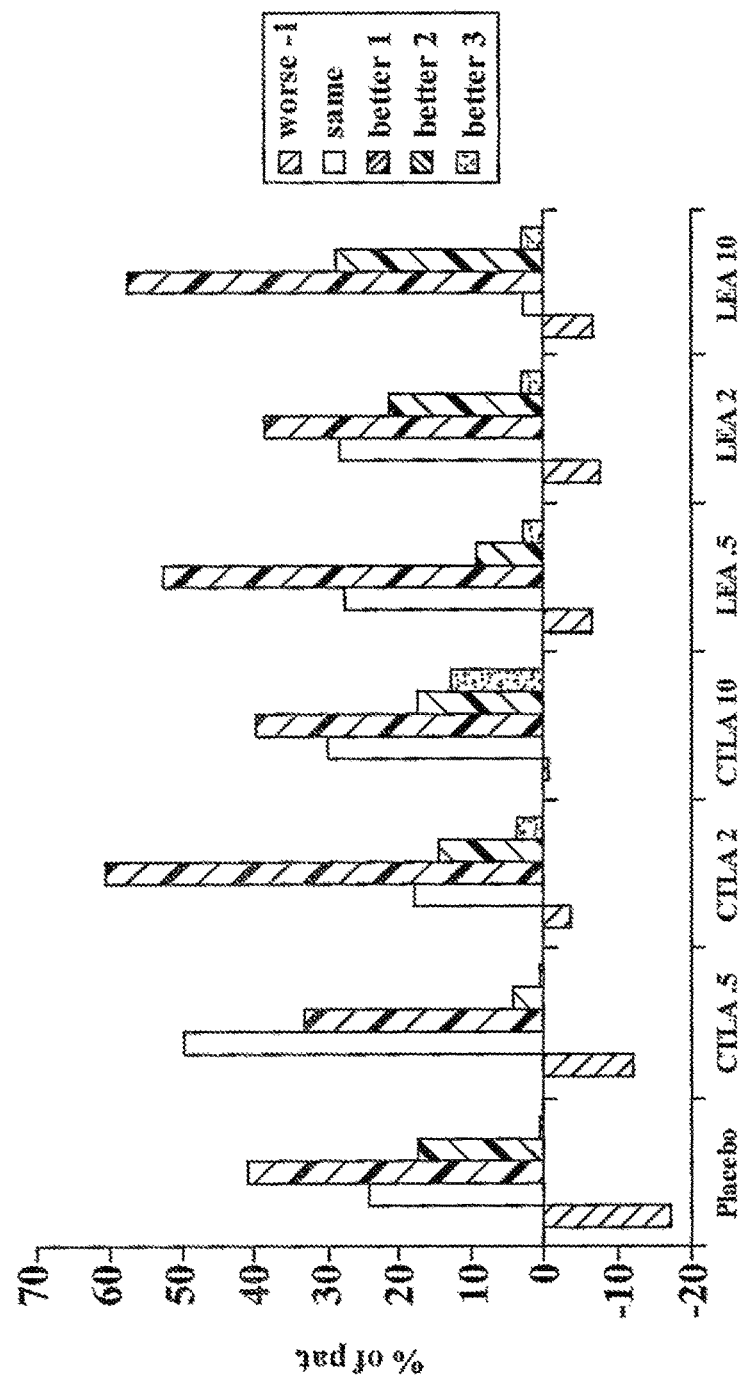
FIG. 5C: Physician global disease changes (by Likert scale by mean unit change from baseline) in percentage of patients at Day 85 as described in Example 3, infra. Physician global disease activity changes.

The percent of patients having reduced swollen and tender joint counts compared to the patients having no response to treatment with CTLA4Ig, L104EA29YIg, or placebo, is shown in FIGS. 4A and 4B. The therapeutic responses appear to be dose-dependent. A larger percentage of patients show improvement of 20, 50, 70, and even 100% in the 2 and 10 mg/kg groups for both products.

The percent of patients having reduced pain, disease activity evaluated by patient and physician mean score units with CTLA4Ig, L104EA29YIg, or placebo, is shown in FIGS. 5A-5D. The therapeutic responses, as monitored by the Likert scale, appear to be dose-dependent in favor of the active treatment groups as compared to placebo on Day 85. The Likert scale is a validated verbal rating scale using adjectives to rank the symptoms ("The American College of Rheumatology Preliminary Core Set of Disease Activity Measures for Rheumatoid Arthritis Clinical Trials", *Arthritis Rheum.*, 36(6):729-740 (June 1993)).

Figure 6B:
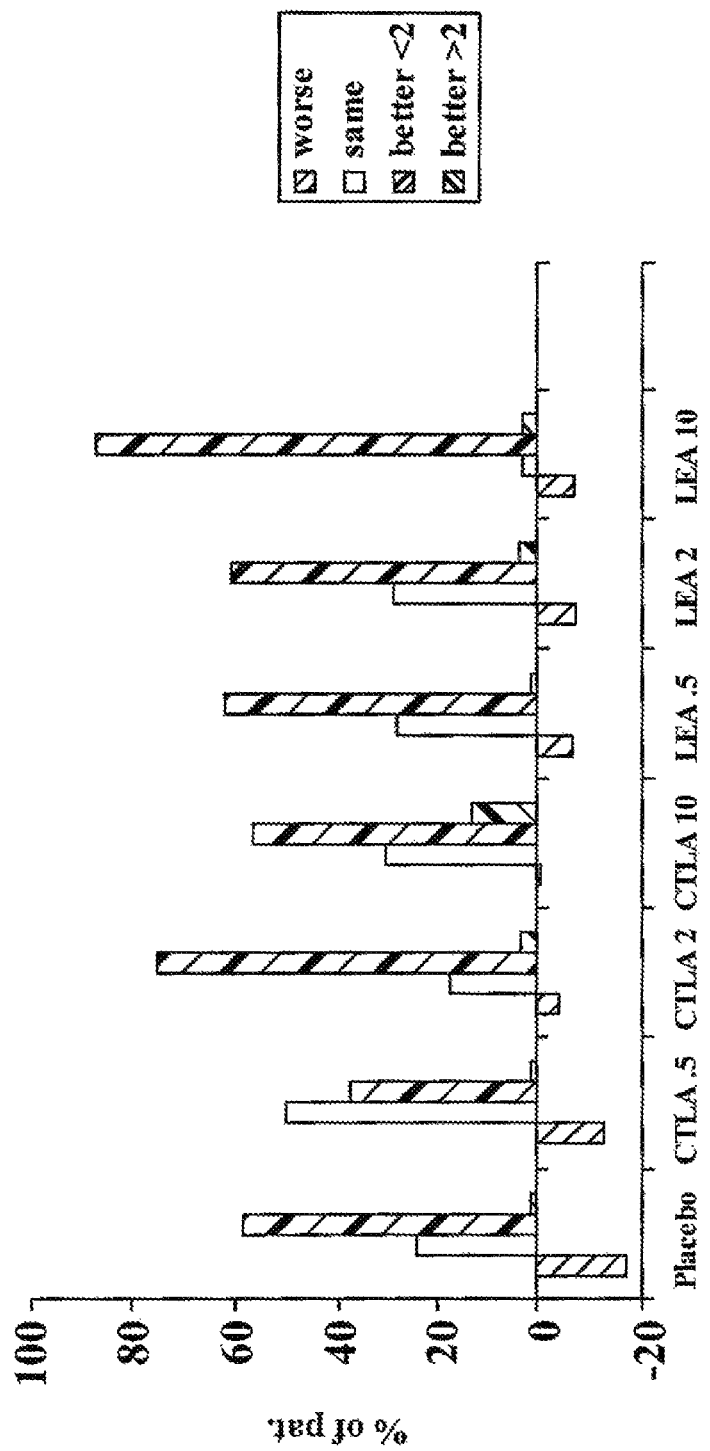
FIG. 6B: Physician global assessment of disease activity change from baseline by range of 2 units at Day 85 as described in Example 3, infra. Disease activity improvement.

The patient and physician assessments of disease activity change from the baseline by at least 2 units, resulting from treatment with CTLA4Ig, L104EA29YIg, or placebo, are shown in FIGS. 6A and 6B. The responses appear to be dose-dependent with more marked improvement for the higher doses of active drugs.

Figure 7A:
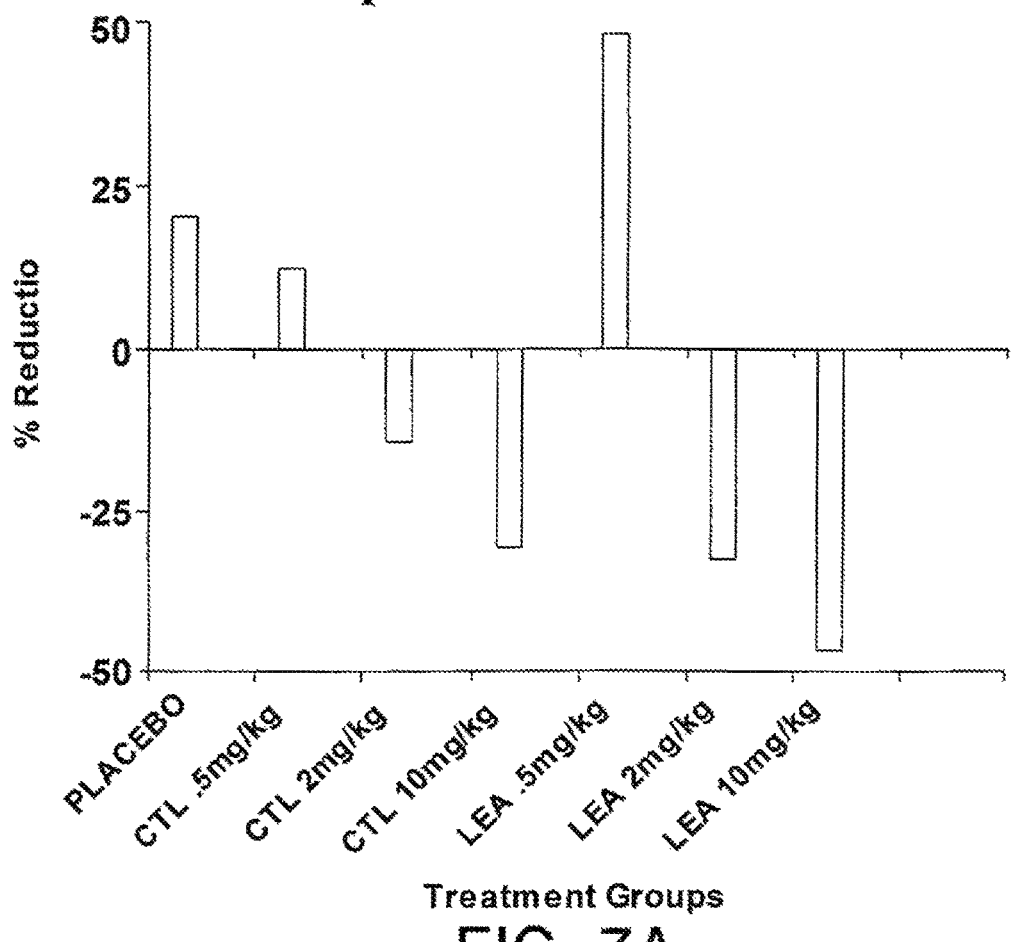
FIG. 7A: Percent reduction in C-reactive protein (CRP) levels at Day 85 as described in Example 3, infra. Percentage reduction in CRP levels from baseline.
Figure 7B:
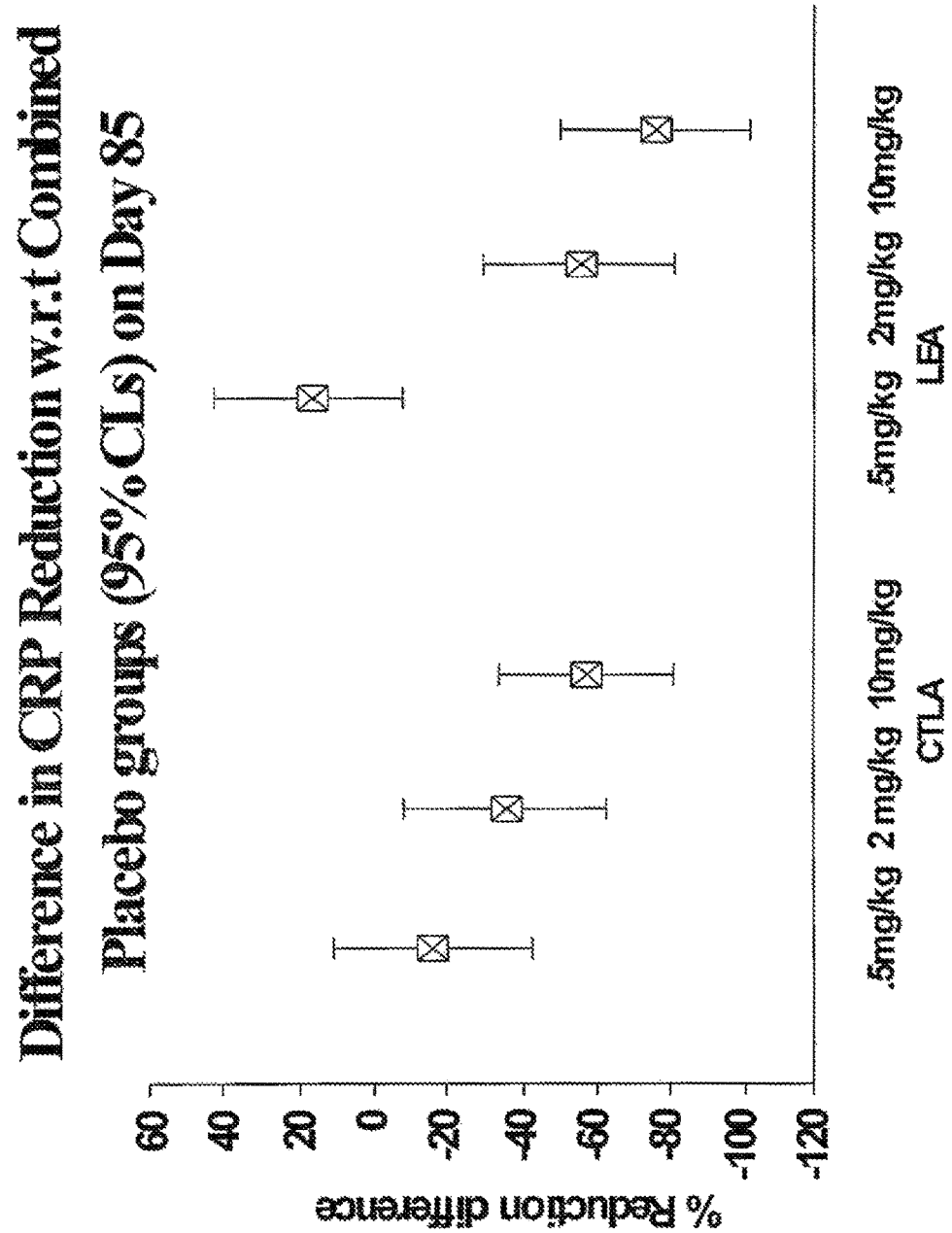
FIG. 7B: Difference in reduction in C-reactive protein (CRP) levels at Day 85 as described in Example 3, infra. Percent reduction difference in CRP levels with 95% confidence intervals.

The percent reduction in C-reactive protein (CRP) levels in patients treated with CTLA4Ig, L104EA29YIg, or placebo, is shown in FIGS. 7A and 7B. The responses appear to be dose-dependent with a clear decrease for the 2 and 10 mg/kg active treatment groups. In addition, FIG. 7B showed that the difference is quite significant compared to placebo with 95% confidence intervals. FIG. 7C shows the changes in serum level changes from baseline at Day 85.

The amount of serum soluble IL-2 receptor in patients treated with CTLA4Ig, L104EA29YIg, or placebo, is shown in FIG. 8. The reduction in soluble IL-2 receptor levels appears to be dose-dependent.

Figure 33B:
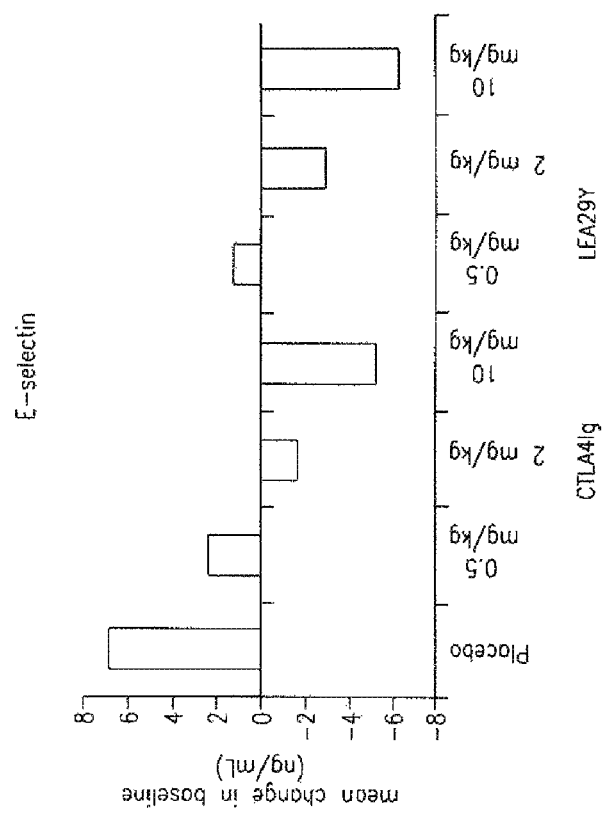
FIGS. 33A and 33B: Reduction in soluble ICAM-1 and soluble E-selectin levels mean change from baseline at Day 85 as described in Example 3, infra.
Figure 33A:
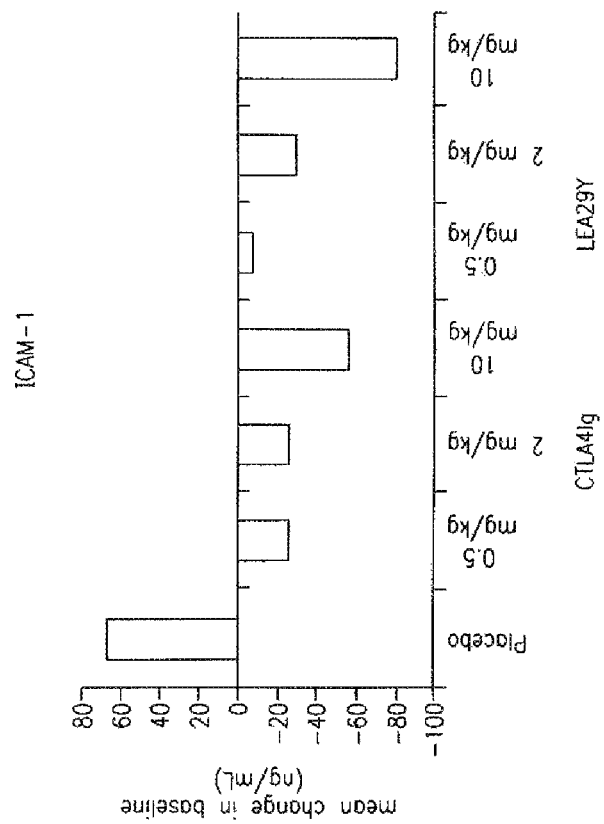
Figure 34:
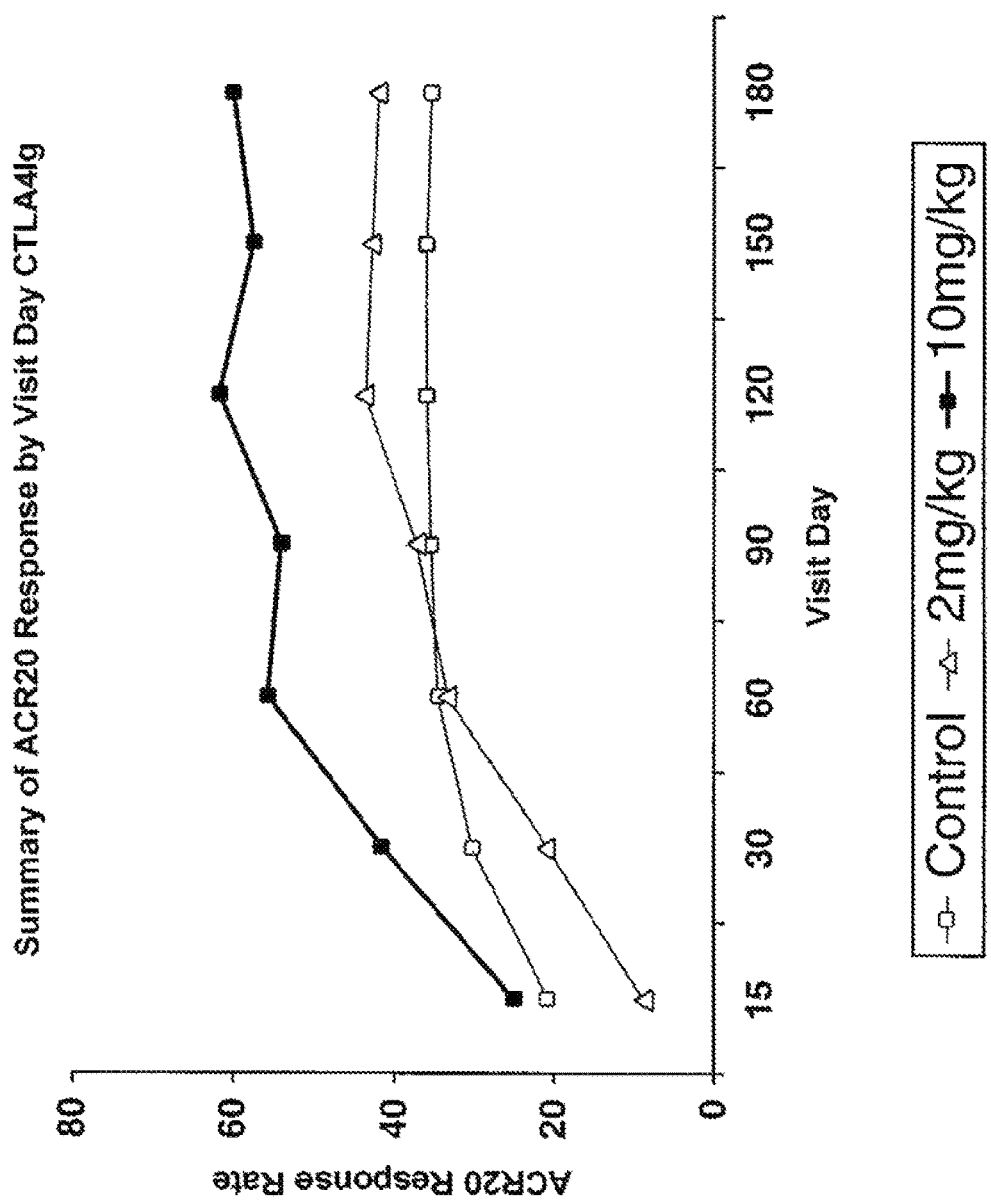
FIG. 34: A graph showing the summary of ACR20 response by visit day in response to methotrexate and CTLA4Ig (2 and 10 mg/kg) therapy, as described in Example 5, infra.
Figure 35:
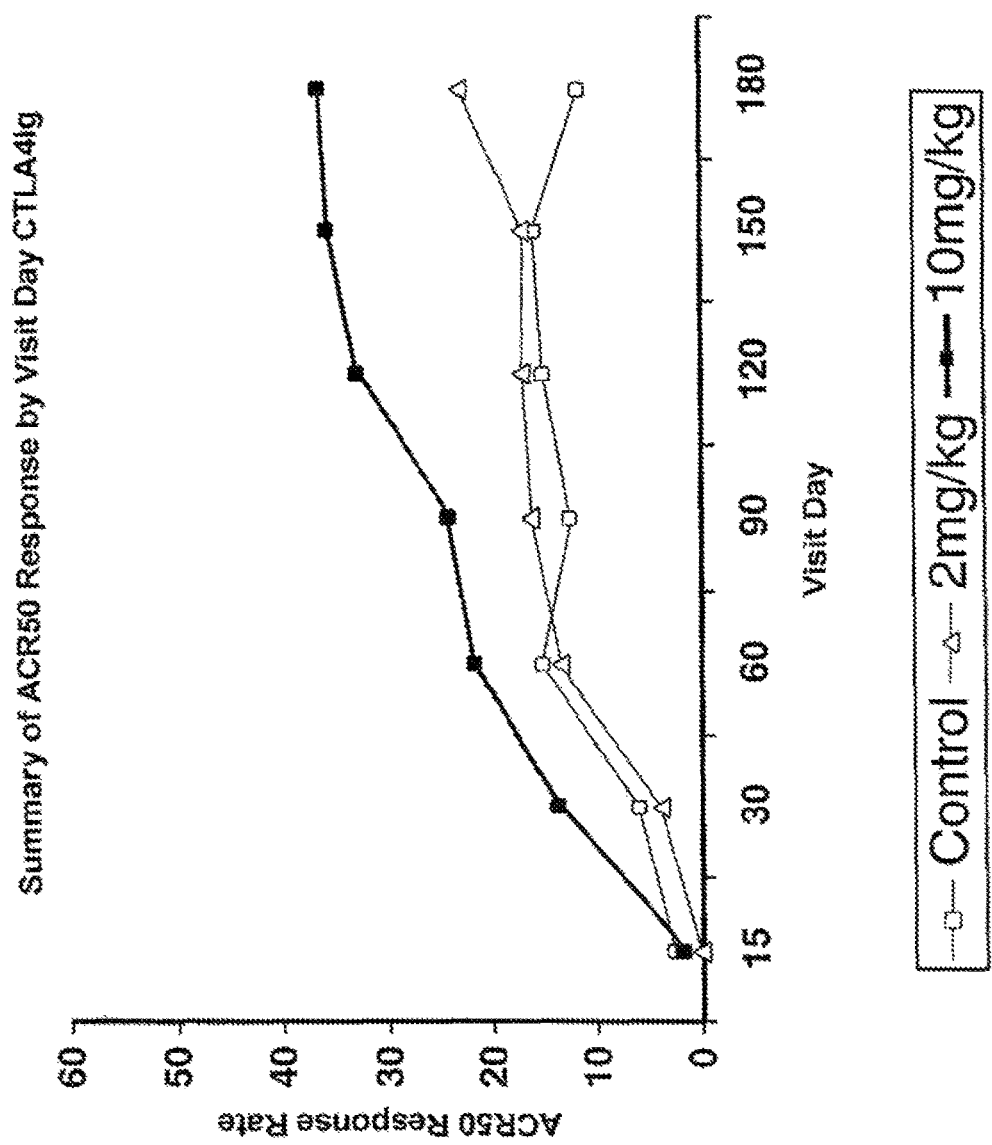
FIG. 35: A graph showing the summary of ACR50 response by visit day in response to methotrexate alone or methotrexate and CTLA4Ig (2 and 10 mg/kg) therapy, as described in Example 5, infra.
Figure 36:
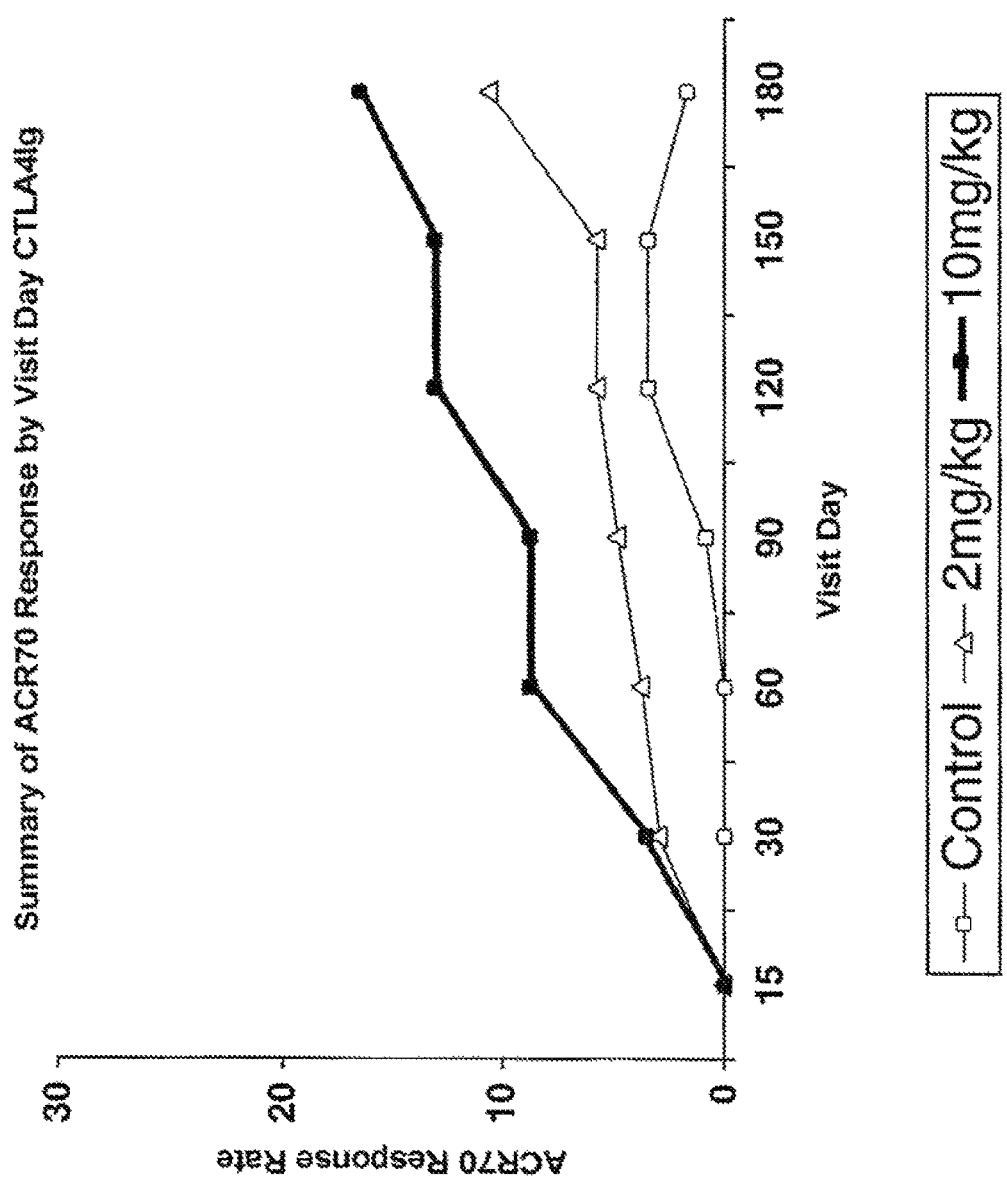
FIG. 36: A graph showing the summary of ACR70 response by visit day in response to methotrexate alone or methotrexate and CTLA4Ig (2 and 10 mg/kg) therapy, as described in Example 5, infra.
Figure 37:
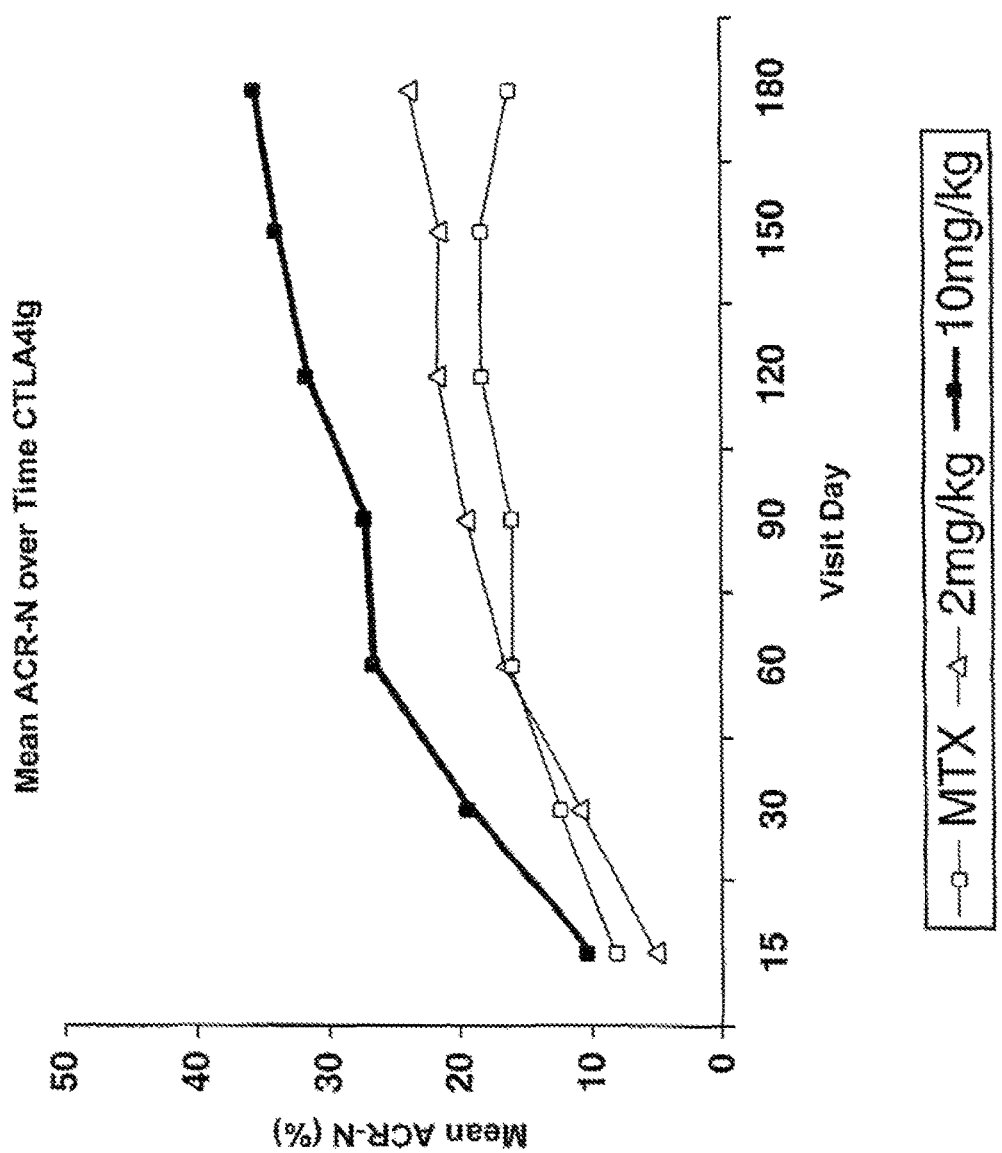
FIG. 37: A graph showing the mean ACR-N over time in response to methotrexate alone or methotrexate and CTLA4Ig (2 and 10 mg/kg) therapy, as described in Example 5, infra.

The amount of serum soluble ICAM-1 and soluble E-selectin in patients treated with CTLA4Ig, L104EA29YIg, or placebo, is shown in FIGS. 33A and 33B. The reduction in soluble ICAM-1 and soluble E-selectin levels appears to be dose-dependent.

Figure 9A:
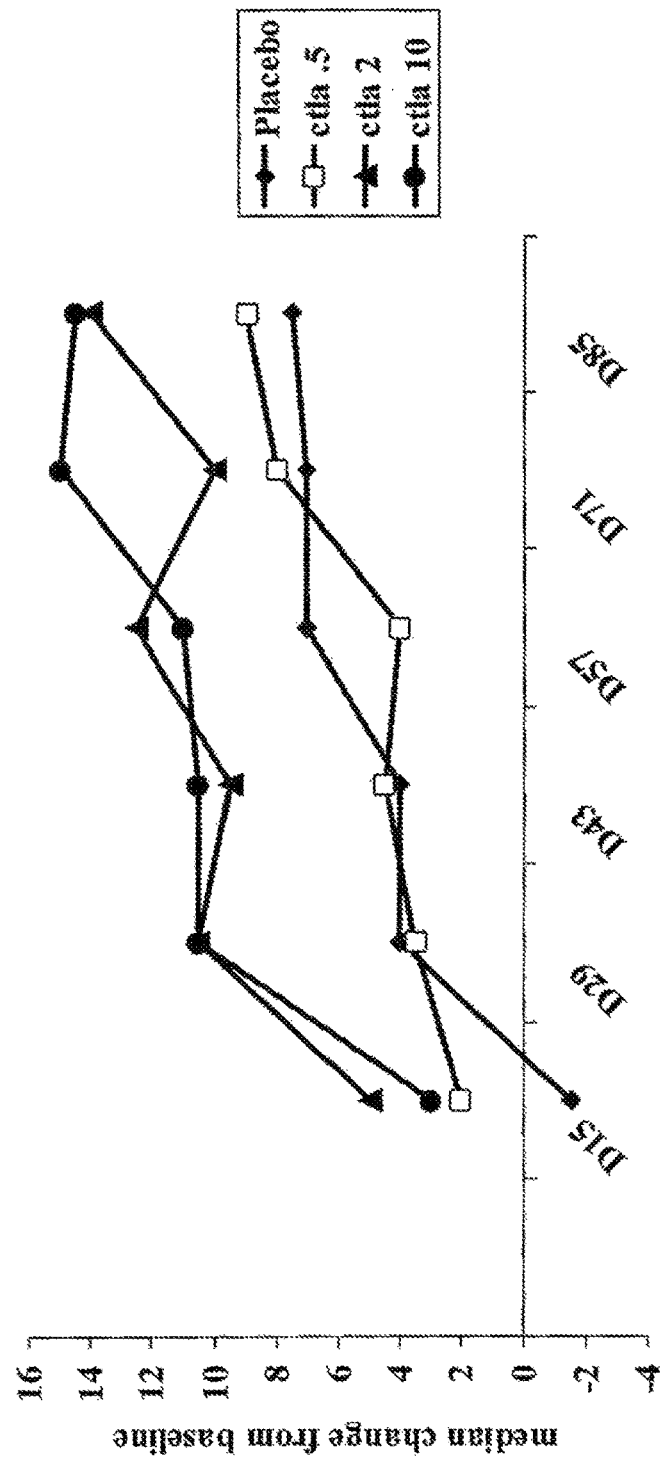
FIG. 9A: The effect of CTLA4Ig on tender joints over time as described in Example 3, infra. Median difference from baseline.
Figure 9B:
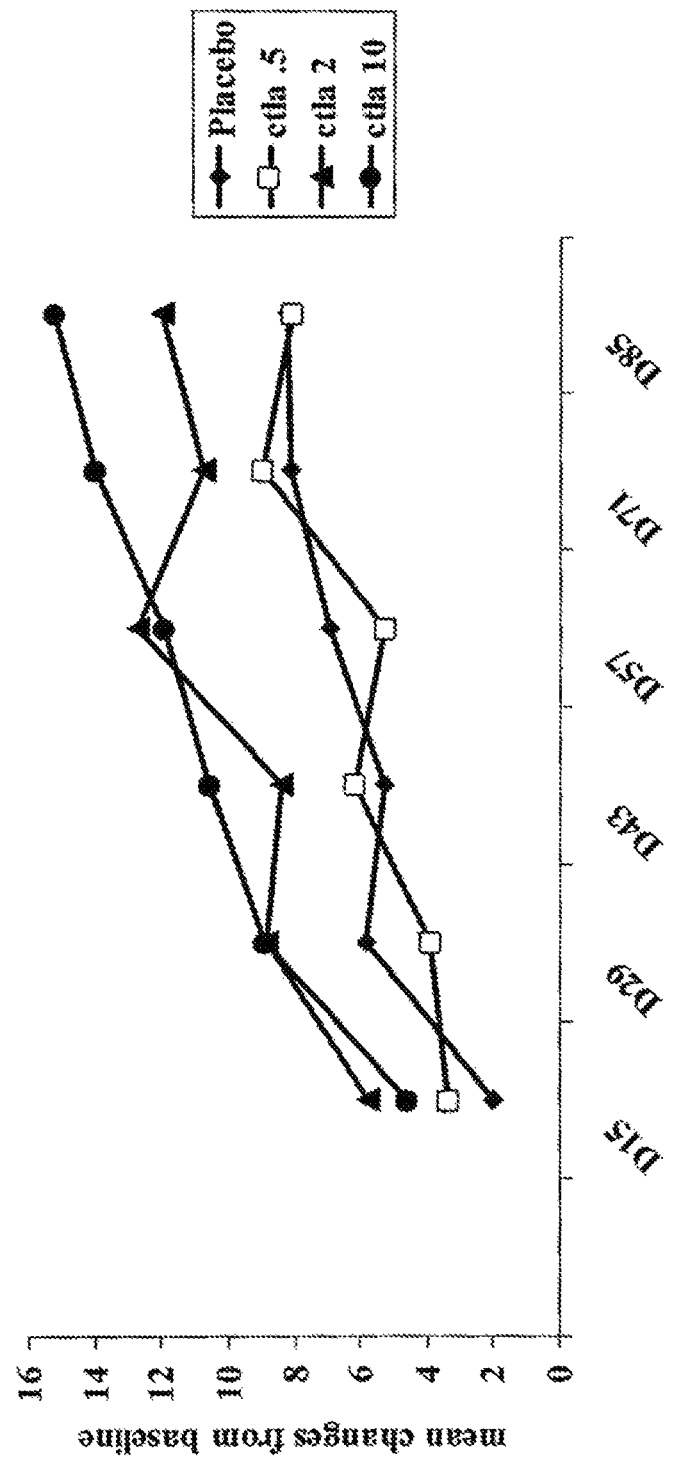
FIG. 9B: The effect of CTLA4Ig on tender joints over time as described in Example 3, infra. Mean difference from baseline.

The median and mean tender joint counts in patients treated with CTLA4Ig or placebo over time are shown in FIGS. 9A and 9B. The change from baseline (e.g., reduction in tender joints) appears to be more important in the 2 and 10 mg/kg treated groups, than in the placebo or 0.5 mg/kg groups.

Figure 10A:
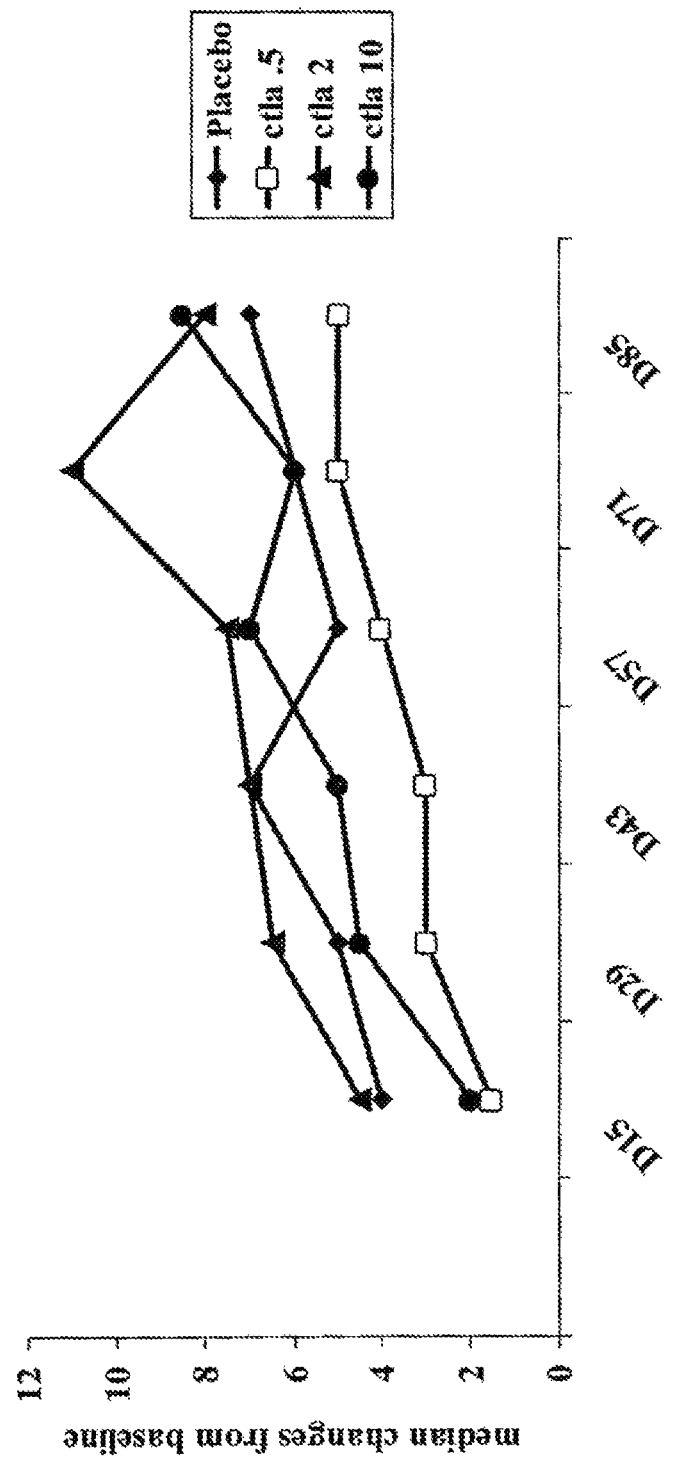
FIG. 10A: The effect of CTLA4Ig on swollen joints over time as described in Example 3, infra. Median difference from baseline.
Figure 10B:
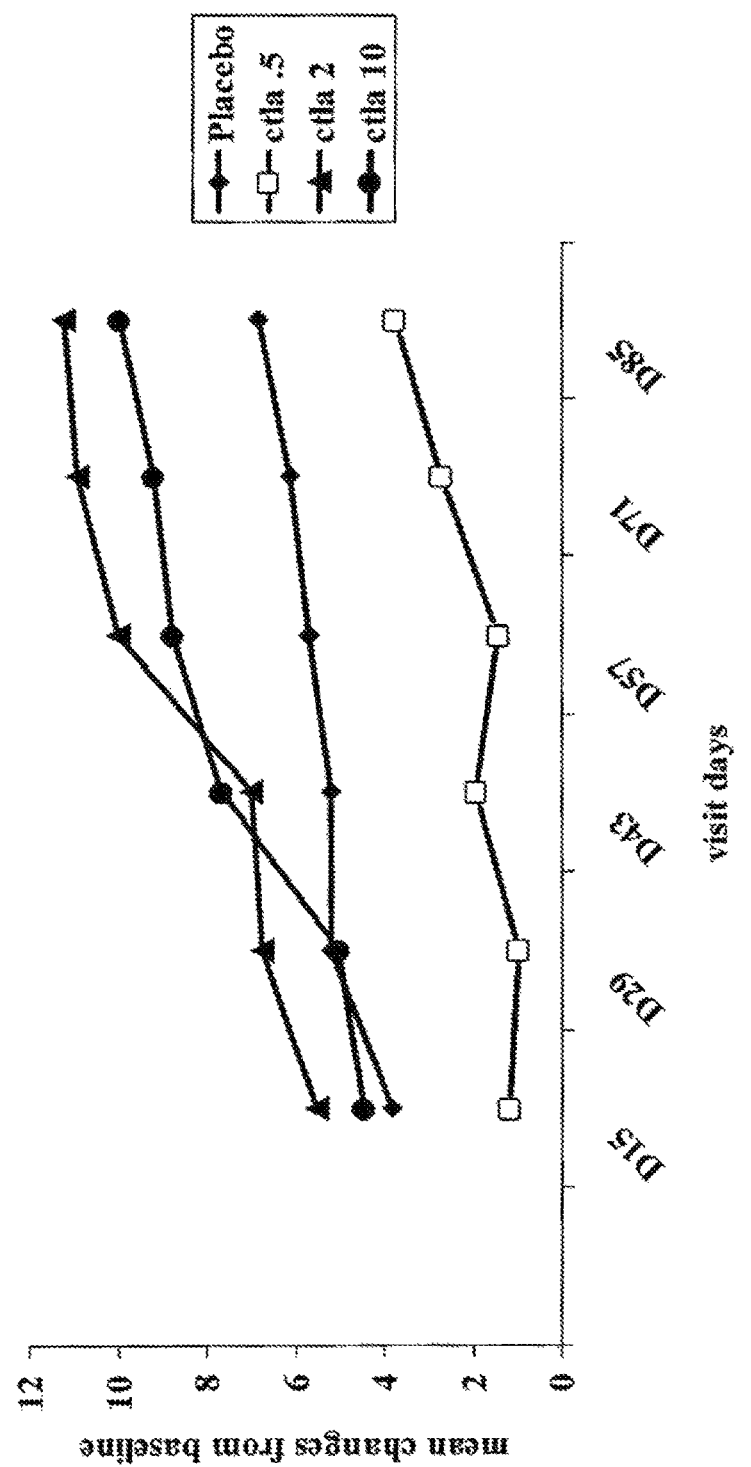
FIG. 10B: The effect of CTLA4Ig on swollen joints over time as described in Example 3, infra. Mean difference from baseline.

The median and mean swollen joint counts in patients treated with CTLA4Ig or placebo over time are shown in FIGS. 10A and 10B. The change from baseline (e.g., reduction in swollen joints) appears to be more important in the 2 and 10 mg/kg treated groups than placebo or 0.5 mg/kg groups.

Figure 11:
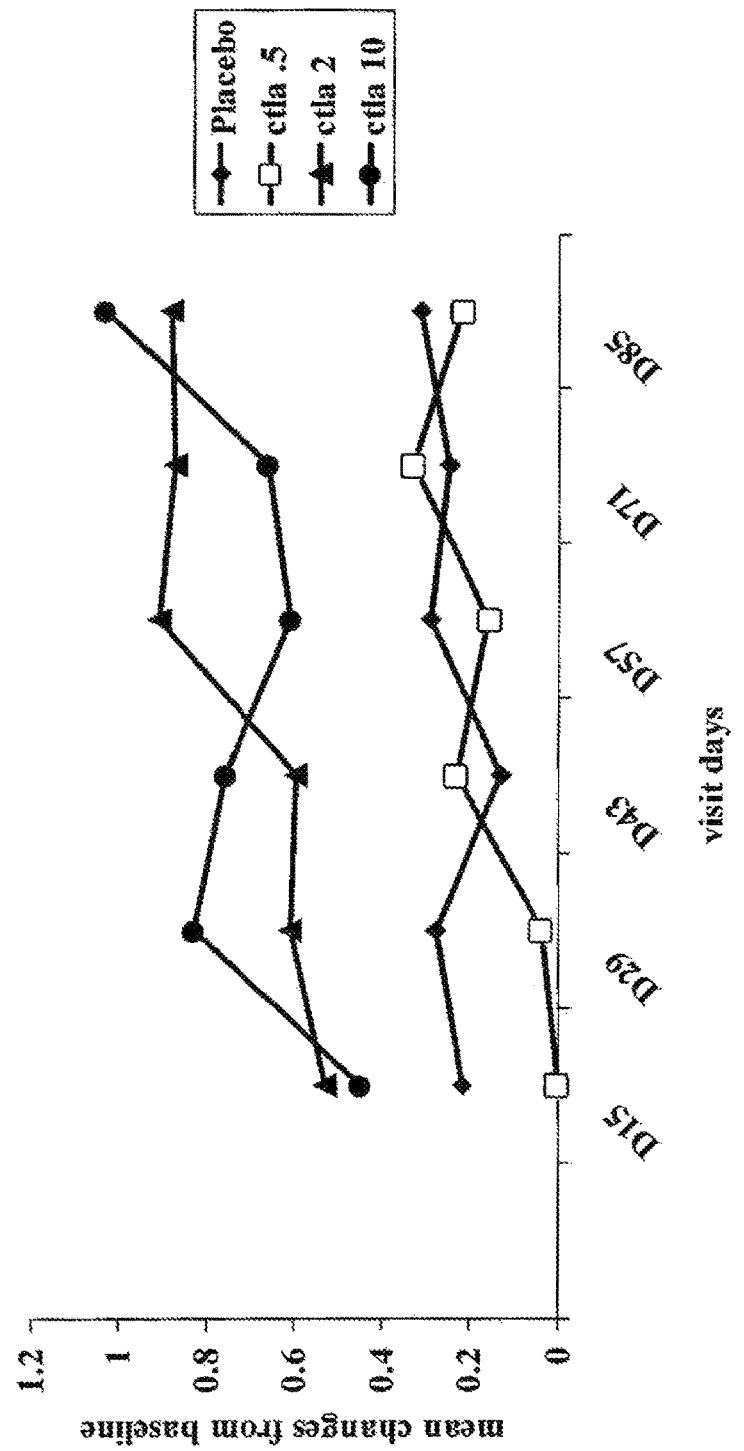
FIG. 11: The effect of CTLA4Ig on pain assessment mean difference from baseline over time as described in Example 3, infra.

The mean pain assessment scores over time in patients treated with CTLA4Ig or placebo are shown in FIG. 11. The change from baseline (e.g., reduction in pain) appears to be more important in the 2 and 10 mg/kg treated groups than placebo or 0.5 mg/kg groups.

Figure 12A:
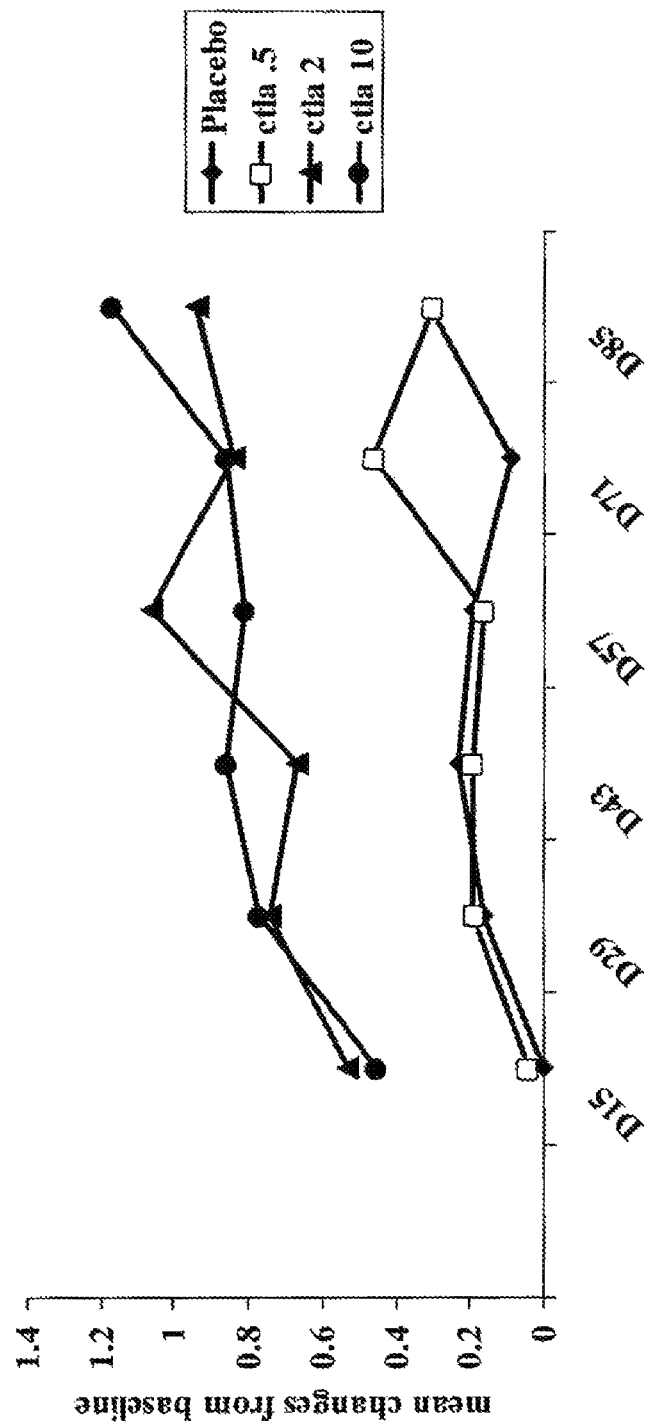
FIG. 12A: The effect of CTLA4Ig on patient assessment of disease activity mean difference from baseline over time as described in Example 3, infra.
Figure 12B:
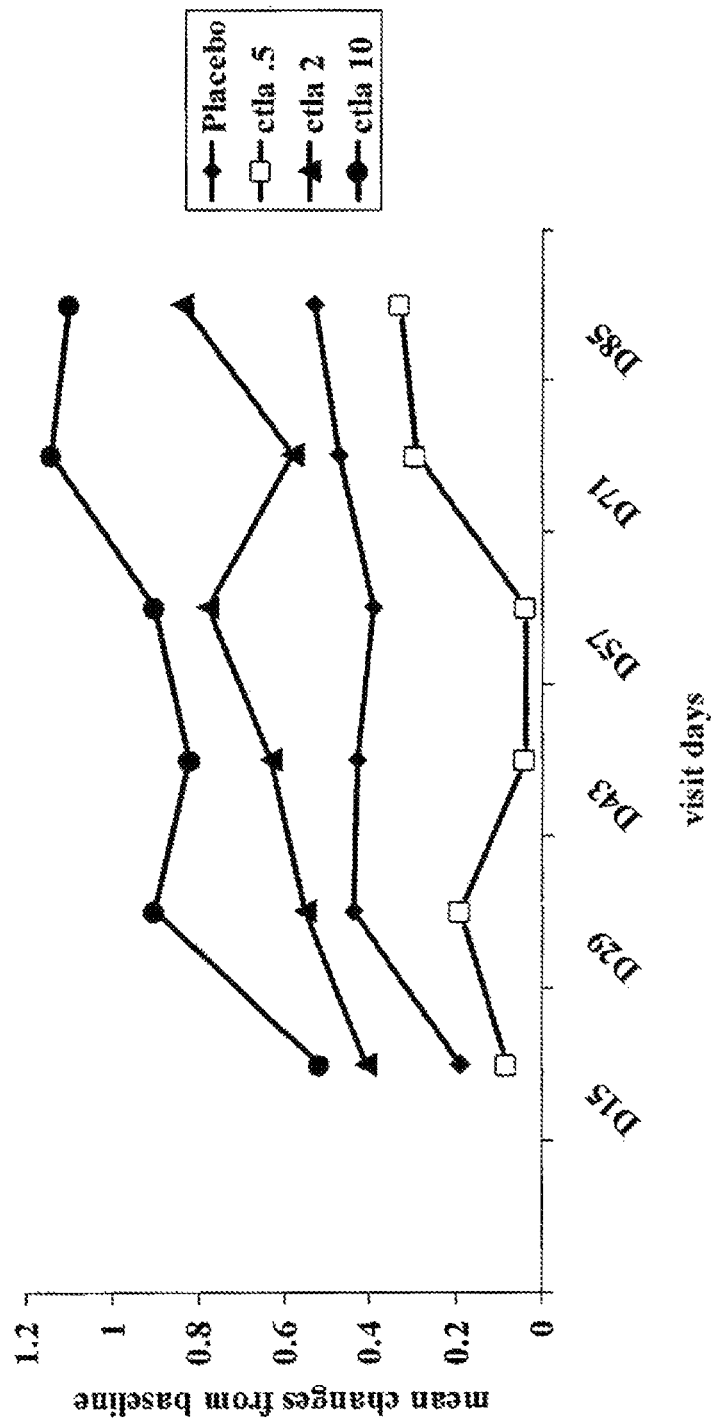
FIG. 12B: The effect of CTLA4Ig on physician assessment of disease activity mean difference from baseline over time as described in Example 3, infra.

The mean disease activity assessment scores assessed by patient or physician in patients treated with CTLA4Ig or placebo over time are shown in FIGS. 12A and 12B. The change from baseline (e.g., reduction in disease activity) appears to be more important in the 2 and 10 mg/kg treated groups than placebo or 0.5 mg/kg groups.

Figure 13A:
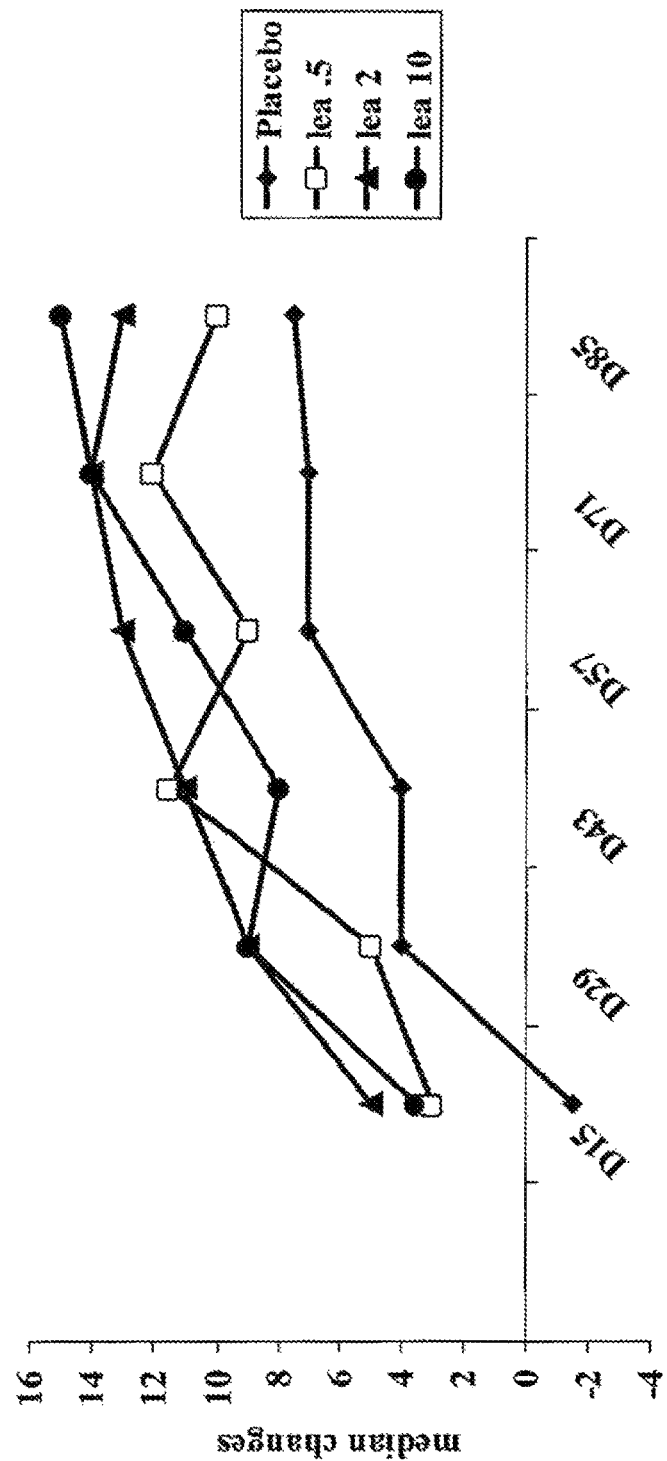
FIG. 13A: The effect of L104EA29YIg on tender joints over time as described in Example 3, infra. Median difference from baseline.
Figure 13B:
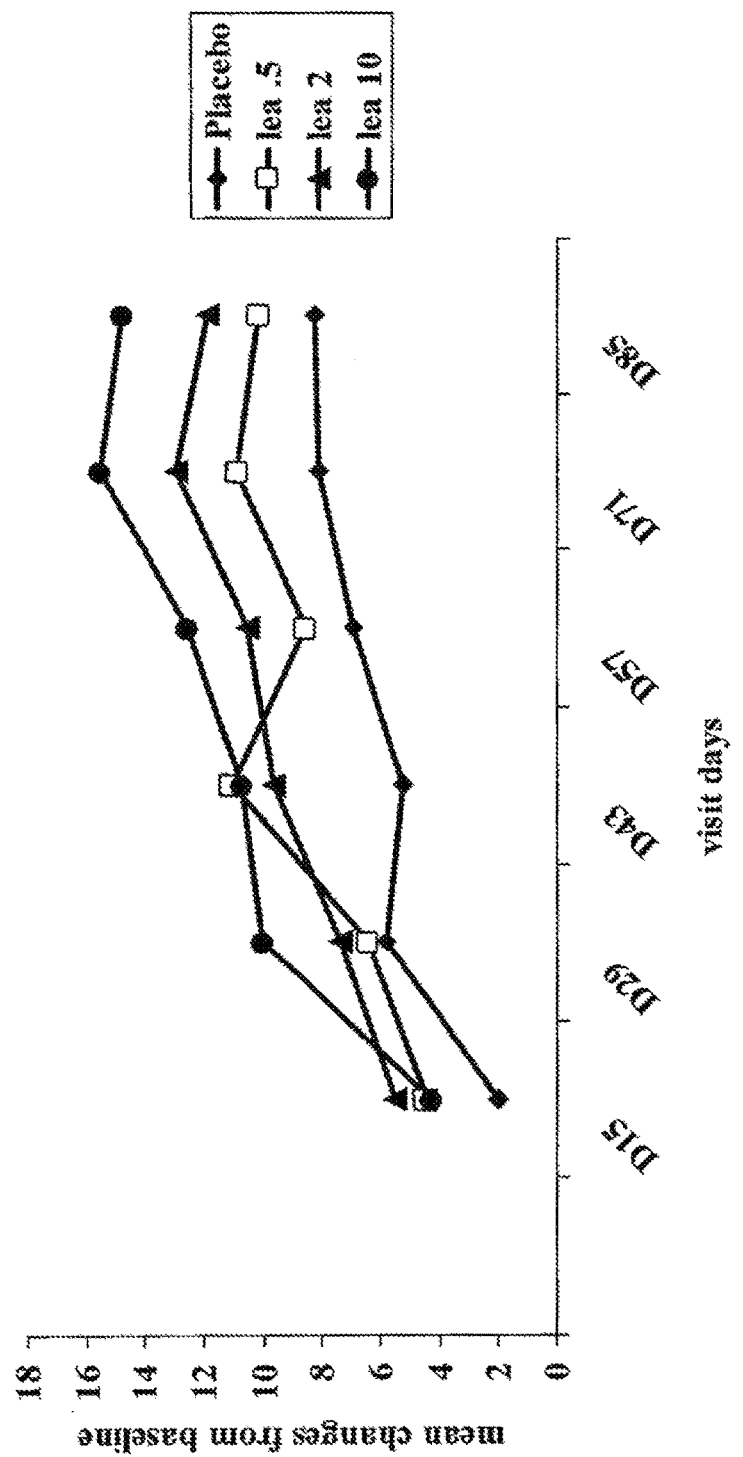
FIG. 13B: The effect of L104EA29YIg on tender joints over time as described in Example 3, infra. Mean change from baseline.

The median and mean tender joint counts in patients treated with L104EA29YIg (denoted as LEA in the figures) or placebo over time are shown in FIGS. 13A and 13B. The change from baseline (e.g., reduction in tender joints) appears to be dose-dependent.

Figure 14A:
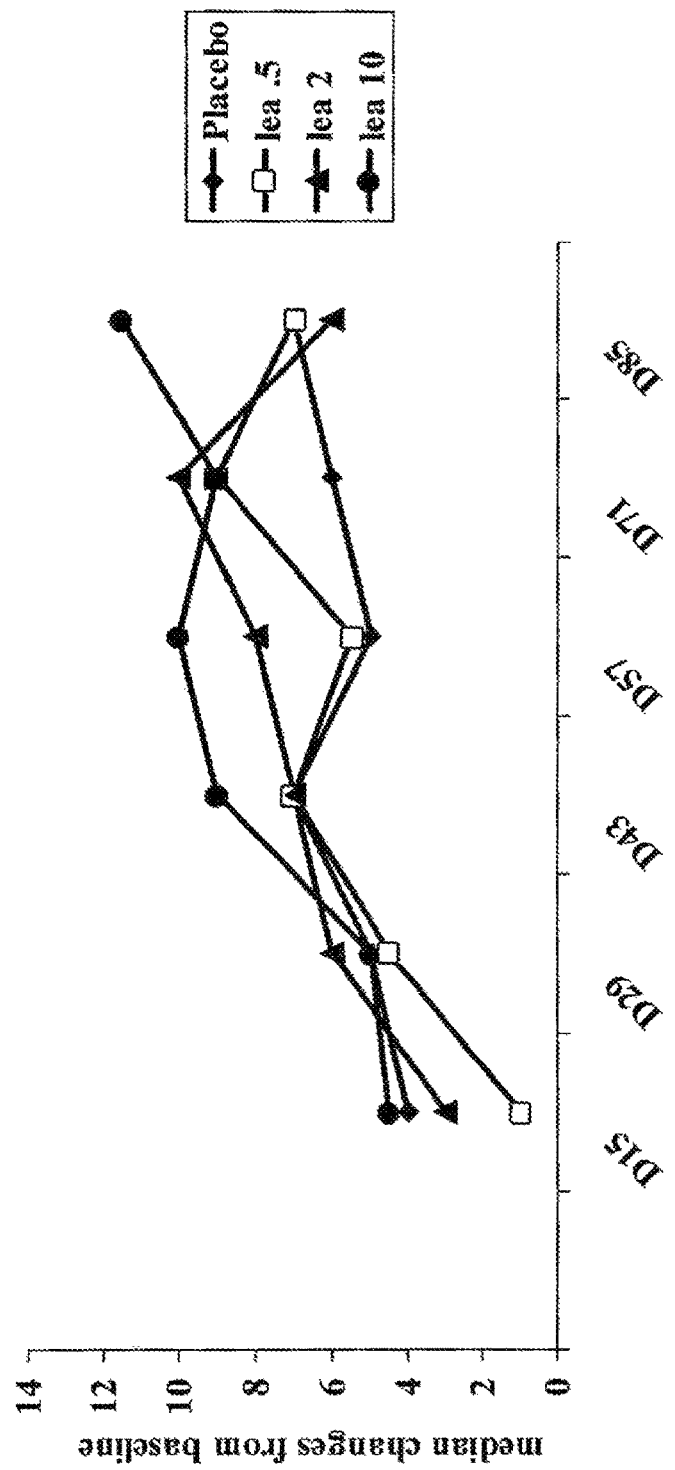
FIG. 14A: The effect of L104EA29YIg on swollen joints over time as described in Example 3, infra. Median difference from baseline.
Figure 14B:
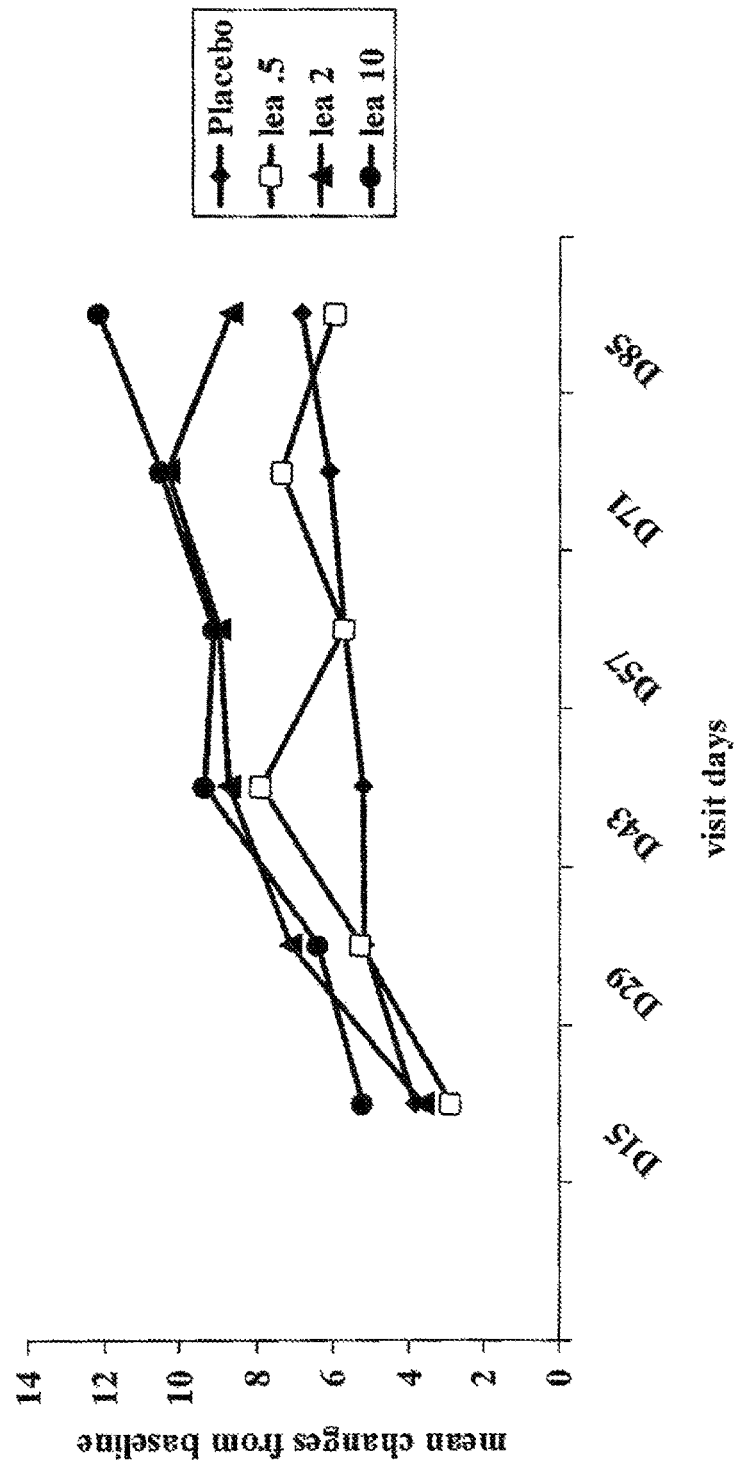
FIG. 14B: The effect of L104EA29YIg on swollen joints over time as described in Example 3, infra. Mean change from baseline.

The median and mean swollen joint counts in patients treated with L104EA29YIg (denoted as LEA in the figures) or placebo over time are shown in FIGS. 14A and 14B. The change from baseline (e.g., reduction in swollen joints) appears to be more important in the 2 and 10 mg/kg treated groups than placebo or 0.5 mg/kg groups.

Figure 15:
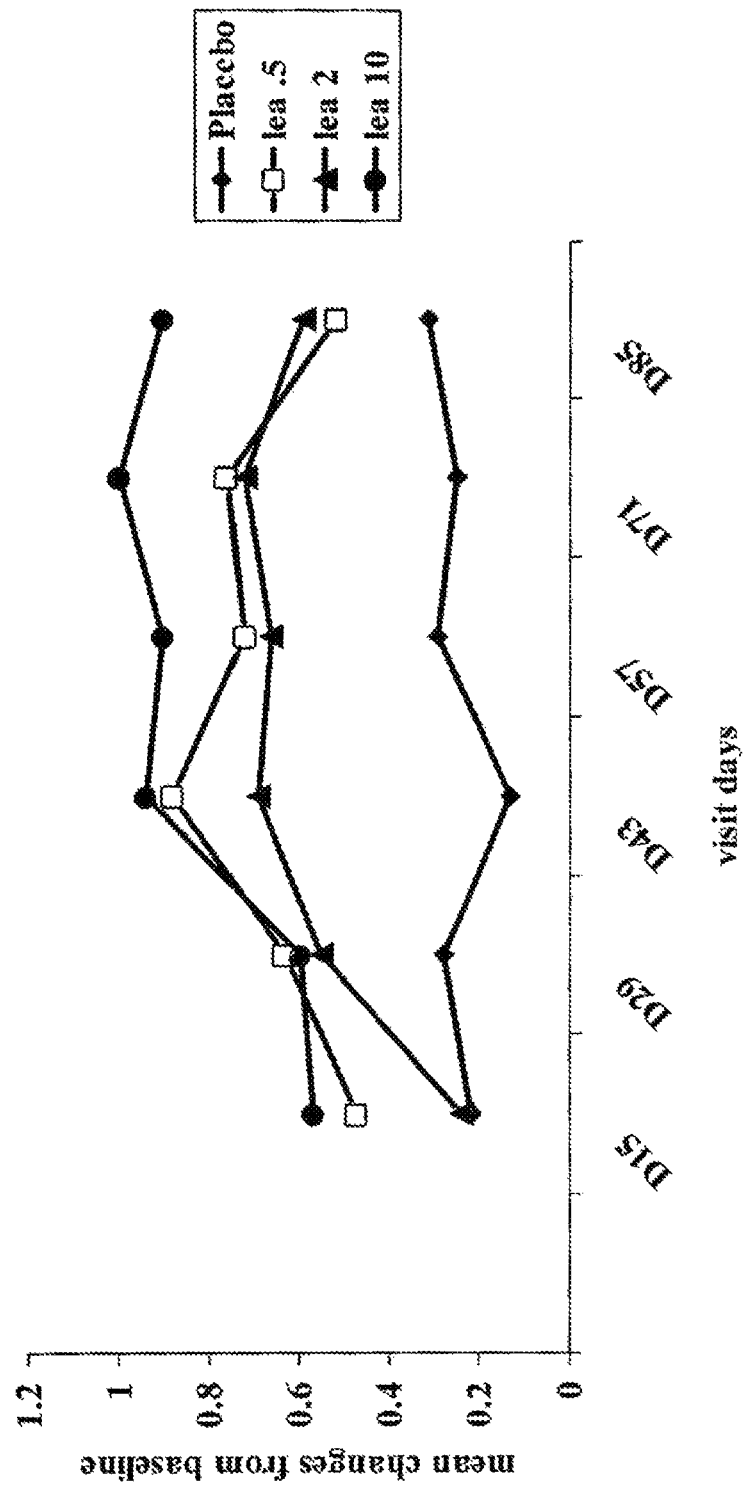
FIG. 15: The effect of L104EA29YIg on pain assessment over time as described in Example 3, infra. Mean change from baseline over time.

The mean pain assessment scores in patients treated with L104EA29YIg (denoted as LEA in the figures) or placebo over time are shown in FIG. 15. The change from baseline (e.g., reduction in pain) appears to be dose-dependent.

Figure 16A:
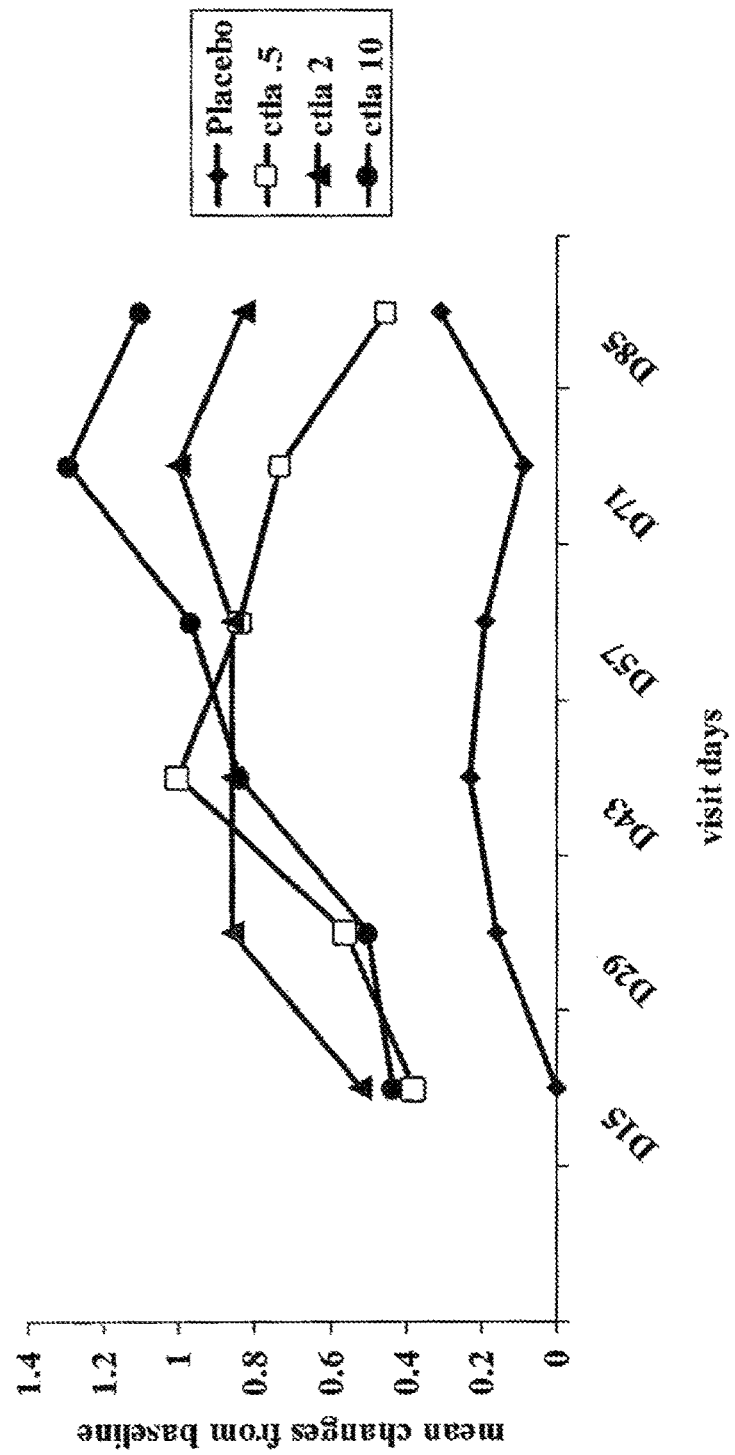
FIG. 16A: The effect of L104EA29YIg on patient assessment of disease activity mean difference from baseline over time as described in Example 3, infra.
Figure 16B:
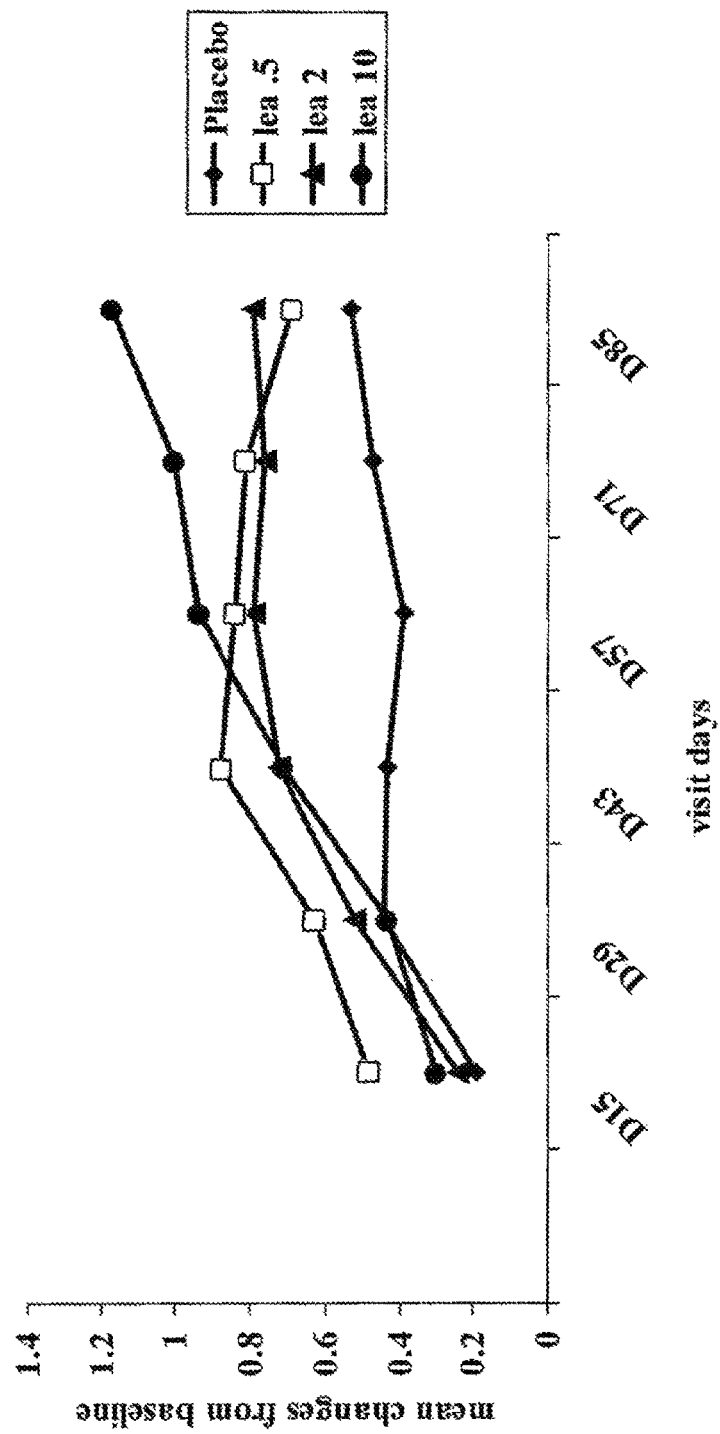
FIG. 16B: The effect of L104EA29YIg on physician assessment of disease activity mean difference from baseline over time as described in Example 3, infra.

The mean disease activity assessment scores evaluated by patient or physician in patients treated with L104EA29YIg (denoted as LEA in the figures) or placebo over time are shown in FIGS. 16A and 16B. The change from baseline (e.g., reduction in disease activity) appears to be dose-dependent.

Figure 17:
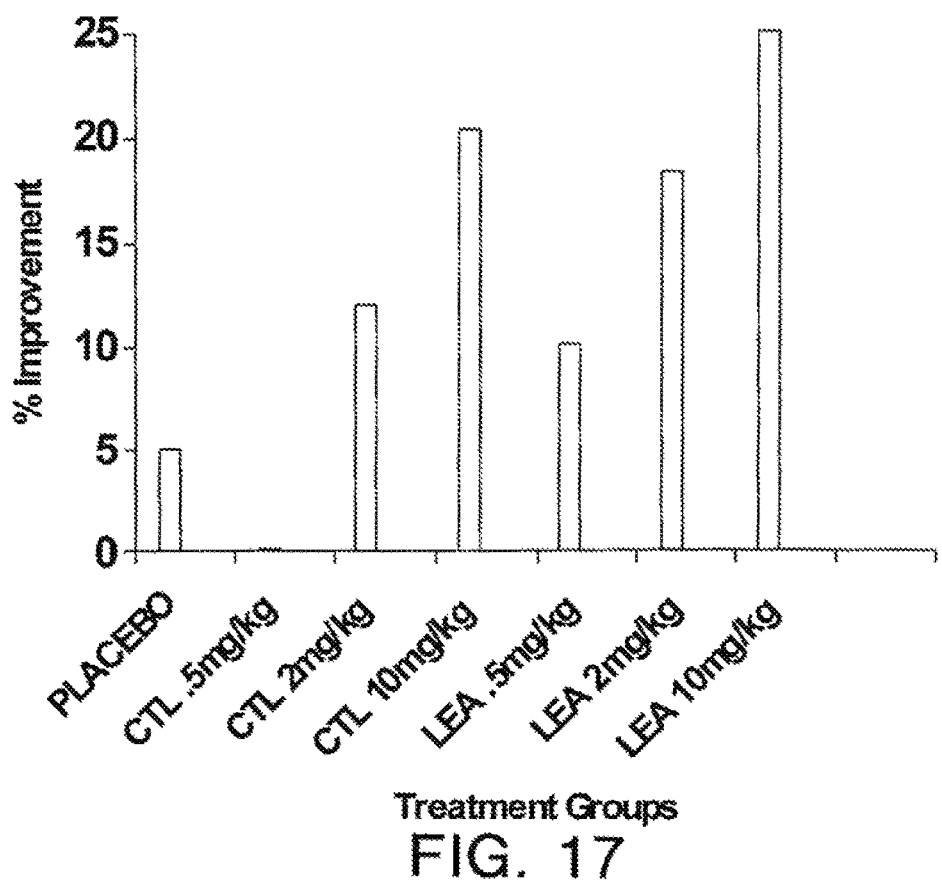
FIG. 17: Percent improvement in patient disability assessed by Health Assessment Questionnaire (HAQ) compared to the baseline at Day 85 with CTLA4Ig and L104EA29YIg treatment as described in Example 3, infra.

The percent improvement of physical disability assessed by HAQ at Day 85 for patients treated with CTLA4Ig, L104EA29YIg, or placebo are shown in FIG. 17 (Health Assessment Questionnaire (HAQ); Fries, J. F. et al., *J. Rheumatol.*, 9:789-793 (1982)). There is a clear dose dependent improvement with this parameter.

The changes from baseline for soluble IL-2r and C-reactive protein levels were dose-dependent in both treatment groups. After treatment, soluble IL-2r levels were −2%, −10%, and −22% for CTLA4Ig and −4%, −18%, and −32% for L104EA29YIg at 0.5, 2.0, and 10.0 mg/kg respectively, compared to +3% for the placebo. C-reactive protein levels were +12%, −15%, and −32% for CTLA4Ig and +47%, −33%, and −47% for L104EA29YIg at 0.5, 2.0, and 10.0 mg/kg respectively, compared to +20% for the placebo (FIG. 7A).

No clinically remarkable findings with respect to routine hematology testing, chemistry laboratory testing with the exception of slight suppressions in IgA and IgG levels at the higher doses of both drugs, physical findings, or vital signs assessments were observed. Notably, neither medication induced drug-specific antibodies.

Example 4

The following Examples describe phase II clinical studies of human patients that will be administered L104EA29YIg, to reduce or prevent structural damage, including bone or joint erosion using validated radiographic scales. This improvement in reducing or preventing structural damage is parallel to the clinical improvement measured by the clinical parameters.

The status of the bone structure is monitored in some of the human patients prior to treatment with CTLA4Ig or L104EA29YIg. These patients are administered from 0.5 to 20 mg/kg of CTLA4Ig or L104EA29YIg chronically every 2 to 12 weeks (alone or in combination with other agents) to maintain their therapeutic improvement over time. Radiographs of patients' hands and feet are taken at predefined intervals: 6 months, and then yearly, as recommended by the FDA guidelines. These patients are monitored in long-term extension after 6 and 12 months to determine if treatment with CTLA4Ig or L104EA29YIg reduces the progression of bone deterioration, and then yearly. The patients are monitored by radiographic methods, including x-ray and/or magnetic resonance imaging (MRI), according to standard practice in the art (Larsen, A. K. et al., *Acta Radiol. Diagn.*, 18:481-491 (1977); Sharp, J. T. et al., *Arthritis Rheum.*, 28:1326-1335 (1985)). The results of the radiographic data are evaluated for prevention of structural damage, including slowing the progression of bone erosion and cartilage damage, with joint space narrowing and/or prevention of new erosions.

Example 5

A Study to Evaluate the Safety and Clinical Efficacy of Two Different Doses of CTLA4Ig Administered Intravenously to Subjects with Active Rheumatoid Arthritis while Receiving Methotrexate Rheumatoid Arthritis (RA) treatment is rapidly changing with an increased willingness to use more aggressive therapies to achieve larger increases in efficacy and higher success rates. The ultimate goal is to improve the subject condition in a more intensive way, by raising the rate of major and complete clinical response, to treatment and maintaining this benefit with acceptable safety.

Methotrexate remains the cornerstone of the RA treatment. It was the first agent that demonstrated early onset of action, superior efficacy and tolerability compared to the classical DMARDs (e.g., gold, hydroxychloroquine, sulfasalazine) used to treat RA. Clinical benefit may be seen as early as 3 weeks after initiating treatment, and the maximal improvement is generally achieved by 6 months. However, methotrexate has a number of limitations. For example, despite its increased tolerability, the window between efficacy and liver toxicity is quite narrow. Subjects treated with methotrexate require careful monitoring and unacceptable toxicity is often the reason for discontinuation of treatment.

Methotrexate also does not appear to efficiently control disease progression or joint deterioration. For some subjects, practitioners feel compelled to add a second DMARD with the hope of increasing efficacy despite the risk of increased toxicity. Alternatively, co-treatment with methotrexate and a costimulator blocker (e.g., CD80 and CD86 blockers such as CTLA4Ig) that target the autoimmune mechanism that lies upstream of the cytokine inflammatory cascade, may also increase efficacy.

As noted in Example 3, above, significant clinical responses and reductions in surrogate markers of disease activity were observed for CTLA4Ig at doses of 2 and 10 mg/kg with a good tolerability profile. It has also been confirmed that the composition CTLA4Ig, used in Example 3 above, did not induce any side effects. As a result, it was decided to continue the clinical development of CTLA4Ig for rheumatoid arthritis in Phase IIB.

The following provides a description of a Phase IIB clinical study of human patients administered soluble CTLA4 molecule with methotrexate, and the results of the study after 6 months.

This Example describes a 12-month study in which primary efficacy was assessed after all subjects completed 6 months of treatment or discontinue therapy. Efficacy, safety, and disease progression were also assessed throughout the duration of the study.

The study utilized a randomized, double blind, placebo controlled, parallel dosing design. The study was designed to evaluate the safety, clinical activity, immunogenicity and pharmacokinetics of two doses of CTLA4Ig: 2 or 10 mg/kg. A total of approximately 330 subjects with active RA and receiving methotrexate were randomized to 1 of 3 dosing arms: CTLA4Ig at 2 mg/kg (N=110), 10 mg/kg (N=110) and placebo control group (N=110) given monthly infusions for 12 months. All groups continued on weekly methotrexate treatment (10-30 mg weekly) (FIGS. 57-62).

CTLA4Ig or a placebo were also administered on Day 15. Each dose of study medication was infused intravenously over approximately 30 minutes. The primary efficacy endpoint was the ACR 20 response rate after 6 months.

For the first 6 months, subjects were not allowed to alter their doses of corticosteroids, glucocorticoids or NSAIDs. Increases in methotrexate were also not permitted during the first 6 months. Decreases in methotrexate were permitted only if it was felt to be causing toxicity. Subjects were treated with methotrexate for at least 6 months, and at a stable dose for 28 days prior to first treatment of CTLA4Ig or placebo. DMARDs other than methotrexate were not permitted. Low-dose stable corticosteroids use (at 10 mg daily or less) and/or use of stable non-steroidal anti-inflammatory drugs (NSAIDs), including acetyl salicylic acid (ASA), was allowed. Analgesics that did not contain ASA or NSAIDs were permitted in subjects experiencing pain not adequately controlled by the baseline and study medications, except for 12 hours before a joint evaluation. Decreases in NSAIDs were permitted but only if due to adverse events such as gastrointestinal toxicity.

Test Product, Dose and Mode of Administration, Duration of Treatment

CTLA4Ig at 2 mg/kg or 10 mg/kg was infused every two weeks for the first month, and monthly thereafter for 12 months.

All subjects received weekly doses of methotrexate (10-30 mg) for at least 6 months prior to randomization and maintained at the entry dose for the first 6 months of the trial. Doses could only be decreased for toxicity during the first 6 months.

Criteria for Evaluation

The primary endpoint of the first stage of the study was the proportion of subjects meeting the American College of Rheumatology criteria for 20% improvement (ACR 20) on Day 180 (month six). The ACR 20 definition of improvement is a 20% improvement from baseline in the number of tender and swollen joint counts, and a 20% improvement from baseline in 3 of the following 5 core set measurements: subject global assessment of pain, subject global assessment of disease activity, physician global assessment of disease activity, subject assessment of physical function and acute phase reactant value (C-reactive protein (CRP)). The evaluation for 50% improvement (ACR 50) and 70% improvement (ACR 70) follow similarly. Subjects who discontinued the study due to lack of efficacy (i.e., worsening RA) were considered as ACR non-responders from that time on. For all subjects who dropped out for other reasons, their ACR response at the time of discontinuation was carried forward.

Statistical Methods

Two doses of CTLA4Ig (2 mg/kg and 10 mg/kg) were compared with the placebo control group. All subjects were maintained at the same stable entry doses of methotrexate. The primary analysis was the comparison of CTLA4Ig 10 mg/kg with placebo. Sample sizes were based on a 5% level (2-tailed) of significance. Based on published studies, the placebo plus methotrexate control ACR 20 response rate at 6 months is about 25%. A sample of 107 subjects (adjusted for a possible 15% dropout) per treatment arm was determined to yield a 94% power to detect a difference of 25% at the 5% level (two-tailed). Similarly, the sample was determined to yield a power of 95% and 90% to detect differences of 20% and 14% in ACR 50 and ACR 70, respectively. If the comparison between CTLA4Ig 10 mg/kg and placebo was significant with regards to ACR 20, then the comparison between CTLA4Ig 2 mg/kg and placebo was carried out. This second testing should have a power of 88%. This sequentially rejective procedure based on Chi-square tests was also used to test for differences in ACR 50 and ACR 70 responses.

All efficacy analyses were based on a data set containing all available assessments from all subjects who received at least one dose of study medication.

Percent changes from baseline were also reported for the individual components of the ACR. For subjects who discontinued, their last observation was carried forward.

Results

Demography and Baseline Characteristics

TABLE III

Subject Disposition and Demographics

|  | Methotrexate + CTLA4Ig 10 mg/kg | Methotrexate + CTLA4Ig 2 mg/kg | Methotrexate + Placebo |
|---|---|---|---|
| Enrolled/Randomized | 115 | 105 | 119 |
| Completed | 99 (86.1%) | 82 (78.1%) | 78 (65.5%) |
| Discontinued | 16 (13.9%) | 23 (21.9%) | 41 (34.5%) |
| Adverse Events | 2 (1.7%) | 7 (6.7%) | 7 (5.9%) |
| Lack of Efficacy | 12 (10.4%) | 13 (12.4%) | 29 (24.4%) |
| Other | 2 (1.7%) | 3 (2.9%) | 5 (4.2%) |
| Age (yrs) - Mean (Range) | 55.8 (17-83) | 54.4 (23-80) | 54.7 (23-80) |
| Weight (kg) - Mean (Range) | 77.8 (40.1-144) | 78.7 (48.4-186.8) | 79.9 (44-140) |
| Sex | 75% females | 63% females | 66% females |
| Race | 87% white | 87% white | 87% white |
| Duration of Disease (yrs) Mean ± SD | 9.7 ± 9.8 | 9.7 ± 8.1 | 8.9 ± 8.3 |

Demographic and baseline clinical characteristics were similar among the treatment groups. 63 to 75 percent of subjects were female, 87% were Caucasian. The mean duration of the disease at entry was 9.7±9.8, 9.7±8.1, and 8.9±8.3 years respectively in the 10, 2 mg/kg and the control group. The mean weight in kg was very similar between 77.8 and 79.9 kg with a range of 40.1 to 186.8 kg (Table III).

After 6 months, more subjects had discontinued from the control group (35.5%) than from the active treatment groups; 13.9% and 21.9% for the 10 and 2 mg/kg treated groups, respectively. The main reason was lack of efficacy: with 24.3% discontinuing in the control group, as opposed to 12.4% and 10.4% discontinuing in the 2 and 10 mg/kg groups, respectively. The discontinuation rate due to adverse events was lower in the 10 mg/kg group with 1.7%, while it was 6.7% and 5.9% in the 2 mg/kg and the control groups, respectively.

During the first 3-4 months, the discontinuations appeared at a faster rate in the control group compared to the active-treatment groups. After Day 120, the discontinuations for all treatment groups stabilized for the duration of the primary treatment period (6 months).

TABLE IV

Baseline Clinical Characteristics

|  | Methotrexate + CTLA4Ig 10 mg/kg (n = 115) | Methotrexate + CTLA4Ig 2 mg/kg (n = 105) | Methotrexate + Placebo (n = 119) |
|---|---|---|---|
| Tender Joints (mean ± SD) | 30.8 ± 12.2 | 28.2 ± 12.0 | 29.2 ± 13.0 |
| Swollen Joints (mean ± SD) | 21.3 ± 8.4 | 20.2 ± 8.9 | 21.8 ± 8.8 |
| Pain (VAS 100 mm) (mean ± SD) | 62.1 ± 21.4 | 64.5 ± 22.3 | 65.2 ± 22.1 |

TABLE IV-continued

Baseline Clinical Characteristics

|  | Methotrexate + CTLA4Ig 10 mg/kg (n = 115) | Methotrexate + CTLA4Ig 2 mg/kg (n = 105) | Methotrexate + Placebo (n = 119) |
|---|---|---|---|
| Physical Function (MHAQ score of 0 to 3) (mean ± SD) | 1.0 ± 0.5 | 1.0 ± 0.5 | 1.0 ± 0.6 |
| Subject Global Assessment (VAS 100 mm) (mean ± SD) | 60.1 ± 20.7 | 59.4 ± 23.7 | 62.8 ± 21.6 |
| Physician Global Assessment (VAS 100 mm) (mean ± SD) | 62.1 ± 14.8 | 61.0 ± 16.7 | 63.3 ± 15.5 |
| CRP (mg/dL) | 2.9 ± 2.8 | 3.2 ± 2.6 | 3.2 ± 3.2 |
| Morning Stiffness (in min.) | 97.9 ± 63.1 | 104.1 ± 63.9 | 106.0 ± 64.2 |

The mean number of tender and swollen joints at baseline was comparable among the three treatment groups. The mean number of tender joints and swollen joints in the 10 mg group was 30.8±12.2 and 21.3±8.4, respectively. The mean number of tender joints and swollen joints in the 2 mg group was 28.2±12.0, and 20.2±8.9, respectively. The mean number of tender joints and swollen joints in the control group was 29.2±13.0, and 21.8±8.8, respectively. These assessments and all other clinical assessments were similar among all treatment groups (Table IV).

ACR Responses and Core Components

TABLE V

ACR Response at 6 Months

|  | Methotrexate + CTLA4Ig 10 mg/kg (n = 115) | Methotrexate + CTLA4Ig 2 mg/kg (n = 105) | Methotrexate + Placebo (n = 119) |
|---|---|---|---|
| ACR 20 | 60.0% | 41.9% | 35.3% |
| Difference from control group | 24.7 | 6.6 | — |
| 95% CI | 11.9, 37.5 | −6.2, 19.4 | — |
| p-value | <0.001 | 0.31 | — |
| ACR 50 | 36.5% | 22.9% | 11.8% |
| Difference from control group | 24.8 | 11.1 | — |
| 95% CI | 13.8, 35.7 | 1.2, 20.9 | — |
| p-value | <0.001 | 0.027 | — |
| ACR 70 | 16.5% | 10.5% | 1.7% |
| Difference from control group | 14.8 | 8.8 | — |
| 95% CI | 7.5, 22.2 | 2.7, 14.9 | — |
| p-value | <0.001 | 0.005 | — |

Figure 49:
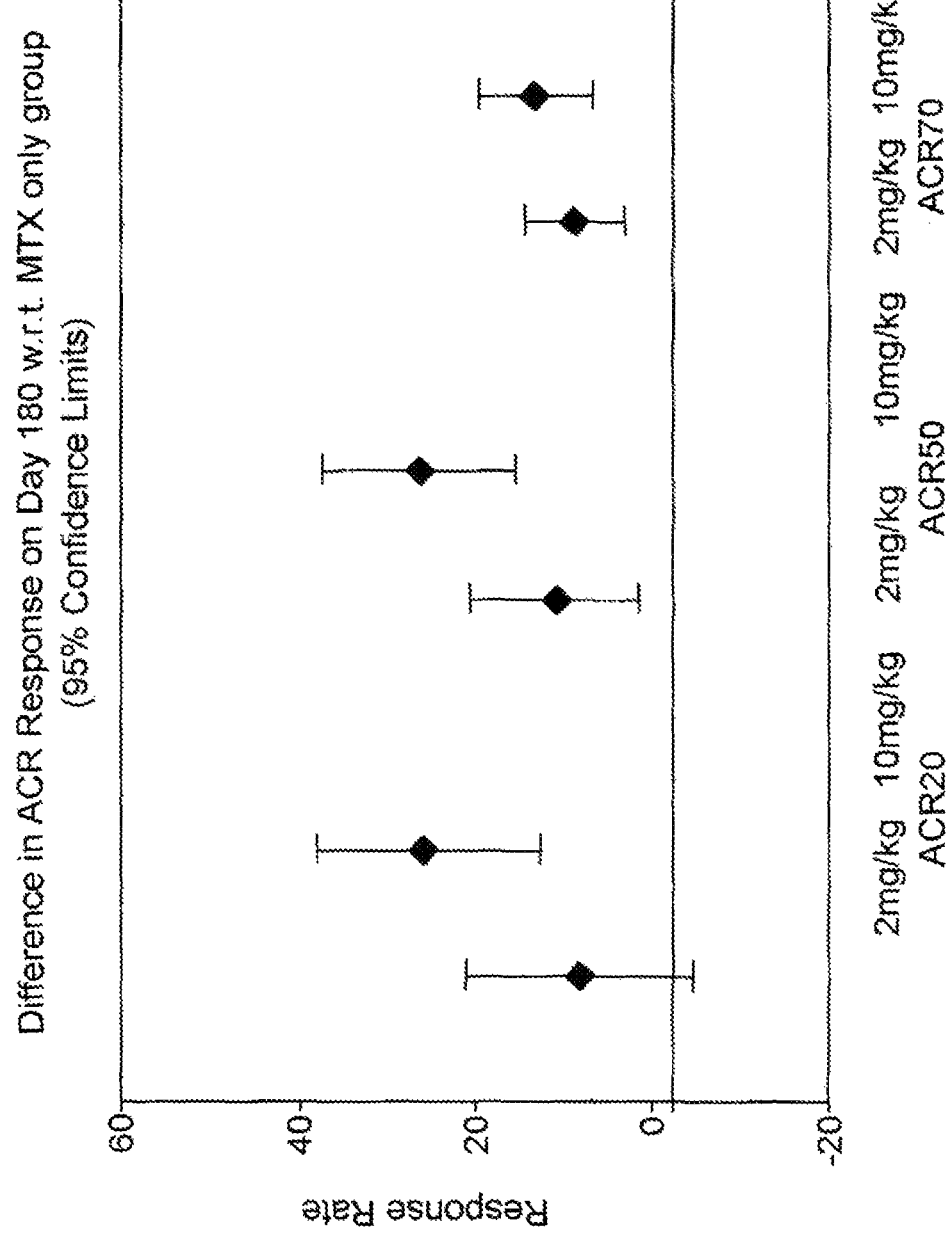
FIG. 49: A graph showing the difference in ACR response rate on Day 180 in two groups after therapy with CTLA4Ig (2 and 10 mg/kg) in comparison to a group treated with methotrexate (MTX) only (95% Confidence Limits), as described in Example 5, infra.

The improvements in ACR 20, 50, and 70 response rates in the 10 mg/kg treatment group, at 6 months relative to the methotrexate control group, were statistically significant (FIGS. 34-38 and 40). The improvements in ACR 50, and ACR 70 for the 2 mg/kg group were also statistically significant. The difference in ACR 20 response between the 2 mg/kg group and the control group was 6.6%. This difference was not statistically significant, p=0.31 (Table V, FIG. 49).

Figure 38:
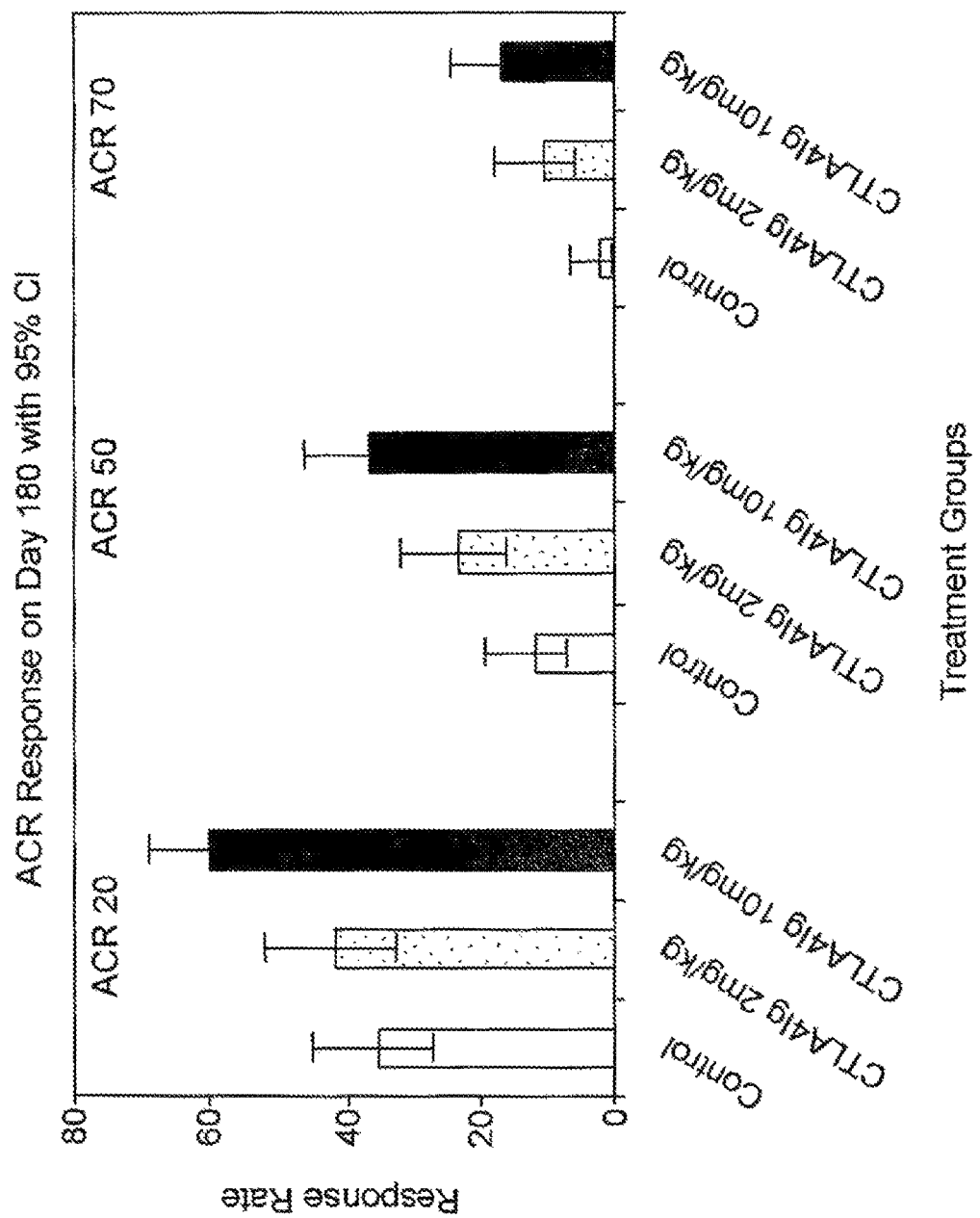
FIG. 38: A bar graph showing the ACR response in response to methotrexate alone or methotrexate and CTLA4Ig (2 and 10 mg/kg) therapy on Day 180 with a 95% confidence interval, as described in Example 5, infra.
Figure 40:
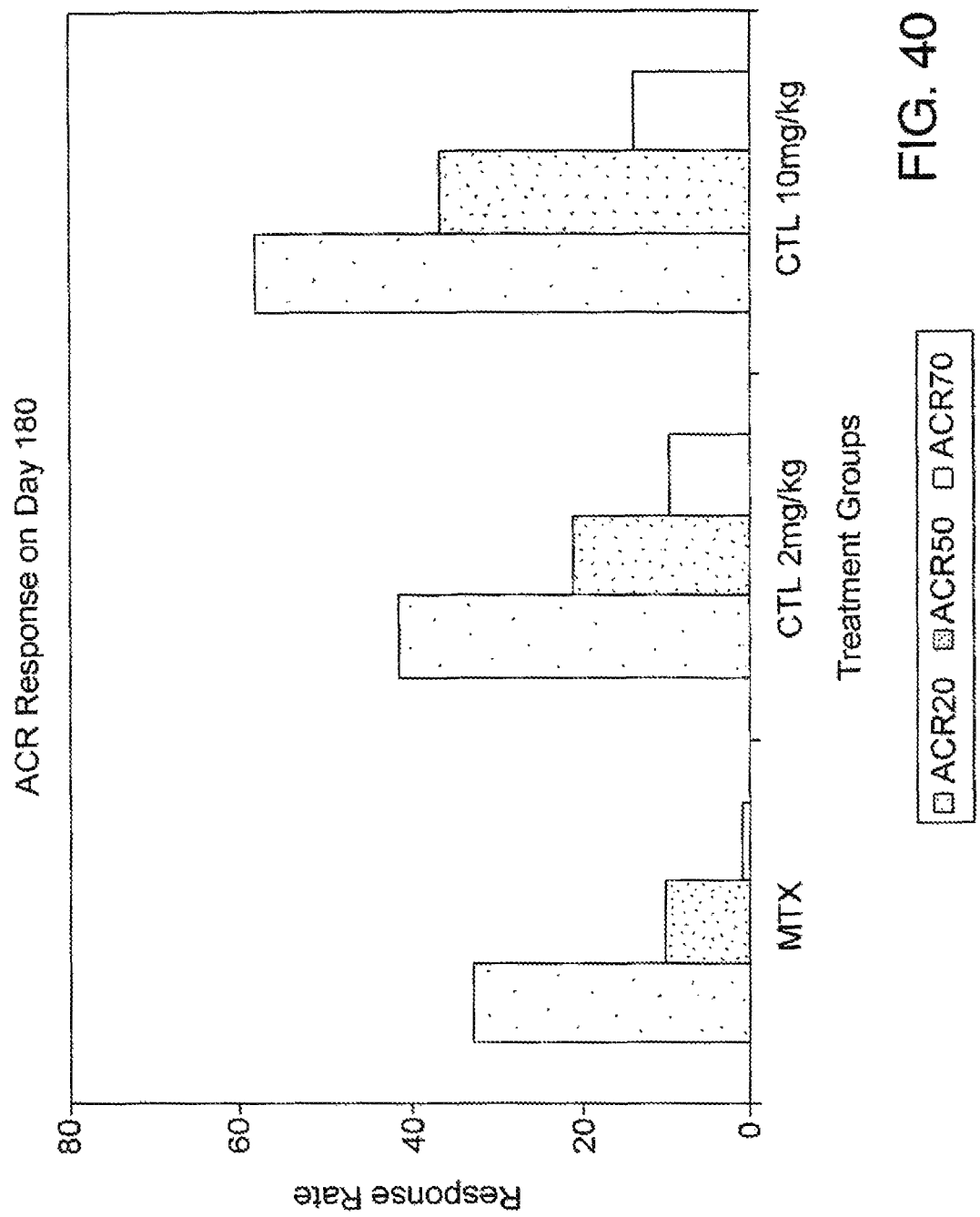
FIG. 40: A bar graph showing ACR response after therapy with methotrexate alone or methotrexate and CTLA4Ig (2 and 10 mg/kg) on Day 180, as described in Example 5, infra.
Figure 41:
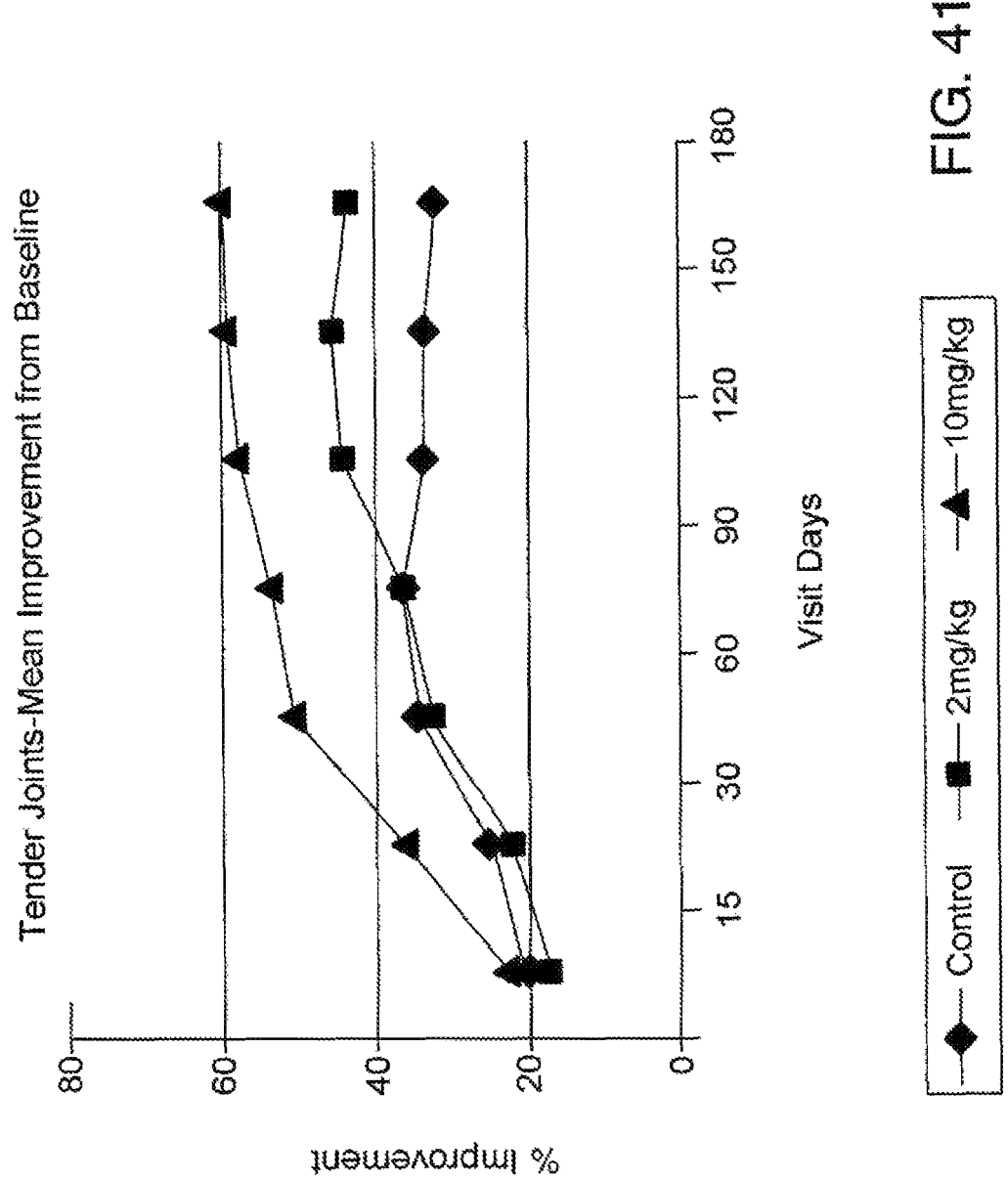
FIG. 41: A graph showing percent improvement in tender joints after therapy with methotrexate alone or methotrexate and CTLA4Ig (2 and 10 mg/kg)—mean percent improvement from baseline, as described in Example 5, infra.
Figure 42:
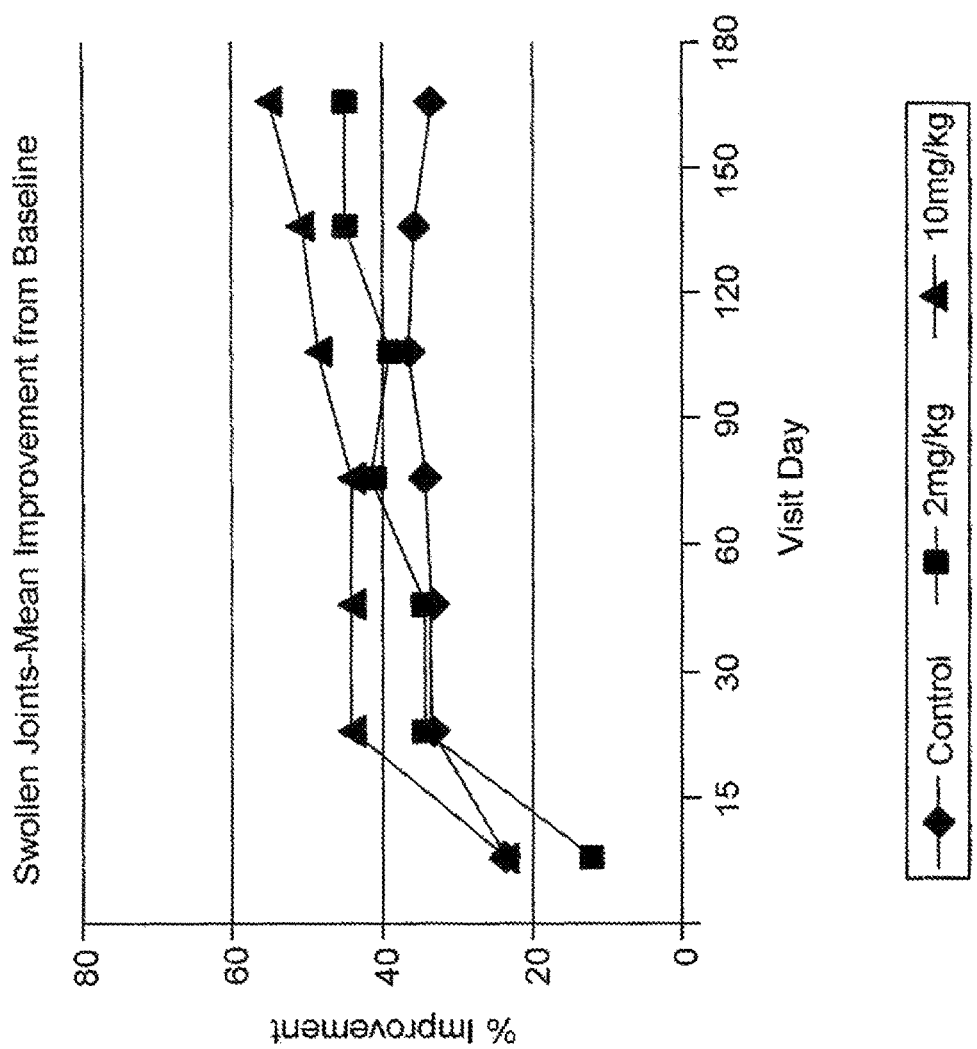
FIG. 42: A graph showing percent improvement in swollen joints after therapy with methotrexate alone or methotrexate and CTLA4Ig (2 and 10 mg/kg)—mean percent improvement from baseline, as described in Example 5, infra.
Figure 43:
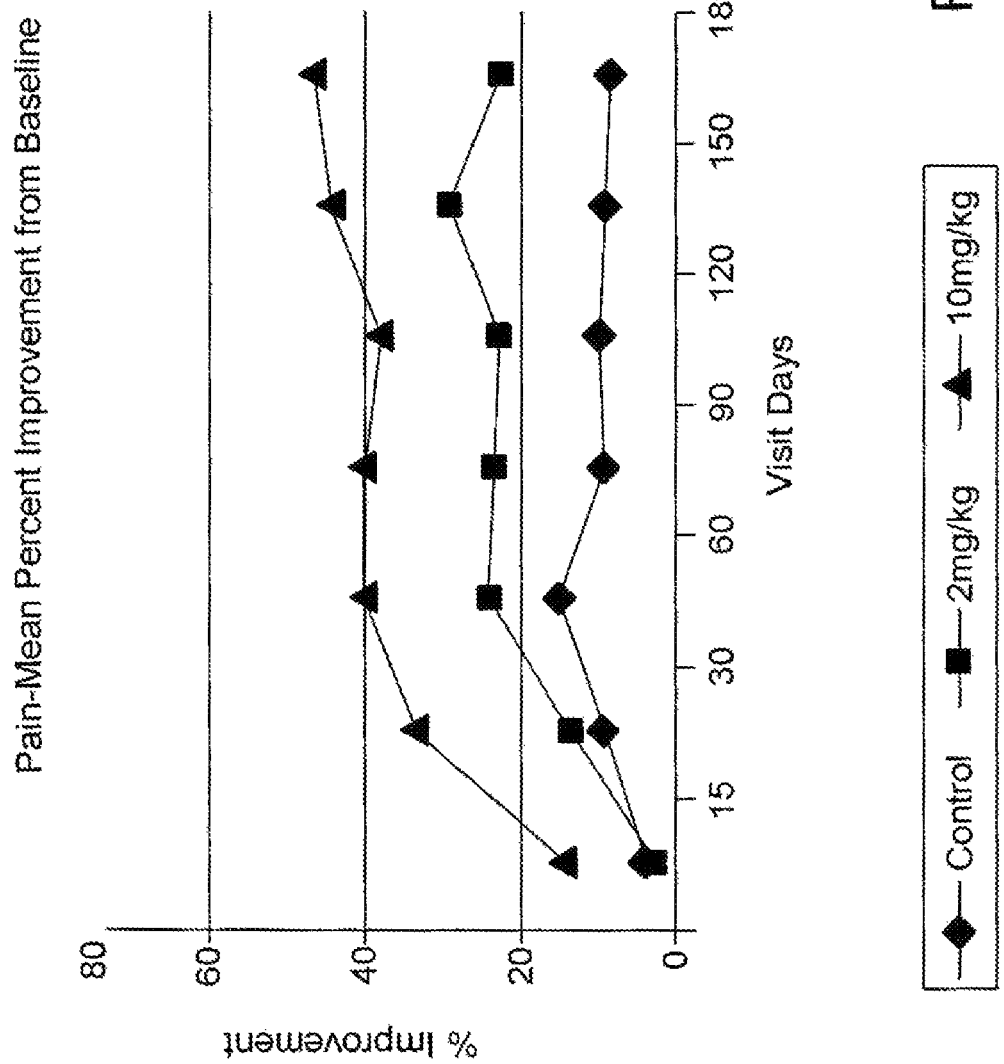
FIG. 43: A graph showing percent improvement in pain after therapy with methotrexate alone or methotrexate and CTLA4Ig (2 and 10 mg/kg)—mean percent improvement from baseline, as described in Example 5, infra.
Figure 44:
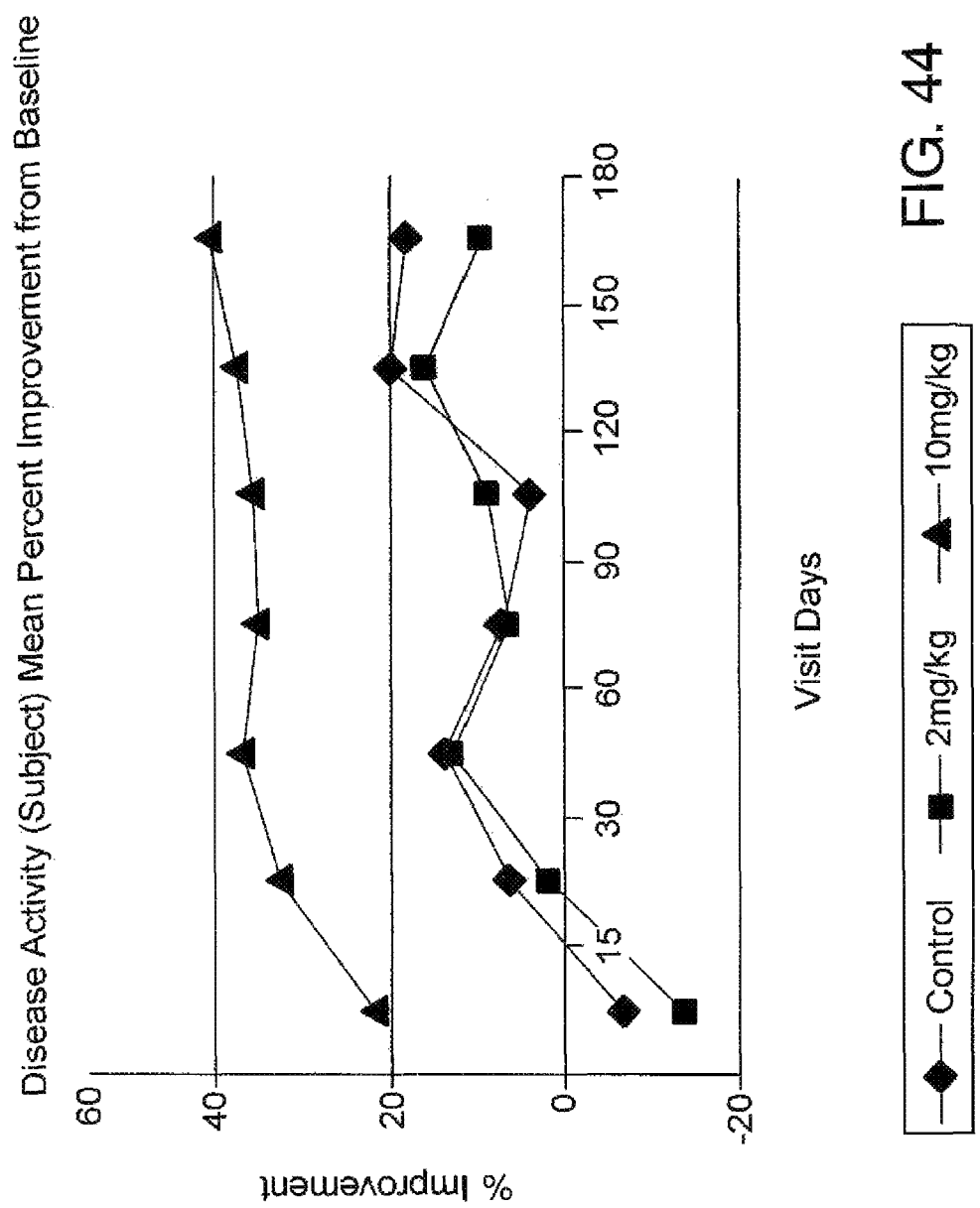
FIG. 44: A graph showing percent improvement in regard to disease activity as reported by the subject after therapy with methotrexate alone or methotrexate and CTLA4Ig (2 and 10 mg/kg)—mean percent improvement from baseline, as described in Example 5, infra.
Figure 45:
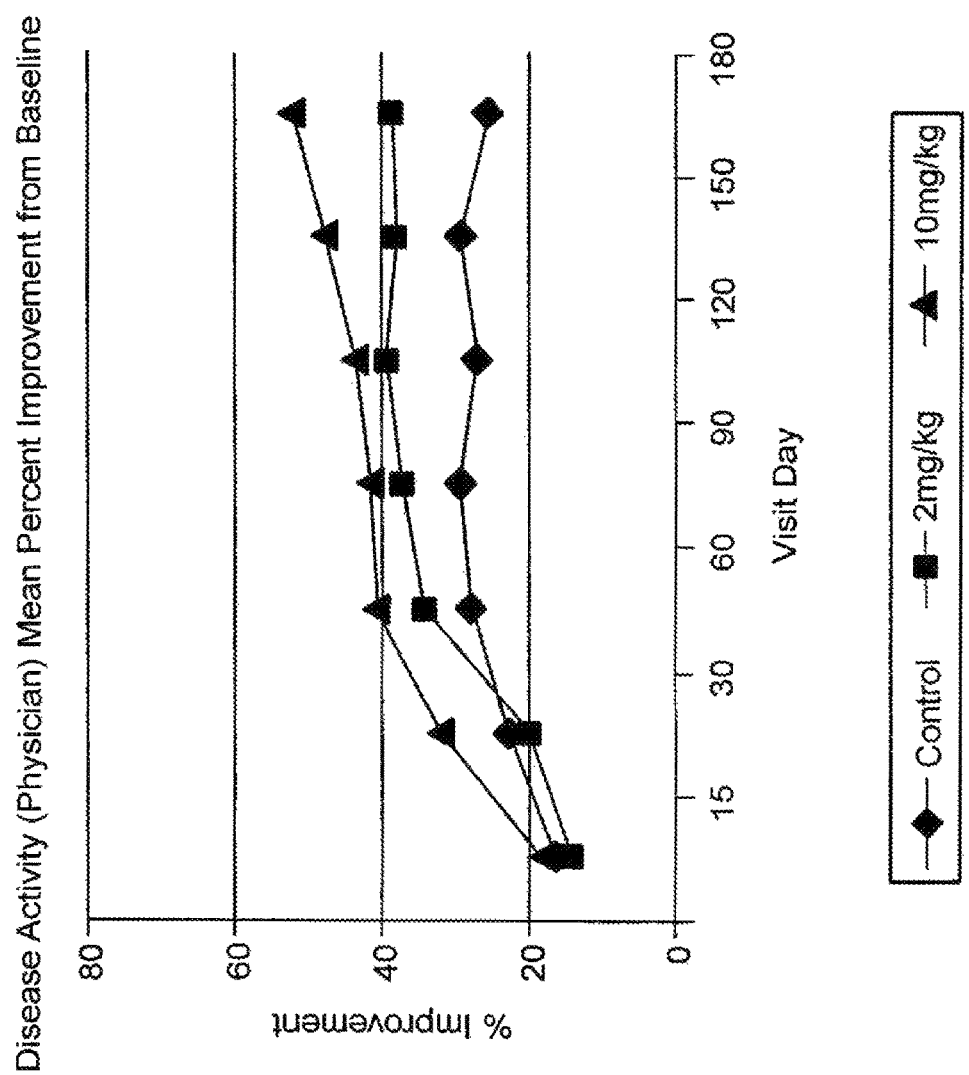
FIG. 45: A graph showing percent improvement in regard to disease activity as reported by the physician after therapy with methotrexate alone or methotrexate and CTLA4Ig (2 and 10 mg/kg)—mean percent improvement from baseline, as described in Example 5, infra.

FIGS. 34-37 presents the ACR response rates from Day 1 to Day 180. FIGS. 38 and 40 presents the ACR20, -50 and -70 response rates on Day 180 for the various treatment groups. The ACR 50 and ACR 70 response rates suggest the possibility that maximal efficacy may not have been achieved at 10 mg/kg.

Figure 39:
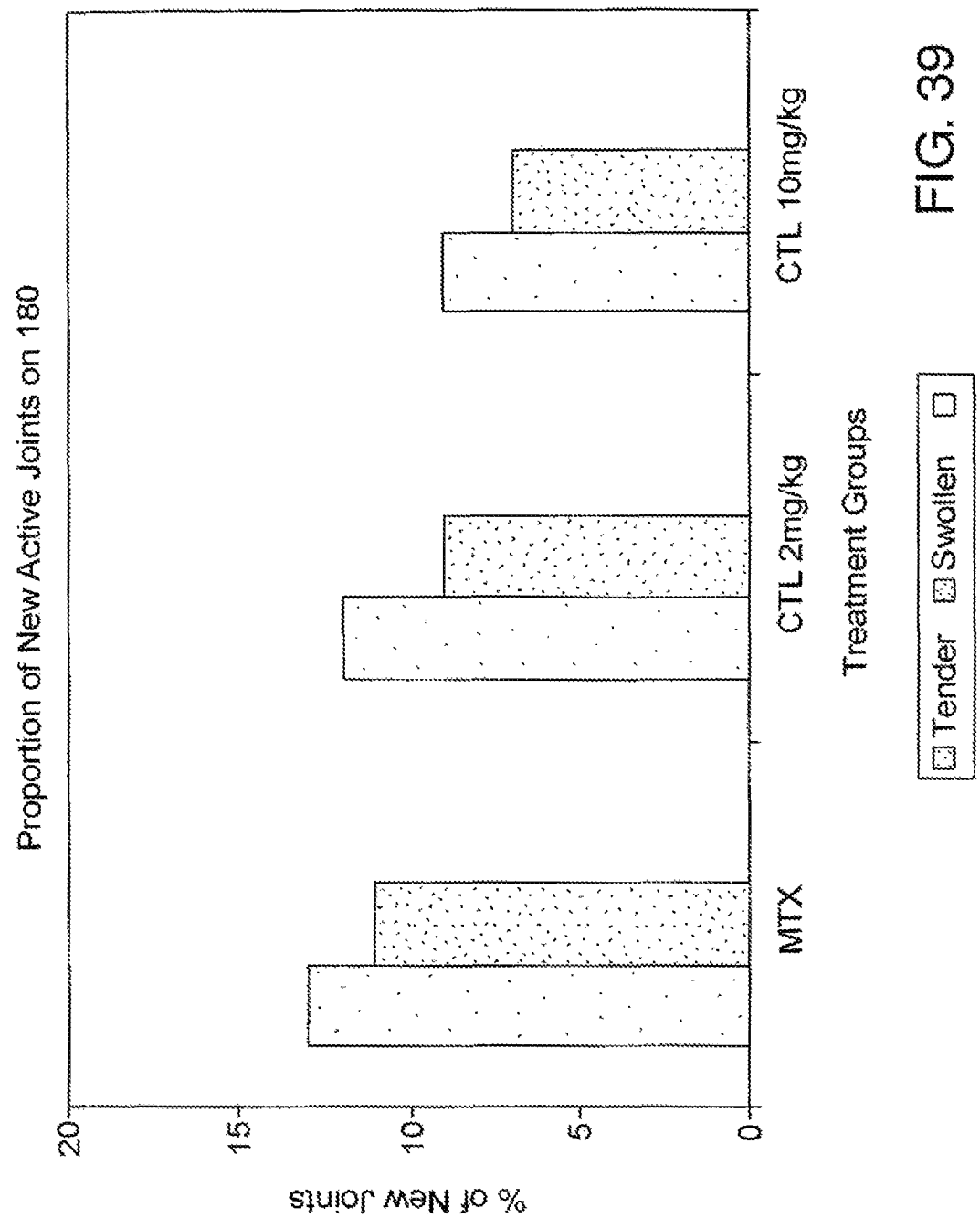
FIG. 39: A bar graph showing the proportion of New Active Joints in response to methotrexate alone or methotrexate and CTLA4Ig (2 and 10 mg/kg) therapy on Day 180, as described in Example 5, infra.

FIG. 39 shows the proportion of new tender and swollen joints at Day 180 of the study after therapy with methotrexate alone or in combination with CTLA4Ig (administered at 2 or 10 mg/kg body weight of subject).

Figure 46:
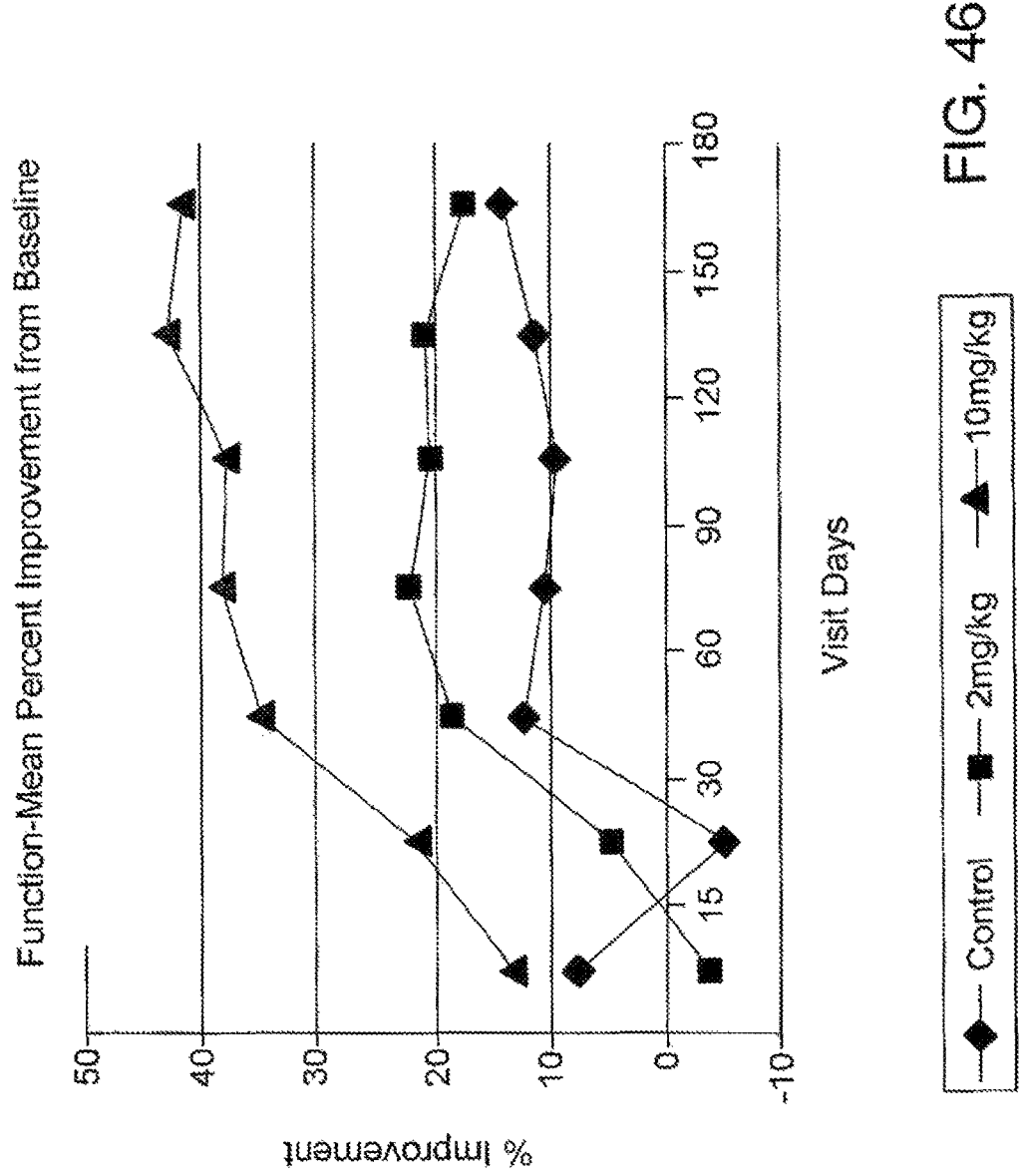
FIG. 46: A graph showing percent improvement regarding physical function after therapy with methotrexate alone or methotrexate and CTLA4Ig (2 and 10 mg/kg)—mean percent improvement from baseline as measured by HAQ, as described in Example 5, infra.

FIG. 46 shows the mean percent improvement in physical function from baseline as measured by HAQ.

TABLE VI

Individual ACR Components at Day 180
(Mean Percent Improvement)

| Core Components | Methotrexate + CTLA4Ig 10 mg/kg (n = 115) | Methotrexate + CTLA4Ig 2 mg/kg (n = 105) | Methotrexate + Placebo (n = 119) |
|---|---|---|---|
| Tender Joints | 59.9% | 43.3% | 32.1% |
| Swollen Joints | 54.9% | 45.1% | 33.4% |
| Pain | 46.4% | 22.7% | 8.4% |
| Physical Function (mHAQ) | 41.5% | 17.3% | 14.1% |
| Subject Global Assessment | 40.8% | 9.6% | 17.6% |
| Physician Global Assessment | 52.0% | 38.6% | 25.6% |
| CRP | 31.5% | 16.2% | −23.6% |

The 2 and 10 mg/kg dose groups demonstrated some degree of efficacy among all clinical components of the ACR response criteria (Table VI; FIGS. 41-45, 47-48); the subject's global assessment in the 2 mg/kg dose group being the only exception. The reduction of tender and swollen joints appears dose-dependent. The number of tender joints was decreased by 59.9%, 43.3% and 32.1% in the 10 mg/kg, 2 mg/kg and control groups, respectively. A similar pattern was observed for the swollen joint counts with a decrease of 54.9%, 45.1% and 33.4% in the 10 mg/kg, 2 mg/kg and control groups, respectively. The greatest differences relative to the control group were observed with the pain assessment which decreased 46.4% and 22.7% relative to baseline for 10 mg and 2 mg/kg CTLA4Ig, respectively, compared to 8.4% in the control group. The mean CRP decreased 31.5% and 16.2% relative to baseline in the 10 and 2 mg/kg groups compared to an increase of 23.6% in the control group.

Health-Related Quality of Life

The impact of CTLA4Ig on health-related quality of life (HRQOL) was measured by the Medical Outcomes Study Short Form-36 (SF-36). The SF-36 was administered to all subjects at baseline, 90 and 180 days. The SF-36 consists of 36 items which covers eight domains (physical function, role-physical, bodily pain, general health, vitality, social function, role emotional, and mental health). These individual domains are used to derive the physical and mental component summary scores which range from 0 to 100, with higher scores indicating better quality of life. Absolute differences of 5 or more in the SF-36 scores were considered clinically meaningful.

Figure 50:
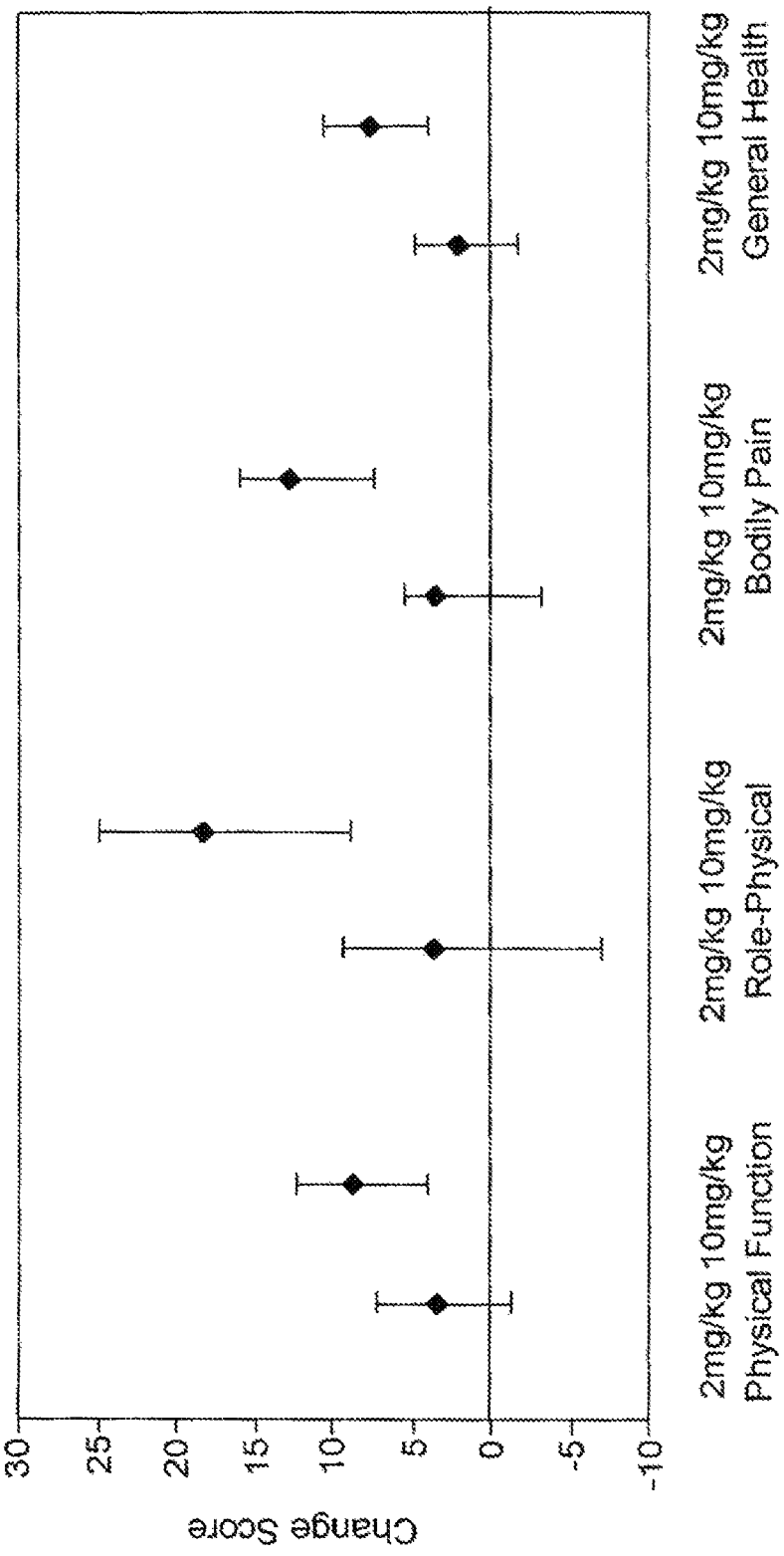
FIG. 50: A graph showing the change from baseline for SF-36 Physical Health Component on Day 180, in two groups after therapy with CTLA4Ig (2 and 10 mg/kg) compared to a group treated with methotrexate only (95% Confidence Limits), as described in Example 5, infra.
Figure 51:
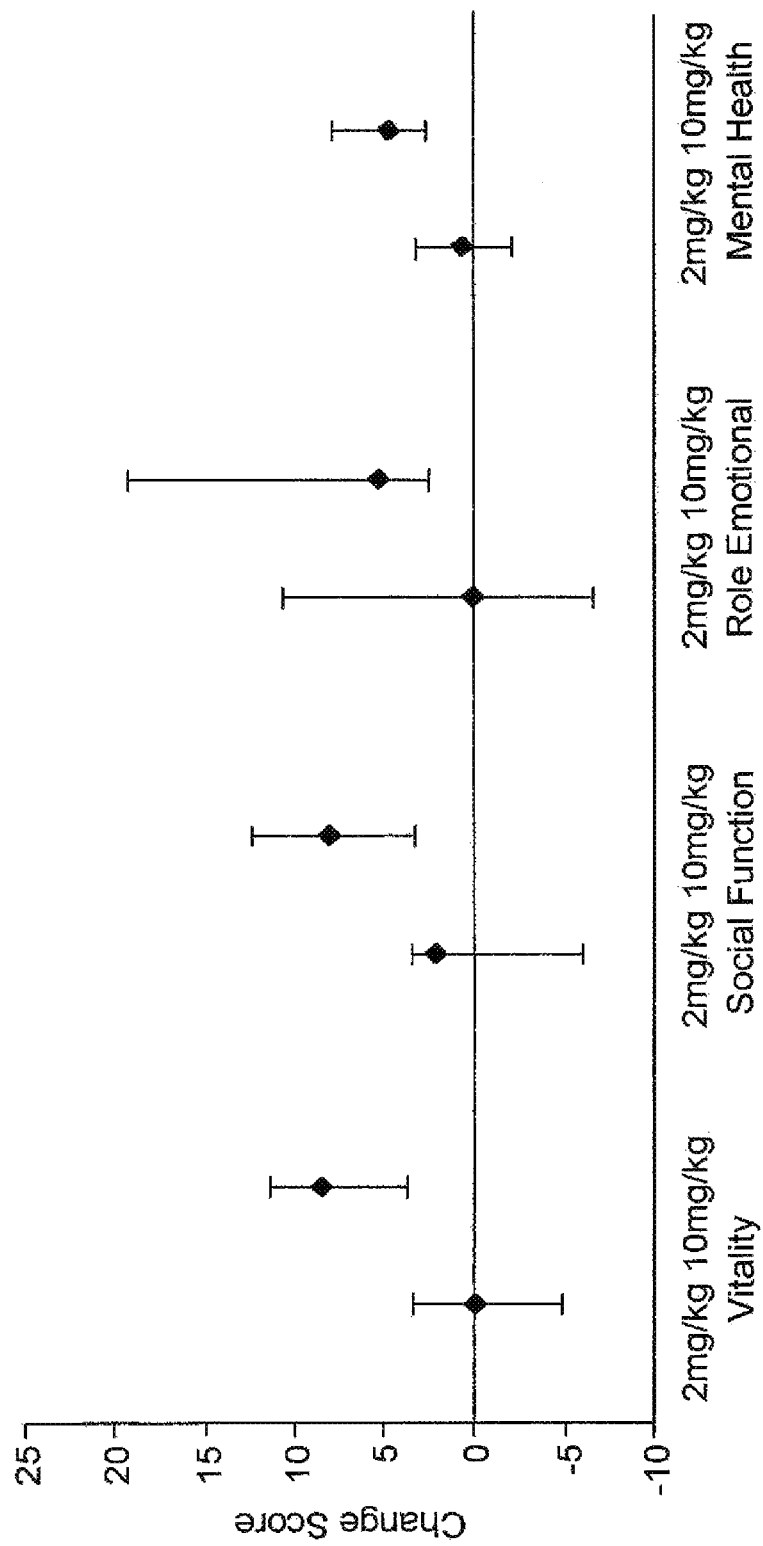
FIG. 51: A graph showing the change from baseline for SF-36 Mental Health Component on Day 180, in two groups after therapy with CTLA4Ig (2 and 10 mg/kg) compared to a group treated with methotrexate only (95% Confidence Limits), as described in Example 5, infra.

Compared to subjects treated with placebo, subjects in the CTLA4Ig 10 mg/kg group also experienced statistically significantly greater improvement in all 8 domains of the SF-36 (FIGS. 50 and 51). For subjects treated with CTLA4Ig 2 mg/kg, the improvements were also greater than those treated with placebo, but the differences were not statistically significant (FIGS. 50 and 51).

Baseline SF-36 scores were comparable between the three treatment groups. Improvements in quality of life show a clear dose-response trend after 6 months of treatment. Subjects in the CTLA4Ig 10 mg/kg treatment group demonstrated clinically and statistically significant improvements from baseline in all 8 domains of the SF-36. The greatest effects were shown in the role-physical, bodily pain, and role-emotional domains. This positive finding was consistent with the efficacy results. For subjects treated with CTLA4Ig 2 mg/kg, improvements from baseline were also statistically significant for all domains except mental health.

Pharmacokinetics

Pharmacokinetic Parameter Values

|  | $C_{max}$ (µG/ML) | $T_{max}$ (H) | $AUC_{tau}$ (µG · H/ML) | T-HALF (Days) | CLT (ML/H/KG) | VSS (L/KG) |
| --- | --- | --- | --- | --- | --- | --- |
| 2 mg/kg | | | | | | |
| MEAN | 57.96 | 0.50* | 10176.14 | 13.50 | 0.23 | 0.07 |
| SD | 16.93 | (0.00, 4.00) | 3069.84 | 5.91 | 0.13 | 0.04 |
| N | 15 | 15 | 15 | 15 | 15 | 15 |
| 10 mg/kg | | | | | | |
| MEAN | 292.09 | 0.50* | 50102.56 | 13.11 | 0.22 | 0.07 |
| SD | 67.78 | (0.00, 4.00) | 15345.95 | 5.32 | 0.09 | 0.03 |
| N | 14 | 14 | 14 | 14 | 14 | 14 |

*Median (minimum, maximum)

The pharmacokinetics of CTLA4Ig were derived from serum concentration versus time data between dosing days 60 and 90. Samples were collected prior to dosing on Day 60, at 0.5, and 4 h after dosing, on Days 67, 74, 81, and prior to dosing on Day 90. The preliminary data indicate that both $C_{max}$ and AUC values increase in a proportion comparable to the dose increment. For nominal doses increasing in a 1:5 proportion, both the $C_{max}$ and AUC values increased in the proportion of 1:5.04 and 1:4.92, respectively. T-HALF, CLT, and $V_{SS}$ values appeared to be comparable and dose independent.

Mean $V_{SS}$ values were 0.07 L/kg for both dose levels, which was approximately 1.6-fold the plasma volume.

Pharmacodynamics

TABLE VII

Mean Baseline Values for Pharmacodynamic Biomarkers

| Biomarker | Methotrexate + CTLA4Ig 10 mg/kg (n = 115) | Methotrexate + CTLA4Ig 2 mg/kg (n = 105) | Methotrexate + Placebo (n = 119) |
| --- | --- | --- | --- |
| CRP (mg/dL) | 2.9 | 3.2 | 3.2 |
| RF (IU/L) | 207 | 274 | 179 |
| IL-2r (pg/ml) | 1388 | 1407 | 1398 |
| IL-6 (pg/ml) | 26.7 | 31.7 | 21.4 |
| TNFα (pg/ml) | 11.8 | 6.0 | 11.9 |

Serum levels of pharmacodynamic biomarkers were analyzed at various times during the study. Baseline values are shown in Table VII. The values on Day 180 relative to baseline are shown in the FIGS. 52-56.

Figure 47:
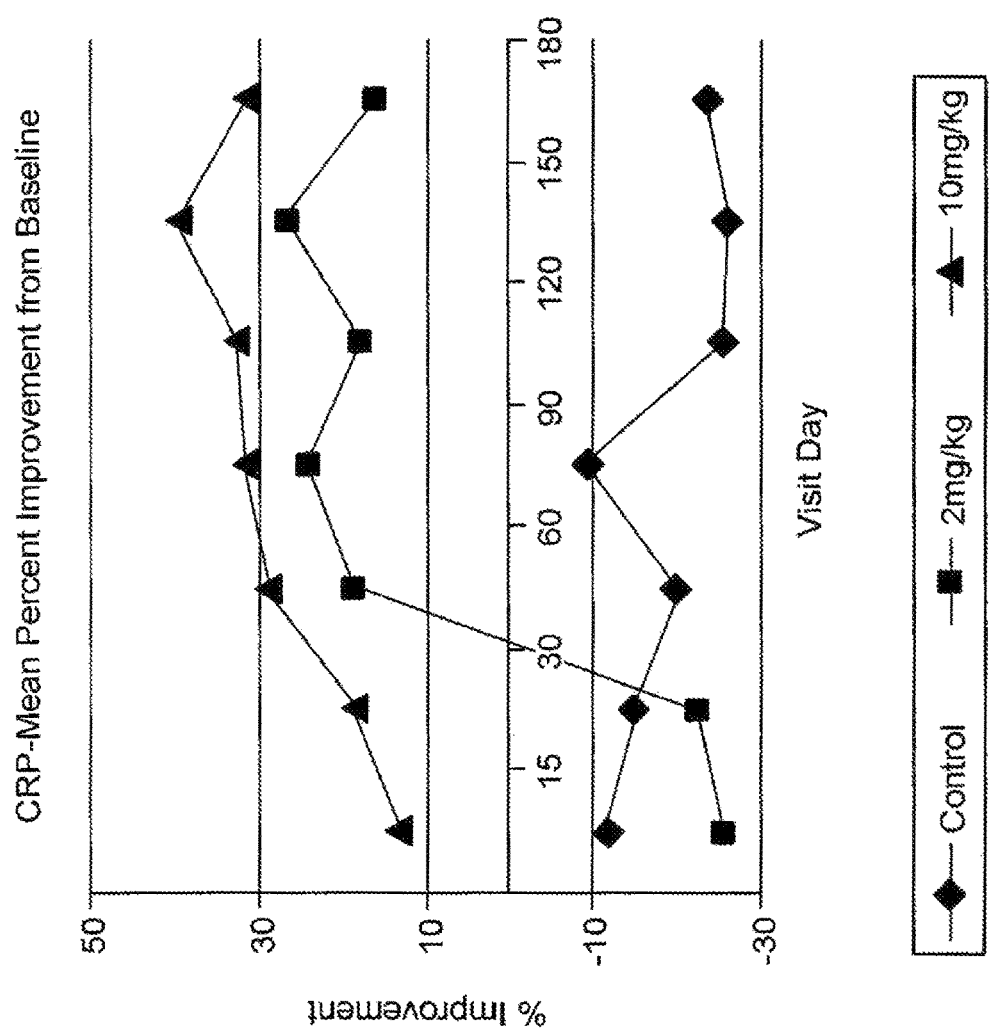
FIG. 47: A graph showing percent improvement in CRP levels function after therapy with methotrexate alone or methotrexate and CTLA4Ig (2 and 10 mg/kg)—mean percent improvement from baseline, as described in Example 5, infra.
Figure 48:
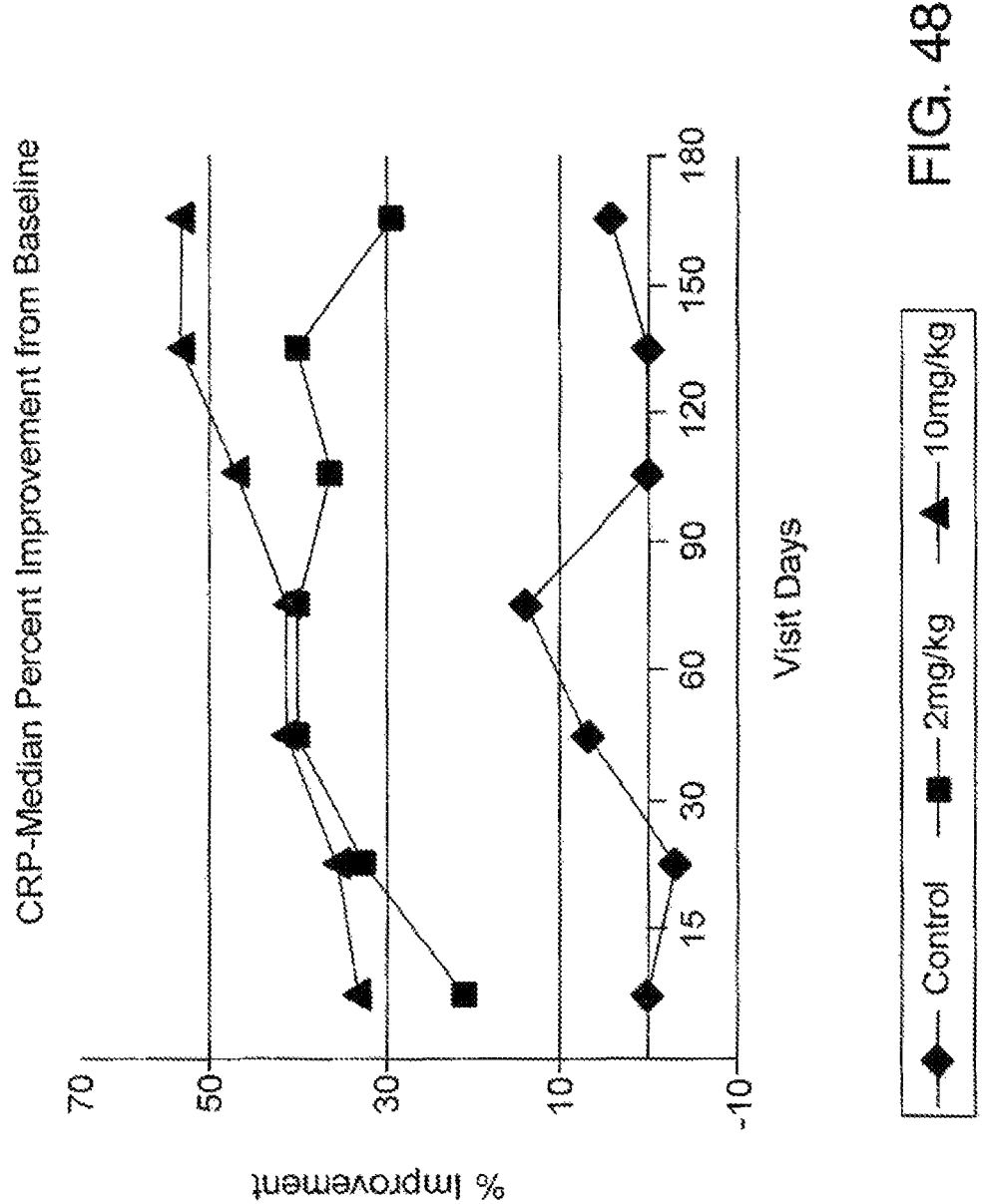
FIG. 48: A graph showing percent improvement in CRP levels function after therapy with methotrexate alone or methotrexate and CTLA4Ig (2 and 10 mg/kg)—median percent improvement from baseline, as described in Example 5, infra.
Figure 52:
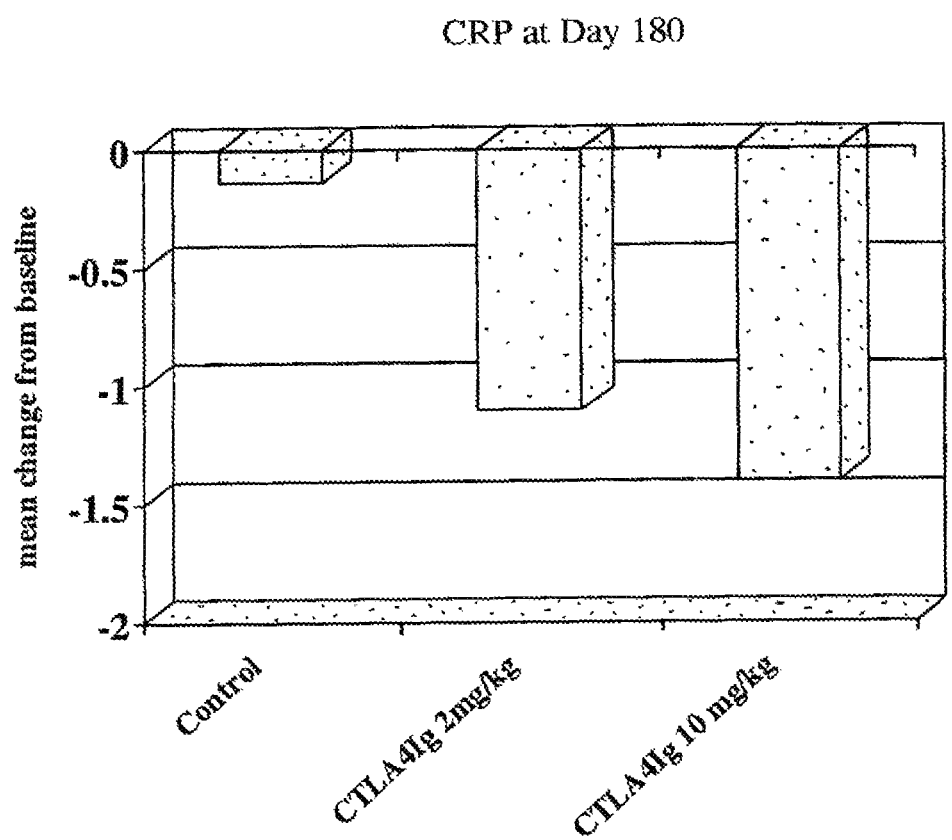
FIG. 52: A bar graph showing CRP levels at Day 180 after therapy with methotrexate alone or methotrexate and CTLA4Ig (2 and 10 mg/kg), as described in Example 5, infra.

CRP levels decreased from baseline in both CTLA4Ig-treated groups more than in the control group, with greater reduction observed in the 10 mg/kg dosing group (see FIGS. 47, 48 and 52).

Figure 53:
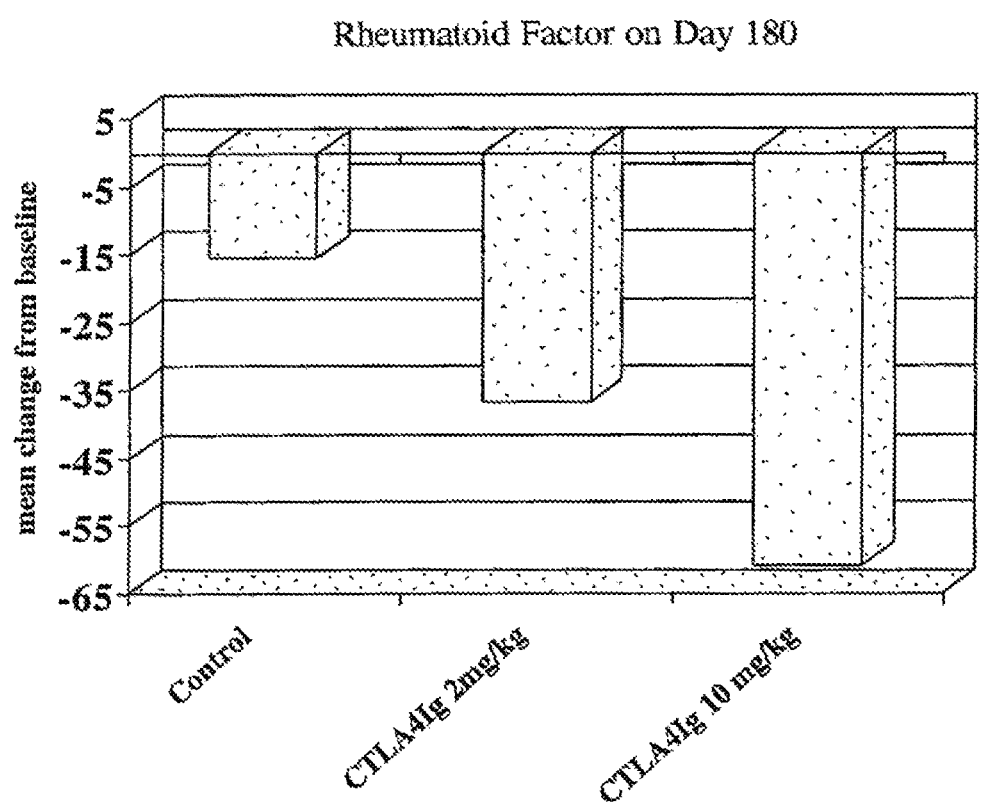
FIG. 53: A bar graph showing Rheumatoid Factor levels on Day 180 after therapy with methotrexate alone or methotrexate and CTLA4Ig (2 and 10 mg/kg), as described in Example 5, infra.

Rheumatoid factor levels decreased from baseline in both CTLA4Ig-treated groups more than in the control group, with greater reduction observed in the 10 mg/kg dosing group (see FIG. 53).

Figure 54:
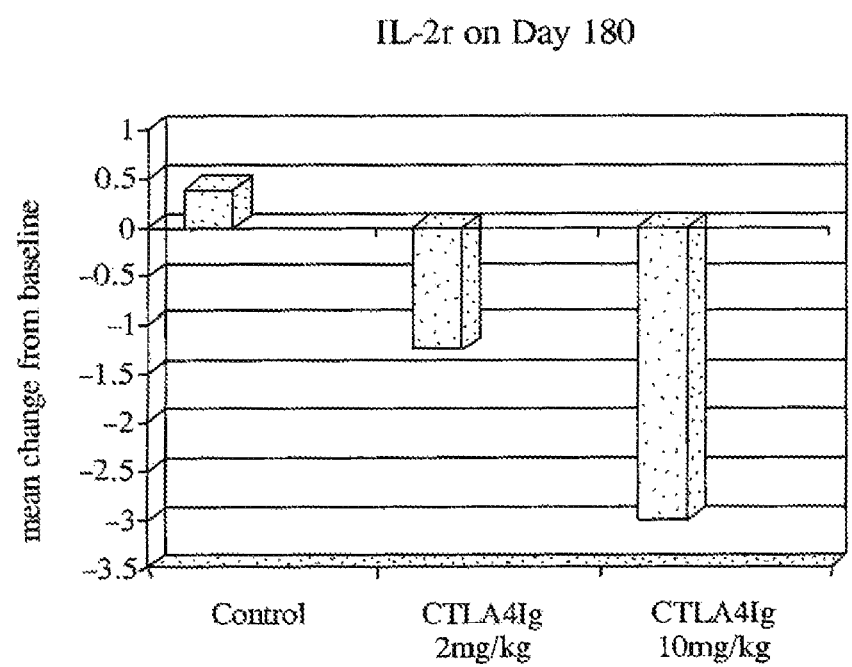
FIG. 54: A bar graph showing IL-2r levels on Day 180 after therapy with methotrexate alone or methotrexate and CTLA4Ig (2 and 10 mg/kg), as described in Example 5, infra.

Soluble IL-2r levels decreased from baseline in both CTLA4Ig-treated groups more than in the control group, with greater reduction observed in the 10 mg/kg dosing group (see FIG. 54).

Figure 55:
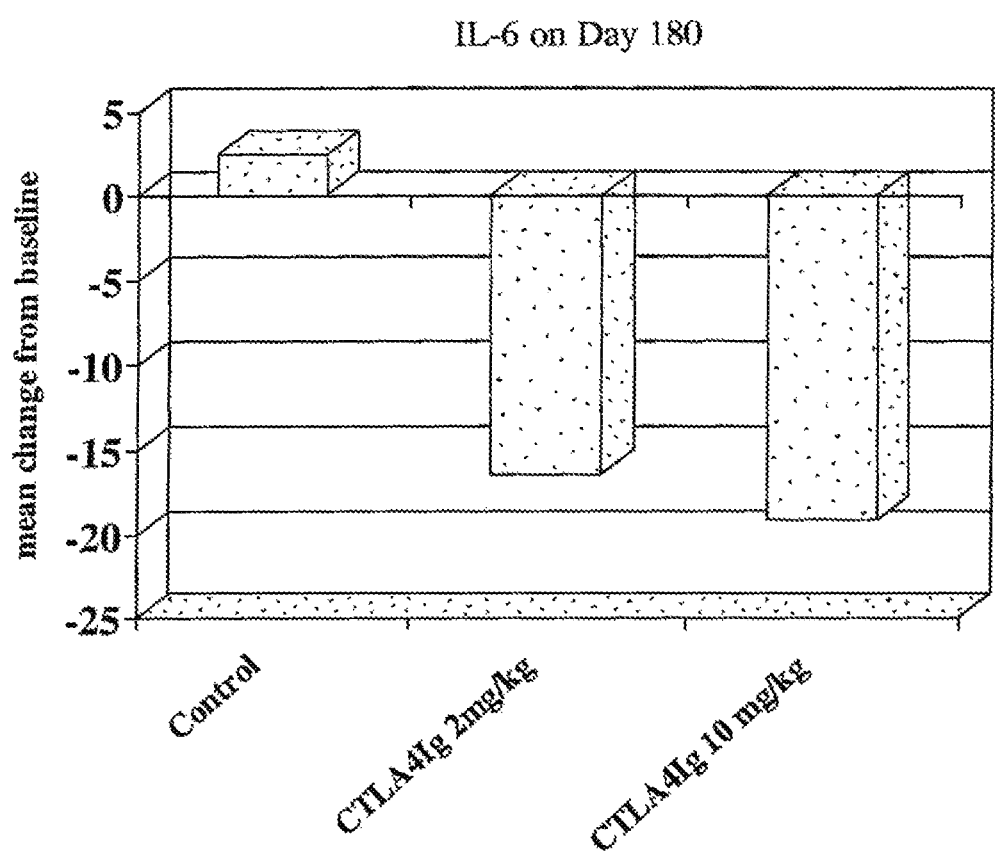
FIG. 55: A bar graph showing IL-6 levels on Day 180 after therapy with methotrexate alone or methotrexate and CTLA4Ig (2 and 10 mg/kg), as described in Example 5, infra.
Figure 56:
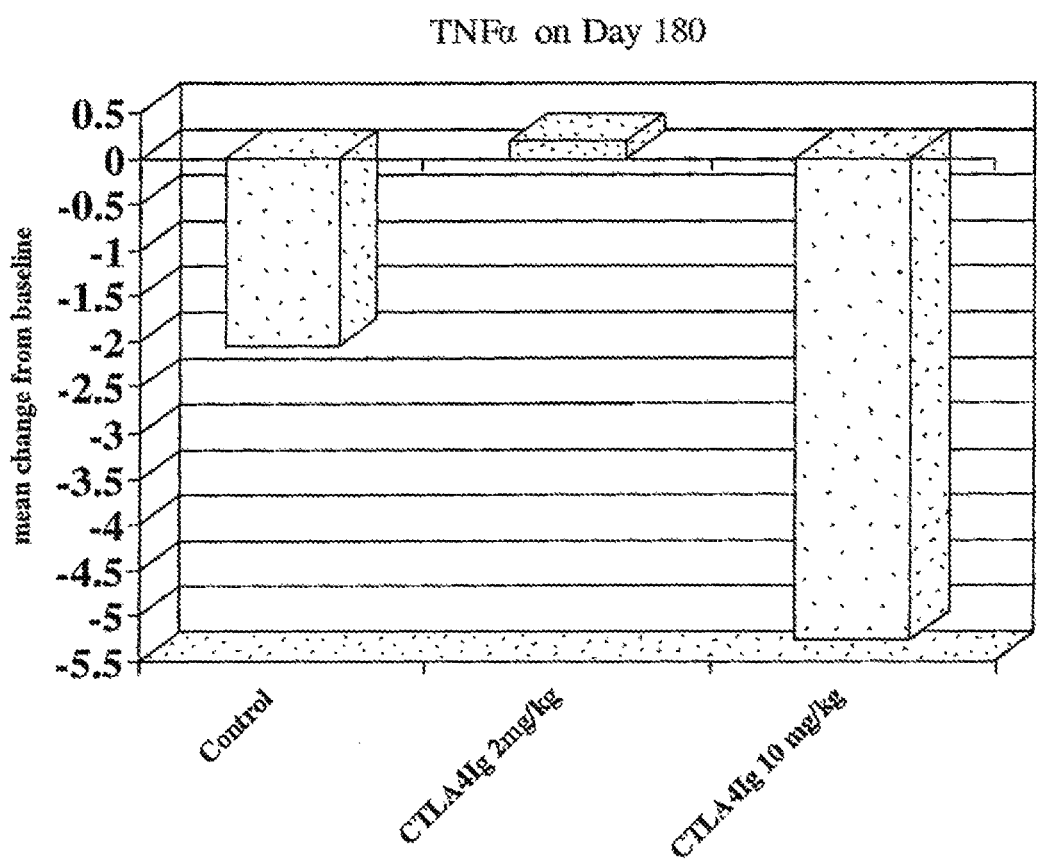
FIG. 56: A bar graph showing TNFα levels on Day 180 after therapy with methotrexate alone or methotrexate and CTLA4Ig (2 and 10 mg/kg), as described in Example 5, infra.

Serum IL-6 levels decreased from in both CTLA4Ig-treated groups more than in the control group (see FIG. 55).

The effects of CTLA4Ig on serum TNFα levels were inconclusive. The 2 mg/kg group increased and the 10 mg/kg group decreased relative to the control group (see FIG. 56).

Safety

CTLA4Ig was well tolerated at all doses. There were no deaths, malignancies or opportunistic infections in any subjects receiving CTLA4Ig. Serious adverse events (SAEs) and non-serious adverse events (NSAEs) were similar or less frequent in the active-treatment groups compared to the control group.

Fewer subjects in the 10 mg/kg group discontinued due to adverse events relative to the control group (1.7% vs 5.9%, respectively). The discontinuations due to adverse events in the 2 mg/kg were similar to the control group (6.7% vs 5.9%, respectively). The SAEs followed a pattern similar to the discontinuations due to adverse events.

No serious adverse events in the 10 mg/kg dose group were considered related to the study drug.

Immunogenicity

No anti-drug antibody responses were detected through Day 180 at both dose levels of CTLA4Ig.

CTLA4Ig significantly reduced the signs and symptoms of rheumatoid arthritis in subjects receiving methotrexate as assessed by ACR response criteria. The effects of CTLA4Ig appear to increase in proportion to dose level. The improvement from baseline in all ACR core components is higher in the 10 mg/kg group than the 2 mg/kg group. CTLA4Ig at 10 mg/kg doses demonstrated clinically and statistically significant improvements in all 8 domains of the SF-36. All pharmacodynamic biomarkers assayed appeared to decrease in proportion to CTLA4Ig dose level except for TNFα. CTLA4Ig was safe and well tolerated in subjects with rheumatoid arthritis receiving methotrexate. The adverse event profile for both CTLA4Ig doses was similar to the control group.

Example 6

A Study of a Co-Stimulation Blocker, CTLA4Ig, Given Monthly in Combination with Etanercept to Patients with Active Rheumatoid Arthritis The following Example provides a description of the administration of CTLA4Ig, in combination with etanercept, to treat patients with active Rheumatoid Arthritis.

Etanercept, along with infliximab, comprises a new generation of Rheumatoid Arthritis drugs which targets Tumor Necrosis Factor (TNF). Etanercept is a dimeric fusion protein having an extracellular portion of the TNF receptor linked to the Fc portion of human immunoglobulin (IgG1). This fusion protein binds to TNF, blocks its interactions with cell surface TNF receptors and render TNF molecules biologically inactive.

This Example describes a 12-month study in which efficacy was assessed after all subjects completed 6 months of treatment or discontinued therapy. Efficacy, safety and disease progression were also assessed throughout the duration of the study.

The study utilized a randomized, double-blind, placebo controlled, parallel dosing design. A total of approximately 141 subjects with active RA and receiving etanercept (25 mg twice weekly) were randomized to 1 of 2 dosing groups: 1) a group receiving CTLA4Ig at 2 mg/kg (n=94) plus etanercept or 2) a placebo group receiving etanercept only (n=47).

Test Product, Dose and Mode of Administration, Duration of Treatment

All subjects received etanercept (25 mg twice weekly) for at least 3 months prior to treatment.

Infusions of CTLA4Ig were given on Days 1, 15, 30, and monthly thereafter, for 6 months (primary treatment phase). Each dose of study medication was infused intravenously for approximately 30 minutes.

The primary treatment phase of the study took place during the first 6 months of treatment. During this period, subjects were required to remain on stable doses of etanercept (25 mg twice weekly). DMARDs other than etanercept were not permitted. Low-dose stable corticosteroid (at 10 mg daily or less) and/or stable non-steroidal anti-inflammatory drug (NSAID), including acetyl salicylic acid (ASA), use was allowed. Analgesics (that do not contain ASA or NSAIDs) were permitted in subjects experiencing pain that was not adequately controlled by the baseline and study medications, except for 12 hours before a joint evaluation.

Criteria for Evaluation

The primary endpoint of this study was to collect data regarding the proportion of subjects meeting modified American College of Rheumatology (ACR) criteria for 20% improvement (ACR 20) after 6 months. The modified ACR 20 criteria were used to accommodate the low CRP levels in this study's subject population. The modified ACR criteria were defined as 1) a greater than 20% improvement in tender and swollen joint count and 2) a greater than 20% improvement in 2 of the remaining 4 core data set measures (global pain, physician, subject, functional assessment). CRP, which is normally a part of the standard ACR core data sets, was not included in the modified ACR criteria due to the low levels of CRP in subjects using TNF blockers, such as etanercept. The standard ACR criteria, and two alternative criteria (SF-36 Physical Health and SF-36 Mental Health) were also evaluated as secondary endpoints.

Statistical Methods

Treatment of a group of patients with CTLA4Ig 2 mg/kg in combination with etanercept was compared with a control group treated with placebo plus etanercept. Based on previous studies with etanercept in similar patient populations, it was assumed that the modified ACR 20 response rate (modified criteria for evaluation) at 6 months would be 35% in the control group. This is the rate of response expected among subjects who did not respond adequately to etanercept therapy. Using a 2:1 randomization, a sample of 141 (adjusted for a possible 10% dropout) subjects (47 control/94 CTLA4Ig) yields a 90% power to detect a difference of 30% at the 5% level of significance (2-tailed, based on a chi-square test with no adjustment for continuity correction).

Similarly, the sample was determined to yield a power of 91% and 83% to detect differences of 30 and 25% in ACR 50 and 70, respectively. However, due to slow enrollment, only 122 subjects were randomized and 121 treated and analyzed (one subject was randomized but never received treatment).

Demography and Baseline Characteristics

TABLE 1

Subject Disposition at Day 180

|  | CTLA4Ig + etanercept | Placebo + etanercept | Total |
| --- | --- | --- | --- |
| Randomized* | 85 | 36 | 121 |
| Completed | 68 (80%) | 22 (61%) | 90 (74%) |
| Discontinued | 17 (20%) | 14 (39%) | 31 (26%) |
| Adverse Events | 6 (7.0%) | 1 (2.7%) | 7 (6%) |
| Lack of Efficacy | 6 (7.0%) | 12 (33%) | 18 (15%) |
| Other | 5 (5.8%) | 1 (2.7%) | 6 (5%) |

*Excludes one subject that did not receive treatment.

After 6 months, the proportion of total discontinuations were higher (39%) in the placebo plus etanercept treatment group compared to the CTLA4Ig plus etanercept group (20%). The difference was driven by a higher rate of discontinuation due to lack of efficacy in the placebo plus etanercept group (Table 1).

Demographic characteristics were similar between treatment groups. The majority of subjects were female and Caucasian. The mean duration of the disease was 13 years and the mean age was 52 years (Table 2).

TABLE 2

Mean Baseline Demographic and Clinical Characteristics

|  | CTLA4Ig + etanercept N = 85 | Placebo + etanercept N = 36 | Total N = 121 |
| --- | --- | --- | --- |
| Mean Age: yrs (Range) | 50 (24-74) | 55 (28-72) | 52 (24-74) |
| Mean Weight: kg (Range) | 81 (45-154) | 79 (46-126) | 81 (45-154) |
| Gender: Female: n (%) | 66 (78%) | 26 (72%) | 92 (76%) |
| Race: Caucasian - n (%) | 80 (94%) | 36 (100%) | 116 (96%) |

TABLE 2-continued

Mean Baseline Demographic and Clinical Characteristics

| | CTLA4Ig + etanercept N = 85 | Placebo + etanercept N = 36 | Total N = 121 |
|---|---|---|---|
| Mean Duration of Disease: yrs ± sd | 13.0 ± 10.1 | 12.8 ± 8.6 | 13.0 ± 9.7 |
| Tender Joints (out of 68) - mean ± sd | 28.7 ± 14.0 | 29.5 ± 13.7 | 28.9 ± 13.8 |
| Swollen Joints - (out of 66) - mean ± sd | 19.6 ± 9.4 | 20.3 ± 11.0 | 19.8 ± 9.9 |

Baseline clinical characteristics were similar between treatment groups including a mean of 29 tender joints and 20 swollen joints. With the exception of CRP values, which were lower, the baseline characteristics were typical of subjects with active rheumatoid arthritis and enrolled in clinical studies (Table 2).

ACR Responses and Core Components

Figure 63:
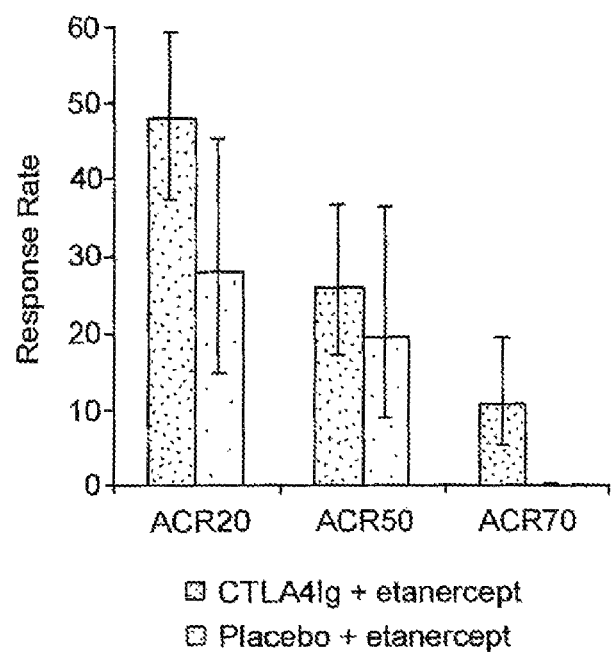
FIG. 63: A bar graph showing the difference in modified ACR response rates on Day 180 in two groups after therapy with etanercept alone (25 mg twice weekly) or in combination with CTLA4Ig (2 mg/kg), as described in Example 6, infra.

The improvements in the ACR 20 and ACR 70 responses in the CTLA4Ig+etanercept group were statistically significant compared to the CTLA4Ig+placebo group (Table 3 and FIG. 63).

TABLE 3

Modified ACR Response at Day 180 - Number of Subjects (%)*

| | ACR 20 | ACR 50 | ACR 70 |
|---|---|---|---|
| CTLA4Ig + etanercept*** | 48.2% | 25.9% | 10.6% |
| Diff. from Placebo + etanercept | 20.5% | 6.4% | 10.6% |
| 95% CI | (1.2, 39.7) | (−10.2, 23.1) | (0.4, 20.8) |
| p-Value | 0.037** | 0.448 | 0.042** |

Figure 64A:
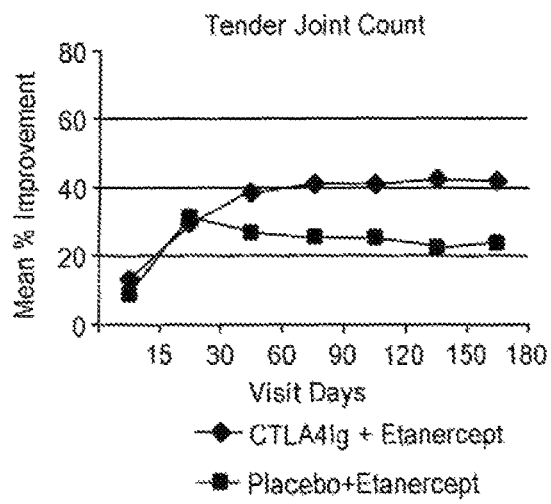
FIGS. 64a-64c: Graphs showing percentage improvement of individual components of the modified ACR criteria as assessed on each visit day after therapy with etanercept alone (25 mg twice weekly) or in combination with CTLA4Ig (2 mg/kg) as described in Example 6, infra.
Figure 64B:
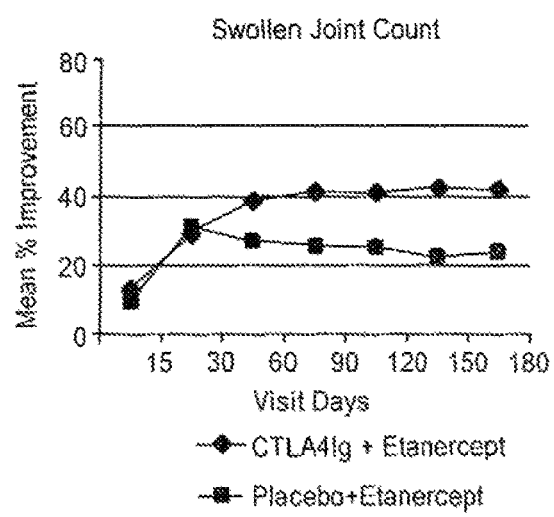
Figure 64C:
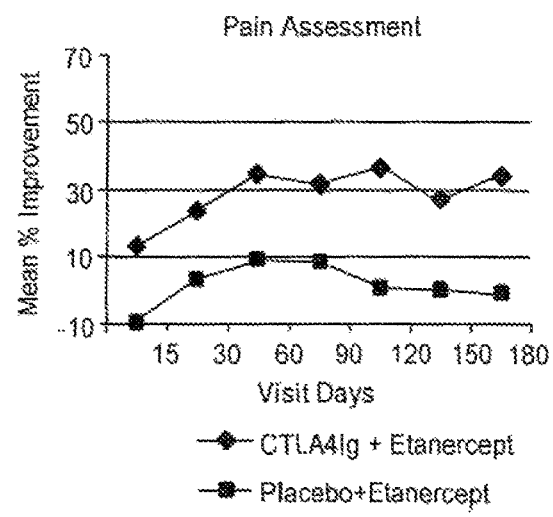

*See Criteria for Evaluation
**$p < 0.05$ (probability for ACR response in CTLA4Ig + etanercept vs. placebo + etanercept)
***N = 85 and N = 36 for CTLA4Ig + etanercept: and Placebo + etanercept, respectively By two months of treatment, numerically higher responses on all components of the ACR criteria were observed for the CTLA4Ig plus etanercept group. Three of the seven ACR components are shown in FIGS. 64a-64c.

The mean improvements in the individual components of the ACR criteria on Day 180 were consistently greater in the CTLA4Ig plus etanercept treatment group compared to the placebo plus etanercept group (Table 4).

TABLE 4

Mean Percent (SE) Improvement in Individual ACR Components at Day 180

| ACR Component | CTLA4Ig + etanercept N = 85 | Placebo + etanercept N = 36 |
|---|---|---|
| Tender Joints | 42% (5.5) | 24% (8.3) |
| Swollen Joints | 37% (5.0) | 21% (8.1) |
| Pain | 34% (4.3) | −1% (10.8) |
| Physical Function (MHAQ) | 31% (5.2) | −5% (13.8) |
| Subject Global Assessment | 27% (5.4) | 3% (9.5) |
| Physician Global Assessment | 43% (4.3) | 27% (5.8) |

Quality of Life

Compared to baseline, subjects in the CTLA4Ig plus etanercept group demonstrated statistically significant improvements at Day 180 in all 8 subscales of the SF-36—compared to only one (physical function) in subjects in the placebo plus etanercept group. The absolute changes in HRQOL subscales were considered clinically meaningful.

Figure 65A:
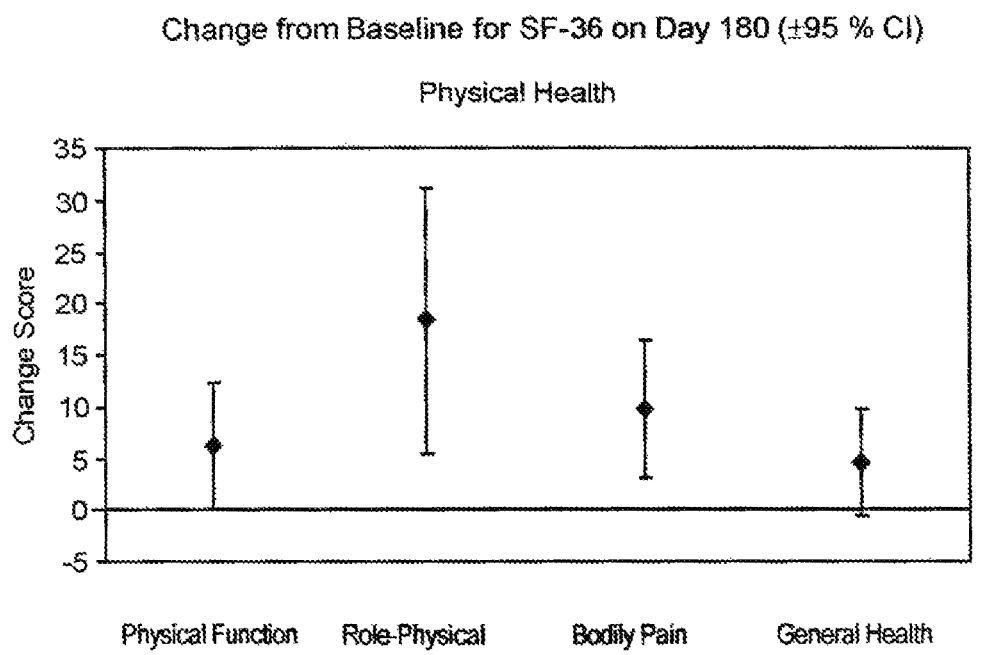
FIG. 65A: A graph showing the change from baseline for SF-36 Physical Health Component on Day 180, in two groups after therapy with etanercept (25 mg biweekly) alone or in combination with CTLA4Ig (2 mg/kg) (95% Confidence Limits), as described in Example 6, infra.
Figure 65B:
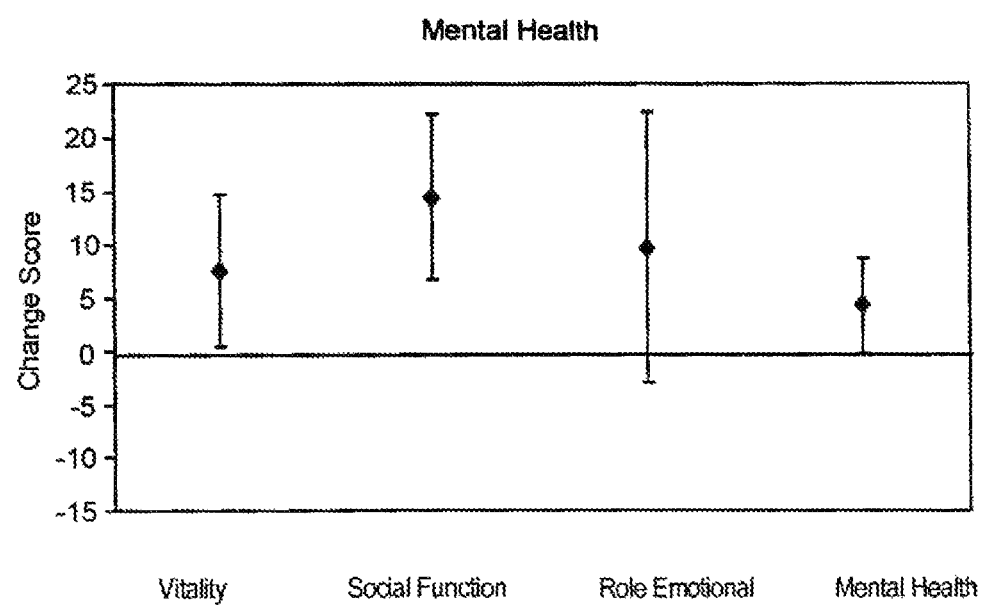
FIG. 65B: A graph showing the change from baseline for SF-36 Mental Health Component on Day 180, in two groups after therapy with etanercept (25 mg biweekly) alone or in combination with CTLA4Ig (2 mg/kg) (95% Confidence Limits), as described in Example 6, infra.

Compared to the placebo plus etanercept group, subjects in the CTLA4Ig plus etanercept group experienced statistically significantly greater improvement in 4 subscales of the SF-36: role-physical, bodily pain, vitality, and social function (FIGS. 65A and 65B). Improvements in the other 4 subscales were also greater than the placebo plus etanercept group, although they were not statistically significant.

Safety

No deaths or opportunistic infections occurred during the first 6 months of this study. Among the most frequently reported adverse events, headache, upper respiratory infection, musculo/skeletal pain, nausea/vomiting, hypertension, and diarrhea occurred at a higher rate in the CTLA4Ig plus etanercept group compared to the placebo plus etanercept group. Sinus abnormalities and rash were slightly higher in the CTLA4Ig plus etanercept group, as well.

More subjects in the CTLA4Ig plus etanercept group experienced serious adverse events (SAE) (7.1%) than the etanercept plus placebo group (2.8%). However, no SAEs were considered related to the study drug.

Two subjects receiving CTLA4Ig and etanercept had a dermatological malignancy. One subject had a basal cell carcinoma that was excised after the Day 150 visit. The other subject had a squamous cell carcinoma which was a pre-existing lesion that the subject decided to have removed after the Day 120 visit. Another subject experienced angioedema that was considered by the investigator to be a drug reaction to azithromycin.

All adverse events (AEs) leading to discontinuation were of either of mild or of moderate intensity. One discontinuation in the CTLA4Ig plus etanercept group, due to a tremor, was considered a serious adverse event.

Immunogenicity

No subjects receiving CTLA4Ig seroconverted for CTLA4Ig or CTLA4-T specific antibodies. No significant change in GMTs for CTLA4Ig or CTLA4-T specific antibodies was observed.

Comparison Between CTLA4Ig/Etanercept and CTLA4Ig/Methotrexate ACR Responses

TABLE 5

CTLA4Ig + Etanercept vs. CTLA4Ig + Methotrexate ACR Responses (% Improvement)

| | CTLA4Ig + Etanercept[a] (IM101-101) | | CTLA4Ig + Methotrexate[b] (IM101-100) | | |
|---|---|---|---|---|---|
| | 2 mg/kg N = 85 | 0 mg/kg[c] N = 36 | 10 mg/kg N = 115 | 2 mg/kg N = 105 | 0 mg/kg[c] N = 119 |
| ACR 20 | 48.2%[d] | 27.8% | 60.0%[d] | 41.9% | 35.3% |
| ACR 50 | 29.3% | 19.4% | 36.5%[d] | 22.9%[d] | 11.8% |
| ACR 70 | 10.6%[d] | 0% | 16.5%[d] | 10.5%[d] | 1.7% |

[a]Modified ACR. See criteria for evaluation.
[b]Standard ACR criteria.
[c]Placebo + Background therapy (etanercept or methotrexate).
[d]$p < 0.05$ for the difference in ACR response vs placebo + background therapy.

The efficacy of CTLA4Ig plus etanercept at 2 mg/kg was similar to that observed in subjects receiving the same dose of CTLA4Ig plus methotrexate therapy (Example 5). However, the criteria for evaluation in the methotrexate (Example 5) trial was the standard ACR, that includes CRP among the core components, while in the etanercept trial (Example 6) the criteria for evaluation was the modified ACR, that excludes CRP.

Conclusion

Preliminary assessment of the study at 6 months found that CTLA4Ig (2 mg/kg) in combination with etanercept reduced the signs and symptoms of rheumatoid arthritis, as compared with etanercept alone. The increases in the modified ACR20 and ACR 70 assays were statistically significant. Efficacy of CTLA4Ig plus etanercept therapy was observed within one month of the start of treatment. CTLA4Ig was generally safe and well tolerated when administered in combination with etanercept with the safety profile similar to etanercept therapy alone. CTLA4Ig was not immunogenic during the six month trial period. Additionally, the efficacy of CTLA4Ig therapy in combination with etanercept (Example 6) was similar to the same dose of CTLA4Ig with methotrexate (Example 5).

Example 7

One-Year Results of a Phase IIB, Multicenter, Randomized, Double-Blind, Placebo-Controlled Study to Evaluate the Safety and Clinical Efficacy of Two Different Doses of BMS-188667 Administered Intravenously to Subjects with Active Rheumatoid Arthritis while Receiving Methotrexate The following Example provides the one-year results from a Phase IIB, multicenter, randomized, double-blind, placebo controlled clinical study to evaluate the safety and clinical efficacy of administering two different doses of CTLA4Ig in combination with methotrexate to treat patients with active Rheumatoid Arthritis (RA). The study presented in this Example is a continuance of the six-month study presented in Example 5.

Based on preliminary efficacy results from Example 3, supra, and the standard practice of adding other therapies to MTX in the treatment of RA, this study was designed to test the hypothesis that CTLA4Ig (BMS-188667) combined with MTX may have greater clinical efficacy when compared with MTX plus placebo in RA subjects who still have active disease despite MTX treatment.

The results presented in this clinical study report are based on data from an analysis performed after all subjects completed 6 months of treatment and again after all subjects completed 12 months of treatment.

Throughout this Example, the 10 mg/kg CTLA4Ig plus MTX group may be referred to as the 10 mg/kg group, the 2 mg/kg plus MTX group is referred to as the 2 mg/kg group, and the CTLA4Ig (BMS-188667) placebo plus MTX group is referred to as the placebo group.

Study Methodology

This study compared the clinical efficacy of two different doses (10 and 2 mg/kg) of CTLA4Ig (BMS-188667) combined with methotrexate (MTX) or with MTX plus placebo in subjects with active RA as assessed by ACR at 6-month and 12-month intervals. This study enrolled adult subjects with active RA who had had an inadequate response to MTX.

Results after one-year of monitoring subjects with active rheumatoid arthritis who were intravenously administered: 1) CTLA4Ig at a dosage of 2 mg/kg body weight with methotrexate, 2) CTLA4Ig at a dosage of 10 mg/kg body weight with methotrexate, or 3) a placebo with methotrexate (hereinafter known as placebo), are presented herein.

Subjects with active RA, despite treatment with MTX and who met the inclusion/exclusion criteria for this study were randomized 1:1:1 to receive one of the following treatments on a background of MTX therapy: CTLA4Ig (BMS-188667) 10 mg/kg, CTLA4Ig (BMS-188667) 2 mg/kg, or placebo. Subjects must have been treated with MTX (10 mg to 30 mg weekly) for at least 6 months, at a stable dose for 28 days prior to Day 1.

Treatment Groups: Subjects were randomized 1:1:1 to one of three treatment groups:

1) Group 1: CTLA4Ig (BMS-188667) 10 mg/kg by intravenous infusion.
2) Group 2: CTLA4Ig (BMS-188667) 2 mg/kg by intravenous infusion.
3) Group 3: CTLA4Ig (BMS-188667) placebo by intravenous infusion.

Infusion doses were based upon the subject's body weight from the pre-treatment visit immediately prior to the Day 1 visit (for a subject on MTX monotherapy, the weight was obtained at the screening visit; for a subject on MTX combination therapy [in combination with other DMARDs], the weight was obtained from the washout visit, Day −2). The infusion doses were not modified during Day 1 to Day 360.

Infusions were to occur at approximately the same time of day throughout the study. All doses of study medication were administered in a fixed volume of 75 mL at a constant rate over approximately 30 minutes. The intravenous bag and line were flushed with 25 mL of dextrose 5% in water (D5W) solution at the end of each infusion. All intravenous infusions were administered with the subject in the seated position. Subjects were observed for Adverse Events (Aes) and changes in vital signs (blood pressure, heart rate, body temperature) from the start of each infusion (pre-dose, 15, 30, 45, 60, 75, 90, 120 minutes) and for a minimum of 2 hours after the start of the infusion. The observation period could be extended, if clinically indicated.

During the primary phase (Day 1 to Day 180) of the study, concomitant administration of selected medications was allowed. The permitted medications included:

MTX: Continued use of current dose (no increases, and decreases only for toxicity)

Systemic (non-topical) corticosteroids: Provided that the dose was stable and the total dose was less than or equal to the equivalent of prednisone 10 mg/day. Intra-articular injections were to be avoided; however, if necessary, up to two intra-articular injections were permitted. NOTE: A joint that received an intra-articular injection was counted as "active" in ALL subsequent assessments/evaluations.

NSAIDs, including ASA: Provided the dose was stable

Acetaminophen, combination products including acetaminophen and narcotic analgesics (i.e., acetaminophen with codeine phosphate, acetaminophen with propoxyphene napsylate, acetaminophen with oxycodone hydrochloride, acetaminophen with oxycodone bitartrate, etc.), or tramadol: For subjects experiencing pain not adequately controlled by baseline or study medication (except for 12 hours before a joint evaluation)

Table 1 is a schedule of study procedures and evaluations.

TABLE 1

Schedule of Study Procedures and Evaluations

| | Pretreatment (Day) | | Treatment Period | | | | | | | | | | | | |
|---|---|---|---|---|---|---|---|---|---|---|---|---|---|---|---|
| | Screen | | Treatment Day[e,f,j,h] | | | | | | | | | | | | |
| Visit Day | (−28 to −2) | (−2) | 1 | 15 | 30 | 60 | 90 | 120 | 150 | 180 | 210 | 240 | 270 | 300 | 330 | 360 |
| *Screening assessments* | | | | | | | | | | | | | | | | |
| Informed consent | X | | | | | | | | | | | | | | | |
| Complete History and Physical | X | | | | | | | | | | | | | | | X[i] |
| CXR | X[a] | | | | | | | | | | | | | | | |
| ECG | X[a] | | | | | | | | | | | | | | | X |
| Stabilize/Withdraw prohibited medications (if necessary)[b] | X | | | | | | | | | | | | | | | |
| Enroll Subject | X | X[m] | | | | | | | | | | | | | | |
| Randomize Subject[k] | | | X | | | | | | | | | | | | | |
| Dosing[h] | | | X | X | X | X | X | X | X | X | | X | | X | X | |
| *Interim Assessments[f]* | | | | | | | | | | | | | | | | |
| Duration of morning stiffness | X | | X | X | X | X | X | X | X | X | | X | | X | | X |
| Interim History and Physical | | | X | X | X | X | X | X | X | X | | X | | X | | |
| Tender joint count | X | X | X | X | X | X | X | X | X | X | | X | | X | | X |
| Swollen joint count | X | X | X | X | X | X | X | X | X | X | | X | | X | | X |
| Subject's assessment of pain | X | | X | X | X | X | X | X | X | X | | X | | X | | X |
| Subject's global assess of disease activity | X | | X | X | X | X | X | X | X | X | | X | | X | | X |
| Physician's global assess of disease activity | X | | X | X | X | X | X | X | X | X | | X | | X | | X |
| Subject's assess of physical function | X | | X | X | X | X | X | X | X | X | | X | | X | | X |
| Short form-36 health questionnaire (SF-36) | X | | X | | | | X | | | X | | | | | | X |
| Subjects response to therapy | | | | | | | X | | | X | | | | | | X |
| *Safety Assessments* | | | | | | | | | | | | | | | | |
| Adverse event monitoring | | | X | X | X | X | X | X | X | X | X | X | X | X | X | X[o] |
| Weight[g] | X | X | | | | | | | | | | | | | | X |
| Mammogram (females only)[l] | X | | | | | | | | | | | | | | | X |
| Vital signs | X | | X | X | X | X | X | X | X | X | X | X | X | X | X | X |
| *Labs* | | | | | | | | | | | | | | | | |
| CBC | X | | X | X | X | X | X | X | X | X | X | X | X | X | X | X |
| Chemistry panel | X | | X | X | X | X | X | X | X | X | X | X | X | X | X | X |
| Urinalysis | X | | | | | | | | | | | | | | | X |
| Urine/serum pregnancy test[d] | X | | X | X | X | X | X | X | X | X | X | X | X | X | X | X |
| Hepatitis B surface antigen | X | | | | | | | | | | | | | | | |
| Hepatitis C antibody | X | | | | | | | | | | | | | | | |
| *Pharmacodynamics (PD)* | | | | | | | | | | | | | | | | |
| Rheumatoid factor | X | | X | | | | | | | X | | | | | | X |
| CRP | X | X | X | X | X | X | X | X | X | X | | X | | X | | X |
| IL-2R | | | X | | X | X | X | X | X | X | | X | | X | | X |
| Exploratory cytokines (ICAM-1 e-Selectin, IL-6 and TNFα) | | | X | | | | X | | | X | | | | | | X |
| Pharmacokinetics | | | X | | X | X | | | | X | | | | | | |
| *Immunoglobulin determinations* | | | | | | | | | | | | | | | | |
| Quantitative immunoglobulins (IgG, IgA, IgM) | | | X | | | | | | | X | | | | | | X |

TABLE 1-continued

Schedule of Study Procedures and Evaluations

| | Pretreatment (Day) | | Treatment Period | | | | | | | | | | | | |
|---|---|---|---|---|---|---|---|---|---|---|---|---|---|---|---|
| | Screen | | Treatment Day[e,f,i,h] | | | | | | | | | | | | |
| Visit Day | (−28 to −2) | (−2) | 1 | 15 | 30 | 60 | 90 | 120 | 150 | 180 | 210 | 240 | 270 | 300 | 330 | 360 |
| | | | Immunogenicity | | | | | | | | | | | | |
| Anti-BMS-188667Ab testing | | | X | X | X | | | | | X | | | X | | | X |
| | | | Radiographic assessments[n] | | | | | | | | | | | | |
| X-rays (hands/wrists and feet) | | | X | | | | | | | X | | | | | | X |

[a]Chest X-ray and ECG was performed if not performed within 6 months or not on file.
[b]If subject was being treated with DMARDs on top of methotrexate therapy and did not meet initial entry criteria, the DMARDs must have been washed out for at least 28 days prior to Day 1.
[c]This visit was required only if the subject was on MTX therapy.
[d]Urine or serum pregnancy test performed within 48 hours prior to dosing, for all women of child bearing potential. Serum pregnancy test was to be processed locally.
[e]Subjects who discontinued must have had an "early termination" visit. Assessments at this visit were identical to assessments performed on Day 360. The assessments for this visit replaced what might have been scheduled on the day of discontinuation. Changes in current DMARD, steroid, or NSAIDs therapy were not permitted until after these assessments were performed. Subjects were to be contacted 30 days after discontinuation to capture safety data (adverse events).
[f]Every effort must have been made to insure the same evaluator completed the assessment for each subject.
[g]Most recent weight should have been used to calculate study drug dosage. All doses administered during the study were be based on this weight.
[h]For Day 15, a +/−3 day visit window was permitted. For subsequent visits, a +/−7 day visit window was permitted.
[i]Complete physical examination only.
[j]All assessments should have been performed or administered prior to study drug administration unless otherwise indicated.
[k]The results of all assessments must have been reviewed for eligibility requirements before contacting the Central Randomization System for randomization.
[l]See Section 2.1.4.3 of the protocol for mammography rationale. If not performed within 6 months (documentation must be on file) prior to signing consent. Subjects who discontinued from the study after Day 1 required a follow-up mammogram on the one year anniversary of the mammogram that was performed during the screening period.
[m]Subject's body weight was provided to central randomization system.
[n]No radiographic assessments were required at the termination visit for subjects who discontinued within the first nine months of treatment.
[o]Subjects who were terminated early had adverse events and concomitant medications recorded 30 and 60 days after the last dose of study medication.

Efficacy Assessments
Clinical Measurements and Responses

Clinical response was assessed using the American College of Rheumatology (ACR) Core Data Set and Response Definitions. For this assessment, data were collected on seven components: 1) tender joint count (standardized 68 joint count); 2) swollen joint count (standardized 66 joint count); 3) subject global assessment of pain; 4) subject global assessment of disease activity; 5) physician global assessment of disease activity; 6) subject assessment of physical function (MHAQ); and 7) an acute phase reactant value CRP.

The ACR 20, ACR 50, and ACR 70 definition of response corresponds to a 20%, 50%, or 70% improvement, respectively, over baseline in tender and swollen joints (components 1 and 2) and a 20%, 50%, and 70% improvement, respectively, in three of the five remaining core data set measures (components 3 to 7). A Major Clinical Response is defined as maintenance of an ACR 70 response over a continuous 6-month period. See Table 1 for the days that data for each component was collected.

The primary efficacy analysis tested for differences in ACR 20 response between the two CTLA4Ig (BMS-188667) treatment groups and the placebo group at 6 months (Day 180). A sequential testing procedure was employed. First, a Chi-square test was used to compare the data for the 10 mg/kg CTLA4Ig group with the data for the placebo group at the 0.05 level of significance. If this was significant, the data for the 2 mg/kg CTLA4Ig group was compared with the placebo group at the 0.05 level. This testing procedure preserved the overall alpha level at 5%. Similar analyses were carried out for the ACR 50 and ACR 70 responses at 6 months. Differences in ACR 20, ACR 50 and ACR 70 responses between each CTLA4Ig (BMS-188667) treatment group and the placebo group were summarized using point estimates and 95% confidence intervals. Subjects who discontinued the study due to lack of efficacy (i.e., worsening RA) were considered ACR non-responders at all subsequent time points. For all subjects who discontinued for other reasons, their last ACR response was carried forward.

ACR 20, ACR 50, and ACR 70 response rates on Day 360 were compared between each CTLA4Ig (BMS-188667) treatment group and placebo at the Dunnett-adjusted 0.027 (two-tailed) level of significance.

The proportion of responders achieving an ACR 20 response at each time point was also plotted over time, and the Cochran Mantel-Haenszel test (Cochran, W. G., "Some Methods of Strengthening the Common Chi-Square Test", *Biometrics,* 10:417-451 (1954); Mantel, N. et al., "Biostatistical Aspects of the Analysis of Data from Retrospective Studies of Disease", *J. Natl. Cancer. Inst.,* 22:719-748 (1959)) was used to compare the frequency of subjects achieving an ACR 20 response in each CTLA4Ig (BMS-188667) group versus the placebo group.

ACR 20, ACR 50, and ACR 70 responses on Days 15, 30, 60, 90, 120, 150, 180, 240, 300, and 360 were also presented for the two CTLA4Ig (BMS-188667) groups and the placebo group. The differences in ACR responses between the CTLA4Ig (BMS-188667) groups and placebo group were summarized using 95% confidence intervals. The ACR data plotted over time were used to assess onset-of-action and to determine time to maximal response.

A Major Clinical Response was defined as the maintenance of an ACR 70 response over a continuous 6-month period. At the 12-month analysis, the proportion of subjects who achieved a Major Clinical Response among the three groups was summarized.

In order to assess the integrity of the planned analyses, all subjects who received study medication and discontinued the study for any reason were considered ACR non-responders at all scheduled study visits subsequent to discontinuation.

The cumulative index, ACR-N, was evaluated at each follow-up assessment, and the AUC was assessed for up to 6 months and up to 12 months. The trapezoidal rule was used to compute the AUC. The ACR-N AUC was compared between the two CTLA4Ig (BMS-188667) treatment groups and the placebo group using an analysis of variance (ANOVA) for 6- and 12-month data. This allowed for the assessment of subject response throughout the study. These analyses were carried out on the LOCF data sets.

The distributional assumptions regarding the normality of the ACR-N AUC data were checked using the Shapiro-Wilks test on standardized residuals from the ANOVA model at the 10% level of significance.

Surrogate biomarkers were also used to assess the efficacy of the CTLA4Ig+MTX or placebo+MTX treatment regimens. Potential biomarkers for immunomodulation or inflammation in RA include CRP, soluble IL-2r, RF, soluble ICAM-1, E-selectin, serum IL-6, and TNFα. These parameters were summarized by treatment group, using frequencies and mean change from baseline to Day 180 and Day 360.

An Adverse Event (AE) was defined as any new or worsening illness, sign symptom or clinically significant laboratory test abnormality noted by the Investigator during the course of the study, regardless of causality. A serious adverse event (SAE) was defined as an AE that met any of the following criteria: was fatal; was life-threatening; resulted in or prolonged hospitalization; resulted in persistent or significant disability or incapacity, was cancer, was a congenital anomaly/birth defect, resulted in an overdose, resulted in the development of drug dependency or drug abuse, or was an important medical event.

Vital sign measurements were obtained at screening and at each study visit during and following study drug administration. Vital sign measurements (seated blood pressure, heart rate, and body temperature) were summarized by treatment group using means.

The two CTLA4Ig (BMS-188667) treatment groups (10 and 2 mg/kg) were compared with the placebo group. The primary analysis was the comparison of 6-month ACR response rate for 10 mg/kg and placebo groups, to be followed by the comparison of 2 mg/kg with placebo only if the former was significant. Sample sizes were based on a 5% level (two-tailed) of significance. The ACR 20 response rate for a placebo group at 6 months was estimated to be about 25% (Weinblatt, M. et al., "A trial of etanercept, a recombinant TNF:Tc fusion protein in patients with RA receiving methotrexate", New Engl. J. Med., 340:253-259 (1999)). A sample of 107 subjects per treatment group (adjusted for a possible 15% discontinuation rate) was determined to yield a 94% power to detect a difference of 25% at the 5% level (two-tailed). Table 2 summarizes the power needed to detect the specified treatment differences in ACR 20, ACR 50, and ACR 70 responses at 6 months.

TABLE 2

Response Rates and Power with 107[a] Subjects per Group

| Response | Control Rate (%) | Treatment Difference | Power (%) |
|---|---|---|---|
| ACR 20 | 25 | 25 | 94 |
| ACR 50 | 5 | 20 | 95 |
| ACR 70 | 1 | 14 | 90 |

[a]Sample size was adjusted for a possible 15% discontinuation rate; actual sample size was 91.

If the primary comparisons of the 10 mg/kg CTLA4Ig with placebo were significant, then for the comparison of the 2 mg/kg CTLA4Ig with placebo groups, the power of the test would be at least 0.88, 0.90, and 0.81 for the comparison involving ACR 20, ACR 50, and ACR 70 responses at 6 months, respectively (Koch, D. D. et al., "Statistical considerations for multiplicity in confirmatory protocols", Drug Inf. J., 30:523-534 (1996)).

Statistical Analyses
Study Population
Disposition of Subjects

Figure 68:
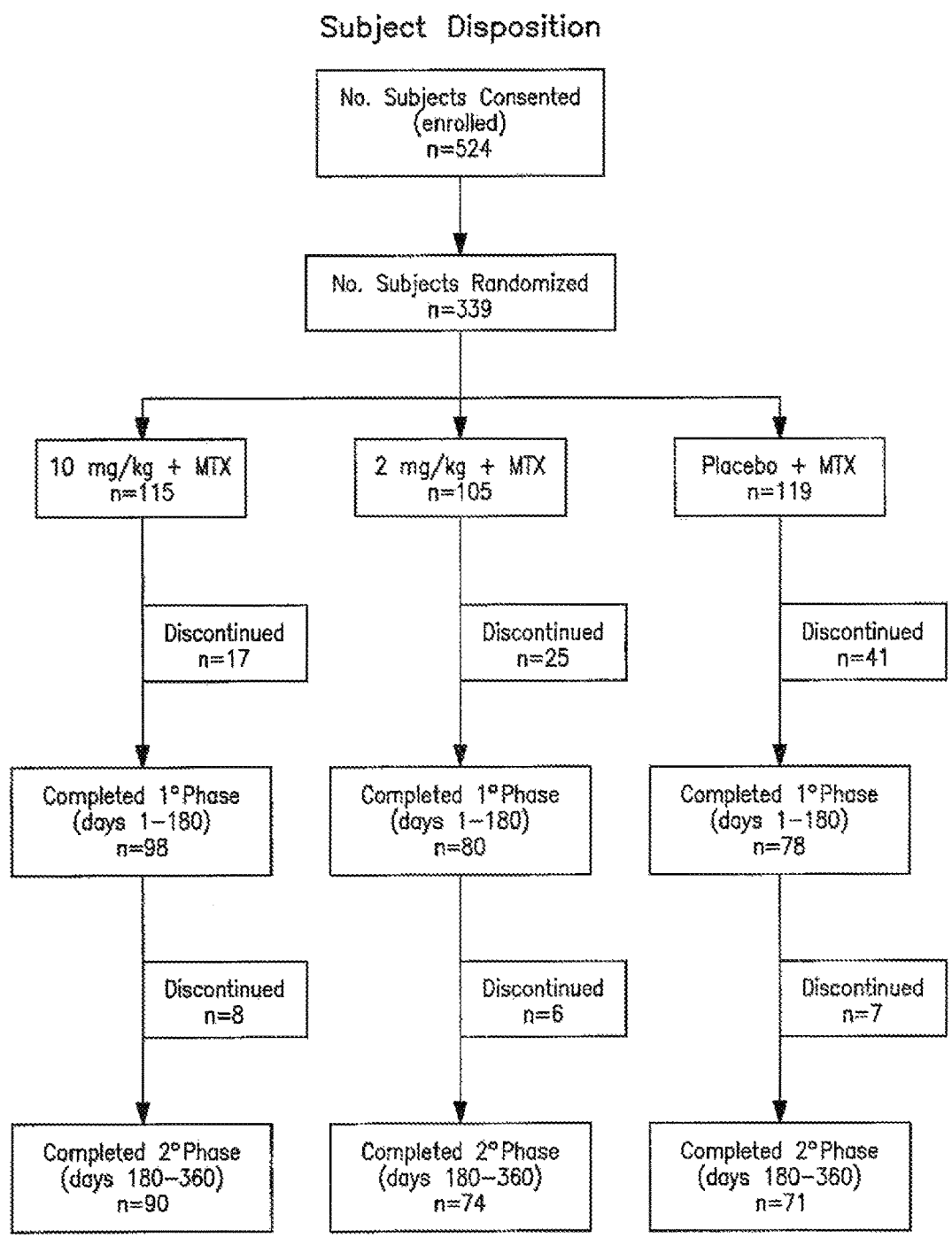
FIG. 68: A schematic diagram showing the disposition of subjects into three cohorts as described in Example 7, infra.

Of 524 subjects who were enrolled in this study, 339 subjects were randomized: 115 to the 10 mg/kg group; 105 to the 2 mg/kg group; and 119 to the placebo group (FIG. 68). The most frequent reason for not being randomized was failure to meet inclusion and/or exclusion criteria.

Primary Phase (Days 1-180)

A total of 256 subjects (75.5% of those randomized) completed the primary phase of the study; 83 subjects discontinued during this period (Table 3). Overall, discontinuation was more than 2-fold higher with placebo compared with 10 mg/kg CTLA4Ig group. Discontinuation due to lack of efficacy and discontinuation due to an AE were also more than 2-fold higher with placebo than with 10 mg/kg CTLA4Ig group.

TABLE 3

Reasons for Discontinuation: Primary Phase (Days 1-180)

| | CTLA4Ig (BMS 188667) | | | |
|---|---|---|---|---|
| | 10 mg/kg | 2 mg/kg | Placebo | Total |
| No. Treated, n | 115 | 105 | 119 | 339 |
| No. Discontinued, n (%) | 17 (14.8) | 25 (23.8) | 41 (34.5) | 83 (24.5) |
| Adverse Event | 3 (2.6) | 7 (6.7) | 9 (7.6) | 19 (5.6) |
| Lack of Efficacy | 12 (10.4) | 16 (15.2) | 28 (23.5) | 56 (16.5) |
| Withdrawal of Consent | 2 (1.7) | 2 (1.9) | 4 (3.4) | 8 (2.4) |
| Completed 180 Days of Therapy, n (%) | 98 (85.2) | 80 (76.2) | 78 (65.5) | 256 (75.5) |

Cumulative Discontinuations (Days 1-360)

A total of 235 subjects (69.3% of those randomized) completed both phases of the study; 104 subjects discontinued by Day 360 (Table 4). The same general pattern in discontinuations noted in the primary phase (2-fold higher incidence with placebo compared with 10 mg/kg CTLA4Ig group) was also observed overall (Days 1-360). This included the overall discontinuation rate, discontinuations due to a lack of efficacy and discontinuations due to an AE.

TABLE 4

Reasons for Discontinuation: Both Phases (Days 1-360)

| | CTLA4Ig (BMS-188667) | | | |
|---|---|---|---|---|
| | 10 mg/kg | 2 mg/kg | Placebo | Total |
| No. Treated, n | 115 | 105 | 119 | 339 |
| No. Discontinued, n (%) | 25 (21.7) | 31 (29.5) | 48 (40.3) | 104 (30.7) |
| Adverse Event | 5 (4.3)[b] | 9 (8.6) | 11 (9.2) | 25 (7.4) |
| Death | 0 | 1 (1.0) | 0 | 1 (0.3) |
| Lost to Follow-up | 1 (0.9) | 2 (1.9) | 0 | 3 (0.9) |
| Other[a] | 1 (0.9) | 0 | 1 (0.8) | 2 (0.6) |
| Lack of Efficacy | 13 (11.3) | 17 (16.2) | 30 (25.2) | 60 (17.7) |
| Withdrawal of Consent | 5 (4.3) | 2 (1.9) | 6 (5.0) | 13 (3.8) |
| Completed 360 Days of Therapy, n (%) | 90 (78.3) | 74 (70.5) | 71 (59.7) | 235 (69.3) |

[a]Other reasons for discontinuation were related to compliance
[b]Subject IM101100-32-5 in the 10 mg/kg CTLA4Ig group reported an AE that was recorded as having resulted in discontinuation from the study; however, this subject was not included in this table.

Figure 69:
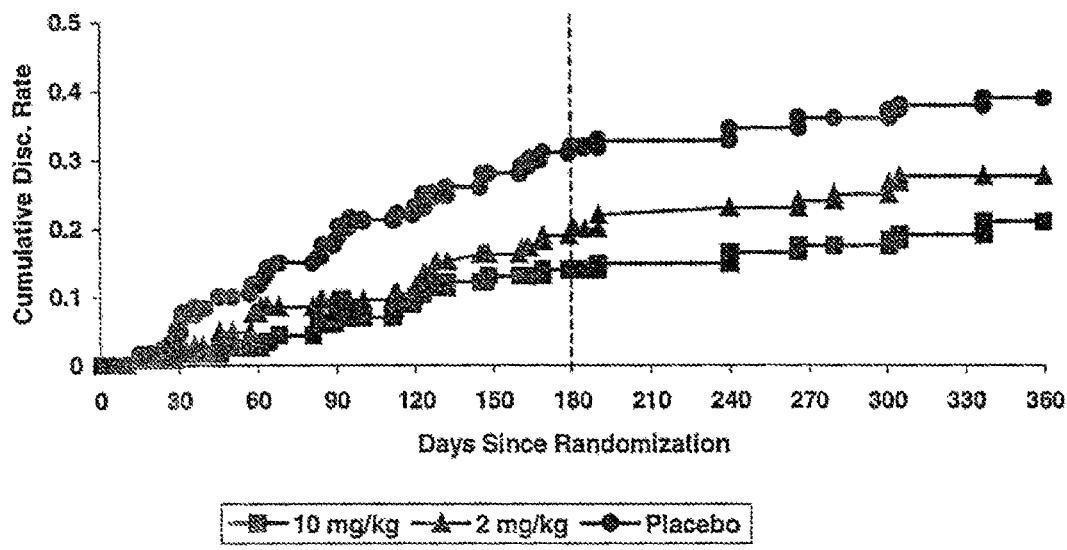
FIG. 69: A Kaplan-Meier plot of the cumulative proportion of subjects who discontinued for any reason during the first 12 months of the study, as described in Example 7, infra.
Figure 70:
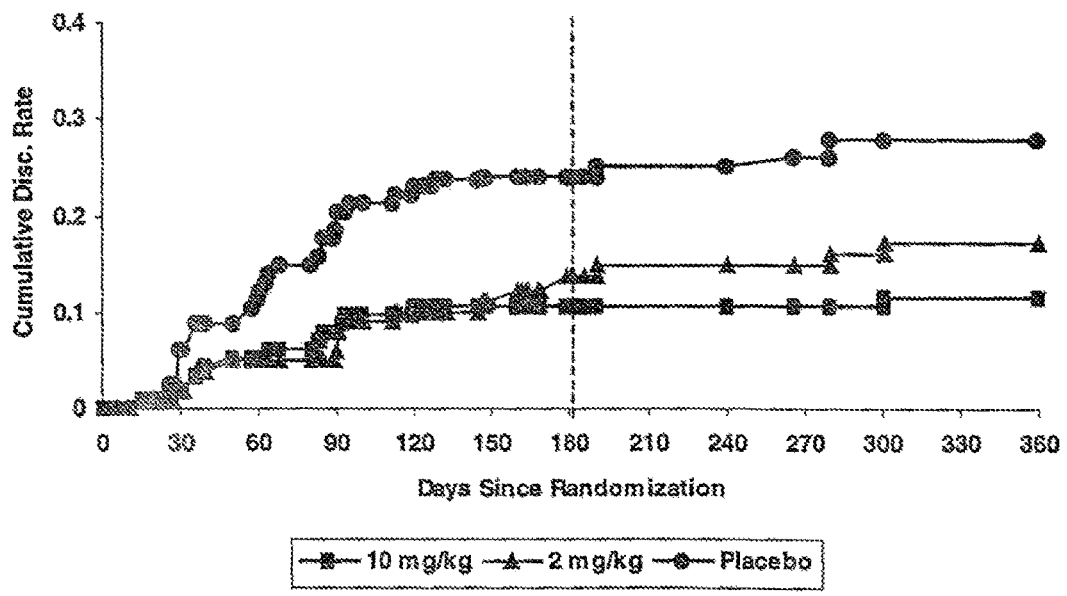
FIG. 70: A Kaplan-Meier plot of the cumulative proportion of subjects who discontinued due to lack of efficacy during the first 12 months of study, as described in Example 7, infra.

A Kaplan-Meier plot of the cumulative proportion of subjects who discontinued for any reason during the first 12 months is presented in FIG. 69; the cumulative proportion of subjects who discontinued due to lack of efficacy in presented in FIG. 70. Note that in both graphs after approximately 30 days of therapy, discontinuation rates with placebo were consistently higher compared with both CTLA4Ig (BMS-188667) groups. Additionally, after approximately 150 days of therapy, discontinuation rates for 2 mg/kg CTLA4Ig group were higher than those for 10 mg/kg.

Demography and Subject Characteristics

Overall, baseline demographic characteristics and baseline clinical RA characteristics were generally comparable across the three treatment groups and were typical of relatively advanced RA encountered in clinical practice (Table 5 and Table 6). The majority of subjects were white females approximately 55 years old with a mean duration of RA of approximately 9 to 10 years, a relatively large number of active joints (approximately 29 tender and 21 swollen joints) and visual analogue scores (VAS) approximately 59-65 mm (100 mm scale).

TABLE 5

Baseline Demographic Characteristics

| | CTLA4Ig (BMS-188667) | | |
|---|---|---|---|
| | 10 mg/kg | 2 mg/kg | Placebo |
| No. Randomized | 115 | 105 | 119 |
| Age (yrs) | | | |
| Mean ± SD | 55.8 ± 12.5 | 54.4 ± 11.3 | 54.7 ± 12.0 |
| (Range) | (17, 83) | (23, 80) | (23, 80) |
| Weight (kg) | | | |
| Mean ± SD | 77.8 ± 18.6 | 78.7 ± 21.4 | 79.9 ± 17.6 |
| (Range) | (40.1, 144.0) | (48.4, 186.8) | (44.0, 140.0) |
| Gender | | | |
| Males, n (%) | 29 (25) | 39 (37) | 40 (34) |
| Females, n (%) | 86 (75) | 66 (63) | 79 (66) |
| Race | | | |
| White, n (%) | 100 (87) | 91 (87) | 104 (87) |
| Black, n (%) | 6 (5) | 0 | 3 (3) |
| Other, n (%) | 9 (8) | 14 (13) | 12 (10) |
| Duration of RA (yrs) | n = 114[a] | n = 105 | n = 117[a] |
| Mean ± SD | 9.7 ± 9.8 | 9.7 ± 8.1 | 8.9 ± 8.3 |
| (Range) | (0, 38) | (0, 36) | (0, 41) |

[a]Duration of RA was not reported for 3 subjects.

Although not a component of the ACR criteria, duration of morning stiffness was also assessed and was nearly 2 hours in each of the three groups. Positive results for RF at baseline were also assessed, and the CTLA4Ig (BMS-188667) treatment groups had higher percentages of subjects who tested positive for RF (86% for both the 10 mg/kg and 2 mg/kg CTLA4Ig groups compared to 76% for the placebo group).

TABLE 6

Baseline Clinical Rheumatoid Arthritis Characteristics

| | CTLA4Ig (BMS-188667) | | |
|---|---|---|---|
| Characteristic | 10 mg/kg (n = 115) | 2 mg/kg (n = 105) | Placebo (n = 119) |
| Tender Joints, n | 115 | 105 | 119 |
| Mean ± SD | 30.8 ± 12.2 | 28.2 ± 12.0 | 29.2 ± 13.0 |
| Range | 11.0, 66.0 | 3.0, 62.0 | 4.0, 68.0 |
| Swollen Joints, n | 115 | 105 | 119 |
| Mean ± SD | 21.3 ± 8.4 | 20.2 ± 8.9 | 21.8 ± 8.8 |
| Range | 9.0, 54.0 | 4.0, 48.0 | 8.0, 64.0 |
| Pain (VAS 100 mm), n | 113 | 104 | 119 |
| Mean ± SD | 62.1 ± 21.4 | 64.3 ± 22.3 | 65.2 ± 22.1 |
| Range | 0.0, 99.0 | 8.0, 100.0 | 3.0, 95.0 |
| Physical Function (MHAQ 0-3), n | 115 | 105 | 119 |
| Mean ± SD | 1.0 ± 0.5 | 1.0 ± 0.5 | 1.0 ± 0.6 |
| Range | 0.0, 2.5 | 0.0, 2.5 | 0.0, 2.3 |
| Subject Global Assess (VAS 100 mm), n | 113 | 105 | 119 |
| Mean ± SD | 60.1 ± 20.7 | 59.4 ± 23.7 | 62.8 ± 21.6 |
| Range | 10.0, 100.0 | 8.0, 99.0 | 4.0, 94.0 |
| MD Global Assess (VAS 100 mm), n | 113 | 105 | 119 |
| Mean ± SD | 62.1 ± 14.8 | 61.0 ± 16.7 | 63.3 ± 15.5 |
| Range | 20.0, 98.0 | 8.0, 95.0 | 18.0, 93.0 |
| CRP (mg/dL), n | 112 | 99 | 115 |
| Mean ± SD | 2.9 ± 2.8 | 3.2 ± 2.5 | 3.2 ± 3.2 |
| Range | 0.2, 19.9 | 0.2, 10.8 | 0.2, 20.9 |

TABLE 6-continued

Baseline Clinical Rheumatoid Arthritis Characteristics

| Characteristic | CTLA4Ig (BMS-188667) | | |
|---|---|---|---|
| | 10 mg/kg (n = 115) | 2 mg/kg (n = 105) | Placebo (n = 119) |
| Morning Stiffness (in minutes), n | 115 | 103 | 119 |
| Mean ± SD | 97.9 ± 63.1 | 104.1 ± 63.9 | 106.0 ± 64.2 |
| Range | 0.0, 180.0 | 0.0, 180.0 | 0.0, 180.0 |
| Rheumatoid Factor (IU/mL), n | 99 | 90 | 90 |
| % Positive | 86% | 86% | 76% |

Baseline demographics and RA characteristics of the overall population of subjects who had at least one dose of study drug and discontinued due to lack of efficacy were generally comparable to the entire study population, however, a greater proportion of subjects in this subpopulation had been diagnosed with RA for >10 years (45%) compared to the overall study population (34%).

Medical History Findings and Prior Medications

Medical history findings for subjects in this study were consistent with relatively advanced RA and were generally similar among treatment groups. The most frequently occurring findings (in >40% of the subjects) were musculoskeletal findings (not including RA symptoms; 59.3%), gastrointestinal findings (45.1%), and genitourinary findings (42.2%). Other important medical history findings included cardiovascular disease in approximately 39% of subjects in all treatment groups and endocrine/metabolic findings in approximately 29% of all subjects.

Overall use of MTX, systemic (non-topical) corticosteroids, DMARDs and biologic RA medications prior to entering the study was generally comparable across the three treatment groups (Table 7). All subjects were to have received prior treatment with rheumatic medications, including MTX, to be eligible for the study. Prior treatment with MTX was not recorded for 4 subjects. Systemic (non-topical) corticosteroid use prior to randomization was comparable among the three treatment groups, with slightly more subjects in the 2 mg/kg CTLA4Ig and placebo groups taking systemic (non-topical) corticosteroids (~67-68%) compared to subjects in the 10 mg/kg CTLA4Ig group (60.0%). Use of other DMARDs and biologic RA medications prior to entering the study varied from 0 to 12% across treatment groups with no overall predominance in any treatment group. Mean dosing of MTX and of systemic (non-topical) corticosteroids on Day 1 were comparable among all three treatment groups (~15-16 mg/wk, ~6-7 mgs/day, respectively.

TABLE 7

Summary of Rheumatic Medications Prior to Enrollment

| Prior Rheumatic Medication, n (%)[a] | CTLA4Ig (BMS-188667) | | |
|---|---|---|---|
| | 10 mg/kg (n = 115) | 2 mg/kg (n = 105) | Placebo (n = 119) |
| No. Subjects on Prior Medications | 114 (99.1) | 103 (98.1) | 118 (99.2) |
| Methotrexate[b] | 114 (99.1) | 103 (98.1) | 118 (99.2) |
| Systemic (non-topical) corticosteroids | 69 (60.0) | 71 (67.6) | 80 (67.2) |
| Other DMARDs | 19 (16.5) | 19 (18.1) | 25 (21.0) |
| Sulfasalazine | 9 (7.8) | 2 (1.9) | 10 (8.4) |

TABLE 7-continued

Summary of Rheumatic Medications Prior to Enrollment

| Prior Rheumatic Medication, n (%)[a] | CTLA4Ig (BMS-188667) | | |
|---|---|---|---|
| | 10 mg/kg (n = 115) | 2 mg/kg (n = 105) | Placebo (n = 119) |
| Hydroxychloroquine | 8 (7.0) | 6 (5.7) | 14 (11.8) |
| Cyclosporine | 2 (1.7) | 4 (3.8) | 4 (3.4) |
| Infliximab | 2 (1.7) | 2 (1.9) | 2 (1.7) |
| Etanercept | 1 (0.9) | 4 (3.8) | 1 (0.8) |
| Chloroquine | 1 (0.9) | 0 | 0 |
| Leflunomide | 0 | 2 (1.9) | 2 (1.7) |

[a]Categories of prior rheumatic medications were not mutually exclusive.
[b]Administration of MTX was not recorded for 4 subjects.

Study Therapy

Of the three treatment groups, the 10 mg/kg CTLA4Ig group had the longest mean duration of exposure for both study phases and the placebo group had the shortest mean duration of exposure for both study phases (Day 180: 163 days, 156 days, 140 days; Day 360: 286 days, 268 days, and 234 days; 10 mg/kg, 2 mg/kg, and placebo, respectively).

At Day 180 (end of the primary phase), the proportion of subjects receiving infusions was higher in the 10 mg/kg CTLA4Ig group (85%) compared with the 2 mg/kg CTLA4Ig group (79%) and the placebo group (66%) (Table 8). At Day 330 (day of last scheduled infusion in the secondary phase), the proportion of subjects receiving infusions was also higher in the 10 mg/kg CTLA4Ig group (78%) compared with the 2 mg/kg CTLA4Ig group (70%) and the placebo group (59%).

TABLE 8

Subjects Who Received Infusions on Given Study Days

| | Number (%) of Subjects | | |
|---|---|---|---|
| | CTLA4Ig (BMS-188667) | | |
| Day | 10 mg/kg (n = 115) | 2 mg/kg (n = 105) | Placebo (n = 119) |
| 1 | 115 (100) | 105 (100) | 119 (100) |
| 15 | 114 (99) | 104 (99) | 117 (98) |
| 30 | 113 (98) | 101 (96) | 111 (93) |
| 60 | 108 (94) | 97 (92) | 103 (87) |
| 90 | 106 (92) | 94 (90) | 94 (79) |
| 120 | 100 (87) | 86 (82) | 83 (70) |
| 150 | 98 (85) | 83 (79) | 81 (68) |
| 180 | 98 (85) | 83 (79) | 78 (66) |
| 210 | 94 (82) | 80 (86) | 78 (66) |
| 240 | 95 (83) | 78 (74) | 76 (64) |
| 270 | 93 (81) | 77 (73) | 73 (61) |
| 300 | 90 (78) | 74 (70) | 72 (61) |
| 330 | 90 (78) | 73 (70) | 70 (59) |

Methotrexate

Subjects were to have been treated with a "stable" dose of MTX (10-30 mg weekly) for at least 6 months, for 28 days prior to Day 1. With the exception of 4 subjects, all subjects received between 10 and 30 mg of MTX weekly in addition to CTLA4Ig (BMS-188667) during the primary phase (Day 1-180). During the secondary phase (Day 181-360), the dose of MTX could have been adjusted provided it remained between 10 and 30 mg weekly.

Measurements of Treatment Compliance

During the primary phase, the number of missed infusions of study drug was at any time point (Table 9). During the secondary phase, subjects in the placebo group appeared to have missed slightly fewer infusions than subjects in the CTLA4Ig (BMS-188667) groups. However, more placebo than CTLA4Ig (BMS-188667) subjects discontinued by these later time points (see, supra).

TABLE 9

Number of Missed Infusions of Study Drug

| | CTLA4Ig (BMS-188667) | | |
|---|---|---|---|
| | 10 mg/kg (n = 115) | 2 mg/kg (n = 105) | Placebo (n = 119) |
| Day 1 | 0 | 0 | 0 |
| Day 15 | 1 | 1 | 0 |
| Day 30 | 0 | 1 | 1 |
| Day 60 | 0 | 0 | 0 |
| Day 90 | 0 | 0 | 0 |
| Day 120 | 0 | 1 | 2 |
| Day 150 | 1 | 2 | 0 |
| Day 180 | 1 | 0 | 1 |
| Day 210 | 4 | 0 | 0 |
| Day 240 | 1 | 2 | 1 |
| Day 270 | 0 | 2 | 0 |
| Day 300 | 1 | 1 | 0 |
| Day 330 | 0 | 0 | 0 |

Concomitant Therapy

Systemic (non-topical) corticosteroid use was generally comparable among the three groups during screening/enrollment (58-67%) and during the primary phase of the study (67-71%), Tables 10 and 11, respectively. While corticosteroid use decreased in all three treatment groups by Day 360, more subjects in the 10 mg/kg CTLA4Ig group took systemic (non-topical) corticosteroids (63.5%) compared to the other two treatment groups (53.3% and 45.4% for the 2 mg/kg CTLA4Ig and placebo groups, respectively). Several subjects (CTLA4Ig: 0-3%, placebo: 0-10%) received DMARDs other than MTX during screening/enrollment.

TABLE 10

Summary of Rheumatic Concomitant Medications During Screening/Enrollment

| | CTLA4Ig (BMS-188667) | | |
|---|---|---|---|
| Rheumatic Medication, n (%)[a] | 10 mg/kg (n = 115) | 2 mg/kg (n = 105) | Placebo (n = 119) |
| No. Subjects on Prior Medications | 114 (99.1) | 103 (98.1) | 118 (99.2) |
| Methotrexate | 114 (99.1) | 103 (98.1) | 118 (99.2) |
| Systemic (non-topical) corticosteroids | 67 (58.3) | 70 (66.7) | 75 (63.0) |
| Other DMARDs | 5 (4.3) | 6 (5.7) | 14 (11.8) |
| Sulfasalazine | 3 (2.6) | 1 (1.0) | 4 (3.4) |
| Hydroxychloroquine | 2 (1.7) | 3 (2.9) | 12 (10.1) |
| Cyclosporine | 1 (0.9) | 1 (1.0) | 2 (1.7) |
| Etanercept | 0 | 1 (1.0) | 0 |

[a]Drug categories were not mutually exclusive.

TABLE 11

Subjects Who Received Clinically Relevant Concomitant Medications During Both Study Phases

| | CTLA4Ig (BMS-188667) | | |
|---|---|---|---|
| Medication[a] | 10 mg/kg (n = 115) | 2 mg/kg (n = 105) | Placebo (n = 119) |
| Systemic (non-topical) corticosteroids (Primary Phase) | 77 (67.0) | 71 (67.6) | 85 (71.4) |
| Systemic (non-topical) corticosteroids (Secondary Phase) | 73 (63.5) | 56 (53.3) | 54 (45.4) |

[a]Drug categories were not mutually exclusive.

Note: Subject IM101100-83-3 (10 mg/kg CTLA4Ig) took mefloquine and subject IM101100-28-7 (placebo) took quinine between Days 1 and 180; subject IM101100-18-11 (10 mg/kg CTLA4Ig) took quinine between Days 181 and 360 as an antimalarial, and was not considered a significant protocol violation.

Efficacy Results

The CTLA4Ig (BMS-188667) 10 mg/kg group had superior efficacy compared to the placebo group at Day 180 and Day 360. For the 2 mg/kg CTLA4Ig group, results for some efficacy parameters were significantly better compared to the placebo group, results for most other efficacy parameters were numerically higher compared to placebo.

ACR Responses at Day 180

Figure 71A:
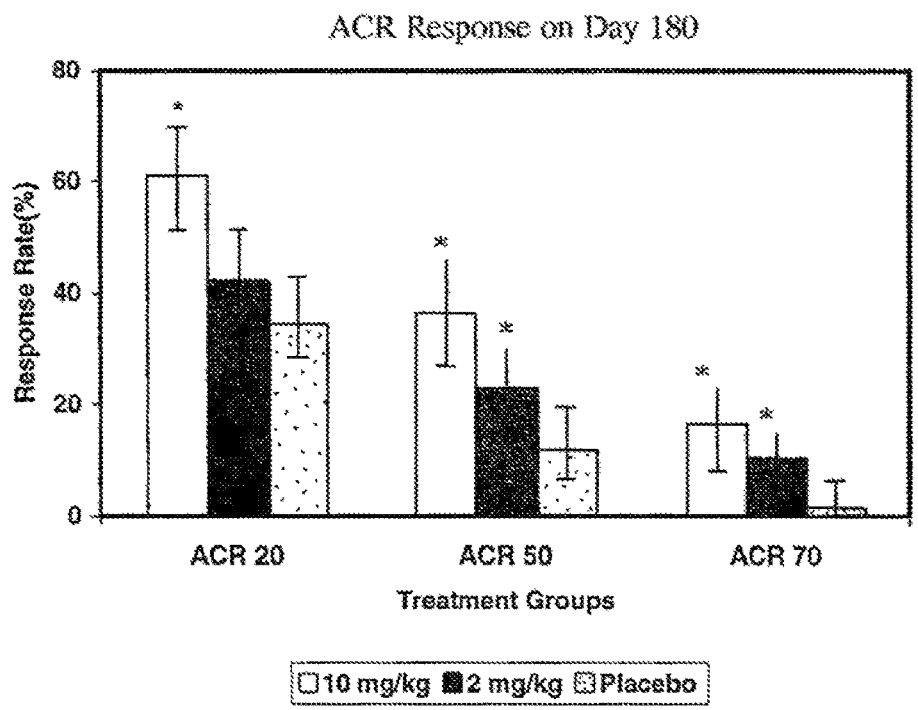
FIG. 71A: A graph showing the ACR Responses on Day 180 for patients administered methotrexate alone or methotrexate and CTLA4Ig (2 or 10 mg/kg body weight) as described in Example 7, infra.
Figure 71B:
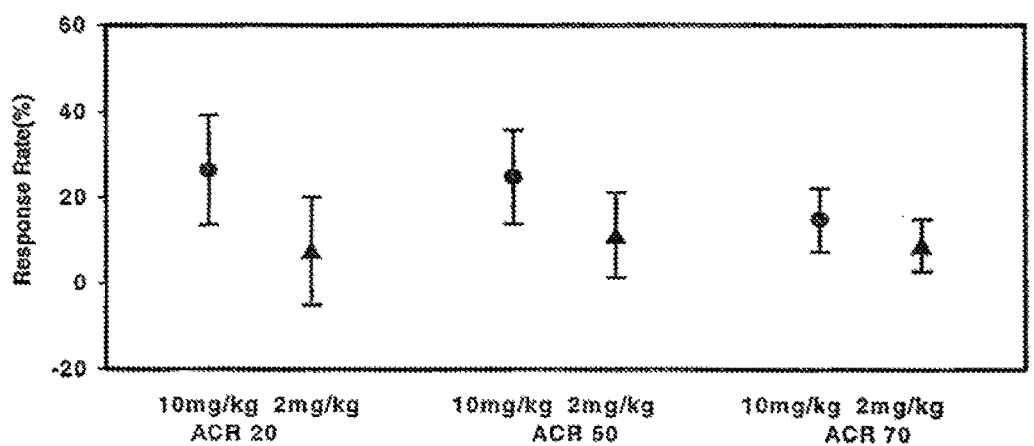
FIG. 71B: A graph showing the 95 Percent Confidence Intervals for Differences in ACR Responses on Day 180 for patients administered methotrexate alone or methotrexate and CTLA4Ig (2 or 10 mg/kg body weight) as described in Example 7, infra.

Analysis of the primary efficacy variable for this study, ACR20 response rate at Day 180, showed that the 10 mg/kg CTLA4Ig group was significantly ($p<0.001$) more effective than placebo (Table 12, FIGS. 71A and 71B).

The ACR50 and ACR70 responses at Day 180 for the 10 mg/kg CTLA4Ig group were also significantly higher compared to the placebo group (Table 12, FIGS. 71A and 71B). The ACR50 and the ACR70 responses at Day 180 for the 2 mg/kg CTLA4Ig group were significantly higher compared to the placebo group. The ACR20 response at Day 180 for the 2 mg/kg CTLA4Ig group was slightly higher compared to the placebo group; however, no statistically significant differences were observed.

TABLE 12

ACR Responses at Day 180

| | CTLA4Ig (BMS-188667) | | |
|---|---|---|---|
| | 10 mg/kg (n = 115) | 2 mg/kg (n = 105) | Placebo (n = 119) |
| ACR 20 | | | |
| n (%) | 70 (60.9) | 44 (41.9) | 42 (35.3) |
| CI | 25.6 (12.8, 38.4) | 6.6 (−6.2, 19.4) | N/A |
| p-value | <0.001[a] | 0.31 | N/A |
| ACR 50 | | | |
| n (%) | 42 (36.5) | 24 (22.9) | 14 (11.8) |
| CI | 24.8 (13.8, 35.7) | 11.1 (1.2, 20.9) | N/A |
| p-value | <0.001[a] | 0.027[a] | N/A |
| ACR 70 | | | |
| n (%) | 19 (16.5) | 11 (10.5) | 2 (1.7) |
| CI | 14.8 (7.5, 22.2) | 8.8 (2.7, 14.9) | N/A |
| p-value | <0.001[a] | 0.005[a] | N/A |

[a]Statistically significant difference for the comparison of BMS-188667 vs placebo.

ACR Responses at Day 360

Figure 72A:
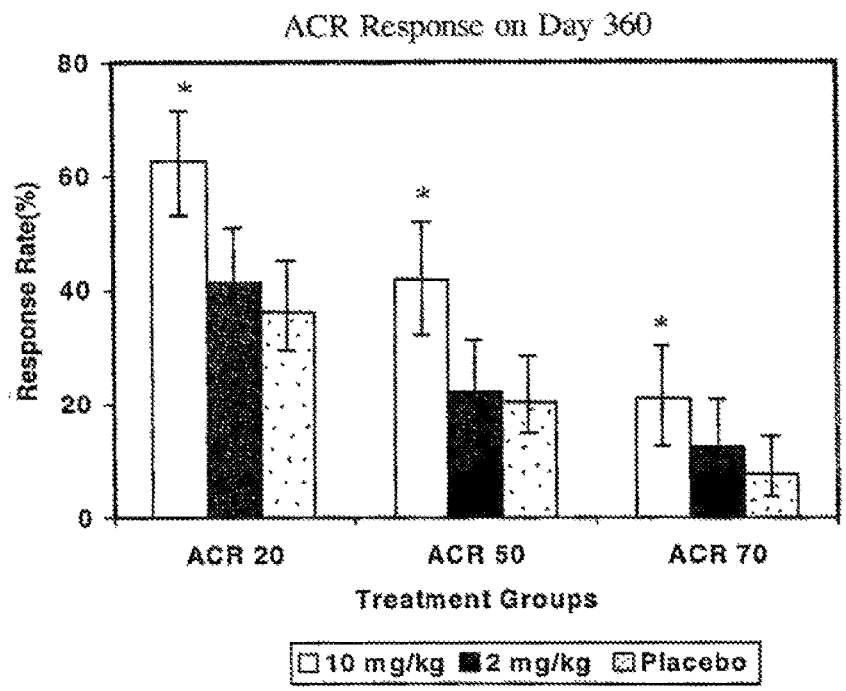
FIG. 72A: A graph showing the ACR Responses on Day 360 for patients administered methotrexate alone or methotrexate and CTLA4Ig (2 or 10 mg/kg body weight) as described in Example 7, infra.
Figure 72B:
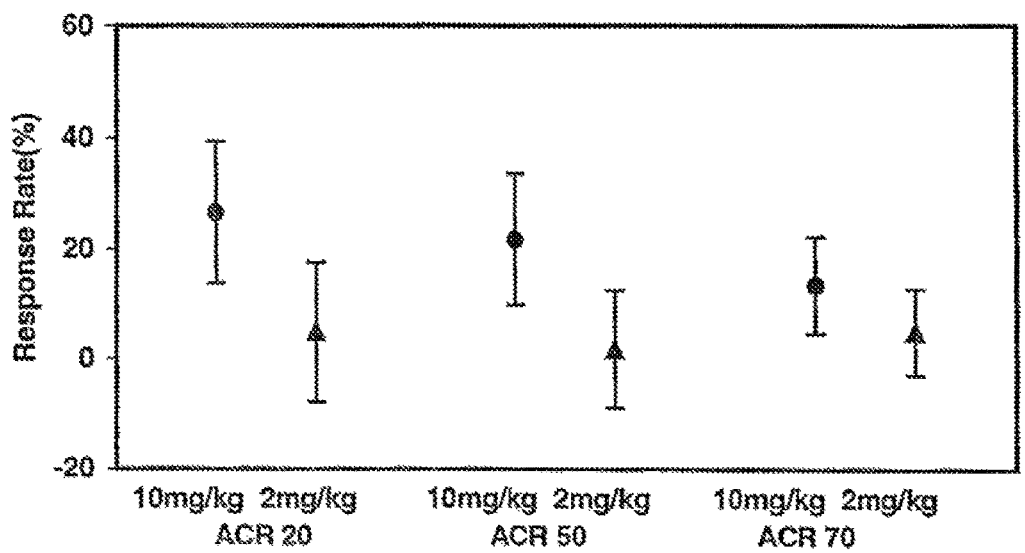
FIG. 72B: A graph showing the 95 Percent Confidence Intervals for Differences in ACR Responses on Day 360 for patients administered methotrexate alone or methotrexate and CTLA4Ig (2 or 10 mg/kg body weight) as described in Example 7, infra.

At Day 360, ACR20, ACR50 and ACR70 responses for the 10 mg/kg CTLA4Ig group were significantly ($p<0.001$) higher compared to the placebo group (Table 13, FIGS. 72A and 72B). Although the same response rates for the 2 mg/kg CTLA4Ig group were numerically higher compared to the placebo group, these differences were not statistically significant.

TABLE 13

ACR Responses at Day 360

| | CTLA4Ig (BMS-188667) | | |
|---|---|---|---|
| | 10 mg/kg (n = 115) | 2 mg/kg (n = 105) | Placebo (n = 119) |
| ACR 20 | | | |
| n (%) | 72 (62.6) | 43 (41.0) | 43 (36.1) |
| CI | 26.5 (13.7, 39.3) | 4.8 (−7.9, 17.6) | N/A |
| p-value | <0.001[a] | 0.459 | N/A |
| ACR 50 | | | |
| n (%) | 48 (41.7) | 23 (21.9) | 24 (20.2) |
| CI | 21.6 (9.7, 33.4) | 1.7 (−8.9, 12.4) | N/A |
| p-value | <0.001[a] | 0.75 | N/A |
| ACR 70 | | | |
| n (%) | 24 (20.9) | 13 (12.4) | 9 (7.6) |
| CI | 13.3 (4.4, 22.2) | 4.8 (−3.0, 12.6) | N/A |
| p-value | 0.003[a] | 0.227 | N/A |

[a]Statistically significant difference for the comparison of 10/mg/kg CTLA4Ig group vs placebo.

ACR Responses by Visit

Figure 73A:
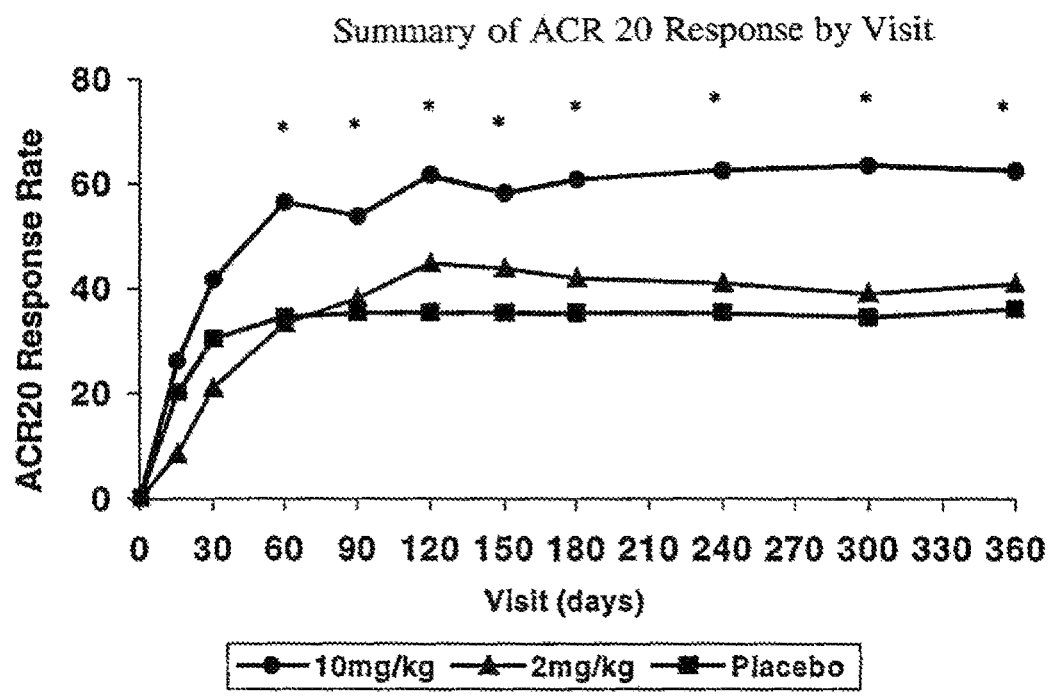
FIG. 73A: A graph summarizing the ACR 20 Response by Visit during a one year interval for patients administered methotrexate alone or methotrexate and CTLA4Ig (2 or 10 mg/kg body weight) as described in Example 7, infra.
Figure 73B:
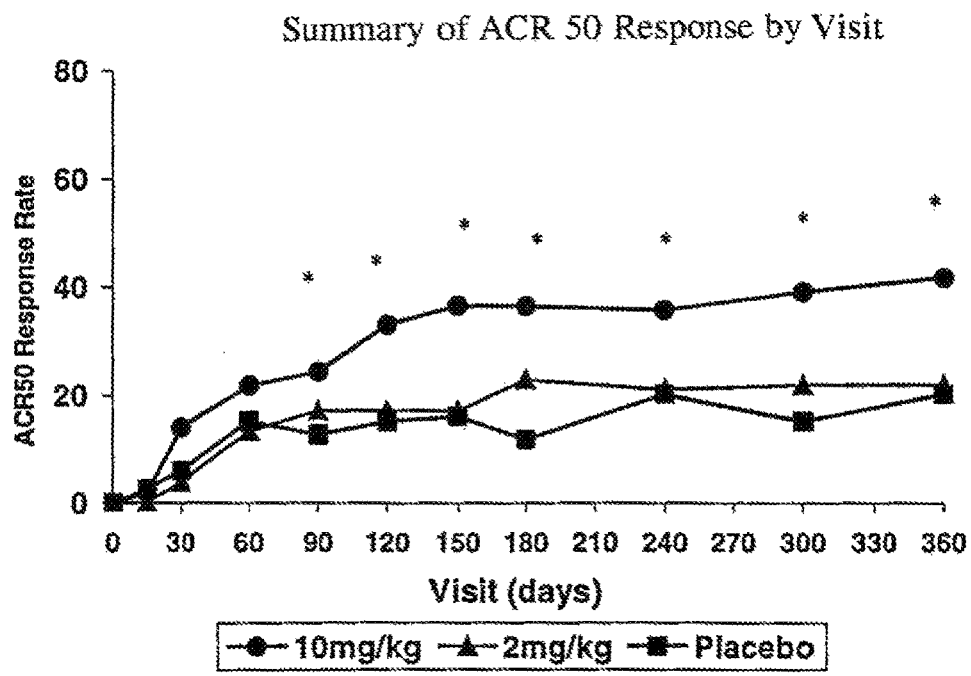
FIG. 73B: A graph summarizing the ACR 50 Response by Visit during a one year interval for patients administered methotrexate alone or methotrexate and CTLA4Ig (2 or 10 mg/kg body weight) as described in Example 7, infra.
Figure 73C:
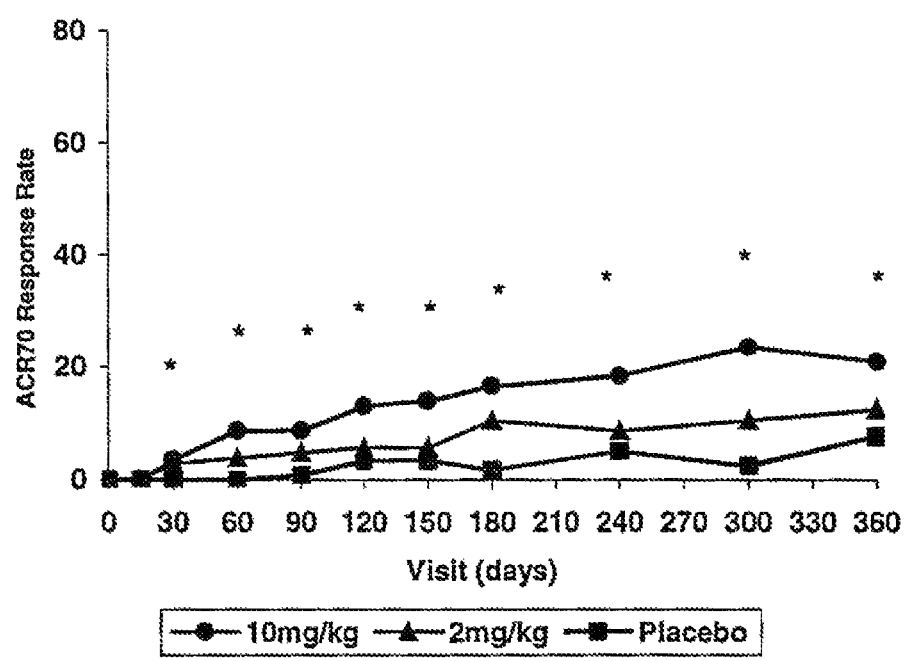
FIG. 73C: A graph summarizing the ACR 70 Response by Visit during a one year interval for patients administered methotrexate alone or methotrexate and CTLA4Ig (2 or 10 mg/kg body weight) as described in Example 7, infra.

For the comparison of the 10 mg/kg CTLA4Ig group to the placebo group, statistically significant improvements were observed for all three response rates (ACR 20, ACR 50, and ACR 70) by Day 90, and these values remained statistically significant at every time point up to and including Day 360 (p0.008 for all three ACR response rates) (FIGS. 73A-73C). In fact, statistically significant improvements in ACR 50 and ACR 70 response for the 10 mg/kg CTLA4Ig group occurred as early as Day 30 (p=0.039 and p=0.04, respectively).

For the 2 mg/kg CTLA4Ig group, statistically significant improvements compared to placebo were observed in ACR 50 and ACR 70 responses at Day 180 (p=0.027 and p=0.005, respectively). At Day 360, improvements in ACR response were slightly greater in the 2 mg/kg CTLA4Ig group compared to the placebo group; however, no statistically significant differences were observed.

After adjusting for visit using the Cochran-Mantel Haenszel test, a significant difference in ACR 20 response was observed for the 10 mg/kg CTLA4Ig group compared to the placebo group at both Day 180 and Day 360. No significant difference was observed between the 2 mg/kg CTLA4Ig and placebo groups at both timepoints. Similar results were obtained for ACR 50 response at both time points. For ACR 70 response at both time points, a significant difference was observed for both CTLA4Ig (BMS-188667) treatment groups compared to the placebo group.

Summary of Major Clinical Response

Major Clinical Response was defined as maintenance of an ACR 70 response over a continuous 6-month period. The percentages of subjects who achieved a Major Clinical Response at Day 360 were significantly higher in both the 10 mg/kg and 2 mg/kg CTLA4Ig groups (7.8% and 5.7%, respectively) when compared to the placebo group (0.8%; p=0.008 and 0.036, respectively) (Table 14).

TABLE 14

Summary of Major Clinical Response by Day 360

| | CTLA4Ig (BMS-188667) | | |
|---|---|---|---|
| | 10 mg/kg (n = 115) | 2 mg/kg (n = 105) | Placebo (n = 119) |
| No. Subjects with a Major Response | 9 (7.8) | 6 (5.7) | 1 (0.8) |
| Diff (CI) | 7.0 (1.8, 12.2) | 4.9 (0.3, 9.4) | N/A |
| p-value | 0.008[a] | 0.036[a] | N/A |

[a]Indicates a statisticall significant difference for the comparison of BMS-188667 vs placebo.

Mean Numeric ACR (ACR-N) and ACR-N Area Under the Curve (ACR-N-AUC)

Figure 74:
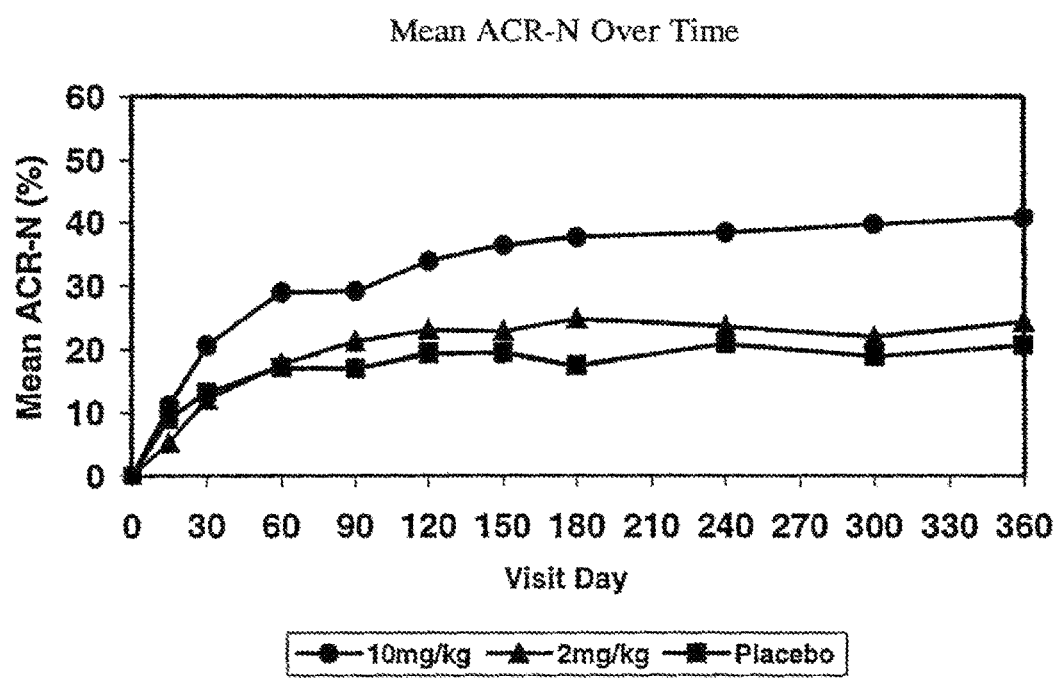
FIG. 74: A graph showing the Mean ACR-N over a one year time interval for patients administered methotrexate alone or methotrexate and CTLA4Ig (2 or 10 mg/kg body weight) as described in Example 7, infra.

Overall, mean numeric ACR (ACR-N) for all treatment groups increased over time during the first 6 months of the study (FIG. 74). During the second 6 months, mean ACR-N increased slightly with 10 mg/kg CTLA4Ig, but remained relatively unchanged with 2 mg/kg CTLA4Ig and placebo. At each study visit, the ACR-N was consistently higher for the 10 mg/kg CTLA4Ig group compared to the 2 mg/kg CTLA4Ig and placebo groups.

Compared to the placebo group, the differences in values for ACR-N AUC (area under the curve) for the 10 mg/kg CTLA4Ig group was significantly (p<0.001) higher by Day 360.

Percentage Improvement from Baseline at Day 180

For the 10 mg/kg CTLA4Ig group, improvements in each individual ACR component (tender and swollen joint counts, CRP, pain, subject global assessment, physician global assessment, and physical function) at Day 180 were statistically significant relative to improvements for the placebo group (Table 15).

For the 2 mg/kg CTLA4Ig group, statistically significant improvements compared to the placebo group were observed in physician global assessment and CRP at Day 180. Furthermore, CRP levels in the placebo group actually worsened at Day 180. Change from baseline in mean duration of morning stiffness was comparable among the three treatment groups at Day 180.

TABLE 15

Mean Percentage Improvement from Baseline at Day 180 (Individual Components of ACR Criteria)

| | CTLA4Ig (BMS-188667) | | |
|---|---|---|---|
| Component | 10 mg/kg (n = 115) | 2 mg/kg (n = 105) | Placebo (n = 119) |
| Tender Joints | n = 114 | n = 104 | n = 118 |
| Mean % Change | 59.78* | 43.15 | 31.88 |
| Swollen Joints | n = 114 | n = 104 | n = 118 |
| Mean % Change | 55.28* | 45.34* | 33.49 |
| CRP | n = 108 | n = 98 | n = 114 |
| Mean % Change | 31.79* | 16.41* | −23.43 |
| Pain | n = 109 | n = 102 | n = 118 |
| Mean % Change | 46.19* | 22.09* | 8.20 |
| Subject Global Assessment | n = 111 | n = 103 | n = 118 |
| Mean % Change | 40.76* | 9.07 | 17.48 |
| MD Global Assessment | n = 111 | n = 103 | n = 116 |
| Mean % Change | 51.91* | 38.71* | 25.14 |
| Physical Function | n = 107 | n = 98 | n = 110 |
| Mean % Change | 41.21* | 21.63 | 13.71 |
| Duration Morning Stiffness | n = 98 | n = 82 | n = 80 |
| Mean ± SD (minutes) | 61.9 ± 55.4 | 60.8 ± 66.1 | 55.9 ± 66.2 |

*Indicates p < 0.05 in comparison with placebo since 95% CIs did not include zero.

Percentage Improvement from Baseline at Day 360

For the 10 mg/kg CTLA4Ig group, improvements in each individual ACR component (tender and swollen joint counts, CRP, pain, subject global assessment, physician global assessment, and physical function) at Day 360 were statistically significant relative to improvements for the placebo group. Mean percentage improvements from baseline to Day 360 are presented in Table 16 for all clinical parameters of the ACR criteria.

For the 2 mg/kg CTLA4Ig group, statistically significant improvements compared to the placebo group were observed in physician global assessment and CRP at Day 360. Furthermore, CRP levels in the placebo group actually worsened at Day 360. At Day 360, the CTLA4Ig (BMS-188667) treatment groups had greater changes from baseline in duration of morning stiffness compared to the placebo group.

TABLE 16

Mean Percentage Improvement from Baseline at Day 360 (Individual Components of ACR Criteria)

| Component | CTLA4Ig (BMS-188667) | | Placebo (n = 119) |
|---|---|---|---|
| | 10 mg/kg (n = 115) | 2 mg/kg (n = 105) | |
| Tender Joints | n = 115 | n = 105 | n = 119 |
| Mean % Change | 66.39* | 43.54* | 29.97 |
| Swollen Joints | n = 115 | n = 105 | n = 119 |
| Mean % Change | 59.74* | 46.40 | 36.17 |
| CRP | n = 112 | n = 98 | n = 115 |
| Mean % Change | 27.59* | 10.31* | −31.26 |
| Pain | n = 112 | n = 104 | n = 119 |
| Mean % Change | 44.93* | 26.26 | 12.55 |
| Subject Global Assessment | n = 113 | n = 105 | n = 119 |
| Mean % Change | 41.01* | 16.08 | 1.99 |
| MD Global Assessment | n = 113 | n = 105 | n = 119 |
| Mean % Change | 53.48* | 37.87* | 24.14 |
| Physical Function | n = 109 | n = 100 | n = 111 |
| Mean % Change | 42.32* | 22.94 | 10.25 |
| Duration Morning Stiffness | n = 88 | n = 71 | n = 72 |
| Mean ± SD | 66.2 ± 59.5* | 66.6 ± 72.2 | 49.7 ± 73.9 |

*Indicates p < 0.05 in comparison with placebo since 95% CIs did not include zero.

New Active Joints

Figure 75:
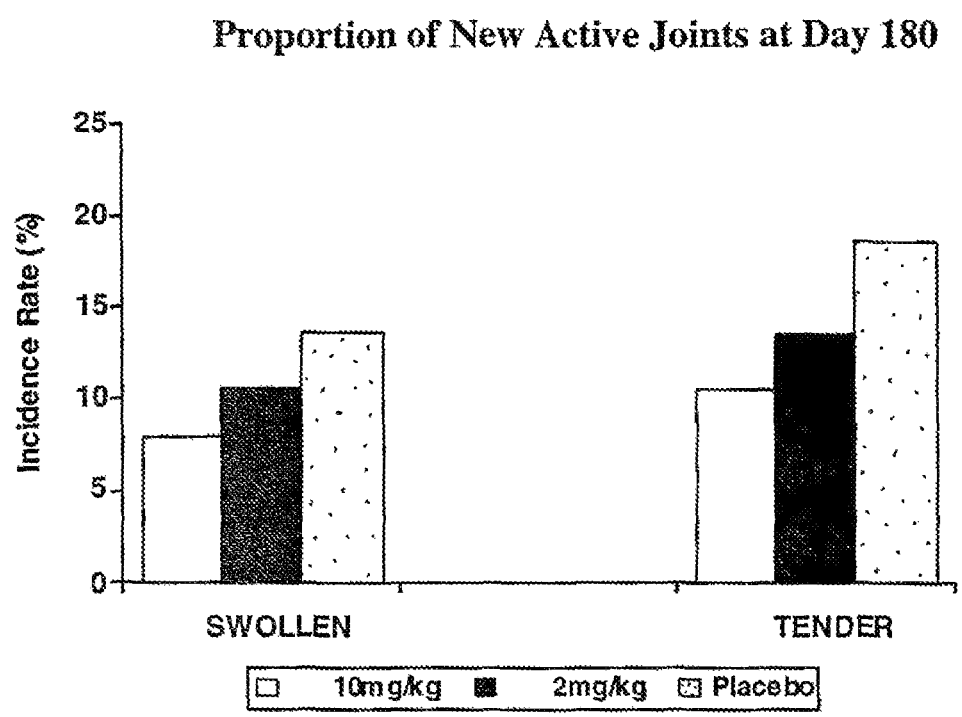
FIG. 75: A graph showing the Proportion of New Active Joints at Day 180 for patients administered methotrexate alone or methotrexate and CTLA4Ig (2 or 10 mg/kg body weight) as described in Example 7, infra.

The proportion of new active joints was determined using the validated 28-joint count (out of 68 total tender joints and out of 66 total swollen joints) proposed by Smollen et al. (Smollen, J. S. et al., "Validity and reliability of the twenty-eight-joint count for the assessment of RA activity", *Arthritis Rheum.*, 38:38-43 (1993)). The proportion of new active joints (both tender and swollen) at Day 180 was lowest for subjects receiving 10 mg/kg CTLA4Ig (FIG. 75).

Figure 76A:
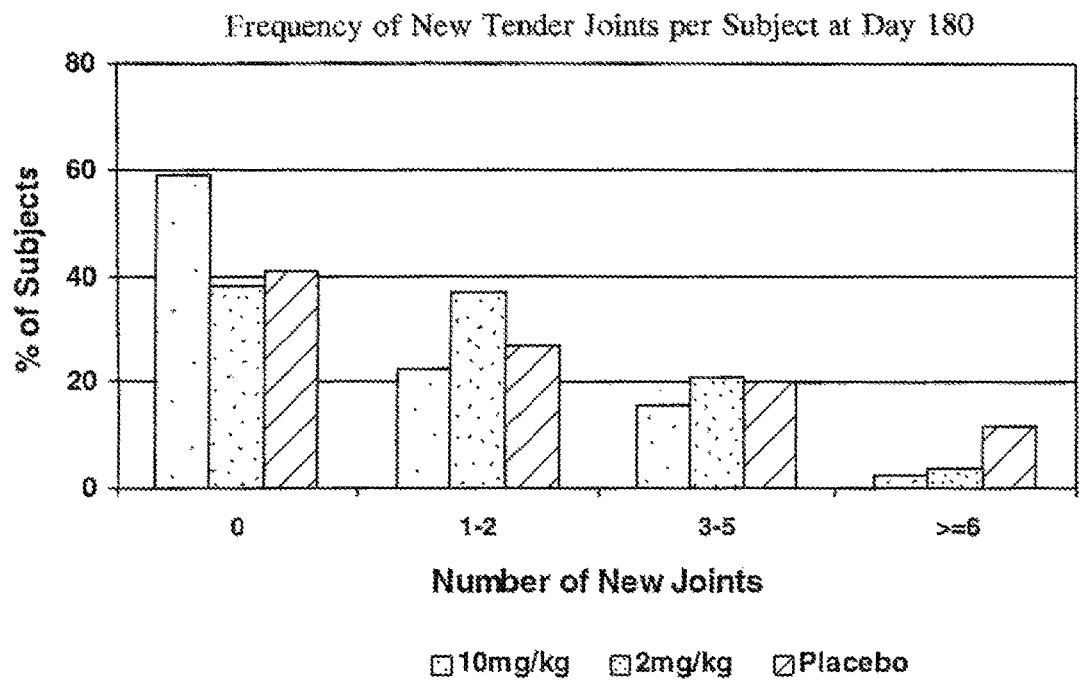
FIG. 76A: A graph showing the Frequency of New Tender Joints per Subject at Day 180 for patients administered methotrexate alone or methotrexate and CTLA4Ig (2 or 10 mg/kg body weight) as described in Example 7, infra.
Figure 77A:
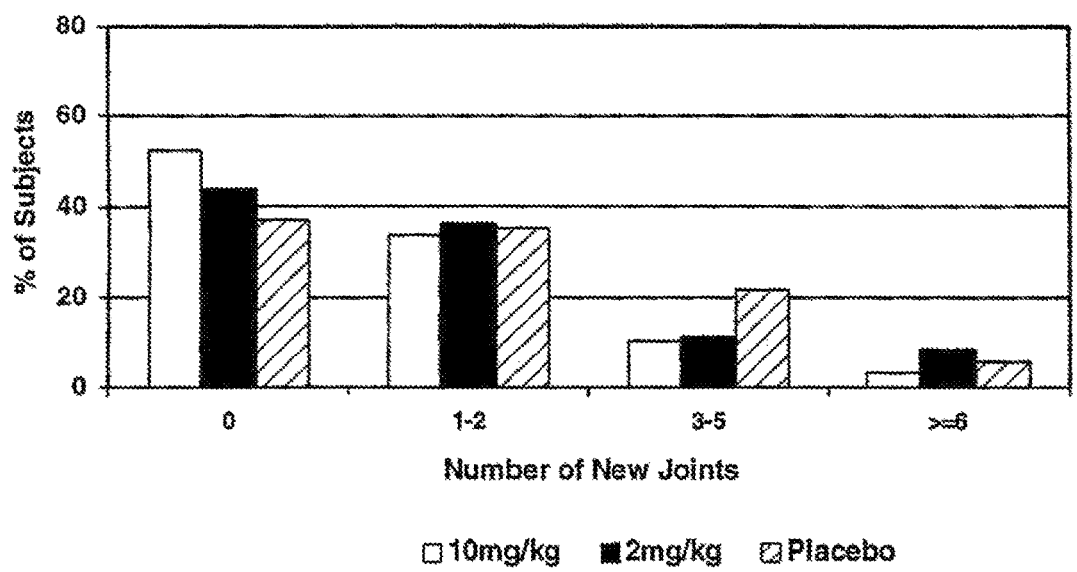
FIG. 77A: A graph showing the Frequency of New Swollen Joints per Subject at Day 180 for patients administered methotrexate alone or methotrexate and CTLA4Ig (2 or 10 mg/kg body weight) as described in Example 7, infra.

At Day 180, the percentages of subjects reporting no new tender joints and no new swollen joints was highest in the 10 mg/kg CTLA4Ig group (FIG. 76A and FIG. 77A). The percentage of subjects who reported no new tender joints and no new swollen joints was approximately 59% and 52%, respectively, in the 10 mg/kg CTLA4Ig group; 38% and 44%, respectively, in the 2 mg/kg CTLA4Ig group; and 41% and 37%, respectively, in the placebo group.

Figure 78:
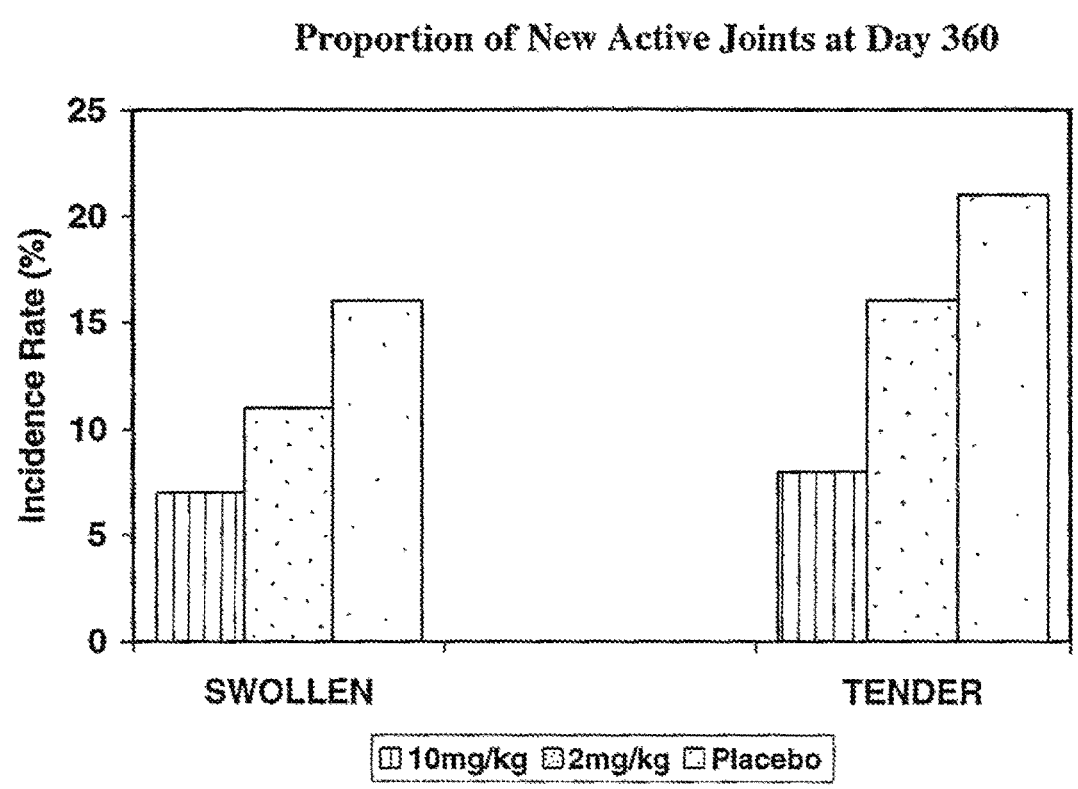
FIG. 78: A graph showing the Proportion of New Active Joints at Day 360 for patients administered methotrexate alone or methotrexate and CTLA4Ig (2 or 10 mg/kg body weight) as described in Example 7, infra.

The proportion of new active joints (both tender and swollen) at Day 360 was lowest for subjects receiving 10 mg/kg CTLA4Ig (FIG. 78). This pattern for the proportion of new active joints mirrored the pattern seen at Day 180.

Figure 76B:
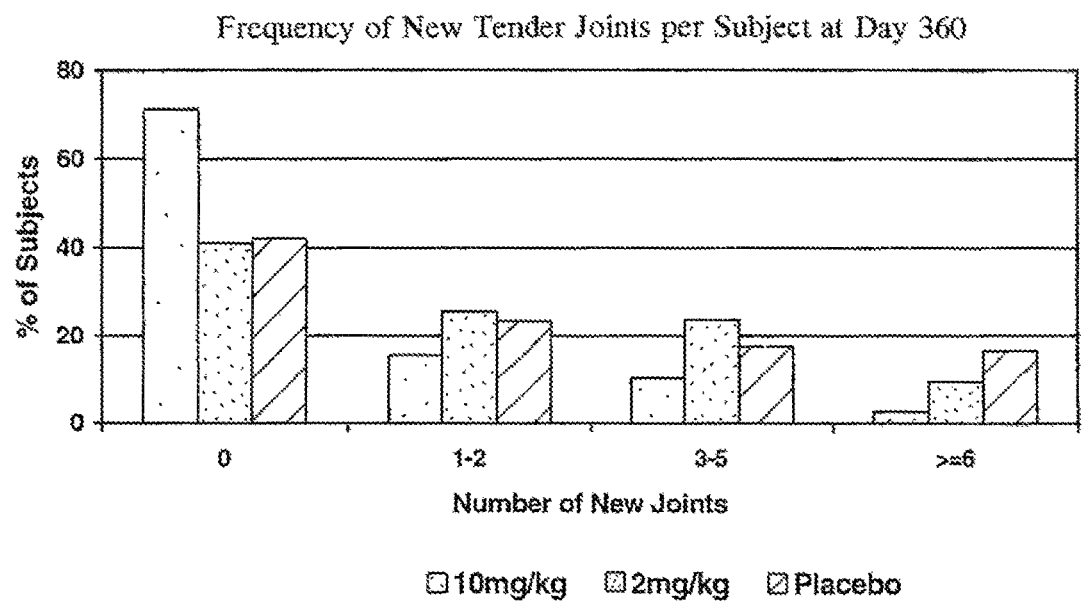
FIG. 76B: A graph showing the Frequency of New Tender Joints per Subject at Day 360 for patients administered methotrexate alone or methotrexate and CTLA4Ig (2 or 10 mg/kg body weight) as described in Example 7, infra.
Figure 77B:
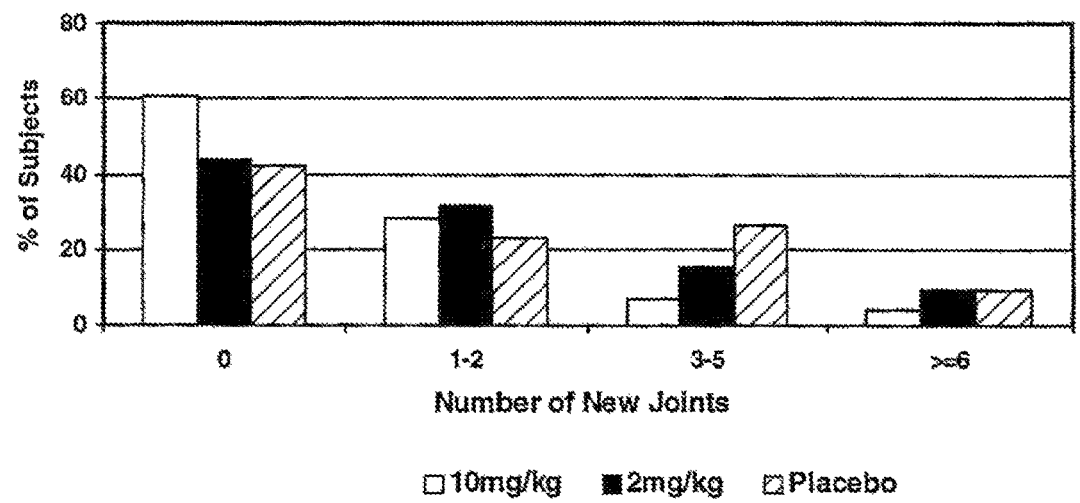
FIG. 77B: A graph showing the Frequency of New Swollen Joints per Subject at Day 360 for patients administered methotrexate alone or methotrexate and CTLA4Ig (2 or 10 mg/kg body weight) as described in Example 7, infra.

Similarly, at Day 360, the proportion of subjects reporting no new tender joints and no new swollen joints was highest in the 10 mg/kg CTLA4Ig group (FIG. 76B and FIG. 77B). The percentage of subjects who reported no new tender and no new swollen joints was approximately 71% and 61%, respectively, in the 10 mg/kg CTLA4Ig group; 41% and 44%, respectively, in the 2 mg/kg CTLA4Ig group; and 42% for both counts in the placebo group.

Improvement in Clinical Parameters Among Subjects with an ACR Response

Among ACR 20, ACR 50, and ACR 70 responders, improvement in the core components of the ACR criteria were slightly greater for the two CTLA4Ig (BMS-188667) treatment groups compared to placebo.

The onset of action for subjects who received the 10 mg/kg CTLA4Ig dose occurred after approximately 15 days, with significant increases in ACR 20 improvement occurring at ≥Day 60 for ACR50 at ≥Day 90 for ACR70 at ≥Day 30 and in each instance, continuing until Day 360 (see FIGS. 73A-73C).

Changes from Baseline for the Health Outcomes Short Form Questionnaire (SF-36)

The impact of CTLA4Ig (BMS-188667) on health-related quality of life was assessed using the Health Outcomes Short Form Questionnaire SF-36 (summary scores range from 0 to 100 with higher scores indicating a better quality of life). Analyses were performed on the LOCF (last observation carried forward) data set as well as the as the observed data set.

Figure 79A:
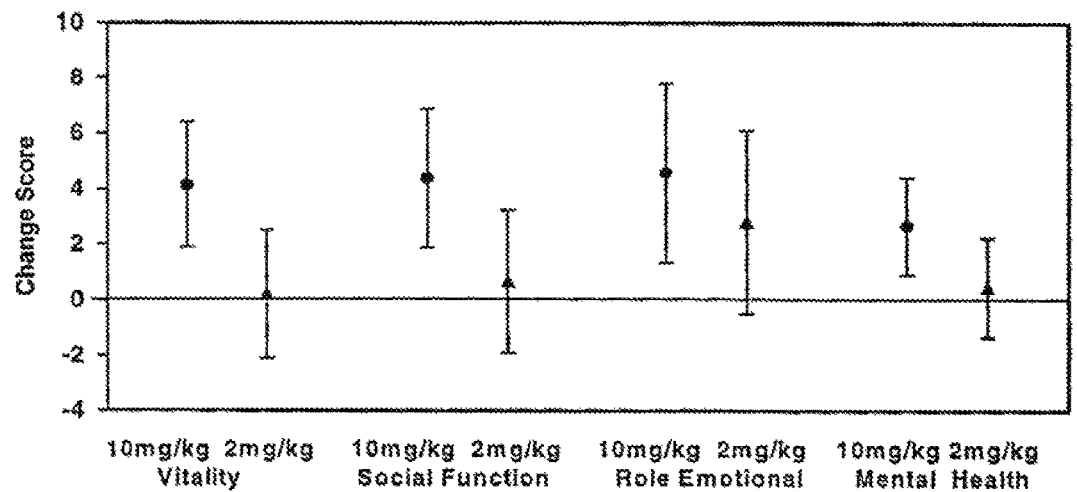
FIGS. 79A and 79B: Graphs showing the: 79A) Change from Baseline in the Physical Health Domains on Day 180, and 79B) Change from Baseline in the Mental Health Domains on 180, for patients administered methotrexate alone or methotrexate and CTLA4Ig (2 or 10 mg/kg body weight) as described in Example 7, infra.
Figure 79B:
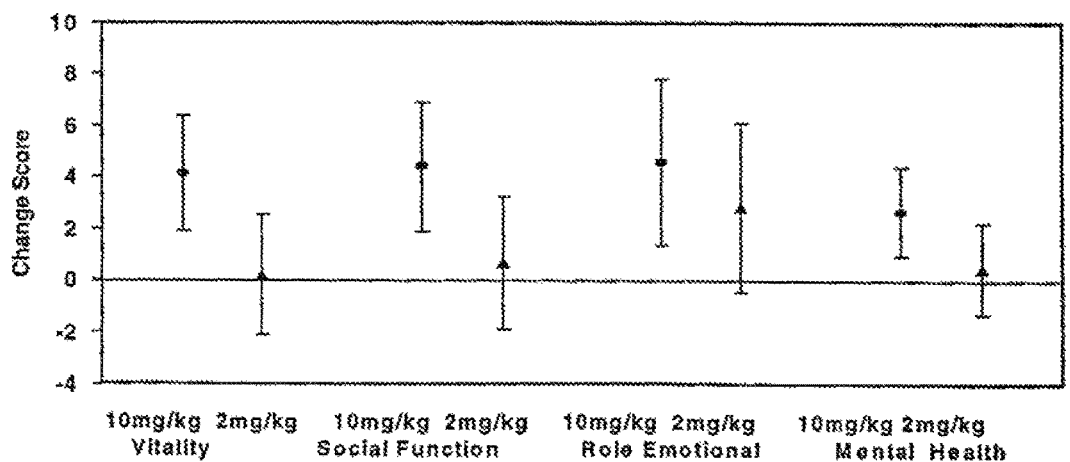
Figure 80A:
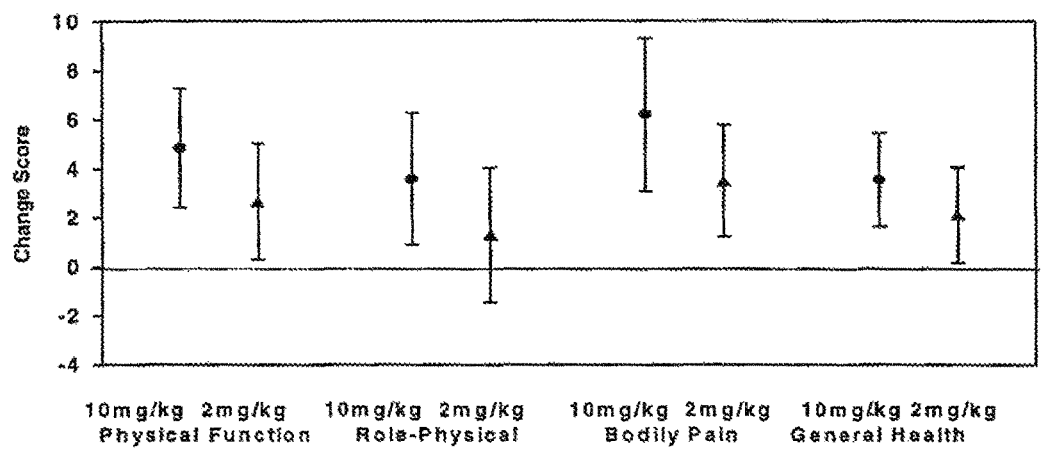
FIGS. 80A and 80B: Graphs showing the: 80A) Change from Baseline in the Physical Health Domains on Day 360, and 80B) Change from Baseline in the Mental Health Domains on Day 360, for patients administered methotrexate alone or methotrexate and CTLA4Ig (2 or 10 mg/kg body weight) as described in Example 7, infra.
Figure 80B:
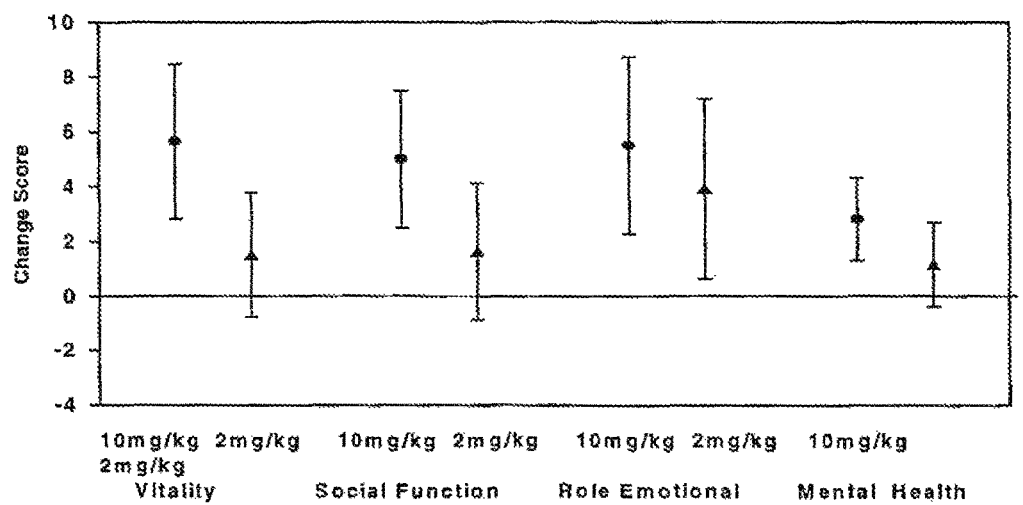
Figure 81:
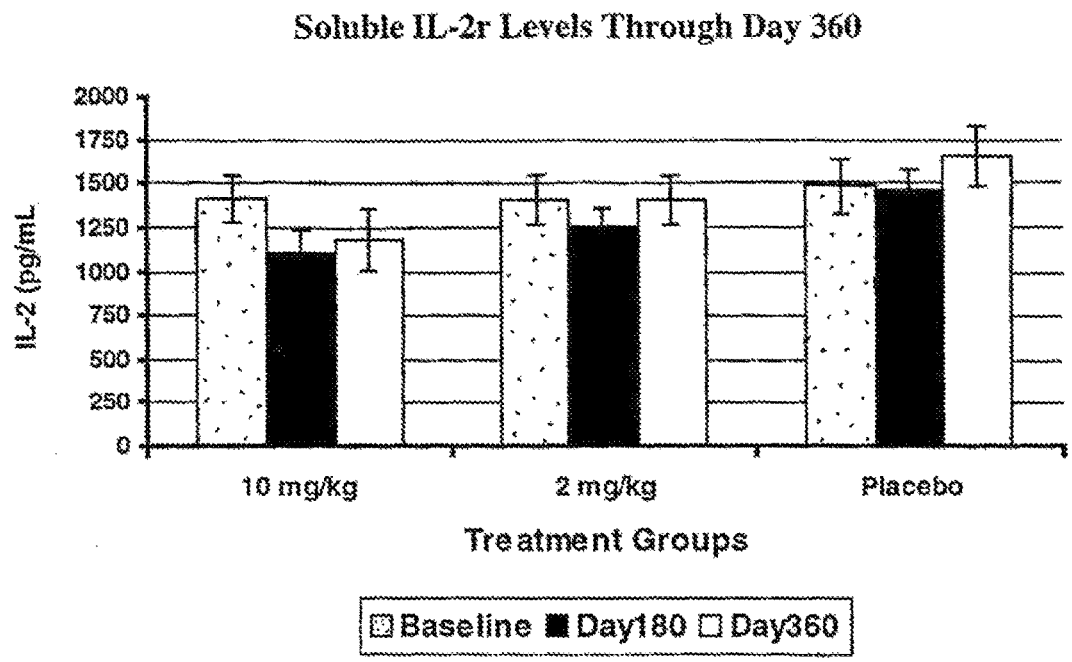
FIG. 81: A graph showing the Soluble IL-2r Levels at Baseline, Days 180 and 360 for patients administered methotrexate alone or methotrexate and CTLA4Ig (2 or 10 mg/kg body weight) as described in Example 7, infra.
Figure 82:
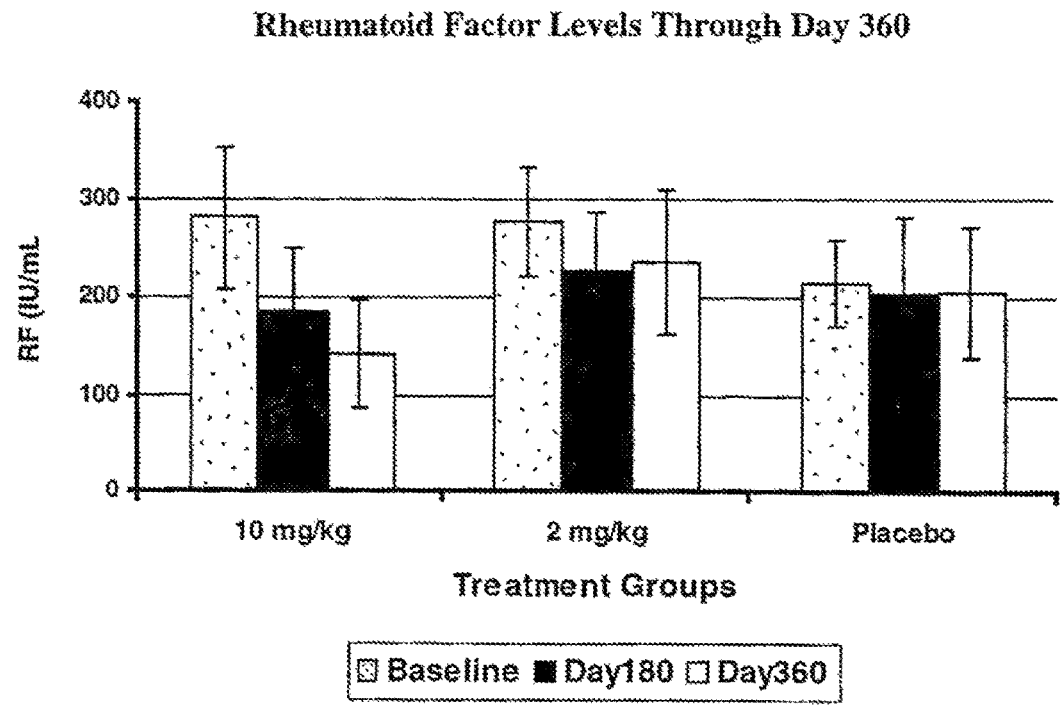
FIG. 82: A graph showing the Rheumatoid Factor Levels at Baseline, Days 180 and 360 for patients administered methotrexate alone or methotrexate and CTLA4Ig (2 or 10 mg/kg body weight) as described in Example 7, infra.
Figure 83:
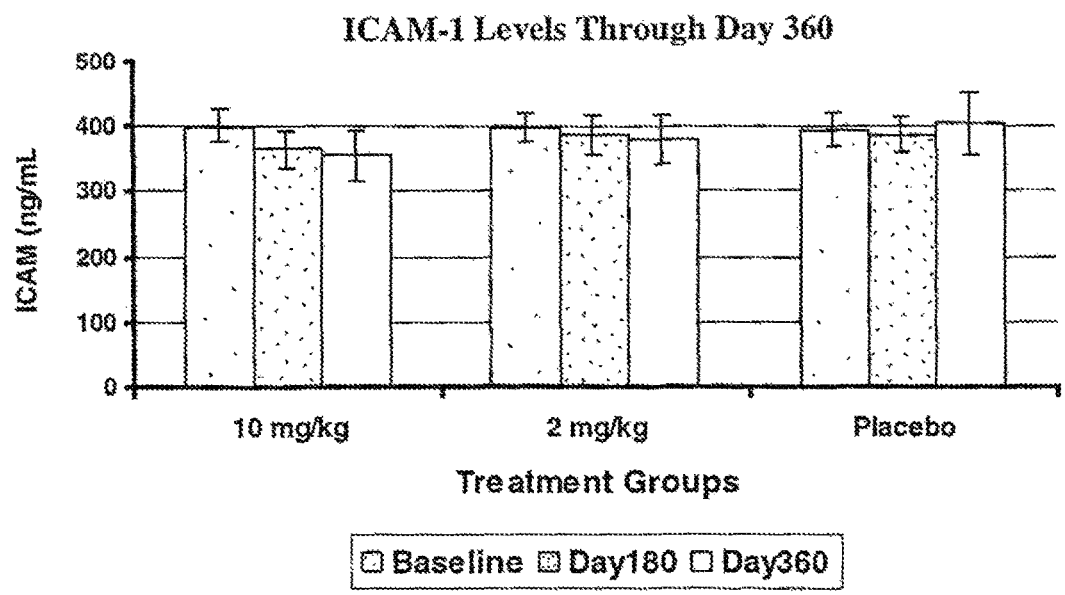
FIG. 83: A graph showing the ICAM-1 Levels at Baseline, Days 180 and 360 for patients administered methotrexate alone or methotrexate and CTLA4Ig (2 or 10 mg/kg body weight) as described in Example 7, infra.
Figure 84:
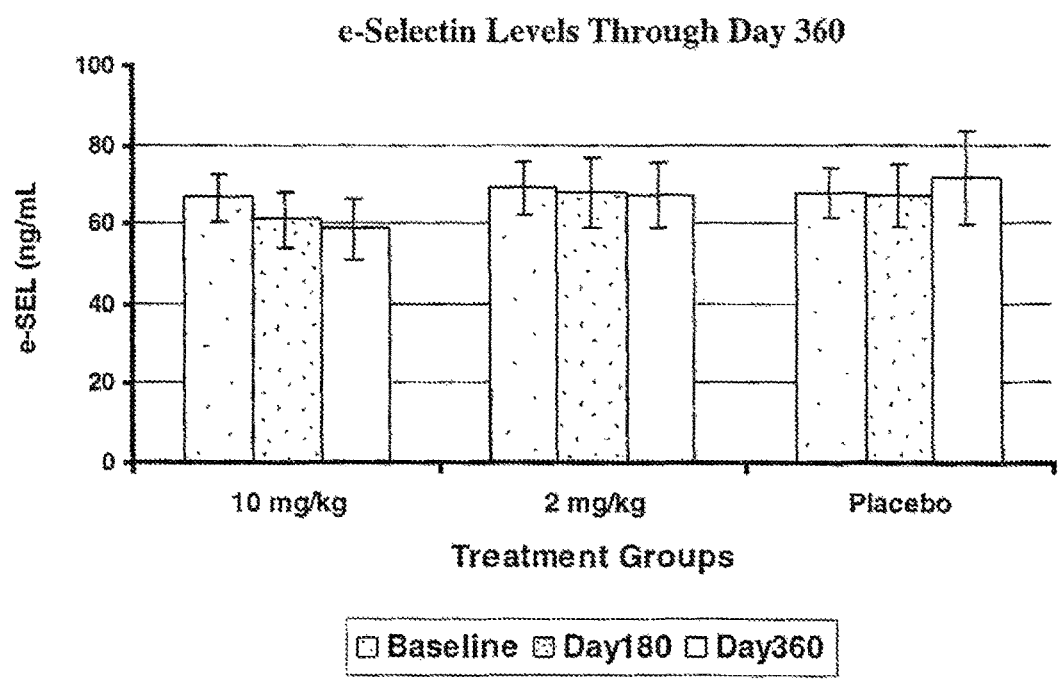
FIG. 84: A graph showing the e-Selectin Levels at Baseline, Days 180 and 360 for patients administered methotrexate alone or methotrexate and CTLA4Ig (2 or 10 mg/kg body weight) as described in Example 7, infra.
Figure 85:
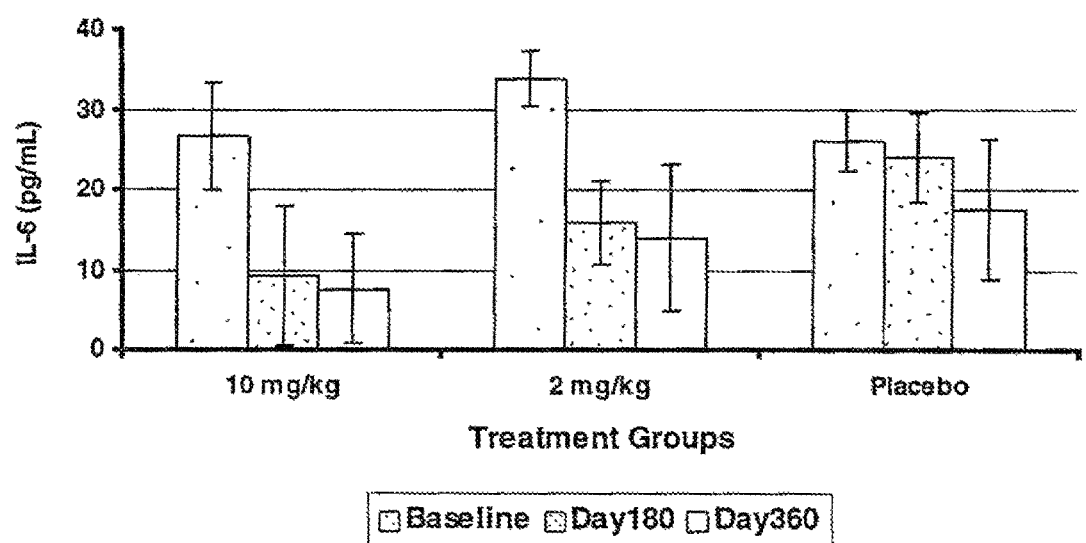
FIG. 85: A graph showing the Serum IL-6 at Baseline, Days 180 and 360 for patients administered methotrexate alone or methotrexate and CTLA4Ig (2 or 10 mg/kg body weight) as described in Example 7, infra.
Figure 86A:
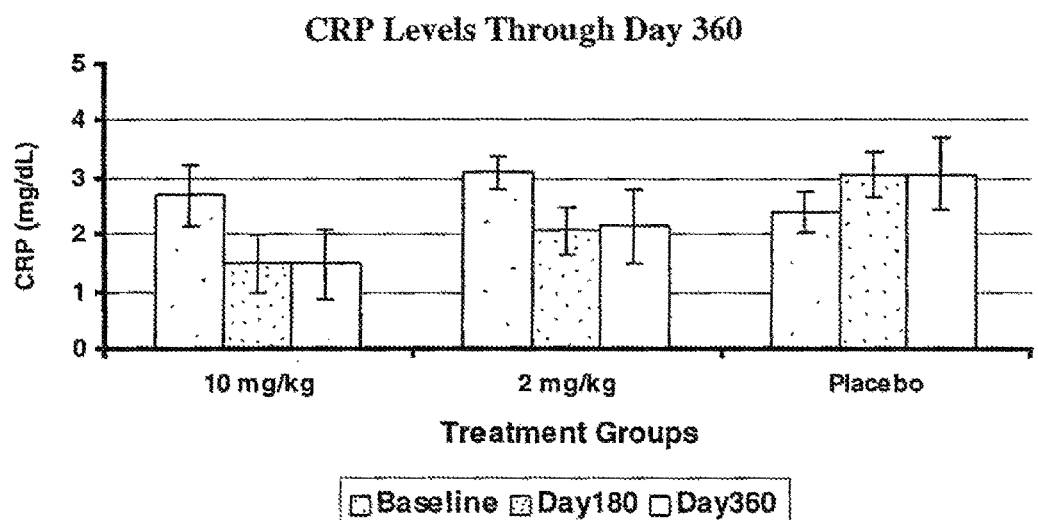
FIG. 86A: A graph showing the CRP Levels at Baseline, Days 180 and 360 for patients administered methotrexate alone or methotrexate and CTLA4Ig (2 or 10 mg/kg body weight) as described in Example 7, infra.
Figure 86B:
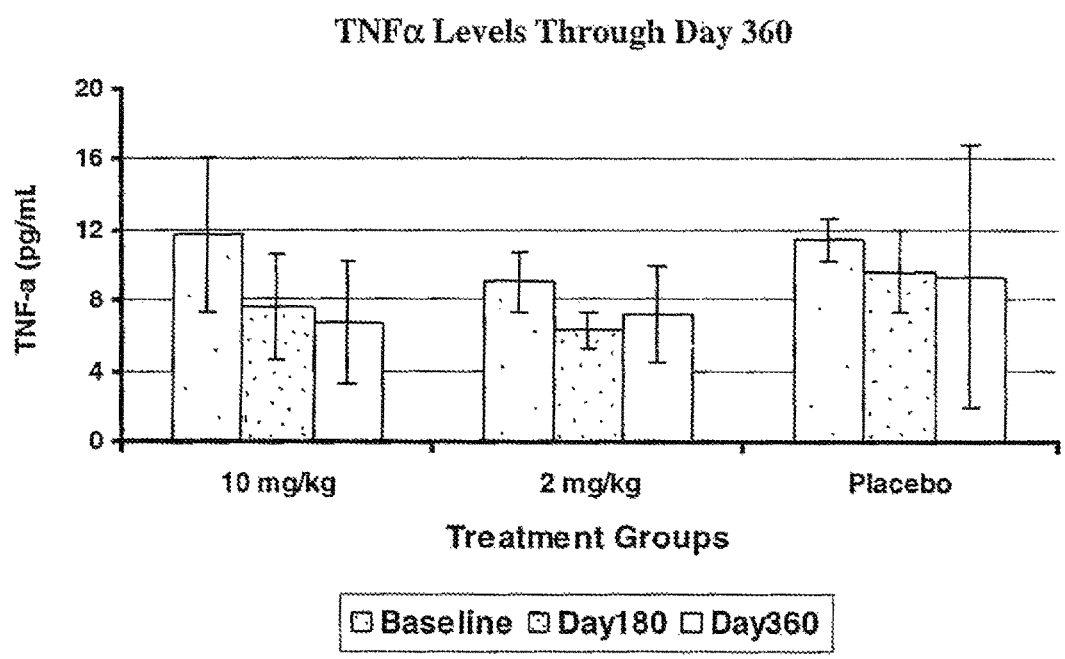
FIG. 86B: A graph showing the TNFα Levels at Baseline, Days 180 and 360 for patients administered methotrexate alone or methotrexate and CTLA4Ig (2 or 10 mg/kg body weight) as described in Example 7, infra.

For the 10 mg/kg CTLA4Ig group, statistically significant improvement from baseline compared to the placebo group was observed in all four mental health and all four physical health domains of the SF-36 at Day 180, using the LOCF analysis (i.e., 95% CIs did not include 0) (FIGS. 79A and 79B). For the 2 mg/kg CTLA4Ig group, there were numerical improvements in the mental health or physical health domains compared to placebo at Day 180, however, these improvements were not statistically significant.

Results of analyses performed on the as-observed data set were similar to those observed for the LOCF data set except that the "role emotional" domain at Day 180 was not significantly improved (but was numerically improved) for the comparison between the 10 mg/kg CTLA4Ig and placebo groups using the as-observed data set.

The physical component and the mental health component summary measures at Day 180 are shown in Table 17.

TABLE 17

Mean Change from Baseline to Day 180 for the SF-36 (Physical and Mental Health Components)

| Summary Score | CTLA4Ig (BMS-188667) | | Placebo (n = 119) |
|---|---|---|---|
| | 10 mg/kg (n = 115) | 2 mg/kg (n = 105) | |
| Mental Health Component | n = 115 | n = 103 | n = 118 |
| Baseline Mean | 44.52 | 43.06 | 41.75 |
| Postbaseline Mean | 48.69 | 45.59 | 44.04 |
| Mean Change from Baseline | 4.17 | 2.53 | 2.30 |
| 95% CI | (2.46, 5.88) | (0.39, 4.67) | (0.42, 4.17) |
| Physical Component | n = 115 | n = 103 | n = 118 |
| Baseline Mean | 31.13 | 30.80 | 32.33 |
| Postbaseline Mean | 39.30 | 35.47 | 35.21 |
| Mean Change from Baseline | 8.16 | 4.67 | 2.88 |
| 95% CI | (6.33, 9.99) | (3.25, 6.09) | (1.54, 4.22) |

Results of the Health Outcomes at Day 360 were similar to those seen at Day 180. For the 10 mg/kg CTLA4Ig group, statistically significant improvements from baseline compared to the placebo group were observed in all four mental and all four physical domains of the SF-36 at Day 360, using the LOCF analysis (i.e., 95% CIs did not include 0) (FIGS.

80A and 80B). For the 2 mg/kg CTLA4Ig group, a statistically significant difference in three of four physical domains at Day 360 and one of four mental domains at Day 360 compared to the placebo group was observed.

Results of analyses performed on the as-observed data set were similar to those observed for the LOCF data set.

The physical component and mental health component summary measures at Day 360 is shown in Table 18.

TABLE 18

Mean Change from Baseline to Day 360 for the SF-36 (Summaries of Physical Component and Mental Health Component)

|  | CTLA4Ig (BMS-188667) | | |
|---|---|---|---|
| Summary Score | 10 mg/kg (n = 115) | 2 mg/kg (n = 105) | Placebo (n = 119) |
| Mental Health Component | n = 115 | n = 103 | n = 118 |
| Baseline Mean | 44.52 | 43.06 | 44.75 |
| Postbaseline Mean | 48.83 | 45.65 | 43.22 |
| Mean Change from Baseline | 4.31 | 2.59 | 1.47 |
| 95% CI | (2.64, 5.98) | (0.64, 4.55) | (−0.14, 3.08) |
| Physical Component | n = 115 | n = 103 | n = 118 |
| Baseline Mean | 31.13 | 30.80 | 32.33 |
| Postbaseline Mean | 38.93 | 36.49 | 34.93 |
| Mean Change from Baseline | 7.79 | 5.69 | 2.60 |
| 95% CI | (5.90, 9.68) | (4.10, 7.28) | (1.09, 4.11) |

Biomarker and Pharmacodynamic Data

There were significant improvements (decreases) in 5 of the 6 biomarker/pharmacodynamic (PD) parameters with 10 mg/kg CTLA4Ig at Day 180 (soluble IL-2r, rheumatoid factor (RF), ICAM-1, E-selectin and IL-6) and a numerical decrease in TNF-α (Table 19). There were significant improvements (decreases) in 3 of the 6 biomarker/PD parameters with 2 mg/kg CTLA4Ig at Day 180 (soluble IL-2r, RF and IL-6) and a numerical improvement in ICAM-1. There were no significant changes in any of the biomarker/PD parameters with placebo at Day 180. There appears to be a dose response relationship with the improvements (decreases) in biomarker/PD parameters.

TABLE 19

Pharmacodynamic Measures at Day 180

|  | CTLA4Ig (BMS-188667) | | |
|---|---|---|---|
| Parameter | 10 mg/kg (n = 115) | 2 mg/kg (n = 105) | Placebo (n = 119) |
| Soluble IL-2r | n = 95 | n = 84 | n = 76 |
| (Normal range: 640-2543 pg/mL) | | | |
| Baseline Mean (±SD) | 1426.19 ± 751.76 | 1396.82 ± 610.21 | 1429.13 ± 667.84 |
| Postbaseline Mean (±SD) | 1112.62 ± 699.68 | 1261.31 ± 473.66 | 1470.03 ± 637.75 |
| Mean Change | −316.23 | −135.51 | 43.59 |
| 95% CI | (−417.73, −214.72) | (−241.48, −29.53) | (−71.24, 158.43) |
| Rheumatoid Factor | n = 95 | n = 84 | n = 74 |
| (Normal Range: 0-20 IU/mL) | | | |
| Baseline Mean (±SD) | 289.71 ± 401.95 | 256.19 ± 307.92 | 196.11 ± 265.48 |
| Postbaseline Mean (±SD) | 185.43 ± 269.52 | 227.82 ± 276.27 | 204.36 ± 320.09 |
| Mean Change | −104.27 | −28.12 | −0.62 |
| 95% CI | (−151.53, −57.01) | (−52.13, −4.11) | (−31.67, 30.43) |
| ICAM-1 | n = 95 | n = 82 | n = 75 |
| Baseline Mean (±SD) | 404.89 ± 137.72 | 393.47 ± 150.85 | 387.33 ± 230.93 |
| Postbaseline Mean (±SD) | 364.74 ± 109.47 | 387.25 ± 142.73 | 386.17 ± 163.82 |
| Mean Change | −40.42 | −6.22 | 1.09 |
| 95% CI | (−58.06, −22.78) | (−27.49, 15.05) | (−31.88, 34.05) |
| E-selectin | n = 89 | n = 80 | n = 71 |
| Baseline Mean (±SD) | 68.07 ± 32.93 | 67.32 ± 37.13 | 68.23 ± 43.09 |
| Postbaseline Mean (±SD) | 61.01 ± 31.53 | 67.86 ± 40.20 | 67.37 ± 35.66 |
| Mean Change | −8.41 | 0.54 | −0.68 |
| 95% CI | (−13.24, −3.58) | (−5.95, 7.03) | (−6.87, 5.51) |
| Serum IL-6 | n = 86 | n = 74 | n = 69 |
| (Normal Range: 0.3-14.8 pg/mL) | | | |
| Baseline Mean (±SD) | 28.47 ± 38.28 | 31.75 ± 42.29 | 21.20 ± 26.51 |
| Postbaseline Mean (±SD) | 9.25 ± 15.85 | 16.00 ± 22.13 | 23.98 ± 37.92 |
| Mean Change | −20.30 | −16.10 | 1.98 |
| 95% CI | (−27.55, −13.06) | (−24.20, −8.00) | (−7.21, 11.17) |
| TNFα | n = 84 | n = 74 | n = 69 |
| (1.2-8.0 pg/mL) | | | |
| Baseline Mean (±SD) | 11.17 ± 23.72 | 7.51 ± 13.25 | 13.12 ± 23.20 |
| Postbaseline Mean (±SD) | 7.57 ± 7.90 | 6.20 ± 4.48 | 9.59 ± 11.21 |
| Mean Change | −3.66 | −1.21 | −3.54 |
| 95% CI | (−8.62, 1.30) | (−4.32, 1.90) | (−7.82, 0.75) |

Overall, the pattern in the changes in biomarker/PD data at Day 360 were similar to that seen at Day 180. There were significant improvements (decreases) in 5 of the 6 biomarker/PD parameters with 10 mg/kg CTLA4Ig at Day 360 (soluble IL-2r, RF, ICAM-1, E-selectin and IL-6) and a numerical, but not statistically significant improvement observed for TNF-α (Table 20). There was a significant improvement (decrease) in IL-6 only with 2 mg/kg CTLA4Ig at Day 360, however, numerical improvements were seen with RF and ICAM-1. There were no significant changes in any of the biomarker/PD parameters with placebo at Day 360. As seen with Day 180 data, it appeared that all of the improvements (decreases) in biomarker/PD parameters occurred in a dose response manner.

A comparison of the postbaseline means for the biomarker/PD parameters at Day 180 to those at Day 360 reveals important trends. For the 10 mg/kg CTLA4Ig group, all biomarkers/PD measures continued to decrease, with the exception of soluble IL-2r which increased slightly. For the 2 mg/kg CTLA4Ig group, mean values for 3 of the biomarkers/PD parameters either decreased slightly (ICAM-1, serum IL-6) or remained relatively constant (E-selectin) and mean values for the other 3 biomarkers/PD measures increased slightly (soluble IL-2r, RF, TNF a). For the placebo group, mean values for all of the biomarkers/PD parameters increased slightly at Day 360, with the exception of TNF a which remained relatively unchanged.

The data are shown graphically for these biomarker/PD measures, as well as for changes in CRP levels, in FIGS. 81-87.

In order to assess the integrity of the planned analyses, all subjects who received study medication and discontinued the study for any reason were considered ACR non-responders at all scheduled study visits subsequent to discontinuation. Results of these analyses (Table 21) were consistent with the efficacy results already presented. The proportion of subjects who received 10 mg/kg CTLA4Ig and achieved an ACR 20, ACR 50, or ACR 70 response at Day 180 was significantly (p<0.001) higher compared to the proportion of subjects who received placebo. For the 2 mg/kg CTLA4Ig group, a significantly (p≤0.009) higher proportion of subjects achieved either an ACR 50 or ACR 70 response.

TABLE 21

ACR Response at Day 180 (Non-Completer Equals Non-Responder)

| | CTLA4Ig (BMS-188667) | | |
|---|---|---|---|
| | 10 mg/kg (n = 115) | 2 mg/kg (n = 105) | Placebo (n = 119) |
| ACR 20, n (%) | 67 (58.3) | 41 (39.0) | 38 (31.9) |
| Diff (CI) | 26.3 (13.6, 39.1) | 7.1 (−5.4, 19.7) | N/A |

TABLE 20

Pharmacodynamic Measures at Day 360

| | CTLA4Ig (BMS-188667) | | |
|---|---|---|---|
| Measure | 10 mg/kg (n = 115) | 2 mg/kg (n = 105) | Placebo (n = 119) |
| Soluble IL-2r | n = 68 | n = 56 | n = 55 |
| (Normal range: 640-2543 pg/mL) | | | |
| Baseline Mean (±SD) | 1372.10 ± 770.11 | 1373.86 ± 567.75 | 1459.93 ± 695.07 |
| Postbaseline Mean (±SD) | 1185.51 ± 638.95 | 1413.84 ± 452.50 | 1666.59 ± 611.97 |
| Mean Change | −194.31 | 39.99 | 206.22 |
| 95% CI | (−305.67, −82.96) | (−69.87, 149.84) | (35.88, 376.56) |
| Rheumatoid Factor | n = 69 | n = 55 | n = 58 |
| (Normal Range: 0-20 IU/mL) | | | |
| Baseline Mean (±SD) | 261.43 ± 333.58 | 258.42 ± 318.65 | 179.12 ± 207.72 |
| Postbaseline Mean (±SD) | 143.13 ± 180.80 | 236.61 ± 287.36 | 206.42 ± 256.27 |
| Mean Change | −118.30 | −25.64 | 20.90 |
| 95% CI | (−175.19, −61.42) | (−58.50, 7.23) | (−10.72, 52.51) |
| ICAM-1 | n = 77 | n = 68 | n = 64 |
| Baseline Mean (±SD) | 406.44 ± 145.22 | 393.41 ± 132.97 | 405.67 ± 245.16 |
| Postbaseline Mean (±SD) | 354.90 ± 111.40 | 380.42 ± 113.20 | 405.07 ± 194.15 |
| Mean Change | −55.15 | −12.98 | 1.47 |
| 95% CI | (−74.80, −35.49) | (−35.36, 9.39) | (−26.41, 29.35) |
| E-selectin | n = 75 | n = 68 | n = 62 |
| Baseline Mean (±SD) | 68.84 ± 34.38 | 66.75 ± 37.10 | 69.72 ± 44.38 |
| Postbaseline Mean (±SD) | 58.77 ± 26.61 | 67.58 ± 31.50 | 71.90 ± 47.43 |
| Mean Change | −10.89 | 0.83 | 2.34 |
| 95% CI | (−15.70, −6.08) | (−5.62, 7.28) | (−4.53, 9.20) |
| Serum IL-6 | n = 56 | n = 47 | n = 48 |
| (Normal Range: 0.3-14.8 pg/mL) | | | |
| Baseline Mean (±SD) | 27.68 ± 38.56 | 27.19 ± 32.45 | 17.27 ± 22.47 |
| Postbaseline Mean (±SD) | 7.64 ± 14.21 | 13.93 ± 19.00 | 17.72 ± 29.76 |
| Mean Change | −20.88 | −12.72 | −0.19 |
| 95% CI | (−31.56, −10.19) | (−22.49, −2.94) | (−7.55, 7.18) |
| TNFα | n = 61 | n = 48 | n = 50 |
| (1.2-8.0 pg/mL) | | | |
| Baseline Mean (±SD) | 9.71 ± 22.80 | 6.27 ± 3.62 | 10.81 ± 21.24 |
| Postbaseline Mean (±SD) | 6.67 ± 4.80 | 7.18 ± 8.14 | 9.36 ± 26.43 |
| Mean Change | −3.02 | 1.08 | −1.41 |
| 95% CI | (−8.70, 2.67) | (−1.26, 3.42) | (−5.14, 2.33) |

TABLE 21-continued

ACR Response at Day 180 (Non-Completer Equals Non-Responder)

| | CTLA4Ig (BMS-188667) | | |
|---|---|---|---|
| | 10 mg/kg (n = 115) | 2 mg/kg (n = 105) | Placebo (n = 119) |
| p-value | <0.001[a] | 0.266 | N/A |
| ACR 50, n (%) | 41 (35.7) | 24 (22.9) | 12 (10.1) |
| Diff (CI) | 25.6 (14.8, 36.3) | 12.8 (3.1, 22.4) | N/A |
| p-value | <0.001[a] | 0.009[a] | N/A |
| ACR 70, n (%) | 19 (16.5) | 11 (10.5) | 2 (1.7) |
| Diff (CI) | 14.8 (7.5, 22.2) | 8.8 (2.7, 14.9) | N/A |
| p-value | <0.001[a] | 0.005[a] | N/A |

[a]Indicates a statistically significant difference for the comparison of BMS-188667 vs placebo.

In addition, all primary efficacy analyses were performed on the WOCF (worst observation carried forward) data set. ACR responses based on the WOCF data set were slightly lower than those reported in Table 13 and were comparable to those presented in Table 21. These findings confirm the consistency of ACR response rates in the CTLA4Ig (BMS-188667) treatment groups.

The dosages of anti-rheumatic concomitant medications were to be collected to assess the need for these medications at 6 and 12 months; however, the available data were inadequate to perform these analyses. Only baseline values for mean dose of methotrexate and systemic (non-topical) corticosteroids are provided.

Efficacy Conclusions

CTLA4Ig (BMS-188667) administered at 10 mg/kg (+MTX) had superior efficacy compared to placebo (+MTX) at Day 180 and Day 360. For the following efficacy parameters, administration of 10 mg/kg CTLA4Ig was significantly better than placebo:

Primary efficacy variable: ACR20 response at Day 180 (p<0.001).
ACR50 and ACR70 responses at Day 180 (p<0.001).
ACR20, ACR50 and ACR70 responses at Day 360 (p≤0.003).
Statistically significant differences in ACR50 and ACR70 responses observed by Day 30 (p=0.039 and p=0.04), statistically significant differences in all 3 response rates (ACR 20, ACR50 and ACR70) observed by Day 90; these values remained statistically significant at every timepoint up to and including Day 360 (p≤0.008).
Proportions of subjects who achieved a Major Clinical Response (maintenance of an ACR 70 response over a continuous 6-month period) at Day 360 (p=0.008).
Mean numeric ACR-AUC by Day 360 (p<0.001).
Mean percentage improvements in each individual ACR component at Day 180 and Day 360 (p<0.05, 95% CIs did not include 0).
Improvements in all four mental and all four physical domains of the Health Outcomes evaluation (SF-36) at both Day 180 and Day 360 (p<0.05, 95% CIs did not include 0).

In addition to the above statistically significant differences, the 10 mg/kg CTLA4Ig group had a lower number of new active joints and a higher number of subjects reporting no new active tender and swollen joints compared with the placebo group at Day 180 and at Day 360.

Significant improvement with 10 mg/kg CTLA4Ig compared with placebo was seen in nearly all measured pharmacodynamic parameters (soluble IL12r, RF, ICAM-1, E-selectin and IL-6) and numerical improvement in TNF-α up to 1 year.

For the 2 mg/kg CTLA4Ig group, some efficacy parameters were significantly better compared to the placebo group:

ACR50 response at Day 180 (p=0.027).
ACR70 response at Day 180 (p=0.005).
Statistically significant differences in ACR70 observed by Day 60 (p=0.032) and statistically significant differences in ACR 50 and ACR 70 at Day 180 (p=0.027 and p=0.005).
Proportions of subjects who achieved a Major Clinical Response (maintenance of an ACR 70 response over a continuous 6-month period) at Day 360 (p=0.036).
Mean percentage improvements in some of the individual ACR component at Day 180 and Day 360 (p<0.05, 95% CIs did not include 0).

For many other efficacy parameters, 2 mg/kg CTLA4Ig was numerically better than placebo.

Safety Results

Overall, the safety profile of CTLA4Ig (BMS-188667) was similar to placebo. There were no major safety problems.

Clinical Laboratory Evaluation

Overall, no new safety issues emerged from the evaluation of mean changes in laboratory values. Mean values for hemoglobin, WBCs, neutrophils, platelets, ALT, AST, GGT and total protein were within the normal range at baseline and remained within the normal range during the study. In general, results of the laboratory tests did not reveal consistent out-of range values or abnormal trends that could be attributed to study medication.

Vital Signs, Physical Findings, and Observations Related to Safety

On each day of study drug administration, vital signs (body temperature, heart rate, and seated blood pressure) were monitored pre-dose and at 15, 30, 45, 60, 75, 90 and 120 minutes post-infusion. Overall, mean values for all vital sign parameters were within normal range and stable throughout the 360-day study period for all treatment groups.

What is claimed:

1. A method of treating autoimmune diseases in a subject comprising administering to the subject a CTLA4 molecule, wherein the CTLA4 molecule comprises:
   (a) an amino acid sequence beginning with methionine at position +1 and ending with aspartic acid at position 124 of SEQ ID NO:17, or
   (b) an amino acid sequence beginning with alanine at position −1 and ending with aspartic acid at position 124 of SEQ ID NO:17 and wherein said autoimmune disease is dermatomyositis.

2. The method of claim 1, wherein the extracellular domain of the CTLA4 molecule is joined to a non-CTLA4 molecule.

3. The method of claim 2, wherein the non-CTLA4 molecule comprises an amino acid sequence which alters the solubility or affinity of the CTLA4 molecule.

4. The method of claim 3, wherein the amino acid sequence which alters the solubility or affinity comprises an immunoglobulin moiety.

5. The method of claim 4, wherein the immunoglobulin moiety is an immunoglobulin constant region or portion thereof.

6. The method of claim 5, wherein the immunoglobulin constant region or portion thereof is mutated to reduce effector function.

7. The method of claim 6, wherein the immunoglobulin constant region or portion thereof comprises a hinge, CH2 and CH3 regions of a human or monkey immunoglobulin molecule.

8. A method of treating autoimmune diseases in a subject comprising administering to the subject a CTLA4 molecule, wherein the CTLA4 molecule comprises:
   (a) an amino acid sequence beginning with methionine at position +1 and ending with lysine at position 357 of SEQ ID NO:19, or
   (b) an amino acid sequence beginning with alanine at position −1 and ending with lysine at position 357 of SEQ ID NO:19 and wherein said autoimmune disease is dermatomyositis.

9. A method of treating autoimmune diseases in a subject comprising administering to the subject a CTLA4 molecule, wherein the CTLA4 molecule comprises:
   (a) an amino acid sequence beginning with methionine at position +1 and ending with aspartic acid at position 124 of SEQ ID NO:17, or
   (b) an amino acid sequence beginning with alanine at position −1 and ending with aspartic acid at position 124 of SEQ ID NO:17 and wherein said autoimmune disease is polymyositis.

10. The method of claim 9, wherein the extracellular domain of the CTLA4 molecule is joined to a non-CTLA4 molecule.

11. The method of claim 10, wherein the non-CTLA4 molecule comprises an amino acid sequence which alters the solubility or affinity of the CTLA4 molecule.

12. The method of claim 11, wherein the amino acid sequence which alters the solubility or affinity comprises an immunoglobulin moiety.

13. The method of claim 12, wherein the immunoglobulin moiety is an immunoglobulin constant region or portion thereof.

14. The method of claim 13, wherein the immunoglobulin constant region or portion thereof is mutated to reduce effector function.

15. The method of claim 14, wherein the immunoglobulin constant region or portion thereof comprises a hinge, CH2 and CH3 regions of a human or monkey immunoglobulin molecule.

16. A method of treating autoimmune diseases in a subject comprising administering to the subject a CTLA4 molecule, wherein the CTLA4 molecule comprises:
   (a) an amino acid sequence beginning with methionine at position +1 and ending with lysine at position 357 of SEQ ID NO:19, or
   (b) an amino acid sequence beginning with alanine at position −1 and ending with lysine at position 357 of SEQ ID NO:19 and wherein said autoimmune disease is polymyositis.

* * * * *

UNITED STATES PATENT AND TRADEMARK OFFICE
CERTIFICATE OF CORRECTION

PATENT NO. : 10,052,360 B2
APPLICATION NO. : 15/047849
DATED : August 21, 2018
INVENTOR(S) : Cohen et al.

Page 1 of 1

It is certified that error appears in the above-identified patent and that said Letters Patent is hereby corrected as shown below:

In the Claims

Claim 16, Column 135, Line 9, delete "and 5" and insert -- and --, thereof.

Signed and Sealed this
Fifth Day of March, 2019

Andrei Iancu
*Director of the United States Patent and Trademark Office*

SEQUENCE LISTING

<160> NUMBER OF SEQ ID NOS: 22

<210> SEQ ID NO 1
<211> LENGTH: 65
<212> TYPE: DNA
<213> ORGANISM: Homo sapiens

<400> SEQUENCE: 1
ctcagtctgg tccttgcact cctgtttcca agcatggcga gcatggcaat gcacgtggcc    60
cagcc                                                                 65

<210> SEQ ID NO 2
<211> LENGTH: 33
<212> TYPE: DNA
<213> ORGANISM: Homo sapiens

<400> SEQUENCE: 2
tttgggctcc tgatcagaat ctgggcacgg ttg                                   33

<210> SEQ ID NO 3
<211> LENGTH: 72
<212> TYPE: DNA
<213> ORGANISM: Homo sapiens

<400> SEQUENCE: 3
ctagccactg aagcttcacc aatgggtgta ctgctcacac agaggacgct gctcagtctg      60
gtccttgcac tc                                                         72

<210> SEQ ID NO 4
<211> LENGTH: 41
<212> TYPE: DNA
<213> ORGANISM: Artificial
<220> FEATURE:
<223> OTHER INFORMATION: Oncostatin M CTLA4 (OMCTLA4) forward primer

<400> SEQUENCE: 4
gaggtgataa agcttcacca atgggtgtac tgctcacaca g                          41

<210> SEQ ID NO 5
<211> LENGTH: 42
<212> TYPE: DNA
<213> ORGANISM: Artificial
<220> FEATURE:
<223> OTHER INFORMATION: Oncostatin M CTLA4 (OMCTLA4) reverse primer

<400> SEQUENCE: 5
gtggtgtatt ggtctagatc aatcagaatc tgggcacggt tc                         42

<210> SEQ ID NO 6
<211> LENGTH: 1152
<212> TYPE: DNA
<213> ORGANISM: Artificial
<220> FEATURE:
<223> OTHER INFORMATION: L104EIg
<220> FEATURE:
<221> NAME/KEY: CDS
<222> LOCATION: (1)..(1149)
<220> FEATURE:
<221> NAME/KEY: mat_peptide
<222> LOCATION: (79)..()

<400> SEQUENCE: 6 atg ggt gta ctg ctc aca cag agg acg ctg ctc agt ctg gtc ctt gca        48
Met Gly Val Leu Leu Thr Gln Arg Thr Leu Leu Ser Leu Val Leu Ala
    -25                 -20                 -15 ctc ctg ttt cca agc atg gcg agc atg gca atg cac gtg gcc cag cct        96
Leu Leu Phe Pro Ser Met Ala Ser Met Ala Met His Val Ala Gln Pro
-10                  -5                  -1 1                  5 gct gtg gta ctg gcc agc agc cga ggc atc gct agc ttt gtg tgt gag       144
Ala Val Val Leu Ala Ser Ser Arg Gly Ile Ala Ser Phe Val Cys Glu
                10                  15                  20 tat gca tct cca ggc aaa gcc act gag gtc cgg gtg aca gtg ctt cgg       192
Tyr Ala Ser Pro Gly Lys Ala Thr Glu Val Arg Val Thr Val Leu Arg

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 25  |     |     |     | 30  |     |     |     | 35  |     |     |     |     |      |
| cag | gct | gac | agc | cag | gtg | act | gaa | gtc | tgt | gcg | gca | acc | tac | atg | atg | 240  |
| Gln | Ala | Asp | Ser | Gln | Val | Thr | Glu | Val | Cys | Ala | Ala | Thr | Tyr | Met | Met |      |
|     | 40  |     |     |     | 45  |     |     |     | 50  |     |     |     |     |     |     |      |
| ggg | aat | gag | ttg | acc | ttc | cta | gat | gat | tcc | atc | tgc | acg | ggc | acc | tcc | 288  |
| Gly | Asn | Glu | Leu | Thr | Phe | Leu | Asp | Asp | Ser | Ile | Cys | Thr | Gly | Thr | Ser |      |
| 55  |     |     |     |     | 60  |     |     |     | 65  |     |     |     |     |     | 70  |      |
| agt | gga | aat | caa | gtg | aac | ctc | act | atc | caa | gga | ctg | agg | gcc | atg | gac | 336  |
| Ser | Gly | Asn | Gln | Val | Asn | Leu | Thr | Ile | Gln | Gly | Leu | Arg | Ala | Met | Asp |      |
|     |     |     |     | 75  |     |     |     |     | 80  |     |     |     |     | 85  |     |      |
| acg | gga | ctc | tac | atc | tgc | aag | gtg | gag | ctc | atg | tac | cca | ccg | cca | tac | 384  |
| Thr | Gly | Leu | Tyr | Ile | Cys | Lys | Val | Glu | Leu | Met | Tyr | Pro | Pro | Pro | Tyr |      |
|     |     |     | 90  |     |     |     |     | 95  |     |     |     |     | 100 |     |     |      |
| tac | gag | ggc | ata | ggc | aac | gga | acc | cag | att | tat | gta | att | gat | cca | gaa | 432  |
| Tyr | Glu | Gly | Ile | Gly | Asn | Gly | Thr | Gln | Ile | Tyr | Val | Ile | Asp | Pro | Glu |      |
|     |     |     |     | 105 |     |     |     |     | 110 |     |     |     |     | 115 |     |      |
| ccg | tgc | cca | gat | tct | gat | cag | gag | ccc | aaa | tct | tct | gac | aaa | act | cac | 480  |
| Pro | Cys | Pro | Asp | Ser | Asp | Gln | Glu | Pro | Lys | Ser | Ser | Asp | Lys | Thr | His |      |
|     |     | 120 |     |     |     |     | 125 |     |     |     |     | 130 |     |     |     |      |
| aca | tcc | cca | ccg | tcc | cca | gca | cct | gaa | ctc | ctg | ggg | gga | tcg | tca | gtc | 528  |
| Thr | Ser | Pro | Pro | Ser | Pro | Ala | Pro | Glu | Leu | Leu | Gly | Gly | Ser | Ser | Val |      |
| 135 |     |     |     | 140 |     |     |     |     | 145 |     |     |     |     |     | 150 |      |
| ttc | ctc | ttc | ccc | cca | aaa | ccc | aag | gac | acc | ctc | atg | atc | tcc | cgg | acc | 576  |
| Phe | Leu | Phe | Pro | Pro | Lys | Pro | Lys | Asp | Thr | Leu | Met | Ile | Ser | Arg | Thr |      |
|     |     |     |     |     | 155 |     |     |     |     | 160 |     |     |     |     | 165 |      |
| cct | gag | gtc | aca | tgc | gtg | gtg | gtg | gac | gtg | agc | cac | gaa | gac | cct | gag | 624  |
| Pro | Glu | Val | Thr | Cys | Val | Val | Val | Asp | Val | Ser | His | Glu | Asp | Pro | Glu |      |
|     |     |     | 170 |     |     |     |     | 175 |     |     |     |     | 180 |     |     |      |
| gtc | aag | ttc | aac | tgg | tac | gtg | gac | ggc | gtg | gag | gtg | cat | aat | gcc | aag | 672  |
| Val | Lys | Phe | Asn | Trp | Tyr | Val | Asp | Gly | Val | Glu | Val | His | Asn | Ala | Lys |      |
|     |     |     | 185 |     |     |     |     | 190 |     |     |     |     | 195 |     |     |      |
| aca | aag | ccg | cgg | gag | gag | cag | tac | aac | agc | acg | tac | cgt | gtg | gtc | agc | 720  |
| Thr | Lys | Pro | Arg | Glu | Glu | Gln | Tyr | Asn | Ser | Thr | Tyr | Arg | Val | Val | Ser |      |
|     | 200 |     |     |     |     | 205 |     |     |     |     | 210 |     |     |     |     |      |
| gtc | ctc | acc | gtc | ctg | cac | cag | gac | tgg | ctg | aat | ggc | aag | gag | tac | aag | 768  |
| Val | Leu | Thr | Val | Leu | His | Gln | Asp | Trp | Leu | Asn | Gly | Lys | Glu | Tyr | Lys |      |
| 215 |     |     |     |     | 220 |     |     |     |     | 225 |     |     |     |     | 230 |      |
| tgc | aag | gtc | tcc | aac | aaa | gcc | ctc | cca | gcc | ccc | atc | gag | aaa | acc | atc | 816  |
| Cys | Lys | Val | Ser | Asn | Lys | Ala | Leu | Pro | Ala | Pro | Ile | Glu | Lys | Thr | Ile |      |
|     |     |     |     | 235 |     |     |     |     | 240 |     |     |     |     | 245 |     |      |
| tcc | aaa | gcc | aaa | ggg | cag | ccc | cga | gaa | cca | cag | gtg | tac | acc | ctg | ccc | 864  |
| Ser | Lys | Ala | Lys | Gly | Gln | Pro | Arg | Glu | Pro | Gln | Val | Tyr | Thr | Leu | Pro |      |
|     |     |     | 250 |     |     |     |     | 255 |     |     |     |     | 260 |     |     |      |
| cca | tcc | cgg | gat | gag | ctg | acc | aag | aac | cag | gtc | agc | ctg | acc | tgc | ctg | 912  |
| Pro | Ser | Arg | Asp | Glu | Leu | Thr | Lys | Asn | Gln | Val | Ser | Leu | Thr | Cys | Leu |      |
|     |     | 265 |     |     |     |     | 270 |     |     |     |     | 275 |     |     |     |      |
| gtc | aaa | ggc | ttc | tat | ccc | agc | gac | atc | gcc | gtg | gag | tgg | gag | agc | aat | 960  |
| Val | Lys | Gly | Phe | Tyr | Pro | Ser | Asp | Ile | Ala | Val | Glu | Trp | Glu | Ser | Asn |      |
|     | 280 |     |     |     |     | 285 |     |     |     |     | 290 |     |     |     |     |      |
| ggg | cag | ccg | gag | aac | aac | tac | aag | acc | acg | cct | ccc | gtg | ctg | gac | tcc | 1008 |
| Gly | Gln | Pro | Glu | Asn | Asn | Tyr | Lys | Thr | Thr | Pro | Pro | Val | Leu | Asp | Ser |      |
| 295 |     |     |     | 300 |     |     |     |     | 305 |     |     |     |     |     | 310 |      |
| gac | ggc | tcc | ttc | ttc | ctc | tac | agc | aag | ctc | acc | gtg | gac | aag | agc | agg | 1056 |
| Asp | Gly | Ser | Phe | Phe | Leu | Tyr | Ser | Lys | Leu | Thr | Val | Asp | Lys | Ser | Arg |      |
|     |     |     |     | 315 |     |     |     |     | 320 |     |     |     |     | 325 |     |      |
| tgg | cag | cag | ggg | aac | gtc | ttc | tca | tgc | tcc | gtg | atg | cat | gag | gct | ctg | 1104 |
| Trp | Gln | Gln | Gly | Asn | Val | Phe | Ser | Cys | Ser | Val | Met | His | Glu | Ala | Leu |      |
|     |     | 330 |     |     |     |     | 335 |     |     |     |     | 340 |     |     |     |      |
| cac | aac | cac | tac | acg | cag | aag | agc | ctc | tcc | ctg | tct | ccg | ggt | aaa | tga | 1152 |

His Asn His Tyr Thr Gln Lys Ser Leu Ser Leu Ser Pro Gly Lys
        345                 350                 355

<210> SEQ ID NO 7
<211> LENGTH: 383
<212> TYPE: PRT
<213> ORGANISM: Artificial
<220> FEATURE:
<223> OTHER INFORMATION: Synthetic Construct

<400> SEQUENCE: 7

Met Gly Val Leu Leu Thr Gln Arg Thr Leu Leu Ser Leu Val Leu Ala
    -25                 -20                 -15

Leu Leu Phe Pro Ser Met Ala Ser Met Ala Met His Val Ala Gln Pro
-10                  -5                  -1  1                 5

Ala Val Val Leu Ala Ser Ser Arg Gly Ile Ala Ser Phe Val Cys Glu
                10                  15                  20

Tyr Ala Ser Pro Gly Lys Ala Thr Glu Val Arg Val Thr Val Leu Arg
            25                  30                  35

Gln Ala Asp Ser Gln Val Thr Glu Val Cys Ala Ala Thr Tyr Met Met
        40                  45                  50

Gly Asn Glu Leu Thr Phe Leu Asp Asp Ser Ile Cys Thr Gly Thr Ser
55                  60                  65                  70

Ser Gly Asn Gln Val Asn Leu Thr Ile Gln Gly Leu Arg Ala Met Asp
                75                  80                  85

Thr Gly Leu Tyr Ile Cys Lys Val Glu Leu Met Tyr Pro Pro Pro Tyr
            90                  95                  100

Tyr Glu Gly Ile Gly Asn Gly Thr Gln Ile Tyr Val Ile Asp Pro Glu
            105                 110                 115

Pro Cys Pro Asp Ser Asp Gln Glu Pro Lys Ser Ser Asp Lys Thr His
        120                 125                 130

Thr Ser Pro Pro Ser Pro Ala Pro Glu Leu Leu Gly Gly Ser Ser Val
135                 140                 145                 150

Phe Leu Phe Pro Pro Lys Pro Lys Asp Thr Leu Met Ile Ser Arg Thr
                155                 160                 165

Pro Glu Val Thr Cys Val Val Val Asp Val Ser His Glu Asp Pro Glu
            170                 175                 180

Val Lys Phe Asn Trp Tyr Val Asp Gly Val Glu Val His Asn Ala Lys
        185                 190                 195

Thr Lys Pro Arg Glu Glu Gln Tyr Asn Ser Thr Tyr Arg Val Val Ser
    200                 205                 210

Val Leu Thr Val Leu His Gln Asp Trp Leu Asn Gly Lys Glu Tyr Lys
215                 220                 225                 230

Cys Lys Val Ser Asn Lys Ala Leu Pro Ala Pro Ile Glu Lys Thr Ile
                235                 240                 245

Ser Lys Ala Lys Gly Gln Pro Arg Glu Pro Gln Val Tyr Thr Leu Pro
            250                 255                 260

Pro Ser Arg Asp Glu Leu Thr Lys Asn Gln Val Ser Leu Thr Cys Leu
        265                 270                 275

Val Lys Gly Phe Tyr Pro Ser Asp Ile Ala Val Glu Trp Glu Ser Asn
    280                 285                 290

Gly Gln Pro Glu Asn Asn Tyr Lys Thr Thr Pro Pro Val Leu Asp Ser
295                 300                 305                 310

Asp Gly Ser Phe Phe Leu Tyr Ser Lys Leu Thr Val Asp Lys Ser Arg
                315                 320                 325

```
Trp Gln Gln Gly Asn Val Phe Ser Cys Ser Val Met His Glu Ala Leu
            330                 335                 340

His Asn His Tyr Thr Gln Lys Ser Leu Ser Leu Ser Pro Gly Lys
            345                 350                 355

<210> SEQ ID NO 8
<211> LENGTH: 1152
<212> TYPE: DNA
<213> ORGANISM: Artificial
<220> FEATURE:
<223> OTHER INFORMATION: L104EA29YIg
<220> FEATURE:
<221> NAME/KEY: CDS
<222> LOCATION: (1)..(1149)
<220> FEATURE:
<221> NAME/KEY: mat_peptide
<222> LOCATION: (79)..()

<400> SEQUENCE: 8 atg ggt gta ctg ctc aca cag agg acg ctg ctc agt ctg gtc ctt gca     48
Met Gly Val Leu Leu Thr Gln Arg Thr Leu Leu Ser Leu Val Leu Ala
    -25                 -20                 -15 ctc ctg ttt cca agc atg gcg agc atg gca atg cac gtg gcc cag cct     96
Leu Leu Phe Pro Ser Met Ala Ser Met Ala Met His Val Ala Gln Pro
-10                  -5              -1   1               5 gct gtg gta ctg gcc agc agc cga ggc atc gct agc ttt gtg tgt gag    144
Ala Val Val Leu Ala Ser Ser Arg Gly Ile Ala Ser Phe Val Cys Glu
                10                  15                  20 tat gca tct cca ggc aaa tat act gag gtc cgg gtg aca gtg ctt cgg    192
Tyr Ala Ser Pro Gly Lys Tyr Thr Glu Val Arg Val Thr Val Leu Arg
            25                  30                  35 cag gct gac agc cag gtg act gaa gtc tgt gcg gca acc tac atg atg    240
Gln Ala Asp Ser Gln Val Thr Glu Val Cys Ala Ala Thr Tyr Met Met
        40                  45                  50 ggg aat gag ttg acc ttc cta gat gat tcc atc tgc acg ggc acc tcc    288
Gly Asn Glu Leu Thr Phe Leu Asp Asp Ser Ile Cys Thr Gly Thr Ser
 55                  60                  65                  70 agt gga aat caa gtg aac ctc act atc caa gga ctg agg gcc atg gac    336
Ser Gly Asn Gln Val Asn Leu Thr Ile Gln Gly Leu Arg Ala Met Asp
                 75                  80                  85 acg gga ctc tac atc tgc aag gtg gag ctc atg tac cca ccg cca tac    384
Thr Gly Leu Tyr Ile Cys Lys Val Glu Leu Met Tyr Pro Pro Pro Tyr
            90                  95                 100 tac gag ggc ata ggc aac gga acc cag att tat gta att gat cca gaa    432
Tyr Glu Gly Ile Gly Asn Gly Thr Gln Ile Tyr Val Ile Asp Pro Glu
        105                 110                 115 ccg tgc cca gat tct gat cag gag ccc aaa tct tct gac aaa act cac    480
Pro Cys Pro Asp Ser Asp Gln Glu Pro Lys Ser Ser Asp Lys Thr His
    120                 125                 130 aca tcc cca ccg tcc cca gca cct gaa ctc ctg ggg gga tcg tca gtc    528
Thr Ser Pro Pro Ser Pro Ala Pro Glu Leu Leu Gly Gly Ser Ser Val
135                 140                 145                 150 ttc ctc ttc ccc cca aaa ccc aag gac acc ctc atg atc tcc cgg acc    576
Phe Leu Phe Pro Pro Lys Pro Lys Asp Thr Leu Met Ile Ser Arg Thr
                155                 160                 165 cct gag gtc aca tgc gtg gtg gtg gac gtg agc cac gaa gac cct gag    624
Pro Glu Val Thr Cys Val Val Val Asp Val Ser His Glu Asp Pro Glu
            170                 175                 180 gtc aag ttc aac tgg tac gtg gac ggc gtg gag gtg cat aat gcc aag    672
Val Lys Phe Asn Trp Tyr Val Asp Gly Val Glu Val His Asn Ala Lys
        185                 190                 195 aca aag ccg cgg gag gag cag tac aac agc acg tac cgt gtg gtc agc    720
```

```
Thr Lys Pro Arg Glu Glu Gln Tyr Asn Ser Thr Tyr Arg Val Val Ser
    200                 205                 210 gtc ctc acc gtc ctg cac cag gac tgg ctg aat ggc aag gag tac aag      768
Val Leu Thr Val Leu His Gln Asp Trp Leu Asn Gly Lys Glu Tyr Lys
215                 220                 225                 230 tgc aag gtc tcc aac aaa gcc ctc cca gcc ccc atc gag aaa acc atc      816
Cys Lys Val Ser Asn Lys Ala Leu Pro Ala Pro Ile Glu Lys Thr Ile
                235                 240                 245 tcc aaa gcc aaa ggg cag ccc cga gaa cca cag gtg tac acc ctg ccc      864
Ser Lys Ala Lys Gly Gln Pro Arg Glu Pro Gln Val Tyr Thr Leu Pro
            250                 255                 260 cca tcc cgg gat gag ctg acc aag aac cag gtc agc ctg acc tgc ctg      912
Pro Ser Arg Asp Glu Leu Thr Lys Asn Gln Val Ser Leu Thr Cys Leu
        265                 270                 275 gtc aaa ggc ttc tat ccc agc gac atc gcc gtg gag tgg gag agc aat      960
Val Lys Gly Phe Tyr Pro Ser Asp Ile Ala Val Glu Trp Glu Ser Asn
    280                 285                 290 ggg cag ccg gag aac aac tac aag acc acg cct ccc gtg ctg gac tcc     1008
Gly Gln Pro Glu Asn Asn Tyr Lys Thr Thr Pro Pro Val Leu Asp Ser
295                 300                 305                 310 gac ggc tcc ttc ttc ctc tac agc aag ctc acc gtg gac aag agc agg     1056
Asp Gly Ser Phe Phe Leu Tyr Ser Lys Leu Thr Val Asp Lys Ser Arg
                315                 320                 325 tgg cag cag ggg aac gtc ttc tca tgc tcc gtg atg cat gag gct ctg     1104
Trp Gln Gln Gly Asn Val Phe Ser Cys Ser Val Met His Glu Ala Leu
            330                 335                 340 cac aac cac tac acg cag aag agc ctc tcc ctg tct ccg ggt aaa tga     1152
His Asn His Tyr Thr Gln Lys Ser Leu Ser Leu Ser Pro Gly Lys
        345                 350                 355

<210> SEQ ID NO 9
<211> LENGTH: 383
<212> TYPE: PRT
<213> ORGANISM: Artificial
<220> FEATURE:
<223> OTHER INFORMATION: Synthetic Construct

<400> SEQUENCE: 9

Met Gly Val Leu Leu Thr Gln Arg Thr Leu Leu Ser Leu Val Leu Ala
    -25                 -20                 -15

Leu Leu Phe Pro Ser Met Ala Ser Met Ala Met His Val Ala Gln Pro
-10                  -5              -1   1                   5

Ala Val Val Leu Ala Ser Ser Arg Gly Ile Ala Ser Phe Val Cys Glu
                10                  15                  20

Tyr Ala Ser Pro Gly Lys Tyr Thr Glu Val Arg Val Thr Val Leu Arg
            25                  30                  35

Gln Ala Asp Ser Gln Val Thr Glu Val Cys Ala Ala Thr Tyr Met Met
    40                  45                  50

Gly Asn Glu Leu Thr Phe Leu Asp Asp Ser Ile Cys Thr Gly Thr Ser
55                  60                  65                  70

Ser Gly Asn Gln Val Asn Leu Thr Ile Gln Gly Leu Arg Ala Met Asp
                75                  80                  85

Thr Gly Leu Tyr Ile Cys Lys Val Glu Leu Met Tyr Pro Pro Pro Tyr
            90                  95                  100

Tyr Glu Gly Ile Gly Asn Gly Thr Gln Ile Tyr Val Ile Asp Pro Glu
        105                 110                 115

Pro Cys Pro Asp Ser Asp Gln Glu Pro Lys Ser Ser Asp Lys Thr His
    120                 125                 130
```

```
Thr Ser Pro Pro Ser Pro Ala Pro Glu Leu Leu Gly Gly Ser Ser Val
135                 140                 145                 150

Phe Leu Phe Pro Pro Lys Pro Lys Asp Thr Leu Met Ile Ser Arg Thr
            155                 160                 165

Pro Glu Val Thr Cys Val Val Val Asp Val Ser His Glu Asp Pro Glu
            170                 175                 180

Val Lys Phe Asn Trp Tyr Val Asp Gly Val Glu Val His Asn Ala Lys
        185                 190                 195

Thr Lys Pro Arg Glu Glu Gln Tyr Asn Ser Thr Tyr Arg Val Val Ser
    200                 205                 210

Val Leu Thr Val Leu His Gln Asp Trp Leu Asn Gly Lys Glu Tyr Lys
215                 220                 225                 230

Cys Lys Val Ser Asn Lys Ala Leu Pro Ala Pro Ile Glu Lys Thr Ile
                235                 240                 245

Ser Lys Ala Lys Gly Gln Pro Arg Glu Pro Gln Val Tyr Thr Leu Pro
            250                 255                 260

Pro Ser Arg Asp Glu Leu Thr Lys Asn Gln Val Ser Leu Thr Cys Leu
        265                 270                 275

Val Lys Gly Phe Tyr Pro Ser Asp Ile Ala Val Glu Trp Glu Ser Asn
    280                 285                 290

Gly Gln Pro Glu Asn Asn Tyr Lys Thr Thr Pro Pro Val Leu Asp Ser
295                 300                 305                 310

Asp Gly Ser Phe Phe Leu Tyr Ser Lys Leu Thr Val Asp Lys Ser Arg
                315                 320                 325

Trp Gln Gln Gly Asn Val Phe Ser Cys Ser Val Met His Glu Ala Leu
            330                 335                 340

His Asn His Tyr Thr Gln Lys Ser Leu Ser Leu Ser Pro Gly Lys
        345                 350                 355

<210> SEQ ID NO 10
<211> LENGTH: 1152
<212> TYPE: DNA
<213> ORGANISM: Artificial
<220> FEATURE:
<223> OTHER INFORMATION: L104EA29LIg
<220> FEATURE:
<221> NAME/KEY: CDS
<222> LOCATION: (1)..(1149)
<220> FEATURE:
<221> NAME/KEY: mat_peptide
<222> LOCATION: (79)..()

<400> SEQUENCE: 10 atg ggt gta ctg ctc aca cag agg acg ctg ctc agt ctg gtc ctt gca     48
Met Gly Val Leu Leu Thr Gln Arg Thr Leu Leu Ser Leu Val Leu Ala
    -25                 -20                 -15 ctc ctg ttt cca agc atg gcg agc atg gca atg cac gtg gcc cag cct     96
Leu Leu Phe Pro Ser Met Ala Ser Met Ala Met His Val Ala Gln Pro
-10                  -5                  -1   1               5 gct gtg gta ctg gcc agc agc cga ggc atc gct agc ttt gtg tgt gag    144
Ala Val Val Leu Ala Ser Ser Arg Gly Ile Ala Ser Phe Val Cys Glu
                10                  15                  20 tat gca tct cca ggc aaa ttg act gag gtc cgg gtg aca gtg ctt cgg    192
Tyr Ala Ser Pro Gly Lys Leu Thr Glu Val Arg Val Thr Val Leu Arg
            25                  30                  35 cag gct gac agc cag gtg act gaa gtc tgt gcg gca acc tac atg atg    240
Gln Ala Asp Ser Gln Val Thr Glu Val Cys Ala Ala Thr Tyr Met Met
    40                  45                  50 ggg aat gag ttg acc ttc cta gat gat tcc atc tgc acg ggc acc tcc    288
Gly Asn Glu Leu Thr Phe Leu Asp Asp Ser Ile Cys Thr Gly Thr Ser
```

```
Gly Asn Glu Leu Thr Phe Leu Asp Asp Ser Ile Cys Thr Gly Thr Ser
 55                  60                  65                  70 agt gga aat caa gtg aac ctc act atc caa gga ctg agg gcc atg gac    336
Ser Gly Asn Gln Val Asn Leu Thr Ile Gln Gly Leu Arg Ala Met Asp
             75                  80                  85 acg gga ctc tac atc tgc aag gtg gag ctc atg tac cca ccg cca tac    384
Thr Gly Leu Tyr Ile Cys Lys Val Glu Leu Met Tyr Pro Pro Pro Tyr
         90                  95                 100 tac gag ggc ata ggc aac gga acc cag att tat gta att gat cca gaa    432
Tyr Glu Gly Ile Gly Asn Gly Thr Gln Ile Tyr Val Ile Asp Pro Glu
            105                 110                 115 ccg tgc cca gat tct gat cag gag ccc aaa tct tct gac aaa act cac    480
Pro Cys Pro Asp Ser Asp Gln Glu Pro Lys Ser Ser Asp Lys Thr His
        120                 125                 130 aca tcc cca ccg tcc cca gca cct gaa ctc ctg ggg gga tcg tca gtc    528
Thr Ser Pro Pro Ser Pro Ala Pro Glu Leu Leu Gly Gly Ser Ser Val
135                 140                 145                 150 ttc ctc ttc ccc cca aaa ccc aag gac acc ctc atg atc tcc cgg acc    576
Phe Leu Phe Pro Pro Lys Pro Lys Asp Thr Leu Met Ile Ser Arg Thr
                155                 160                 165 cct gag gtc aca tgc gtg gtg gtg gac gtg agc cac gaa gac cct gag    624
Pro Glu Val Thr Cys Val Val Val Asp Val Ser His Glu Asp Pro Glu
            170                 175                 180 gtc aag ttc aac tgg tac gtg gac ggc gtg gag gtg cat aat gcc aag    672
Val Lys Phe Asn Trp Tyr Val Asp Gly Val Glu Val His Asn Ala Lys
        185                 190                 195 aca aag ccg cgg gag gag cag tac aac agc acg tac cgt gtg gtc agc    720
Thr Lys Pro Arg Glu Glu Gln Tyr Asn Ser Thr Tyr Arg Val Val Ser
200                 205                 210 gtc ctc acc gtc ctg cac cag gac tgg ctg aat ggc aag gag tac aag    768
Val Leu Thr Val Leu His Gln Asp Trp Leu Asn Gly Lys Glu Tyr Lys
215                 220                 225                 230 tgc aag gtc tcc aac aaa gcc ctc cca gcc ccc atc gag aaa acc atc    816
Cys Lys Val Ser Asn Lys Ala Leu Pro Ala Pro Ile Glu Lys Thr Ile
                235                 240                 245 tcc aaa gcc aaa ggg cag ccc cga gaa cca cag gtg tac acc ctg ccc    864
Ser Lys Ala Lys Gly Gln Pro Arg Glu Pro Gln Val Tyr Thr Leu Pro
            250                 255                 260 cca tcc cgg gat gag ctg acc aag aac cag gtc agc ctg acc tgc ctg    912
Pro Ser Arg Asp Glu Leu Thr Lys Asn Gln Val Ser Leu Thr Cys Leu
        265                 270                 275 gtc aaa ggc ttc tat ccc agc gac atc gcc gtg gag tgg gag agc aat    960
Val Lys Gly Phe Tyr Pro Ser Asp Ile Ala Val Glu Trp Glu Ser Asn
280                 285                 290 ggg cag ccg gag aac aac tac aag acc acg cct ccc gtg ctg gac tcc   1008
Gly Gln Pro Glu Asn Asn Tyr Lys Thr Thr Pro Pro Val Leu Asp Ser
295                 300                 305                 310 gac ggc tcc ttc ttc ctc tac agc aag ctc acc gtg gac aag agc agg   1056
Asp Gly Ser Phe Phe Leu Tyr Ser Lys Leu Thr Val Asp Lys Ser Arg
                315                 320                 325 tgg cag cag ggg aac gtc ttc tca tgc tcc gtg atg cat gag gct ctg   1104
Trp Gln Gln Gly Asn Val Phe Ser Cys Ser Val Met His Glu Ala Leu
            330                 335                 340 cac aac cac tac acg cag aag agc ctc tcc ctg tct ccg ggt aaa tga   1152
His Asn His Tyr Thr Gln Lys Ser Leu Ser Leu Ser Pro Gly Lys
        345                 350                 355

<210> SEQ ID NO 11
<211> LENGTH: 383
<212> TYPE: PRT
```

<213> ORGANISM: Artificial
<220> FEATURE:
<223> OTHER INFORMATION: Synthetic Construct

<400> SEQUENCE: 11

```
Met Gly Val Leu Leu Thr Gln Arg Thr Leu Leu Ser Leu Val Leu Ala
    -25                 -20                 -15
Leu Leu Phe Pro Ser Met Ala Ser Met Ala Met His Val Ala Gln Pro
-10             -5                  -1  1                   5
Ala Val Val Leu Ala Ser Ser Arg Gly Ile Ala Ser Phe Val Cys Glu
                10                  15                  20
Tyr Ala Ser Pro Gly Lys Leu Thr Glu Val Arg Val Thr Val Leu Arg
            25                  30                  35
Gln Ala Asp Ser Gln Val Thr Glu Val Cys Ala Ala Thr Tyr Met Met
        40                  45                  50
Gly Asn Glu Leu Thr Phe Leu Asp Asp Ser Ile Cys Thr Gly Thr Ser
55                  60                  65                  70
Ser Gly Asn Gln Val Asn Leu Thr Ile Gln Gly Leu Arg Ala Met Asp
                75                  80                  85
Thr Gly Leu Tyr Ile Cys Lys Val Glu Leu Met Tyr Pro Pro Pro Tyr
            90                  95                  100
Tyr Glu Gly Ile Gly Asn Gly Thr Gln Ile Tyr Val Ile Asp Pro Glu
        105                 110                 115
Pro Cys Pro Asp Ser Asp Gln Glu Pro Lys Ser Ser Asp Lys Thr His
        120                 125                 130
Thr Ser Pro Pro Ser Pro Ala Pro Glu Leu Leu Gly Gly Ser Ser Val
135                 140                 145                 150
Phe Leu Phe Pro Pro Lys Pro Lys Asp Thr Leu Met Ile Ser Arg Thr
                155                 160                 165
Pro Glu Val Thr Cys Val Val Val Asp Val Ser His Glu Asp Pro Glu
            170                 175                 180
Val Lys Phe Asn Trp Tyr Val Asp Gly Val Glu Val His Asn Ala Lys
        185                 190                 195
Thr Lys Pro Arg Glu Glu Gln Tyr Asn Ser Thr Tyr Arg Val Val Ser
        200                 205                 210
Val Leu Thr Val Leu His Gln Asp Trp Leu Asn Gly Lys Glu Tyr Lys
215                 220                 225                 230
Cys Lys Val Ser Asn Lys Ala Leu Pro Ala Pro Ile Glu Lys Thr Ile
                235                 240                 245
Ser Lys Ala Lys Gly Gln Pro Arg Glu Pro Gln Val Tyr Thr Leu Pro
            250                 255                 260
Pro Ser Arg Asp Glu Leu Thr Lys Asn Gln Val Ser Leu Thr Cys Leu
        265                 270                 275
Val Lys Gly Phe Tyr Pro Ser Asp Ile Ala Val Glu Trp Glu Ser Asn
        280                 285                 290
Gly Gln Pro Glu Asn Asn Tyr Lys Thr Thr Pro Pro Val Leu Asp Ser
295                 300                 305                 310
Asp Gly Ser Phe Phe Leu Tyr Ser Lys Leu Thr Val Asp Lys Ser Arg
                315                 320                 325
Trp Gln Gln Gly Asn Val Phe Ser Cys Ser Val Met His Glu Ala Leu
            330                 335                 340
His Asn His Tyr Thr Gln Lys Ser Leu Ser Leu Ser Pro Gly Lys
        345                 350                 355
```

-continued

```
<210> SEQ ID NO 12
<211> LENGTH: 1152
<212> TYPE: DNA
<213> ORGANISM: Artificial
<220> FEATURE:
<223> OTHER INFORMATION: L104EA29TIg
<220> FEATURE:
<221> NAME/KEY: CDS
<222> LOCATION: (1)..(1149)
<220> FEATURE:
<221> NAME/KEY: mat_peptide
<222> LOCATION: (79)..()

<400> SEQUENCE: 12
```

| | | | | | | | | | | | | | | | | |
|---|---|---|---|---|---|---|---|---|---|---|---|---|---|---|---|---|
| atg | ggt | gta | ctg | ctc | aca | cag | agg | acg | ctg | ctc | agt | ctg | gtc | ctt | gca | 48 |
| Met | Gly | Val | Leu | Leu | Thr | Gln | Arg | Thr | Leu | Leu | Ser | Leu | Val | Leu | Ala | |
| -25 | | | | | -20 | | | | | -15 | | | | | | |
| ctc | ctg | ttt | cca | agc | atg | gcg | agc | atg | gca | atg | cac | gtg | gcc | cag | cct | 96 |
| Leu | Leu | Phe | Pro | Ser | Met | Ala | Ser | Met | Ala | Met | His | Val | Ala | Gln | Pro | |
| -10 | | | | -5 | | | | -1 | 1 | | | | 5 | | | |
| gct | gtg | gta | ctg | gcc | agc | agc | cga | ggc | atc | gct | agc | ttt | gtg | tgt | gag | 144 |
| Ala | Val | Val | Leu | Ala | Ser | Ser | Arg | Gly | Ile | Ala | Ser | Phe | Val | Cys | Glu | |
| | | | 10 | | | | | 15 | | | | | 20 | | | |
| tat | gca | tct | cca | ggc | aaa | act | act | gag | gtc | cgg | gtg | aca | gtg | ctt | cgg | 192 |
| Tyr | Ala | Ser | Pro | Gly | Lys | Thr | Thr | Glu | Val | Arg | Val | Thr | Val | Leu | Arg | |
| | | 25 | | | | | 30 | | | | | 35 | | | | |
| cag | gct | gac | agc | cag | gtg | act | gaa | gtc | tgt | gcg | gca | acc | tac | atg | atg | 240 |
| Gln | Ala | Asp | Ser | Gln | Val | Thr | Glu | Val | Cys | Ala | Ala | Thr | Tyr | Met | Met | |
| | 40 | | | | | 45 | | | | | 50 | | | | | |
| ggg | aat | gag | ttg | acc | ttc | cta | gat | gat | tcc | atc | tgc | acg | ggc | acc | tcc | 288 |
| Gly | Asn | Glu | Leu | Thr | Phe | Leu | Asp | Asp | Ser | Ile | Cys | Thr | Gly | Thr | Ser | |
| 55 | | | | | 60 | | | | | 65 | | | | | 70 | |
| agt | gga | aat | caa | gtg | aac | ctc | act | atc | caa | gga | ctg | agg | gcc | atg | gac | 336 |
| Ser | Gly | Asn | Gln | Val | Asn | Leu | Thr | Ile | Gln | Gly | Leu | Arg | Ala | Met | Asp |  |
| | | | 75 | | | | | 80 | | | | | 85 | | | |
| acg | gga | ctc | tac | atc | tgc | aag | gtg | gag | ctc | atg | tac | cca | ccg | cca | tac | 384 |
| Thr | Gly | Leu | Tyr | Ile | Cys | Lys | Val | Glu | Leu | Met | Tyr | Pro | Pro | Pro | Tyr | |
| | | | 90 | | | | | 95 | | | | | 100 | | | |
| tac | gag | ggc | ata | ggc | aac | gga | acc | cag | att | tat | gta | att | gat | cca | gaa | 432 |
| Tyr | Glu | Gly | Ile | Gly | Asn | Gly | Thr | Gln | Ile | Tyr | Val | Ile | Asp | Pro | Glu | |
| | | | 105 | | | | | 110 | | | | | 115 | | | |
| ccg | tgc | cca | gat | tct | gat | cag | gag | ccc | aaa | tct | tct | gac | aaa | act | cac | 480 |
| Pro | Cys | Pro | Asp | Ser | Asp | Gln | Glu | Pro | Lys | Ser | Ser | Asp | Lys | Thr | His | |
| | 120 | | | | | 125 | | | | | 130 | | | | | |
| aca | tcc | cca | ccg | tcc | cca | gca | cct | gaa | ctc | ctg | ggg | gga | tcg | tca | gtc | 528 |
| Thr | Ser | Pro | Pro | Ser | Pro | Ala | Pro | Glu | Leu | Leu | Gly | Gly | Ser | Ser | Val | |
| 135 | | | | | 140 | | | | | 145 | | | | | 150 | |
| ttc | ctc | ttc | ccc | cca | aaa | ccc | aag | gac | acc | ctc | atg | atc | tcc | cgg | acc | 576 |
| Phe | Leu | Phe | Pro | Pro | Lys | Pro | Lys | Asp | Thr | Leu | Met | Ile | Ser | Arg | Thr | |
| | | | 155 | | | | | 160 | | | | | 165 | | | |
| cct | gag | gtc | aca | tgc | gtg | gtg | gtg | gac | gtg | agc | cac | gaa | gac | cct | gag | 624 |
| Pro | Glu | Val | Thr | Cys | Val | Val | Val | Asp | Val | Ser | His | Glu | Asp | Pro | Glu | |
| | | | 170 | | | | | 175 | | | | | 180 | | | |
| gtc | aag | ttc | aac | tgg | tac | gtg | gac | ggc | gtg | gag | gtg | cat | aat | gcc | aag | 672 |
| Val | Lys | Phe | Asn | Trp | Tyr | Val | Asp | Gly | Val | Glu | Val | His | Asn | Ala | Lys | |
| | | 185 | | | | | 190 | | | | | 195 | | | | |
| aca | aag | ccg | cgg | gag | gag | cag | tac | aac | agc | acg | tac | cgt | gtg | gtc | agc | 720 |
| Thr | Lys | Pro | Arg | Glu | Glu | Gln | Tyr | Asn | Ser | Thr | Tyr | Arg | Val | Val | Ser | |
| | 200 | | | | | 205 | | | | | 210 | | | | | |
| gtc | ctc | acc | gtc | ctg | cac | cag | gac | tgg | ctg | aat | ggc | aag | gag | tac | aag | 768 |
| Val | Leu | Thr | Val | Leu | His | Gln | Asp | Trp | Leu | Asn | Gly | Lys | Glu | Tyr | Lys | |
| 215 | | | | | 220 | | | | | 225 | | | | | 230 | |

| | | | | | | | | | | | | | | | |
|---|---|---|---|---|---|---|---|---|---|---|---|---|---|---|---|
| tgc | aag | gtc | tcc | aac | aaa | gcc | ctc | cca | gcc | ccc | atc | gag | aaa | acc | atc | 816
| Cys | Lys | Val | Ser | Asn | Lys | Ala | Leu | Pro | Ala | Pro | Ile | Glu | Lys | Thr | Ile |
| | | | 235 | | | | 240 | | | | 245 | | | | |

```
tgc aag gtc tcc aac aaa gcc ctc cca gcc ccc atc gag aaa acc atc     816
Cys Lys Val Ser Asn Lys Ala Leu Pro Ala Pro Ile Glu Lys Thr Ile
            235                 240                 245 tcc aaa gcc aaa ggg cag ccc cga gaa cca cag gtg tac acc ctg ccc     864
Ser Lys Ala Lys Gly Gln Pro Arg Glu Pro Gln Val Tyr Thr Leu Pro
            250                 255                 260 cca tcc cgg gat gag ctg acc aag aac cag gtc agc ctg acc tgc ctg     912
Pro Ser Arg Asp Glu Leu Thr Lys Asn Gln Val Ser Leu Thr Cys Leu
            265                 270                 275 gtc aaa ggc ttc tat ccc agc gac atc gcc gtg gag tgg gag agc aat     960
Val Lys Gly Phe Tyr Pro Ser Asp Ile Ala Val Glu Trp Glu Ser Asn
            280                 285                 290 ggg cag ccg gag aac aac tac aag acc acg cct ccc gtg ctg gac tcc    1008
Gly Gln Pro Glu Asn Asn Tyr Lys Thr Thr Pro Pro Val Leu Asp Ser
295                 300                 305                 310 gac ggc tcc ttc ttc ctc tac agc aag ctc acc gtg gac aag agc agg    1056
Asp Gly Ser Phe Phe Leu Tyr Ser Lys Leu Thr Val Asp Lys Ser Arg
            315                 320                 325 tgg cag cag ggg aac gtc ttc tca tgc tcc gtg atg cat gag gct ctg    1104
Trp Gln Gln Gly Asn Val Phe Ser Cys Ser Val Met His Glu Ala Leu
            330                 335                 340 cac aac cac tac acg cag aag agc ctc tcc ctg tct ccg ggt aaa tga    1152
His Asn His Tyr Thr Gln Lys Ser Leu Ser Leu Ser Pro Gly Lys
            345                 350                 355
```

<210> SEQ ID NO 13
<211> LENGTH: 383
<212> TYPE: PRT
<213> ORGANISM: Artificial
<220> FEATURE:
<223> OTHER INFORMATION: Synthetic Construct

<400> SEQUENCE: 13

```
Met Gly Val Leu Leu Thr Gln Arg Thr Leu Leu Ser Leu Val Leu Ala
    -25                 -20                 -15

Leu Leu Phe Pro Ser Met Ala Ser Met Ala Met His Val Ala Gln Pro
-10                  -5                  -1   1               5

Ala Val Val Leu Ala Ser Ser Arg Gly Ile Ala Ser Phe Val Cys Glu
                10                  15                  20

Tyr Ala Ser Pro Gly Lys Thr Thr Glu Val Arg Val Thr Val Leu Arg
            25                  30                  35

Gln Ala Asp Ser Gln Val Thr Glu Val Cys Ala Ala Thr Tyr Met Met
        40                  45                  50

Gly Asn Glu Leu Thr Phe Leu Asp Asp Ser Ile Cys Thr Gly Thr Ser
55                  60                  65                  70

Ser Gly Asn Gln Val Asn Leu Thr Ile Gln Gly Leu Arg Ala Met Asp
                75                  80                  85

Thr Gly Leu Tyr Ile Cys Lys Val Glu Leu Met Tyr Pro Pro Pro Tyr
            90                  95                  100

Tyr Glu Gly Ile Gly Asn Gly Thr Gln Ile Tyr Val Ile Asp Pro Glu
            105                 110                 115

Pro Cys Pro Asp Ser Asp Gln Glu Pro Lys Ser Ser Asp Lys Thr His
            120                 125                 130

Thr Ser Pro Pro Ser Pro Ala Pro Glu Leu Leu Gly Gly Ser Ser Val
135                 140                 145                 150

Phe Leu Phe Pro Pro Lys Pro Lys Asp Thr Leu Met Ile Ser Arg Thr
            155                 160                 165

Pro Glu Val Thr Cys Val Val Val Asp Val Ser His Glu Asp Pro Glu
```

```
                    170                 175                 180
Val Lys Phe Asn Trp Tyr Val Asp Gly Val Glu Val His Asn Ala Lys
            185                 190                 195

Thr Lys Pro Arg Glu Glu Gln Tyr Asn Ser Thr Tyr Arg Val Val Ser
        200                 205                 210

Val Leu Thr Val Leu His Gln Asp Trp Leu Asn Gly Lys Glu Tyr Lys
215                 220                 225                 230

Cys Lys Val Ser Asn Lys Ala Leu Pro Ala Pro Ile Glu Lys Thr Ile
                235                 240                 245

Ser Lys Ala Lys Gly Gln Pro Arg Glu Pro Gln Val Tyr Thr Leu Pro
            250                 255                 260

Pro Ser Arg Asp Glu Leu Thr Lys Asn Gln Val Ser Leu Thr Cys Leu
        265                 270                 275

Val Lys Gly Phe Tyr Pro Ser Asp Ile Ala Val Glu Trp Glu Ser Asn
280                 285                 290

Gly Gln Pro Glu Asn Asn Tyr Lys Thr Thr Pro Pro Val Leu Asp Ser
295                 300                 305                 310

Asp Gly Ser Phe Phe Leu Tyr Ser Lys Leu Thr Val Asp Lys Ser Arg
                315                 320                 325

Trp Gln Gln Gly Asn Val Phe Ser Cys Ser Val Met His Glu Ala Leu
            330                 335                 340

His Asn His Tyr Thr Gln Lys Ser Leu Ser Leu Ser Pro Gly Lys
        345                 350                 355

<210> SEQ ID NO 14
<211> LENGTH: 1152
<212> TYPE: DNA
<213> ORGANISM: Artificial
<220> FEATURE:
<223> OTHER INFORMATION: L104EA29WIg
<220> FEATURE:
<221> NAME/KEY: CDS
<222> LOCATION: (1)..(1149)
<220> FEATURE:
<221> NAME/KEY: mat_peptide
<222> LOCATION: (79)..()

<400> SEQUENCE: 14 atg ggt gta ctg ctc aca cag agg acg ctg ctc agt ctg gtc ctt gca      48
Met Gly Val Leu Leu Thr Gln Arg Thr Leu Leu Ser Leu Val Leu Ala
        -25                 -20                 -15 ctc ctg ttt cca agc atg gcg agc atg gca atg cac gtg gcc cag cct      96
Leu Leu Phe Pro Ser Met Ala Ser Met Ala Met His Val Ala Gln Pro
-10                  -5                  -1  1                 5 gct gtg gta ctg gcc agc agc cga ggc atc gct agc ttt gtg tgt gag     144
Ala Val Val Leu Ala Ser Ser Arg Gly Ile Ala Ser Phe Val Cys Glu
                10                  15                  20 tat gca tct cca ggc aaa tgg act gag gtc cgg gtg aca gtg ctt cgg     192
Tyr Ala Ser Pro Gly Lys Trp Thr Glu Val Arg Val Thr Val Leu Arg
            25                  30                  35 cag gct gac agc cag gtg act gaa gtc tgt gcg gca acc tac atg atg     240
Gln Ala Asp Ser Gln Val Thr Glu Val Cys Ala Ala Thr Tyr Met Met
        40                  45                  50 ggg aat gag ttg acc ttc cta gat gat tcc atc tgc acg ggc acc tcc     288
Gly Asn Glu Leu Thr Phe Leu Asp Asp Ser Ile Cys Thr Gly Thr Ser
55                  60                  65                  70 agt gga aat caa gtg aac ctc act atc caa gga ctg agg gcc atg gac     336
Ser Gly Asn Gln Val Asn Leu Thr Ile Gln Gly Leu Arg Ala Met Asp
                75                  80                  85
```

| | | | | | | | | | | | | | | | | |
|---|---|---|---|---|---|---|---|---|---|---|---|---|---|---|---|---|
| acg | gga | ctc | tac | atc | tgc | aag | gtg | gag | ctc | atg | tac | cca | ccg | cca | tac | 384 |
| Thr | Gly | Leu | Tyr | Ile | Cys | Lys | Val | Glu | Leu | Met | Tyr | Pro | Pro | Pro | Tyr | |
| | | | 90 | | | | 95 | | | | 100 | | | | | |
| tac | gag | ggc | ata | ggc | aac | gga | acc | cag | att | tat | gta | att | gat | cca | gaa | 432 |
| Tyr | Glu | Gly | Ile | Gly | Asn | Gly | Thr | Gln | Ile | Tyr | Val | Ile | Asp | Pro | Glu | |
| | | 105 | | | | | 110 | | | | 115 | | | | | |
| ccg | tgc | cca | gat | tct | gat | cag | gag | ccc | aaa | tct | tct | gac | aaa | act | cac | 480 |
| Pro | Cys | Pro | Asp | Ser | Asp | Gln | Glu | Pro | Lys | Ser | Ser | Asp | Lys | Thr | His | |
| | 120 | | | | | 125 | | | | | 130 | | | | | |
| aca | tcc | cca | ccg | tcc | cca | gca | cct | gaa | ctc | ctg | ggg | gga | tcg | tca | gtc | 528 |
| Thr | Ser | Pro | Pro | Ser | Pro | Ala | Pro | Glu | Leu | Leu | Gly | Gly | Ser | Ser | Val | |
| 135 | | | | | 140 | | | | | 145 | | | | | 150 | |
| ttc | ctc | ttc | ccc | cca | aaa | ccc | aag | gac | acc | ctc | atg | atc | tcc | cgg | acc | 576 |
| Phe | Leu | Phe | Pro | Pro | Lys | Pro | Lys | Asp | Thr | Leu | Met | Ile | Ser | Arg | Thr | |
| | | | | 155 | | | | | 160 | | | | | 165 | | |
| cct | gag | gtc | aca | tgc | gtg | gtg | gtg | gac | gtg | agc | cac | gaa | gac | cct | gag | 624 |
| Pro | Glu | Val | Thr | Cys | Val | Val | Val | Asp | Val | Ser | His | Glu | Asp | Pro | Glu | |
| | | | 170 | | | | | 175 | | | | | 180 | | | |
| gtc | aag | ttc | aac | tgg | tac | gtg | gac | ggc | gtg | gag | gtg | cat | aat | gcc | aag | 672 |
| Val | Lys | Phe | Asn | Trp | Tyr | Val | Asp | Gly | Val | Glu | Val | His | Asn | Ala | Lys | |
| | | 185 | | | | | 190 | | | | | 195 | | | | |
| aca | aag | ccg | cgg | gag | gag | cag | tac | aac | agc | acg | tac | cgt | gtg | gtc | agc | 720 |
| Thr | Lys | Pro | Arg | Glu | Glu | Gln | Tyr | Asn | Ser | Thr | Tyr | Arg | Val | Val | Ser | |
| | 200 | | | | | 205 | | | | | 210 | | | | | |
| gtc | ctc | acc | gtc | ctg | cac | cag | gac | tgg | ctg | aat | ggc | aag | gag | tac | aag | 768 |
| Val | Leu | Thr | Val | Leu | His | Gln | Asp | Trp | Leu | Asn | Gly | Lys | Glu | Tyr | Lys | |
| 215 | | | | | 220 | | | | | 225 | | | | | 230 | |
| tgc | aag | gtc | tcc | aac | aaa | gcc | ctc | cca | gcc | ccc | atc | gag | aaa | acc | atc | 816 |
| Cys | Lys | Val | Ser | Asn | Lys | Ala | Leu | Pro | Ala | Pro | Ile | Glu | Lys | Thr | Ile | |
| | | | | 235 | | | | | 240 | | | | | 245 | | |
| tcc | aaa | gcc | aaa | ggg | cag | ccc | cga | gaa | cca | cag | gtg | tac | acc | ctg | ccc | 864 |
| Ser | Lys | Ala | Lys | Gly | Gln | Pro | Arg | Glu | Pro | Gln | Val | Tyr | Thr | Leu | Pro | |
| | | | 250 | | | | | 255 | | | | | 260 | | | |
| cca | tcc | cgg | gat | gag | ctg | acc | aag | aac | cag | gtc | agc | ctg | acc | tgc | ctg | 912 |
| Pro | Ser | Arg | Asp | Glu | Leu | Thr | Lys | Asn | Gln | Val | Ser | Leu | Thr | Cys | Leu | |
| | | 265 | | | | | 270 | | | | | 275 | | | | |
| gtc | aaa | ggc | ttc | tat | ccc | agc | gac | atc | gcc | gtg | gag | tgg | gag | agc | aat | 960 |
| Val | Lys | Gly | Phe | Tyr | Pro | Ser | Asp | Ile | Ala | Val | Glu | Trp | Glu | Ser | Asn | |
| | 280 | | | | | 285 | | | | | 290 | | | | | |
| ggg | cag | ccg | gag | aac | aac | tac | aag | acc | acg | cct | ccc | gtg | ctg | gac | tcc | 1008 |
| Gly | Gln | Pro | Glu | Asn | Asn | Tyr | Lys | Thr | Thr | Pro | Pro | Val | Leu | Asp | Ser | |
| 295 | | | | | 300 | | | | | 305 | | | | | 310 | |
| gac | ggc | tcc | ttc | ttc | ctc | tac | agc | aag | ctc | acc | gtg | gac | aag | agc | agg | 1056 |
| Asp | Gly | Ser | Phe | Phe | Leu | Tyr | Ser | Lys | Leu | Thr | Val | Asp | Lys | Ser | Arg | |
| | | | | 315 | | | | | 320 | | | | | 325 | | |
| tgg | cag | cag | ggg | aac | gtc | ttc | tca | tgc | tcc | gtg | atg | cat | gag | gct | ctg | 1104 |
| Trp | Gln | Gln | Gly | Asn | Val | Phe | Ser | Cys | Ser | Val | Met | His | Glu | Ala | Leu | |
| | | | 330 | | | | | 335 | | | | | 340 | | | |
| cac | aac | cac | tac | acg | cag | aag | agc | ctc | tcc | ctg | tct | ccg | ggt | aaa | tga | 1152 |
| His | Asn | His | Tyr | Thr | Gln | Lys | Ser | Leu | Ser | Leu | Ser | Pro | Gly | Lys | | |
| | | 345 | | | | | 350 | | | | | 355 | | | | |

<210> SEQ ID NO 15
<211> LENGTH: 383
<212> TYPE: PRT
<213> ORGANISM: Artificial
<220> FEATURE:
<223> OTHER INFORMATION: Synthetic Construct

<400> SEQUENCE: 15

Met Gly Val Leu Leu Thr Gln Arg Thr Leu Leu Ser Leu Val Leu Ala

|       | -25 |     |     |     | -20 |     |     |     | -15 |     |     |     |
|-------|-----|-----|-----|-----|-----|-----|-----|-----|-----|-----|-----|-----|

Leu Leu Phe Pro Ser Met Ala Ser Met Ala Met His Val Ala Gln Pro
-10             -5              -1  1               5

Ala Val Val Leu Ala Ser Ser Arg Gly Ile Ala Ser Phe Val Cys Glu
            10              15              20

Tyr Ala Ser Pro Gly Lys Trp Thr Glu Val Arg Val Thr Val Leu Arg
        25              30              35

Gln Ala Asp Ser Gln Val Thr Glu Val Cys Ala Ala Thr Tyr Met Met
    40              45              50

Gly Asn Glu Leu Thr Phe Leu Asp Asp Ser Ile Cys Thr Gly Thr Ser
55              60              65              70

Ser Gly Asn Gln Val Asn Leu Thr Ile Gln Gly Leu Arg Ala Met Asp
            75              80              85

Thr Gly Leu Tyr Ile Cys Lys Val Glu Leu Met Tyr Pro Pro Pro Tyr
        90              95              100

Tyr Glu Gly Ile Gly Asn Gly Thr Gln Ile Tyr Val Ile Asp Pro Glu
        105             110             115

Pro Cys Pro Asp Ser Asp Gln Glu Pro Lys Ser Ser Asp Lys Thr His
        120             125             130

Thr Ser Pro Pro Ser Pro Ala Pro Glu Leu Leu Gly Gly Ser Ser Val
135             140             145             150

Phe Leu Phe Pro Pro Lys Pro Lys Asp Thr Leu Met Ile Ser Arg Thr
            155             160             165

Pro Glu Val Thr Cys Val Val Val Asp Val Ser His Glu Asp Pro Glu
        170             175             180

Val Lys Phe Asn Trp Tyr Val Asp Gly Val Glu Val His Asn Ala Lys
        185             190             195

Thr Lys Pro Arg Glu Glu Gln Tyr Asn Ser Thr Tyr Arg Val Val Ser
    200             205             210

Val Leu Thr Val Leu His Gln Asp Trp Leu Asn Gly Lys Glu Tyr Lys
215             220             225             230

Cys Lys Val Ser Asn Lys Ala Leu Pro Ala Pro Ile Glu Lys Thr Ile
            235             240             245

Ser Lys Ala Lys Gly Gln Pro Arg Glu Pro Gln Val Tyr Thr Leu Pro
        250             255             260

Pro Ser Arg Asp Glu Leu Thr Lys Asn Gln Val Ser Leu Thr Cys Leu
        265             270             275

Val Lys Gly Phe Tyr Pro Ser Asp Ile Ala Val Glu Trp Glu Ser Asn
    280             285             290

Gly Gln Pro Glu Asn Asn Tyr Lys Thr Thr Pro Pro Val Leu Asp Ser
295             300             305             310

Asp Gly Ser Phe Phe Leu Tyr Ser Lys Leu Thr Val Asp Lys Ser Arg
            315             320             325

Trp Gln Gln Gly Asn Val Phe Ser Cys Ser Val Met His Glu Ala Leu
        330             335             340

His Asn His Tyr Thr Gln Lys Ser Leu Ser Leu Ser Pro Gly Lys
        345             350             355

<210> SEQ ID NO 16
<211> LENGTH: 636
<212> TYPE: DNA
<213> ORGANISM: Homo sapiens
<220> FEATURE:
<221> NAME/KEY: CDS
<222> LOCATION: (1)..(636)

```
<220> FEATURE:
<221> NAME/KEY: mat_peptide
<222> LOCATION: (79)..()

<400> SEQUENCE: 16 atg ggt gta ctg ctc aca cag agg acg ctg ctc agt ctg gtc ctt gca      48
Met Gly Val Leu Leu Thr Gln Arg Thr Leu Leu Ser Leu Val Leu Ala
    -25                 -20                 -15 ctc ctg ttt cca agc atg gcg agc atg gca atg cac gtg gcc cag cct      96
Leu Leu Phe Pro Ser Met Ala Ser Met Ala Met His Val Ala Gln Pro
-10                  -5                  -1  1               5 gct gta gta ctg gcc agc agc cga ggc atc gcc agc ttt gtg tgt gag     144
Ala Val Val Leu Ala Ser Ser Arg Gly Ile Ala Ser Phe Val Cys Glu
            10                  15                  20 tat gca tct cca ggc aaa gcc act gag gtc cgg gtg aca gtg ctt cgg     192
Tyr Ala Ser Pro Gly Lys Ala Thr Glu Val Arg Val Thr Val Leu Arg
        25                  30                  35 cag gct gac agc cag gtg act gaa gtc tgt gcg gca acc tac atg atg     240
Gln Ala Asp Ser Gln Val Thr Glu Val Cys Ala Ala Thr Tyr Met Met
    40                  45                  50 ggg aat gag ttg acc ttc cta gat gat tcc atc tgc acg ggc acc tcc     288
Gly Asn Glu Leu Thr Phe Leu Asp Asp Ser Ile Cys Thr Gly Thr Ser
55                  60                  65                  70 agt gga aat caa gtg aac ctc act atc caa gga ctg agg gcc atg gac     336
Ser Gly Asn Gln Val Asn Leu Thr Ile Gln Gly Leu Arg Ala Met Asp
                75                  80                  85 acg gga ctc tac atc tgc aag gtg gag ctc atg tac cca ccg cca tac     384
Thr Gly Leu Tyr Ile Cys Lys Val Glu Leu Met Tyr Pro Pro Pro Tyr
            90                  95                  100 tac ctg ggc ata ggc aac gga acc cag att tat gta att gat cca gaa     432
Tyr Leu Gly Ile Gly Asn Gly Thr Gln Ile Tyr Val Ile Asp Pro Glu
        105                 110                 115 ccg tgc cca gat tct gac ttc ctc ctc tgg atc ctt gca gca gtt agt     480
Pro Cys Pro Asp Ser Asp Phe Leu Leu Trp Ile Leu Ala Ala Val Ser
    120                 125                 130 tcg ggg ttg ttt ttt tat agc ttt ctc ctc aca gct gtt tct ttg agc     528
Ser Gly Leu Phe Phe Tyr Ser Phe Leu Leu Thr Ala Val Ser Leu Ser
135                 140                 145                 150 aaa atg cta aag aaa aga agc cct ctt aca aca ggg gtc tat gtg aaa     576
Lys Met Leu Lys Lys Arg Ser Pro Leu Thr Thr Gly Val Tyr Val Lys
                155                 160                 165 atg ccc cca aca gag cca gaa tgt gaa aag caa ttt cag cct tat ttt     624
Met Pro Pro Thr Glu Pro Glu Cys Glu Lys Gln Phe Gln Pro Tyr Phe
            170                 175                 180 att ccc atc aat                                                     636
Ile Pro Ile Asn
        185

<210> SEQ ID NO 17
<211> LENGTH: 212
<212> TYPE: PRT
<213> ORGANISM: Homo sapiens

<400> SEQUENCE: 17

Met Gly Val Leu Leu Thr Gln Arg Thr Leu Leu Ser Leu Val Leu Ala
    -25                 -20                 -15

Leu Leu Phe Pro Ser Met Ala Ser Met Ala Met His Val Ala Gln Pro
-10                  -5                  -1  1               5

Ala Val Val Leu Ala Ser Ser Arg Gly Ile Ala Ser Phe Val Cys Glu
            10                  15                  20
```

-continued

```
Tyr Ala Ser Pro Gly Lys Ala Thr Glu Val Arg Val Thr Val Leu Arg
         25                   30                  35

Gln Ala Asp Ser Gln Val Thr Glu Val Cys Ala Ala Thr Tyr Met Met
 40                      45                  50

Gly Asn Glu Leu Thr Phe Leu Asp Asp Ser Ile Cys Thr Gly Thr Ser
 55                  60                  65                  70

Ser Gly Asn Gln Val Asn Leu Thr Ile Gln Gly Leu Arg Ala Met Asp
             75                  80                  85

Thr Gly Leu Tyr Ile Cys Lys Val Glu Leu Met Tyr Pro Pro Pro Tyr
             90                  95                  100

Tyr Leu Gly Ile Gly Asn Gly Thr Gln Ile Tyr Val Ile Asp Pro Glu
             105                 110                 115

Pro Cys Pro Asp Ser Asp Phe Leu Leu Trp Ile Leu Ala Ala Val Ser
         120                 125                 130

Ser Gly Leu Phe Phe Tyr Ser Phe Leu Leu Thr Ala Val Ser Leu Ser
135                 140                 145                 150

Lys Met Leu Lys Lys Arg Ser Pro Leu Thr Thr Gly Val Tyr Val Lys
             155                 160                 165

Met Pro Pro Thr Glu Pro Glu Cys Glu Lys Gln Phe Gln Pro Tyr Phe
             170                 175                 180

Ile Pro Ile Asn
         185

<210> SEQ ID NO 18
<211> LENGTH: 1152
<212> TYPE: DNA
<213> ORGANISM: Artificial
<220> FEATURE:
<223> OTHER INFORMATION: CTLA4Ig
<220> FEATURE:
<221> NAME/KEY: CDS
<222> LOCATION: (1)..(1149)
<220> FEATURE:
<221> NAME/KEY: mat_peptide
<222> LOCATION: (79)..()

<400> SEQUENCE: 18 atg ggt gta ctg ctc aca cag agg acg ctg ctc agt ctg gtc ctt gca    48
Met Gly Val Leu Leu Thr Gln Arg Thr Leu Leu Ser Leu Val Leu Ala
 -25                  -20                 -15 ctc ctg ttt cca agc atg gcg agc atg gca atg cac gtg gcc cag cct    96
Leu Leu Phe Pro Ser Met Ala Ser Met Ala Met His Val Ala Gln Pro
-10                  -5                  -1  1               5 gct gtg gta ctg gcc agc agc cga ggc atc gct agc ttt gtg tgt gag   144
Ala Val Val Leu Ala Ser Ser Arg Gly Ile Ala Ser Phe Val Cys Glu
                 10                  15                  20 tat gca tct cca ggc aaa gcc act gag gtc cgg gtg aca gtg ctt cgg   192
Tyr Ala Ser Pro Gly Lys Ala Thr Glu Val Arg Val Thr Val Leu Arg
         25                  30                  35 cag gct gac agc cag gtg act gaa gtc tgt gcg gca acc tac atg atg   240
Gln Ala Asp Ser Gln Val Thr Glu Val Cys Ala Ala Thr Tyr Met Met
 40                  45                  50 ggg aat gag ttg acc ttc cta gat gat tcc atc tgc acg ggc acc tcc   288
Gly Asn Glu Leu Thr Phe Leu Asp Asp Ser Ile Cys Thr Gly Thr Ser
 55                  60                  65                  70 agt gga aat caa gtg aac ctc act atc caa gga ctg agg gcc atg gac   336
Ser Gly Asn Gln Val Asn Leu Thr Ile Gln Gly Leu Arg Ala Met Asp
             75                  80                  85 acg gga ctc tac atc tgc aag gtg gag ctc atg tac cca ccg cca tac   384
Thr Gly Leu Tyr Ile Cys Lys Val Glu Leu Met Tyr Pro Pro Pro Tyr
```

```
                      90                   95                      100
tac ctg ggc ata ggc aac gga acc cag att tat gta att gat cca gaa       432
Tyr Leu Gly Ile Gly Asn Gly Thr Gln Ile Tyr Val Ile Asp Pro Glu
            105                 110                 115 ccg tgc cca gat tct gat cag gag ccc aaa tct tct gac aaa act cac       480
Pro Cys Pro Asp Ser Asp Gln Glu Pro Lys Ser Ser Asp Lys Thr His
        120                 125                 130 aca tcc cca ccg tcc cca gca cct gaa ctc ctg ggt gga tcg tca gtc       528
Thr Ser Pro Pro Ser Pro Ala Pro Glu Leu Leu Gly Gly Ser Ser Val
135                 140                 145                 150 ttc ctc ttc ccc cca aaa ccc aag gac acc ctc atg atc tcc cgg acc       576
Phe Leu Phe Pro Pro Lys Pro Lys Asp Thr Leu Met Ile Ser Arg Thr
                155                 160                 165 cct gag gtc aca tgc gtg gtg gtg gac gtg agc cac gaa gac cct gag       624
Pro Glu Val Thr Cys Val Val Val Asp Val Ser His Glu Asp Pro Glu
            170                 175                 180 gtc aag ttc aac tgg tac gtg gac ggc gtg gag gtg cat aat gcc aag       672
Val Lys Phe Asn Trp Tyr Val Asp Gly Val Glu Val His Asn Ala Lys
        185                 190                 195 aca aag ccg cgg gag gag cag tac aac agc acg tac cgg gtg gtc agc       720
Thr Lys Pro Arg Glu Glu Gln Tyr Asn Ser Thr Tyr Arg Val Val Ser
200                 205                 210 gtc ctc acc gtc ctg cac cag gac tgg ctg aat ggc aag gag tac aag       768
Val Leu Thr Val Leu His Gln Asp Trp Leu Asn Gly Lys Glu Tyr Lys
215                 220                 225                 230 tgc aag gtc tcc aac aaa gcc ctc cca gcc ccc atc gag aaa acc atc       816
Cys Lys Val Ser Asn Lys Ala Leu Pro Ala Pro Ile Glu Lys Thr Ile
                235                 240                 245 tcc aaa gcc aaa ggg cag ccc cga gaa cca cag gtg tac acc ctg ccc       864
Ser Lys Ala Lys Gly Gln Pro Arg Glu Pro Gln Val Tyr Thr Leu Pro
            250                 255                 260 cca tcc cgg gat gag ctg acc aag aac cag gtc agc ctg acc tgc ctg       912
Pro Ser Arg Asp Glu Leu Thr Lys Asn Gln Val Ser Leu Thr Cys Leu
        265                 270                 275 gtc aaa ggc ttc tat ccc agc gac atc gcc gtg gag tgg gag agc aat       960
Val Lys Gly Phe Tyr Pro Ser Asp Ile Ala Val Glu Trp Glu Ser Asn
280                 285                 290 ggg cag ccg gag aac aac tac aag acc acg cct ccc gtg ctg gac tcc      1008
Gly Gln Pro Glu Asn Asn Tyr Lys Thr Thr Pro Pro Val Leu Asp Ser
295                 300                 305                 310 gac ggc tcc ttc ttc ctc tac agc aag ctc acc gtg gac aag agc agg      1056
Asp Gly Ser Phe Phe Leu Tyr Ser Lys Leu Thr Val Asp Lys Ser Arg
                315                 320                 325 tgg cag cag ggg aac gtc ttc tca tgc tcc gtg atg cat gag gct ctg      1104
Trp Gln Gln Gly Asn Val Phe Ser Cys Ser Val Met His Glu Ala Leu
            330                 335                 340 cac aac cac tac acg cag aag agc ctc tcc ctg tct ccg ggt aaa tga      1152
His Asn His Tyr Thr Gln Lys Ser Leu Ser Leu Ser Pro Gly Lys
        345                 350                 355

<210> SEQ ID NO 19
<211> LENGTH: 383
<212> TYPE: PRT
<213> ORGANISM: Artificial
<220> FEATURE:
<223> OTHER INFORMATION: Synthetic Construct

<400> SEQUENCE: 19

Met Gly Val Leu Leu Thr Gln Arg Thr Leu Leu Ser Leu Val Leu Ala
        -25                 -20                 -15
```

```
Leu Leu Phe Pro Ser Met Ala Ser Met Ala Met His Val Ala Gln Pro
-10              -5                  -1   1                   5

Ala Val Val Leu Ala Ser Ser Arg Gly Ile Ala Ser Phe Val Cys Glu
            10              15                  20

Tyr Ala Ser Pro Gly Lys Ala Thr Glu Val Arg Val Thr Val Leu Arg
            25              30                  35

Gln Ala Asp Ser Gln Val Thr Glu Val Cys Ala Ala Thr Tyr Met Met
            40              45                  50

Gly Asn Glu Leu Thr Phe Leu Asp Asp Ser Ile Cys Thr Gly Thr Ser
 55              60              65                  70

Ser Gly Asn Gln Val Asn Leu Thr Ile Gln Gly Leu Arg Ala Met Asp
            75              80                  85

Thr Gly Leu Tyr Ile Cys Lys Val Glu Leu Met Tyr Pro Pro Pro Tyr
            90              95                  100

Tyr Leu Gly Ile Gly Asn Gly Thr Gln Ile Tyr Val Ile Asp Pro Glu
            105             110                 115

Pro Cys Pro Asp Ser Asp Gln Glu Pro Lys Ser Ser Asp Lys Thr His
            120             125                 130

Thr Ser Pro Pro Ser Pro Ala Pro Glu Leu Leu Gly Gly Ser Ser Val
135             140             145                 150

Phe Leu Phe Pro Pro Lys Pro Lys Asp Thr Leu Met Ile Ser Arg Thr
                155             160                 165

Pro Glu Val Thr Cys Val Val Val Asp Val Ser His Glu Asp Pro Glu
            170             175                 180

Val Lys Phe Asn Trp Tyr Val Asp Gly Val Glu Val His Asn Ala Lys
            185             190                 195

Thr Lys Pro Arg Glu Glu Gln Tyr Asn Ser Thr Tyr Arg Val Val Ser
200             205                 210

Val Leu Thr Val Leu His Gln Asp Trp Leu Asn Gly Lys Glu Tyr Lys
215             220                 225                 230

Cys Lys Val Ser Asn Lys Ala Leu Pro Ala Pro Ile Glu Lys Thr Ile
            235             240                 245

Ser Lys Ala Lys Gly Gln Pro Arg Glu Pro Gln Val Tyr Thr Leu Pro
            250             255                 260

Pro Ser Arg Asp Glu Leu Thr Lys Asn Gln Val Ser Leu Thr Cys Leu
            265             270                 275

Val Lys Gly Phe Tyr Pro Ser Asp Ile Ala Val Glu Trp Glu Ser Asn
            280             285                 290

Gly Gln Pro Glu Asn Asn Tyr Lys Thr Thr Pro Pro Val Leu Asp Ser
295             300                 305                 310

Asp Gly Ser Phe Phe Leu Tyr Ser Lys Leu Thr Val Asp Lys Ser Arg
            315             320                 325

Trp Gln Gln Gly Asn Val Phe Ser Cys Ser Val Met His Glu Ala Leu
            330             335                 340

His Asn His Tyr Thr Gln Lys Ser Leu Ser Leu Ser Pro Gly Lys
            345             350                 355

<210> SEQ ID NO 20
<211> LENGTH: 6
<212> TYPE: PRT
<213> ORGANISM: Artificial
<220> FEATURE:
<223> OTHER INFORMATION: MYPPPY amino acid sequence

<400> SEQUENCE: 20
```

```
Met Tyr Pro Pro Tyr
 1               5
```

<210> SEQ ID NO 21
<211> LENGTH: 1152
<212> TYPE: DNA
<213> ORGANISM: Artificial
<220> FEATURE:
<223> OTHER INFORMATION: CTLA4Ig
<220> FEATURE:
<221> NAME/KEY: CDS
<222> LOCATION: (1)..(1149)
<220> FEATURE:
<221> NAME/KEY: mat_peptide
<222> LOCATION: (79)..()

<400> SEQUENCE: 21

```
atg ggt gta ctg ctc aca cag agg acg ctg ctc agt ctg gtc ctt gca        48
Met Gly Val Leu Leu Thr Gln Arg Thr Leu Leu Ser Leu Val Leu Ala
-25             -20                 -15 ctc ctg ttt cca agc atg gcg agc atg gca atg cac gtg gcc cag cct        96
Leu Leu Phe Pro Ser Met Ala Ser Met Ala Met His Val Ala Gln Pro
-10              -5                 -1  1                   5 gct gtg gta ctg gcc agc agc cga ggc atc gcc agc ttt gtg tgt gag       144
Ala Val Val Leu Ala Ser Ser Arg Gly Ile Ala Ser Phe Val Cys Glu
                10                  15                  20 tat gca tct cca ggc aaa gcc act gag gtc cgg gtg aca gtg ctt cgg       192
Tyr Ala Ser Pro Gly Lys Ala Thr Glu Val Arg Val Thr Val Leu Arg
         25                  30                  35 cag gct gac agc cag gtg act gaa gtc tgt gcg gca acc tac atg atg       240
Gln Ala Asp Ser Gln Val Thr Glu Val Cys Ala Ala Thr Tyr Met Met
 40                  45                  50 ggg aat gag ttg acc ttc cta gat gat tcc atc tgc acg ggc acc tcc       288
Gly Asn Glu Leu Thr Phe Leu Asp Asp Ser Ile Cys Thr Gly Thr Ser
 55                  60                  65                  70 agt gga aat caa gtg aac ctc act atc caa gga ctg agg gcc atg gac       336
Ser Gly Asn Gln Val Asn Leu Thr Ile Gln Gly Leu Arg Ala Met Asp
                 75                  80                  85 acg gga ctc tac atc tgc aag gtg gag ctc atg tac cca ccg cca tac       384
Thr Gly Leu Tyr Ile Cys Lys Val Glu Leu Met Tyr Pro Pro Pro Tyr
             90                  95                 100 tac ctg ggc ata ggc aac gga acc cag att tat gta att gat cca gaa       432
Tyr Leu Gly Ile Gly Asn Gly Thr Gln Ile Tyr Val Ile Asp Pro Glu
        105                 110                 115 ccg tgc cca gat tct gat cag gag ccc aaa tct tct gac aaa act cac       480
Pro Cys Pro Asp Ser Asp Gln Glu Pro Lys Ser Ser Asp Lys Thr His
120                 125                 130 aca tcc cca ccg tcc cca gca cct gaa ctc ctg ggg gga tcg tca gtc       528
Thr Ser Pro Pro Ser Pro Ala Pro Glu Leu Leu Gly Gly Ser Ser Val
135                 140                 145                 150 ttc ctc ttc ccc cca aaa ccc aag gac acc ctc atg atc tcc cgg acc       576
Phe Leu Phe Pro Pro Lys Pro Lys Asp Thr Leu Met Ile Ser Arg Thr
                155                 160                 165 cct gag gtc aca tgc gtg gtg gtg gac gtg agc cac gaa gac cct gag       624
Pro Glu Val Thr Cys Val Val Val Asp Val Ser His Glu Asp Pro Glu
            170                 175                 180 gtc aag ttc aac tgg tac gtg gac ggc gtg gag gtg cat aat gcc aag       672
Val Lys Phe Asn Trp Tyr Val Asp Gly Val Glu Val His Asn Ala Lys
        185                 190                 195 aca aag ccg cgg gag gag cag tac aac agc acg tac cgt gtg gtc agc       720
Thr Lys Pro Arg Glu Glu Gln Tyr Asn Ser Thr Tyr Arg Val Val Ser
200                 205                 210
```

| | | | | | | | | | | | | | | | | |
|---|---|---|---|---|---|---|---|---|---|---|---|---|---|---|---|---|
| gtc | ctc | acc | gtc | ctg | cac | cag | gac | tgg | ctg | aat | ggc | aag | gag | tac | aag | 768 |
| Val | Leu | Thr | Val | Leu | His | Gln | Asp | Trp | Leu | Asn | Gly | Lys | Glu | Tyr | Lys | |
| 215 | | | | 220 | | | | | 225 | | | | | 230 | | |
| tgc | aag | gtc | tcc | aac | aaa | gcc | ctc | cca | gcc | ccc | atc | gag | aaa | acc | atc | 816 |
| Cys | Lys | Val | Ser | Asn | Lys | Ala | Leu | Pro | Ala | Pro | Ile | Glu | Lys | Thr | Ile | |
| | | | | 235 | | | | | 240 | | | | | 245 | | |
| tcc | aaa | gcc | aaa | ggg | cag | ccc | cga | gaa | cca | cag | gtg | tac | acc | ctg | ccc | 864 |
| Ser | Lys | Ala | Lys | Gly | Gln | Pro | Arg | Glu | Pro | Gln | Val | Tyr | Thr | Leu | Pro | |
| | | | 250 | | | | | 255 | | | | | 260 | | | |
| cca | tcc | cgg | gat | gag | ctg | acc | aag | aac | cag | gtc | agc | ctg | acc | tgc | ctg | 912 |
| Pro | Ser | Arg | Asp | Glu | Leu | Thr | Lys | Asn | Gln | Val | Ser | Leu | Thr | Cys | Leu | |
| | | 265 | | | | | 270 | | | | | 275 | | | | |
| gtc | aaa | ggc | ttc | tat | ccc | agc | gac | atc | gcc | gtg | gag | tgg | gag | agc | aat | 960 |
| Val | Lys | Gly | Phe | Tyr | Pro | Ser | Asp | Ile | Ala | Val | Glu | Trp | Glu | Ser | Asn | |
| | 280 | | | | | 285 | | | | | 290 | | | | | |
| ggg | cag | ccg | gag | aac | aac | tac | aag | acc | acg | cct | ccc | gtg | ctg | gac | tcc | 1008 |
| Gly | Gln | Pro | Glu | Asn | Asn | Tyr | Lys | Thr | Thr | Pro | Pro | Val | Leu | Asp | Ser | |
| 295 | | | | 300 | | | | | 305 | | | | | 310 | | |
| gac | ggc | tcc | ttc | ttc | ctc | tac | agc | aag | ctc | acc | gtg | gac | aag | agc | agg | 1056 |
| Asp | Gly | Ser | Phe | Phe | Leu | Tyr | Ser | Lys | Leu | Thr | Val | Asp | Lys | Ser | Arg | |
| | | | | 315 | | | | | 320 | | | | | 325 | | |
| tgg | cag | cag | ggg | aac | gtc | ttc | tca | tgc | tcc | gtg | atg | cat | gag | gct | ctg | 1104 |
| Trp | Gln | Gln | Gly | Asn | Val | Phe | Ser | Cys | Ser | Val | Met | His | Glu | Ala | Leu | |
| | | | 330 | | | | | 335 | | | | | 340 | | | |
| cac | aac | cac | tac | acg | cag | aag | agc | ctc | tcc | ctg | tct | ccg | ggt | aaa | tga | 1152 |
| His | Asn | His | Tyr | Thr | Gln | Lys | Ser | Leu | Ser | Leu | Ser | Pro | Gly | Lys | | |
| | | 345 | | | | | 350 | | | | | 355 | | | | |

<210> SEQ ID NO 22
<211> LENGTH: 383
<212> TYPE: PRT
<213> ORGANISM: Artificial
<220> FEATURE:
<223> OTHER INFORMATION: Synthetic Construct

<400> SEQUENCE: 22

Met Gly Val Leu Leu Thr Gln Arg Thr Leu Leu Ser Leu Val Leu Ala
    -25                 -20                 -15

Leu Leu Phe Pro Ser Met Ala Ser Met Ala Met His Val Ala Gln Pro
-10                  -5                  -1   1                   5

Ala Val Val Leu Ala Ser Ser Arg Gly Ile Ala Ser Phe Val Cys Glu
                10                  15                  20

Tyr Ala Ser Pro Gly Lys Ala Thr Glu Val Arg Val Thr Val Leu Arg
                25                  30                  35

Gln Ala Asp Ser Gln Val Thr Glu Val Cys Ala Ala Thr Tyr Met Met
        40                  45                  50

Gly Asn Glu Leu Thr Phe Leu Asp Asp Ser Ile Cys Thr Gly Thr Ser
55                  60                  65                  70

Ser Gly Asn Gln Val Asn Leu Thr Ile Gln Gly Leu Arg Ala Met Asp
                75                  80                  85

Thr Gly Leu Tyr Ile Cys Lys Val Glu Leu Met Tyr Pro Pro Pro Tyr
                90                  95                  100

Tyr Leu Gly Ile Gly Asn Gly Thr Gln Ile Tyr Val Ile Asp Pro Glu
                105                 110                 115

Pro Cys Pro Asp Ser Asp Gln Glu Pro Lys Ser Ser Asp Lys Thr His
            120                 125                 130

Thr Ser Pro Pro Ser Pro Ala Pro Glu Leu Leu Gly Gly Ser Ser Val
135                 140                 145                 150

-continued

```
Phe Leu Phe Pro Pro Lys Pro Lys Asp Thr Leu Met Ile Ser Arg Thr
            155             160                 165

Pro Glu Val Thr Cys Val Val Val Asp Val Ser His Glu Asp Pro Glu
            170             175                 180

Val Lys Phe Asn Trp Tyr Val Asp Gly Val Glu Val His Asn Ala Lys
        185             190                 195

Thr Lys Pro Arg Glu Glu Gln Tyr Asn Ser Thr Tyr Arg Val Val Ser
        200             205             210

Val Leu Thr Val Leu His Gln Asp Trp Leu Asn Gly Lys Glu Tyr Lys
215             220             225                 230

Cys Lys Val Ser Asn Lys Ala Leu Pro Ala Pro Ile Glu Lys Thr Ile
            235             240                 245

Ser Lys Ala Lys Gly Gln Pro Arg Glu Pro Gln Val Tyr Thr Leu Pro
            250             255                 260

Pro Ser Arg Asp Glu Leu Thr Lys Asn Gln Val Ser Leu Thr Cys Leu
            265             270             275

Val Lys Gly Phe Tyr Pro Ser Asp Ile Ala Val Glu Trp Glu Ser Asn
        280             285             290

Gly Gln Pro Glu Asn Asn Tyr Lys Thr Thr Pro Pro Val Leu Asp Ser
295             300             305                 310

Asp Gly Ser Phe Phe Leu Tyr Ser Lys Leu Thr Val Asp Lys Ser Arg
            315             320                 325

Trp Gln Gln Gly Asn Val Phe Ser Cys Ser Val Met His Glu Ala Leu
            330             335                 340

His Asn His Tyr Thr Gln Lys Ser Leu Ser Leu Ser Pro Gly Lys
            345             350             355
```